(12) United States Patent
Luo et al.

(10) Patent No.: US 11,473,110 B2
(45) Date of Patent: *Oct. 18, 2022

(54) **XYLITOL PRODUCING *METSCHNIKOWIA* SPECIES**

(71) Applicant: Creatus Biosciences Inc., West Vancouver (CA)

(72) Inventors: Zongli Luo, Vancouver (CA); Hendrik Jurgens Jansen Van Vuuren, Brentwood Bay (CA); Allan George DeBono, Vancouver (CA); Andrew Taplin Ferguson, Vancouver (CA)

(73) Assignee: Creatus Biosciences Inc., West Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/573,758

(22) Filed: Sep. 17, 2019

(65) Prior Publication Data

US 2020/0239915 A1    Jul. 30, 2020

Related U.S. Application Data

(62) Division of application No. 15/849,079, filed on Dec. 20, 2017, now Pat. No. 10,435,721.

(60) Provisional application No. 62/437,606, filed on Dec. 21, 2016.

(51) Int. Cl.
  *C12P 7/18*    (2006.01)
  *C12N 15/81*   (2006.01)
  *C12N 9/00*    (2006.01)
  *C12N 9/04*    (2006.01)

(52) U.S. Cl.
  CPC .............. *C12P 7/18* (2013.01); *C12N 9/0006* (2013.01); *C12N 15/81* (2013.01); *C12Y 101/01009* (2013.01); *C12Y 101/01113* (2013.01); *C12Y 101/01307* (2013.01)

(58) Field of Classification Search
  None
  See application file for complete search history.

(56) References Cited

U.S. PATENT DOCUMENTS

| | | |
|---|---|---|
| 3,619,369 A | 11/1971 | Onishi et al. |
| 3,627,636 A | 12/1971 | Jaffe et al. |
| 3,854,995 A | 12/1974 | Okabe et al. |
| 3,970,712 A | 7/1976 | Friese |
| 3,990,904 A | 11/1976 | Friese et al. |
| 4,008,285 A | 2/1977 | Melaja et al. |
| 4,072,628 A | 2/1978 | Kruse et al. |
| 4,075,406 A | 2/1978 | Melaja et al. |
| 4,087,316 A | 5/1978 | Jividen et al. |
| 4,105,467 A | 8/1978 | Buckl et al. |
| 4,350,766 A | 9/1982 | Mehlberg |
| 4,429,140 A | 1/1984 | Murai et al. |
| 4,950,366 A | 8/1990 | Jiricny et al. |
| 5,081,026 A | 1/1992 | Heikkila et al. |
| 5,084,104 A | 1/1992 | Heikkilä et al. |
| 5,144,024 A | 9/1992 | Pepper et al. |
| 5,158,789 A | 10/1992 | DuRoss |
| 5,162,517 A | 11/1992 | Darsow |
| 5,238,826 A | 8/1993 | Leleu et al. |
| 5,340,403 A | 8/1994 | Fields et al. |
| 5,536,526 A | 7/1996 | Virtanen et al. |
| 5,563,303 A | 10/1996 | Vuorinen |
| 5,616,361 A | 4/1997 | Virtanen et al. |
| 5,631,150 A | 5/1997 | Harkki et al. |
| 5,637,225 A | 6/1997 | Heikkilä et al. |
| 5,686,277 A | 11/1997 | Kim et al. |
| 5,714,602 A | 2/1998 | Beck et al. |
| 5,728,225 A | 3/1998 | Duflot et al. |
| 5,730,877 A | 3/1998 | Heikkilä et al. |
| 5,789,210 A | 8/1998 | Ho et al. |
| 5,831,078 A | 11/1998 | Elseviers et al. |
| 5,866,382 A | 2/1999 | Hallborn et al. |
| 5,965,408 A | 10/1999 | Short |
| 5,980,640 A | 11/1999 | Nurmi et al. |
| 5,998,181 A | 12/1999 | Kim et al. |
| 5,998,607 A | 12/1999 | Heikkilä et al. |
| 5,998,608 A | 12/1999 | Tamion |
| 6,057,438 A | 5/2000 | Hyatt et al. |
| 6,093,326 A | 7/2000 | Heikkilä et al. |
| 6,187,204 B1 | 2/2001 | Heikkild et al. |
| 6,214,125 B1 | 4/2001 | Hyöky et al. |
| 6,221,634 B1 | 4/2001 | Takeuchi et al. |
| 6,224,776 B1 | 5/2001 | Heikkilä et al. |
| 6,239,274 B1 | 5/2001 | Heikkilä et al. |
| 6,242,228 B1 | 6/2001 | Sugiyama et al. |
| 6,262,318 B1 | 7/2001 | Heikkilä et al. |
| 6,271,007 B1 | 8/2001 | Apajalahti et al. |
| 6,303,353 B1 | 10/2001 | Sugiyama et al. |
| 6,335,177 B1 | 1/2002 | Mihara et al. |

(Continued)

FOREIGN PATENT DOCUMENTS

| | | |
|---|---|---|
| CN | 1381585 A | 11/2002 |
| CN | 1699587 A | 11/2005 |

(Continued)

OTHER PUBLICATIONS

Ahmad et al., "Enhancement of xylitol production in Candida tropicalis by co-expression of two genes involved in pentose phosphate pathway," *Bioprocess Biosyst. Eng.*, 35:199-204 (2012).

Ahmad et al., "Enhancement of xylitol production in glycerol kinase disrupted Candida tropicalis by co-expression of three genes involved in glycerol metabolic pathway," *Bioprocess Biosyst. Eng.*, 36:1279-1284 (2013).

Azarpazhooh et al., "Xylitol for preventing acute otitis media in children up to 12 years of age," *Cochrane Database Syst. Rev.*, 11:CD007095 (2016).

Barbosa et al., "Screening of yeasts for production of xylitol fromd-xylose and some factors which affect xylitol yield inCandida guilliermondii," *J. Ind. Microbiol.*, 3:241-251 (1988).

(Continued)

*Primary Examiner* — Suzanne M Noakes

(74) *Attorney, Agent, or Firm* — Greenberg Traurig, LLP

(57) ABSTRACT

Provided herein are *Metschnikowia* species that produce xylitol from xylose when cultured, as well as methods to make and use these *Metschnikowia* species.

19 Claims, 19 Drawing Sheets

Specification includes a Sequence Listing.

(56) References Cited

U.S. PATENT DOCUMENTS

| | | |
|---|---|---|
| 6,340,582 B1 | 1/2002 | Suzuki et al. |
| 6,458,570 B1 | 10/2002 | Elseviers et al. |
| 6,476,217 B1 | 11/2002 | Tamion |
| 6,538,133 B1 | 3/2003 | Aoki et al. |
| 6,572,775 B2 | 6/2003 | Heikkilä et al. |
| 6,649,066 B2 | 11/2003 | Heikkilä et al. |
| 6,663,780 B2 | 12/2003 | Heikkilä et al. |
| 6,685,781 B2 | 2/2004 | Hyöky et al. |
| 6,723,540 B1 | 4/2004 | Harkki et al. |
| 6,752,902 B2 | 6/2004 | Heikkilä et al. |
| 6,773,512 B2 | 8/2004 | Ennelin et al. |
| 6,846,657 B2 | 1/2005 | Heikkilä et al. |
| 6,875,349 B2 | 4/2005 | Heikkilä et al. |
| 6,894,199 B2 | 5/2005 | Heikkilä et al. |
| 6,896,811 B2 | 5/2005 | Heikkilä et al. |
| 6,911,565 B2 | 6/2005 | Heikkilä et al. |
| 6,924,131 B2 | 8/2005 | Sugiyama et al. |
| 6,987,183 B2 | 1/2006 | Heikkilä et al. |
| 6,994,849 B2 | 2/2006 | Droby |
| 7,008,485 B2 | 3/2006 | Heikkilä et al. |
| 7,022,239 B2 | 4/2006 | Heikkilä et al. |
| 7,109,005 B2 | 9/2006 | Eroma et al. |
| 7,127,379 B2 | 10/2006 | Palsson et al. |
| 7,226,735 B2 | 6/2007 | Jeffries et al. |
| 7,226,761 B2 | 6/2007 | Miasnikov et al. |
| 7,229,558 B2 | 6/2007 | Heikkilä et al. |
| 7,427,500 B2 | 9/2008 | Oh et al. |
| 7,482,144 B2 | 1/2009 | Ojamo et al. |
| 7,625,728 B2 | 12/2009 | Eroma et al. |
| 7,820,414 B2 | 10/2010 | Kim et al. |
| 7,901,511 B2 | 3/2011 | Griffin et al. |
| 7,960,152 B2 | 6/2011 | Taylor et al. |
| 7,977,083 B1 | 7/2011 | Sakakibara et al. |
| 8,247,200 B2 | 8/2012 | Foody et al. |
| 8,283,139 B2 | 10/2012 | Park et al. |
| 8,287,652 B2 | 10/2012 | Heikkilä et al. |
| 8,343,736 B2 | 1/2013 | Kim et al. |
| 8,367,346 B2 | 2/2013 | Taylor et al. |
| 8,383,374 B2 | 2/2013 | Causey et al. |
| 8,409,835 B2 | 4/2013 | Huang et al. |
| 2001/0034049 A1 | 10/2001 | Sugiyama et al. |
| 2002/0012939 A1 | 1/2002 | Palsson |
| 2002/0061561 A1 | 5/2002 | Mihara et al. |
| 2002/0076772 A1 | 6/2002 | Elseviers et al. |
| 2002/0168654 A1 | 11/2002 | Maranas et al. |
| 2003/0041352 A1 | 2/2003 | Parrott et al. |
| 2003/0059792 A1 | 3/2003 | Palsson et al. |
| 2003/0097029 A1 | 5/2003 | Heikkilä et al. |
| 2003/0125588 A1 | 7/2003 | Heikkilä et al. |
| 2003/0148482 A1 | 8/2003 | Takenaka et al. |
| 2003/0224363 A1 | 12/2003 | Park et al. |
| 2003/0235881 A1 | 12/2003 | Heikkilä et al. |
| 2004/0009466 A1 | 1/2004 | Maranas et al. |
| 2004/0014185 A1 | 1/2004 | Ojamo et al. |
| 2004/0029149 A1 | 2/2004 | Palsson et al. |
| 2004/0072723 A1 | 4/2004 | Palsson et al. |
| 2004/0142456 A1 | 7/2004 | Jeffries et al. |
| 2004/0191881 A1 | 9/2004 | Raj et al. |
| 2005/0148055 A1 | 7/2005 | Walther et al. |
| 2006/0110805 A1 | 5/2006 | Fotheringham et al. |
| 2006/0281913 A1 | 12/2006 | Ferreira et al. |
| 2009/0047719 A1 | 2/2009 | Burgard et al. |
| 2011/0003356 A1 | 1/2011 | Jain et al. |
| 2011/0172411 A1 | 7/2011 | Heikkila et al. |
| 2011/0207190 A1 | 8/2011 | Subramanian et al. |
| 2012/0021467 A1 | 1/2012 | Zhang et al. |
| 2013/0217070 A1 | 8/2013 | Zhao et al. |
| 2014/0342418 A1 | 11/2014 | Jin et al. |
| 2015/0017696 A1 | 1/2015 | Davis et al. |

FOREIGN PATENT DOCUMENTS

| | | |
|---|---|---|
| CN | 101857886 B | 12/2012 |
| CN | 101914591 B | 5/2013 |
| CN | 103184243 A | 7/2013 |
| CN | 102936576 B | 8/2015 |
| DE | 10258089 A1 | 6/2004 |
| EP | 0450430 A2 | 10/1991 |
| EP | 0553222 B2 | 8/1993 |
| EP | 0754758 A1 | 1/1997 |
| EP | 0527758 B1 | 1/1998 |
| EP | 1029925 A1 | 8/2000 |
| EP | 1065276 B1 | 1/2001 |
| EP | 1306442 A2 | 7/2006 |
| EP | 1721988 A2 | 11/2006 |
| EP | 2332414 A2 | 6/2011 |
| EP | 2460871 A1 | 6/2012 |
| JP | A-H06-339383 | 12/1994 |
| WO | WO 1988/005467 A1 | 7/1988 |
| WO | WO 1990/008193 A1 | 7/1990 |
| WO | WO 1995/033063 A1 | 12/1995 |
| WO | WO 1999/031241 A1 | 6/1999 |
| WO | WO 1999/034021 A1 | 7/1999 |
| WO | WO 2001/004362 A1 | 1/2001 |
| WO | WO 2001/053306 A2 | 7/2001 |
| WO | WO 2002/006504 A1 | 1/2002 |
| WO | WO 2003/097848 A1 | 11/2003 |
| WO | WO 2004/052813 A1 | 6/2004 |
| WO | WO 2004/085627 A1 | 10/2004 |
| WO | WO 2004/108739 A2 | 12/2004 |
| WO | WO 2005/010171 A1 | 2/2005 |
| WO | WO 2009/040862 A1 | 4/2009 |
| WO | WO 2009/116066 A2 | 9/2009 |
| WO | WO 2010/017059 A2 | 2/2010 |
| WO | WO 2012/045088 A9 | 4/2012 |
| WO | WO 2013/059326 A1 | 4/2013 |
| WO | WO 2014/013506 A1 | 1/2014 |
| WO | WO 2014/045297 A2 | 3/2014 |
| WO | WO 2019/038565 A1 | 2/2019 |

OTHER PUBLICATIONS

Belda et al., "Unraveling the Enzymatic Basis of Wine "Flavorome": A Phylo-Functional Study of Wine Related Yeast Species," *Front. Microbiol.*, 7:Article 12 (2016).
Bergquist et al., "Degenerate oligonucleotide gene shuffling (DOGS) and random drift mutagenesis (RNDM): two complementary techniques for enzyme evolution" *Biomol. Eng.*, 22:63-72 (2005).
Bergquist et al., "Degenerate oligonucleotide gene shuffling," *Methods Mol. Biol.*, 352:191-204 (2007).
Bowie et al., "Deciphering the message in protein sequences: tolerance to amino acid substitutions," *Science*, 247:1306-1310 (1990).
Bura et al., "Novel endophytic yeast Rhodotorula mucilaginosa strain PTD3 I: production of xylitol and ethanol" *J. Ind. Microbiol. Biotechnol.*, 39:1003-1011 (2012).
Cadete et al., "*Cyberlindnera xylosilytica* sp. nov., a xylitol-producing yeast species isolated from lignocellulosic materials," *Int. J. Syst. Evol. Microbiol.*, 65(9):2968-2974 (2015).
Cheng et al., "Genetically engineered *Pichia pastoris* yeast for conversion of glucose to xylitol by a single-fermentation process," *Appl. Microbiol. Biotechnol.*, 98(8):3539-3552 (2014).
Chiang et al., A new pathway of pentose metabolism *Biochem. Biophys. Res. Commun.*, 3(5):554-559 (1960).
Chiang et al., "Metabolism of d-xylose by moulds," *Nature*, 188:79-81 (1960).
Chiang et al., "The conversion of D-xylose to xylitol by Penicillum chrysogenum," *Biochim. Biophys. Acta*, 29:664-665 (1958).
Chin et al., "Analysis of NADPH supply during xylitol production by engineered *Escherichia coli*," *Biotechnol. Bioeng.*, 102(1):209-220 (2009).
Chin et al., "Codon Optimization OnLine (COOL): a web-based multi-objective optimization platform for synthetic gene design," *Bioinformatics*, 30(15):2210-2212 (2014).
Chin et al., "Improved NADPH supply for xylitol production by engineered *Escherichia coli* with glycolytic mutations," *Biotechnol. Prog.*, 27:333-341 (2011).
Choi et al., "Production of xylitol in cell recycle fermentations of Candida tropicalis," *Biotechnol. Lett.*, 22:1625-1628 (2000).
Chung et al., "Computational codon optimization of synthetic gene for protein expression," *BMC Syst Biol.*, 6:134 (2012).

(56) References Cited

OTHER PUBLICATIONS

Chung et al., "Stable expression of xylose reductase gene enhances xylitol production in recombinant *Saccharomyces cerevisiae*," *Enzyme Microb. Technol.*, 30:809-816 (2002).
Cirino et al., Engineering *Escherichia coli* for xylitol production from glucose-xylose mixtures *Biotechnol. Bioeng.*, 95(6):1167-1176 (2006).
Coco et al., "DNA shuffling method for generating highly recombined genes and evolved enzymes" *Nat. Biotechnol.*, 19:354-359 (2001).
Colonna et al., "Synthesis and radiocarbon evidence of terephthalate polyesters completely prepared from renewable resources," *Green Chemistry*, 13:2543-2548 (2011).
Cosman et al., "ULBPs, novel MHC class I-related molecules, bind to CMV glycoprotein UL16 and stimulate NK cytotoxicity through the NKG2D receptor," *Immunity*, 14:123-133 (2001).
Crameri et al., "DNA shuffling of a family of genes from diverse species accelerates directed evolution," *Nature*, 391:288-291 (1998).
Currie et al., "Authentication and dating of biomass components of industrial materials; links to sustainable technology," *Nucl. Instr. Meth. Phys. Res. B*, 172:281-287 (2000).
Dahiya et al., "Xylitol production from sugar cane bagasse by fermentation," *Modernisation of Indian Sugar Industry*, Gehlawat ed., Arnold Publishers, New Dehli, pp. 292-303 (1990).
Dahiya, "Xylitol production by Petromyces albertensis grown on medium containing D-xylose," *Can. J. Microbiol.*, 37:14-18 (1991).
Dashtban et al., "Xylitol Production by Genetically Engineered Trichoderma reesei Strains Using Barley Straw as Feedstock," *Appl. Biochem. Biotechnol.*, 169:554-569 (2013).
Dhar et al., "Engineering of Corynebacterium glutamicum for xylitol production from lignocellulosic pentose sugars." *J. Biotechnol.*, 230:63-71 (2016).
Drucker et al., "Comparative effects of the substance-sweeteners glucose, sorbitol, sucrose, xylitol and trichlorosucrose on lowering of pH by two oral *Streptococcus mutans* strains in vitro," *Arch Oral Biol.*, 24(12):965-970 (1979).
Fujii et al., "Error-prone rolling circle amplification: the simplest random mutagenesis protocol," *Nat. Protoc.*, 1(5):2493-2497 (2006).
Fujii et al., "One-step random mutagenesis by error-prone rolling circle amplification," *Nucleic Acids Res.*, 32(19):e145 (2004).
Genbank Accession No. ANFW02000029.1, "Metschnikowia fructicola 277 unitig_191, whole genome shotgun sequence," (Jun. 7, 2016).
Gibbs et al., "Degenerate oligonucleotide gene shuffling (DOGS): a method for enhancing the frequency of recombination with family shuffling," *Gene*, 271:13-20 (2001).
Gong et al., "Conversion of pentoses by yeasts," *Biotechnol. Bioeng.*, 25:85-102 (1983).
Gong et al., "Quantitative production of xylitol from D-xylose by a high-xylitol producing yeast mutant Candida tropicalis HXP2," *Biotechnol. Lett.*, 3:125-130 (1981).
Govinden et al., "Xylitol production by recombinant *Saccharomyces cerevisiae* expressing the Pichia stipitis and Candida shehatae XYL1 genes," *Appl. Microbiol. Biotechnol.*, 55:76-80 (2001).
Grillaud et al., "The polyols in pediatric dentistry: advantages of xylitol," *Arch. Pediatr.*, 12(7):1180-1186 (2005). (English abstract attached).
Guamán-Burneo et al., "Xylitol production by yeasts isolated from rotting wood in the Galápagos Islands, Ecuador, and description of *Cyberlindnera galapagoensis* f.a., sp. Nov," *Antonie Van Leeuwenhoek*, 108(4):919-931 (2015).
Guirimand et al., "Cell surface engineering of *Saccharomyces cerevisiae* combined with membrane separation technology for xylitol production from rice straw hydrolysate," *Appl. Microbiol. Biotechnol.*, 100(8):3477-3487 (2016).
Güldener et al., "A new efficient gene disruption cassette for repeated use in budding yeast," *Nucleic Acids Res.*, 24(13):2519-2524 (1996).
Guo et al., "Screening and characterization of yeasts for xylitol production," *J. Appl. Microbiol.*, 101(5):1096-1104 (2006).

Hallborn et al., "The influence of cosubstrate and aeration on xylitol formation by recombinant*Saccharomyces cerevisiae* expressing the*XYL1* gene," *Appl. Microbiol. Biotechnol.*, 42:326-333 (1994).
Hallborn et al., "Xylitol production by recombinant *Saccharomyces cerevisiae*," *Bio/Technology*, 9:1090-1095 (1991).
Haresaku et al., "Long-term effect of xylitol gum use on mutans streptococci in adults," *Caries Res.*, 41(3):198-203 (2007).
Hayes et al., "Combining computational and experimental screening for rapid optimization of protein properties," *Proc. Natl. Acad. Sci. USA*, 99(25):15926-15931 (2002).
Hellinga, "Computational protein engineering," *Nat. Struct. Biol.*, 5(7):525-527 (1998).
Hershkovitz et al., "De-novo assembly and characterization of the transcriptome of Metschnikowia fructicola reveals differences in gene expression following interaction with Penicillium digitatum and grapefruit peel," *BMC Genomics*, 14:168 (2013).
Hibbert et al., "Directed evolution of biocatalytic processes," *Biomol. Eng.*, 22:11-19 (2005).
Hirabayashi et al., "Improving xylitol production through recombinant expression of xylose reductase in the white-rot fungus *Phanerochaete sordida* YK-624," *J. Biosci. Bioeng.*, 120:6-8 (2015).
Hong et al., "Overexpression of D-xylose reductase (xyl1) gene and antisense inhibition of D-xylulokinase (xyiH) gene increase xylitol production in Trichoderma reesei," *Biomed. Res. Int.*, 2014:169705 (2014).
Huisman et al., "Enzyme Evolution for Chemical Process Applications," *Biocatalysis in the Pharmaceutical and Biotechnology Industries*, Patel Ed., CRC Press, Boca Raton, Florida, pp. 717-742 (2007).
Iverson et al., "Engineering a synthetic anaerobic respiration for reduction of xylose to xylitol using NADH output of glucose catabolism by *Escherichia coli* AI21," *BMC Syst. Biol.*, 10:31 (2016).
Iverson et al., "Increasing reducing power output (NADH) of glucose catabolism for reduction of xylose to xylitol by genetically engineered *Escherichia coli* AI05," *World J. Microbiol. Biotechnol.*, 29:1225-1232 (2013).
Izumori et al., "Production of xylitol from D-xylulose by *Mycobacterium smegmatis*" *J. Ferment. Technol.*, 66(1):33-36 (1988).
Jeffries et al., "Strain selection, taxonomy, and genetics of xylose-fermenting yeasts," *Enzyme Microb. Technol.*, 16:922-932 (1994).
Jeon et al., "Effect of heterologous xylose transporter expression in Candida tropicalis on xylitol production rate," *Bioprocess Biosyst. Eng.*, 36:809-817 (2013).
Jeon et al., "Xylitol production is increased by expression of codon-optimized Neurospora crassa xylose reductase gene in Candida tropicalis," *Bioprocess Biosyst. Eng.*, 35:191-198 (2012).
Jo et al., "Dual utilization of NADPH and NADH cofactors enhances xylitol production in engineered *Saccharomyces cerevisiae*," *Biotechnol. J.*, 10:1935-1943 (2015).
Junyapate et al., "*Yamadazyma ubonensis* f.a., sp. nov., a novel xylitol-producing yeast species isolated in Thailand," *Antonie Van Leeuwenhoek*, 105:471-480 (2014).
Kamat et al., "Xylitol production by Cyberlindnera (*Williopsis*) *saturnus*, a tropical mangrove yeast from xylose and corn cob hydrolysate," *J. Appl. Microbiol.*, 115(6):1357-1367 (2013).
Karlen et al., "Absolute determination of the activity of two C-14 dating standards," *Arkiv Geofysik*, 4:465-471 (1964).
Khankal et al., "Role of xylose transporters in xylitol production from engineered *Escherichia coli.*," *J. Biotechnol.*, 134:246-252 (2008).
Kim et al., "Increased xylitol production rate during long-term cell recycle fermentation of Candida tropicalis" *Biotechnol. Lett.*, 26:623-627 (2004).
Kim et al., "Production of xylitol from D-xylose and glucose with recombinant Corynebacterium glutamicum," *Enzyme Microb. Technol.*, 46:366-371 (2010).
Ko et al., "Enhancement of xylitol productivity and yield using a xylitol dehydrogenase gene-disrupted mutant of Candida tropicalis under fully aerobic conditions," *Biotechnol. Lett.*, 28(15):1159-1162 (2006).

(56) References Cited

OTHER PUBLICATIONS

Ko et al., "Production of xylitol from D-xylose by a xylitol dehydrogenase gene-disrupted mutant of Candida tropicalis," *Appl. Environ. Microbiol.*, 72(6):4207-4213 (2006).
Kretz et al., "Gene site saturation mutagenesis: a comprehensive mutagenesis approach," *Methods Enzymol.*, 388:3-11 (2004).
Kwon et al., "Increase of xylitol productivity by cell-recycle fermentation of Candida tropicalis using submerged membrane bioreactor" *J. Biosci. Bioeng.*, 101(1):13-18 (2006).
Landschulz et al., "The leucine zipper: a hypothetical structure common to a new class of DNA binding proteins," *Science*, 240:1759-1764 (1988).
Lee et al., "A new approach to directed gene evolution by recombined extension on truncated templates (RETT)," *J. Molec. Catalysis B:Enzym.*, 26:119-129 (2003).
Lee et al., "Characterization of two-substrate fermentation processes for xylitol production using recombinant *Saccharomyces cerevisiae* containing xylose reductase gene," *Process Biochem.*, 35:1199-1203 (2000).
Lee et al., "Cloning and characterization of the xyl1 gene, encoding an NADH-preferring xylose reductase from Candida parapsilosis, and its functional expression in Candida tropicalis," *Appl. Environ. Microbiol.*, 69:6179-6188 (2003).
Low et al., "Mimicking somatic hypermutation: affinity maturation of antibodies displayed on bacteriophage using a bacterial mutator strain," *J. Mol. Biol.*, 260(3):359-368 (1996).
Lutz et al., "Creating multiple-crossover DNA libraries independent of sequence identity," *Proc. Natl. Acad. Sci. USA*, 98(20):11248-11253 (2001).
Lutz et al., "Rapid generation of incremental truncation libraries for protein engineering using α-phosphothioate nucleotides," *Nucleic Acids Res.*, 29(4):e16 (2001).
Maguire et al., "Xylitol and caries prevention—is it a magic bullet?," *Br. Dent. J.*, 194(8):429-436 (2003).
Mann, "An International Reference Material for Radiocarbon Dating," *Radiocarbon*, 25(2):519-527 (1983).
Manso et al., "Metschnikowia andauensis as a new biocontrol agent of fruit postharvest diseases," *Postharvest Biol. Technol.*, 61:64-71 (2011).
Matsushika et al., "Ethanol production from xylose in engineered *Saccharomyces cerevisiae* strains: current state and perspectives," *Appl. Microbiol. Biotechnol.*, 84(1):37-53 (2009).
Muller et al., "Nucleotide exchange and excision technology (NExT) DNA shuffling: a robust method for DNA fragmentation and directed evolution," *Nucleic Acids Res.*, 33(13):e117 (2005).
Nair et al., "Evolution in Reverse: Engineering a D-Xylose-Specific Xylose Reductase," *ChemBioChem*, 9(8):1213-1215 (2008).
Ness et al., "Synthetic shuffling expands functional protein diversity by allowing amino acids to recombine independently" *Nat. Biotechnol.*, 20(12):1251-1255 (2002).
Nozaki et al., "Production of D-arabitol by Metschnikowia reukaufii AJ14787," *Biosci. Biotechnol. Biochem.*, 67:1923-1929 (2003).
Nyyssölä et al., "Production of xylitol from D-xylose by recombinant Lactococcus lactis," *J. Biotechnol.*, 118:55-66 (2005).
Oh et al., "Enhanced xylitol production through simultaneous co-utilization of cellobiose and xylose by engineered *Saccharomyces cerevisiae*," *Metab. Eng.*, 15:226-234 (2013).
Oh et al., "Increase of xylitol yield by feeding xylose and glucose in Candida tropicalis," *Appl. Microbiol. Biotechnol.*, 50:419-425 (1998).
Onishi et al., "Microbial production of xylitol from glucose.," *Appl. Microbiol.*, 18(6):1031-1035 (1969).
Onishi et al., "The production of xylitol, L-arabinitol and ribitol by yeasts," *Agr. Biol. Chem.*, 30(11):1139-1144 (1966).
Osawa et al., "Recent evidence for evolution of the genetic code.," *Microbiol Rev.*, 56(1):229-264 (1992).
Ostermeier et al., "A combinatorial approach to hybrid enzymes independent of DNA homology," *Nat. Biotechnol.*, 17:1205-1209 (1999).
Ostermeier et al., "Combinatorial protein engineering by incremental truncation," *Proc. Natl. Acad. Sci. USA*, 96:3562-3567 (1999).
Otten et al., "Directed evolution: selecting today's biocatalysts," *Biomol. Eng.*, 22:1-9 (2005).
Pal et al., "Studies on xylitol production by metabolic pathway engineered Debaryomyces hansenii," *Bioresour. Technol.*, 147:449-455 (2013).
Pourmir et al., "Production of xylitol by recombinant microalgae," *J. Biotechnol.*, 165:178-183 (2013).
Povelainen et al., "Production of D-arabitol by a metabolic engineered strain of Bacillus subtilis," *Biotechnol. J.*, 1:214-219 (2006).
Povelainen et al., "Production of xylitol by metabolically engineered strains of Bacillus subtilis," *J. Biotechnol.*, 128:24-31 (2007).
Prakash et al., "Microbial production of xylitol from D-xylose and sugarcane bagasse hemicellulose using newly isolated thermotolerant yeast *Debaryomyces hansenii*," *Bioresour. Technol.*, 102:3304-3308 (2011).
Pritchard et al., "A general model of error-prone PCR," *J. Theor. Biol.*, 234:497-509 (2005).
Rajpal et al., "A general method for greatly improving the affinity of antibodies by using combinatorial libraries" *Proc. Natl. Acad. Sci. USA*, 102(24):8466-8471 (2005).
Rangaswamy et al., "Screening of facultative anaerobic bacteria utilizing D-xylose for xylitol production," *Appl. Microbiol. Biotechnol.*, 60:88-93 (2002).
Rao et al., "Isolation and characterization of ethanol-producing yeasts from fruits and tree barks," *Lett. Appl. Microbiol.*, 47(1):19-24 (2008).
Reetz et al., "Directed Evolution of an Enantioselective Enzyme through Combinatorial Multiple-Cassette Mutagenesis" *Angew. Chem. Int. Ed Engl.*, 40(19):3589-3591 (2001).
Reetz et al., "Iterative saturation mutagenesis (ISM) for rapid directed evolution of functional enzymes.," *Nat. Protoc.*, 2(4):891-903 (2007).
Reetz et al., "Iterative saturation mutagenesis on the basis of B factors as a strategy for increasing protein thermostability," *Angew. Chem. Int. Ed Engl.*, 45:7745-7751 (2006).
Reidhaar-Olson et al. "Combinatorial cassette mutagenesis as a probe of the informational content of protein sequences," *Science*, 241:53-57 (1988).
Reidhaar-Olson et al., "Random mutagenesis of protein sequences using oligonucleotide cassettes," *Methods Enzymol.*, 208:564-586 (1991).
Rivas et al., "Carbon material and bioenergetic balances of xylitol production from corncobs by Debaryomyces hansenii," *Biotechnol. Prog.*, 19(3):706-713 (2003).
Sampaio et al., "Screening of filamentous fungi for production of xylitol from D-xylose," *Brazilian J. Microbiol.*, 34:325-328 (2003).
Santamauro et al., "Low-cost lipid production by an oleaginous yeast cultured in non-sterile conditions using model waste resources," *Biotechnol. Biofuels.*, 7(1):34-44 (2014).
Santos et al., "The genetic code of the fungal CTG clade," *C.R. Biol.*, 334:607-611 (2011).
Sasaki et al., "Engineering of pentose transport in Corynebacterium glutamicum to improve simultaneous utilization of mixed sugars," *Appl. Microbiol. Biotechnol.*, 85:105-115 (2009).
Sasaki et al., "Xylitol production by recombinant Corynebacterium glutamicum under oxygen deprivation" *Appl. Microbiol. Biotechnol.*, 86:1057-1066 (2010).
Selifonova et al., "Rapid evolution of novel traits in microorganisms" *Appl. Environ. Microbiol.*, 67(8):3645-3649 (2001).
Sen et al., "Developments in directed evolution for improving enzyme functions," *Appl. Biochem. Biotechnol.*, 143:212-223 (2007).
Shao et al., "Random-priming in vitro recombination: an effective tool for directed evolution" *Nucleic Acids Res.*, 26(2):681-683 (1998).
Sharma et al., "Enhancement in xylose utilization using Kluyveromyces marxianus NIRE-K1 through evolutionary adaptation approach," *Bioprocess Biosyst. Eng.*, 39:835-843 (2016).
Sieber et al., "Libraries of hybrid proteins from distantly related sequences," *Nat. Biotechnol.*, 19:456-460 (2001).
Sirisansaneeyakul et al., "Screening of Yeasts for Production of Xylitol from D-Xylose," *J. Ferment. Bioeng.*, 80(6):565-570 (1995).

(56) References Cited

OTHER PUBLICATIONS

Steinberg et al., "Remineralizing potential, antiplaque and antigingivitis effects of xylitol and sorbitol sweetened chewing gum," *Clin. Prev. Dent.*, 14(5):31-34 (1992).
Stemmer, "DNA shuffling by random fragmentation and reassembly: in vitro recombination for molecular evolution," *Proc Natl Acad Sci USA*, 91:10747-10751 (1994).
Stemmer, "Rapid evolution of a protein in vitro by DNA shuffling," *Nature*, 370:389-391 (1994).
Su et al., "Efficient production of xylitol from hemicellulosic hydrolysate using engineered *Escherichia coli*," *Metab. Eng.*, 31:112-122 (2015).
Suzuki et al., "Novel Enzymatic Method for the Production of Xylitol from D-Arabitol by Gluconobacter oxydans," *Biosci. Biotechnol. Biochem.*, 66(12):2614-2620 (2002).
Suzuki et al.,"Expression of xyrA gene encoding for D-xylose reductase of Candida tropicalis and production of xylitol in *Escherichia coli*," *J. Biosci. Bioeng.*, 87(3):280-284 (1999).
Toivari et al., "Metabolic engineering of *Saccharomyces cerevisiae* for conversion of D-glucose to xylitol and other five-carbon sugars and sugar alcohols," *Appl. Environ. Microbiol.*, 73(17):5471-5476 (2007).
Ur-Rehman et al., "Xylitol; A review on Bio-production, Application, Health Benefits and Related Safety Issues," *Crit. Rev. Food Sci. Nutr.*, 55:1514-1528 (2015).
Van Den Burg et al., "Engineering an enzyme to resist boiling," *Proc. Natl. Acad. Sci USA*, 95:2056-2060 (1998).
Vandeska et al., "Effects of environmental conditions on production of xylitol by Candida boidinii," *World J. Microbiol. Biotechnol.*, 11:213-218 (1995).
Volkov et al, "Recombination and chimeragenesis by in vitro heteroduplex formation and in vivo repair" *Nucleic Acids Res.*, 27(18):e18 (1999).
Volkov et al., "Random chimeragenesis by heteroduplex recombination" *Methods Enzymol.*, 328:456-463 (2000).
West, "Xylitol production by Candida species grown on a grass hydrolysate," *World J. Microbiol. Biotechnol.*, 25:913-916 (2009).
Wong et al., "Sequence saturation mutagenesis (SeSaM): a novel method for directed evolution" *Nucleic Acids Res.*, 32(3):e26 (2004).
Wong et al., "Sequence saturation mutagenesis with tunable mutation frequencies" *Anal. Biochem.*, 341:187-189 (2005).
Wong et al., "Transversion-enriched sequence saturation mutagenesis (SeSaM-Tv+): a random mutagenesis method with consecutive nucleotide exchanges that complements the bias of error-prone PCR." *Biotechnol. J.*, 3:74-82 (2008).
Yoon et al., "L-arabinose pathway engineering for arabitol-free xylitol production in Candida tropicalis," *Biotechnol. Lett.*, 33:747-753 (2011).
Yoshitake et al., "Production of Polyalcohol by a *Corynebacterium* sp. Part I. Production of Pentitol from Aldopentose" *Agric. Biol. Chem.*, 35(6):905-911 (1971).
Yoshitake et al., "Xylitol Production by an Enterobacter Species," *Agric. Biol. Chem.*, 37(10):2261-2267 (1973).
Yoshitake et al., Xylitol Production by Enterobacter liquefaciens, *Agric. Biol. Chem.*, 40(8):1493-1503 (1976).
Young et al., "Rewiring yeast sugar transporter preference through modifying a conserved protein motif," *Proc. Natl. Acad. Sci. USA*, 111(1):131-136 (2014).
Young et al., "STE12 homolog is required for mating but dispensable for filamentation in candida lusitaniae" *Genetics*, 155:17-29 (2000).
Zha et al., "Optimization of CDT-1 and XYL1 expression for balanced co-production of ethanol and xylitol from cellobiose and xylose by engineered *Saccharomyces cerevisiae*," *PLoS One*, 8(7):e68317 (2013).
Zhang et al., "Improving xylitol production at elevated temperature with engineered Kluyveromyces marxianus through overexpressing transporters," *Bioresour. Technol.*, 1-17 (2014).
Zhang et al., "Xylitol production at high temperature by engineered Kluyveromyces marxianus," *Bioresour. Technol.*, 152:192-201 (2014).
Zhao et al., "Molecular evolution by staggered extension process (StEP) in vitro recombination," *Nat. Biotechnol.*, 16:258-261 (1998).

XYLITOL PRODUCING *METSCHNIKOWIA* SPECIES

CROSS-REFERENCE TO RELATED APPLICATION

This application is a divisional of application Ser. No. 15/849,079, filed Dec. 20, 2017, which claims the benefit of priority of U.S. Provisional Application No. 62/437,606, filed on Dec. 21, 2016, the entire contents of each of which is incorporated herein by reference.

FIELD

The present invention relates to the field of molecular biology and microbiology. Provided herein are *Metschnikowia* species that produce xylitol from xylose when cultured, as well as methods to make and use these *Metschnikowia* species.

REFERENCE TO SEQUENCE LISTING

The instant application contains a Sequence Listing which has been submitted in ASCII format via EFS-Web and is hereby incorporated by reference in its entirety. Said ASCII copy, created on Sep. 16, 2019, is named 14305-013-999_Sequence_Listing.txt and is 170,380 bytes in size.

BACKGROUND

Xylose is an abundant sugar present in lignocellulosic biomass, a renewable feedstock for producing bioderived chemicals. However, the use of lignocellulosic biomass and the production of bioderived chemicals are limited by the naturally low xylose uptake in microbial organisms. Therefore, a microbial organism that can use xylose to produce bioderived compounds, such as xylitol, represents an unmet need.

Xylitol is a five-carbon sugar alcohol widely used as a low-calorie, low-carbohydrate alternative to sugar (Drucker et al., *Arch of Oral Biol.* 24:965-970 (1979)). Xylitol is approximately as sweet as sucrose but has 33% fewer calories. Xylitol has been reported to not affect insulin levels of people with diabetes and individuals with hyperglycemia. The consumption of xylitol is also reportedly beneficial for dental health, reducing the incidence of caries. For example, xylitol in chewing gum is reported to inhibit growth of *Streptoccocus mutans* (Haresaku et al., *Caries Res.* 41:198-203 (2007)), and to reduce the incidence of acute middle ear infection (Azarpazhooh et al., *Cochrane Database of Systematic Reviews* 11:CD007095 (2011)). Moreover, xylitol has been reported to inhibit demineralization of healthy tooth enamel and to re-mineralize damaged tooth enamel (Steinberg et al., *Clinical Preventive Dentistry* 14:31-34 (1992); Maguire et al., *British Dental J.* 194:429-436 (2003); Grillaud et al., *Arch of Pediatrics and Adolescent Medicine* 12:1180-1186 (2005)).

Commercially, xylitol may be produced by chemical reduction of xylose, although this can present difficulties associated with separation and purification of xylose or xylitol from hydrolysates. Microbial systems for the production of xylitol have been described (Sirisansaneeyakul et al., *J. Ferment. Bioeng.* 80:565-570 (1995); Onishi et al., *Agric. Biol. Chem.* 30:1139-1144 (1966); Barbosa et al., *J. Ind. Microbiol.* 3:241-251 (1988); Gong et al., *Biotechnol. Lett.* 3:125-130 (1981); Vandeska et al., *World J. Microbiol. Biotechnol.* 11:213-218 (1995); Dahiya et al., *Cabdirect.org* 292-303 (1990); Gong et al., *Biotechnol. Bioeng.* 25:85-102 (1983)). For example, yeast from the genus *Candida* has been described as being useful for xylitol production. However, *Candida* spp. may be opportunistic pathogens, so the use of these organisms in processes related to food products are not desirable.

The *Metschnikowia* species, methods and compositions provided herein meet these needs and provide other related advantages.

SUMMARY OF THE INVENTION

Provided herein is an isolated *Metschnikowia* species having a xylitol pathway. Such *Metschnikowia* species can produce xylitol from xylose when cultured in medium having xylose. In some embodiments, a xylitol pathway described herein includes a xylose reductase, which converts xylose to xylitol. Additionally, in some embodiments, the isolated *Metschnikowia* species includes a genetic modification to a xylitol dehydrogenase, which would normally convert xylitol to xylulose. Accordingly, in some embodiments, provided herein is an isolated *Metschnikowia* species having at least one exogenous nucleic acid encoding a xylose reductase or, alternatively or additionally, at least one exogenous nucleic acid that results in overexpression of a xylose reductase of the isolated *Metschnikowia* species. In some embodiments, also provided herein is an isolated *Metschnikowia* species having a genetic modification that attenuates or inactivates a xylitol dehydrogenase of the isolated *Metschnikowia* species. In some embodiments, provided herein is an isolated *Metschnikowia* species having: (a) at least one exogenous nucleic acid encoding a xylose reductase or that results in overexpression of a xylose reductase of the isolated *Metschnikowia* species; and (b) a genetic modification that attenuates or inactivates a xylitol dehydrogenase of the isolated *Metschnikowia* species.

Also provided herein is an isolated *Metschnikowia* species that can produce xylitol from xylose at a specific rate. For example, in some embodiments, the isolated *Metschnikowia* species provided herein produces at least 0.50 g/L/h, at least 0.60 g/L/h, at least 0.70 g/L/h, at least 0.80 g/L/h, at least 0.90 g/L/h, at least 1.00 g/L/h, at least 1.50 g/L/h, at least 2.00 g/L/h, at least 2.50 g/L/h, at least 3.00 g/L/h, at least 3.50 g/L/h, at least 4.00 g/L/h, at least 5.00 g/L/h, at least 6.00 g/L/h, at least 7.00 g/L/h, at least 8.00 g/L/h, at least 9.00 g/L/h, or at least 10.00 g/L/h of xylitol from xylose when cultured.

Still further provided herein is an isolated *Metschnikowia* species that can produce xylitol from xylose at a specific concentration. For example, in some embodiments, the isolated *Metschnikowia* species provided herein produces at least 75 g/L, at least 80 g/L, at least 85 g/L, at least 90 g/L, at least 95 g/L, at least 100 g/L, at least 110 g/L, at least 120 g/L, at least 130 g/L, at least 140 g/L, at least 150 g/L, at least 160 g/L, at least 170 g/L, at least 180 g/L, at least 190 g/L, at least 200 g/L, at least 250 g/L, or at least 300 g/L of xylitol from xylose when cultured.

The isolated *Metschnikowia* species provided herein can be a *Metschnikowia* species selected from *Metschnikowia pulcherrima*, *Metschnikowia fructicola*, *Metschnikowia chrysoperlae*, *Metschnikowia reukaufii*, *Metschnikowia andauensis*, *Metschnikowia shanxiensis*, *Metschnikowia sinensis*, *Metschnikowia zizyphicola*, *Metschnikowia bicuspidata*, *Metschnikowia lunata*, *Metschnikowia zobellii*, *Metschnikowia australis*, *Metschnikowia agaveae*, *Metschnikowia gruessii*, *Metschnikowia hawaiiensis*, *Metschnikowia krissii*, *Metschnikowia* sp. strain NS-O-85, and *Metschnikowia* sp. strain NS-O-89. In a particular embodiment, the isolated *Metschnikowia* species is the *Metschnikowia* species designated Accession No. 081116-01, deposited at the International Depositary Authority of Canada, an International Depositary Authority, on Nov. 8, 2016, under the terms of the Budapest Treaty.

In some embodiments, the at least one exogenous nucleic acid encoding a xylose reductase that is introduced into the isolated *Metschnikowia* species is a heterologous nucleic acid.

In some embodiments, the xylose reductase has the amino acid sequence selected from SEQ ID NOS: 11-18. In a particular embodiment, the xylose reductase has the amino acid sequence of SEQ ID NO: 11 or an amino acid sequence with at least 95% sequence identity to SEQ ID NO: 11.

In some aspects, the isolated *Metschnikowia* species provided herein includes a genetic modification, wherein the genetic modification includes the deletion of at least one allele encoding the xylitol dehydrogenase or a portion thereof of the isolated *Metschnikowia* species. In a particular embodiment, the genetic modification includes the deletion of both alleles encoding the xylitol dehydrogenase or a portion thereof of the isolated *Metschnikowia* species.

In some aspects, the isolated *Metschnikowia* species provided herein further includes at least one exogenous nucleic acid encoding a xylose transporter or that results in overexpression of a xylose transporter of the isolated *Metschnikowia* species. The xylose transporter, in some embodiments, has the amino acid sequence selected from SEQ ID NO: 27-40. In a particular embodiment, the xylose transporter has the amino acid sequence of any one of SEQ ID NOS: 27-36 or an amino acid sequence with at least 30% sequence identity to any one of SEQ ID NOS: 27-36.

In some aspects, provided herein is a method for producing xylitol. In some embodiments, the method includes culturing the isolated *Metschnikowia* species provided herein under conditions and for a sufficient period of time to produce xylitol from xylose. The method can include culturing the isolated *Metschnikowia* species in medium having xylose and a C3 carbon source, a C4 carbon source, a C5 carbon source, a C6 carbon source, or a combination thereof. In some embodiments, the conditions include culturing the isolated *Metschnikowia* species in medium comprising xylose and a co-substrate selected from cellobiose, galactose, glucose, ethanol, acetate, arabitol, sorbitol and glycerol, or a combination thereof. In a particular embodiment, the co-substrate is glucose. In yet another particular embodiment, the medium comprises a combination of xylose and cellobiose, or a combination of xylose and galactose, or a combination of xylose and glycerol. The culturing conditions can also include aerobic culturing conditions. The culturing can include batch cultivation, fed-batch cultivation or continuous cultivation. In some embodiments, the method includes separating the xylitol from other components in the culture using, for example, extraction, continuous liquid-liquid extraction, pervaporation, membrane filtration, membrane separation, reverse osmosis, electrodialysis, distillation, crystallization, centrifugation, extractive filtration, ion exchange chromatography, absorption chromatography, or ultrafiltration.

In some aspects, provided herein is bioderived xylitol produced by a method provided herein.

In some aspects, provided herein is a composition having the isolated *Metschnikowia* species provided herein. Additionally or alternatively, also provided herein is a composition having the bioderived xylitol provided herein. The composition is, in some embodiments, culture medium comprising xylose. In a particular embodiment, the composition is culture medium from which the isolated *Metschnikowia* species provided herein has been removed.

In some embodiments, the composition includes glycerol, arabitol, a C7 sugar alcohol, or a combination thereof, as impurities from the method described herein. In a particular embodiment, the C7 sugar alcohol is volemitol or an isomer thereof. In some embodiments, the amount of glycerol or arabitol, or both, is at least 10%, 20%, 30% or 40% greater than the amount of the respective glycerol or arabitol, or both, produced by a microbial organism other than the isolated *Metschnikowia* species provided herein.

BRIEF DESCRIPTION OF THE DRAWINGS

FIG. 14A uses feeding medium having 36% xylose, 12% galactose, 1.5% glucose, 1.5% peptone, 0.075% yeast extract, 0.075% $KH_2PO_4$, 0.075% $MgSO_4$, and 0.075% $(NH_4)_2SO_4$. The aeration rate was automatically adjusted to keep the dissolved oxygen (DO) to 50% of saturation. FIG. 14B uses feeding medium having 36% xylose, 12% galactose, 3% glucose, 3% peptone, 1.5% yeast extract, 0.075% $KH_2PO_4$, 0.075% $MgSO_4$, and 0.075% $(NH_4)_2SO_4$. More solid medium compounds were added at day 10 to increase the xylose concentration to 7%. The aeration rate was automatically adjusted to keep the dissolved oxygen (DO) to 70% of saturation.

FIG. 15A is YNB medium with 4% glucose (YNBG). FIG. 15B is YNB medium with 4% xylose (YNBX). FIG. 15C is YNB medium with 2% glucose and 2% xylose (YNBGX). FIG. 15D is YPD medium with 4% xylose (YPDX).

DETAILED DESCRIPTION

Figure 1:
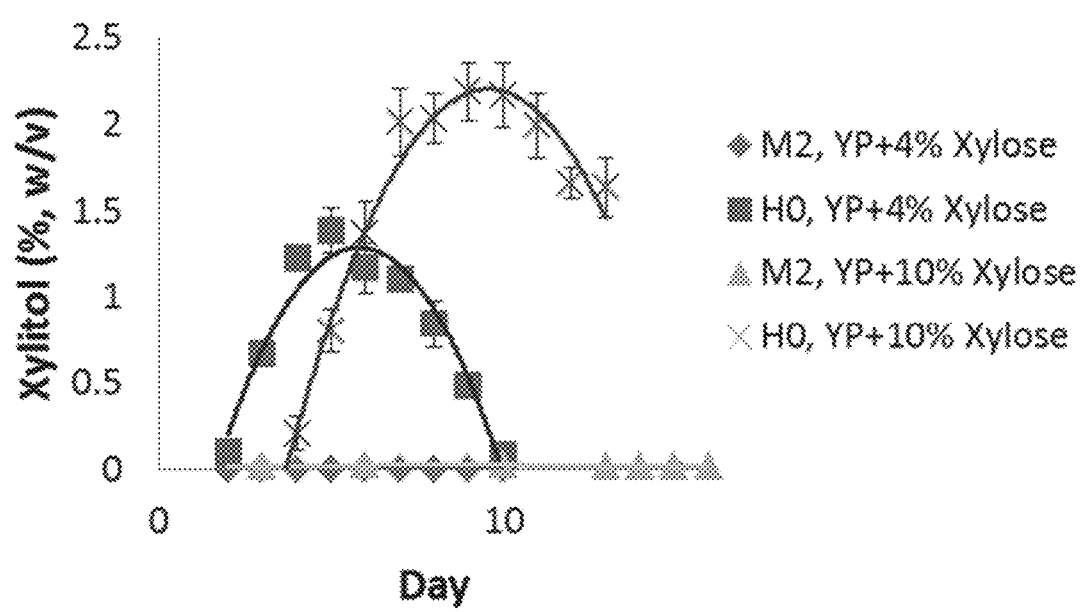
FIG. 1 shows the production of xylitol from xylose for wild-type H0 *Metschnikowia* sp. and *S. cerevisiae* M2 strain. YP+4% Xylose indicates yeast extract peptone medium having 4% xylose. YP+10% Xylose indicates yeast extract peptone medium having 10% xylose.

The compositions and methods provided herein are based, in part, on the discovery, isolation and characterization of a novel yeast species within the *Metschnikowia* genus. Isolation and characterization of this novel *Metschnikowia* species, referred to herein as "H0" or the "H0 *Metschnikowia* sp.," has revealed novel genes and proteins, in particular a novel xylose reductase and novel xylose transporters, which provide a *Metschnikowia* species the ability to utilize xylose for the production of xylitol. Uses for these novel genes and proteins include, for example, the introduction of an exogenous nucleic acid that results in overexpression of xylitol pathway enzymes and proteins, such as a xylose reductase or a xylose transport, in a *Metschnikowia* species, and the introduction of a genetic modification that attenuates or inactivates the xylitol dehydrogenase of the *Metschnikowia* species. Introduction of such modifications to a *Metschnikowia* species, including the H0 *Metschnikowia* sp. described herein, can result in significant increases in xylitol production. Accordingly, the *Metschnikowia* species described herein can be used in a method for producing xylitol by culturing the *Metschnikowia* species in medium having xylose as the carbon source for production of the xylitol. Also provided herein are compositions having the xylitol produced by the methods that use the recombinant *Metschnikowia* species described herein to produce the xylitol. Still further provided herein are isolated polypeptides directed to the novel proteins of the H0 *Metschnikowia* sp. and isolated nucleic acids directed to the novel genes of the H0 *Metschnikowia* sp., as well as host cells including such nucleic acids.

As used herein, the term "aerobic" when used in reference to a culture or growth condition is intended to mean that free oxygen (02) is available in the culture or growth condition. This includes when the dissolved oxygen in the liquid medium is more than 50% of saturation.

As used herein, the term "anaerobic" when used in reference to a culture or growth condition is intended to mean that the culture or growth condition lacks free oxygen (02).

As used herein, the term "attenuate," or grammatical equivalents thereof, is intended to mean to weaken, reduce or diminish the activity or amount of an enzyme or protein. Attenuation of the activity or amount of an enzyme or protein can mimic complete disruption if the attenuation causes the activity or amount to fall below a critical level required for a given pathway to function. However, the attenuation of the activity or amount of an enzyme or protein that mimics complete disruption for one pathway can still be sufficient for a separate pathway to continue to function. For example, attenuation of an endogenous enzyme or protein can be sufficient to mimic the complete disruption of the same enzyme or protein for production of a particular compound (e.g., xylitol), but the remaining activity or amount of enzyme or protein can still be sufficient to maintain other pathways or reactions, such as a pathway that is critical for the host *Metschnikowia* species to survive, reproduce or grow. Attenuation of an enzyme or protein can also be weakening, reducing or diminishing the activity or amount of the enzyme or protein in an amount that is sufficient to increase yield of xylitol, but does not necessarily mimic complete disruption of the enzyme or protein.

As used herein, the term "biobased" means a product that is composed, in whole or in part, of a bioderived compound. A biobased or bioderived product is in contrast to a petroleum derived product, wherein such a product is derived from or synthesized from petroleum or a petrochemical feedstock.

As used herein, the term "bioderived" means derived from or synthesized by a biological organism and can be considered a renewable resource since it can be generated by a biological organism. Such a biological organism, in particular the *Metschnikowia* species disclosed herein, can utilize feedstock or biomass, such as, sugars (e.g., xylose, glucose, fructose, galactose (e.g., galactose from marine plant biomass), sucrose, and arabinose), carbohydrates obtained from an agricultural, plant, bacterial, or animal source, and glycerol (e.g., crude glycerol byproduct from biodiesel manufacturing).

As used herein, the term "carbon source" refers to any carbon containing molecule used by an organism for the synthesis of its organic molecules, including, but not limited to the bioderived compounds described herein. This includes molecules with different amounts of carbon atoms. Specific examples include a C3 carbon source, a C4 carbon source, a C5 carbon source and a C6 carbon source. A "C3 carbon source" refers to a carbon source containing three carbon atoms, such as glycerol. A "C4 carbon source" refers to a carbon source containing four carbon atoms, such as erythrose or threose. A "C5 carbon source" refers to a carbon source containing five carbon atoms, such as xylose, arabinose, arabitol, ribose or lyxose. A "C6 carbon source" refers to a carbon source containing six carbon atoms, such as glucose, galactose, mannose, allose, altrose, gulose, or idose.

The term "exogenous" as it is used herein is intended to mean that the referenced molecule or the referenced activity is introduced into the *Metschnikowia* species described herein. The molecule can be introduced, for example, by introduction of an encoding nucleic acid into the host *Metschnikowia* species' genetic material, such as by integration into a host chromosome or as non-chromosomal genetic material such as a plasmid. Alternatively or additionally, the molecule introduced can be or include, for example, a non-coding nucleic acid that modulates (e.g., increases, decreases or makes constitutive) the expression of an encoding nucleic acid, such as a promoter or enhancer. Therefore, the term as it is used in reference to expression of an encoding nucleic acid refers to introduction of the encoding nucleic acid in an expressible form into the host *Metschnikowia* species and/or introduction of a nucleic acid that increases expression (e.g., overexpresses) of an encoding nucleic acid of the host *Metschnikowia* species. When used in reference to a biosynthetic activity, the term refers to an activity that is introduced into the host *Metschnikowia* species. The source can be, for example, a homologous or heterologous encoding nucleic acid that expresses the referenced activity following introduction into the *Metschnikowia* species. Therefore, the term "endogenous" refers to a referenced molecule or activity that is present in the host *Metschnikowia* species. Similarly, the term when used in reference to expression of an encoding nucleic acid refers to expression of an encoding nucleic acid contained within the microbial organism. The term "heterologous" refers to a molecule or activity derived from a source other than the referenced *Metschnikowia* species, whereas "homologous" refers to a molecule or activity derived from the host *Metschnikowia* species. Accordingly, exogenous expression of an encoding nucleic acid disclosed herein can utilize either or both a heterologous or homologous encoding nucleic acid.

It is understood that when more than one exogenous nucleic acid is included in a *Metschnikowia* species that the more than one exogenous nucleic acid refers to the referenced encoding nucleic acid or biosynthetic activity, as discussed above. It is also understood that a microbial organism can have one or multiple copies of the same exogenous nucleic acid. It is further understood, as disclosed herein, that such more than one exogenous nucleic acid can be introduced into the host *Metschnikowia* species on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host *Metschnikowia* species, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

As used herein, the term "genetic modification," "gene disruption," or grammatical equivalents thereof, is intended to mean a genetic alteration that renders the encoded gene product functionally inactive, or active but attenuated. The genetic alteration can be, for example, deletion of the entire gene, deletion of a regulatory sequence required for transcription or translation, deletion of a portion of the gene that results in a truncated gene product, or by any of the various mutation strategies that inactivate or attenuate the encoded gene product well known in the art. One particularly useful method of gene disruption is complete gene deletion because it reduces or eliminates the occurrence of genetic reversions in the *Metschnikowia* species provided herein. A gene disruption also includes a null mutation, which refers to a mutation within a gene or a region containing a gene that results in the gene not being transcribed into RNA and/or translated into a functional gene product. Such a null mutation can arise from many types of mutations including, for example, inactivating point mutations, deletion of a portion of a gene, entire gene deletions, or deletion of chromosomal segments.

As used herein, the term "inactivate," or grammatical equivalents thereof, is intended to mean to stop the activity of the enzyme or protein. Such inactivation can be accomplished by deletion of the entire nucleic acid sequence encoding the enzyme or protein. Inactivation can also be accomplished by deletion of a portion of the nucleic acid sequence encoding the enzyme or protein such that the resulting enzyme or protein encoded by the nucleic acid sequence does not have the activity of the full length enzyme or protein. Additionally, inactivation of an enzyme or protein can be accomplished by substitutions or insertions, including in combination with deletions, into the nucleic acid sequence encoding the enzyme or protein. Insertions can include heterologous nucleic acids, such as those described herein.

As used herein, the term "isolated" when used in reference to a *Metschnikowia* species described herein is intended to mean an organism that is substantially free of at least one component as the referenced microbial organism is found in nature. The term includes a *Metschnikowia* species that is removed from some or all components as it is found in its natural environment. The term also includes a microbial organism that is removed from some or all components as the microbial organism is found in non-naturally occurring environments. Therefore, an isolated *Metschnikowia* species is partly or completely separated from other substances as it is found in nature or as it is grown, stored or subsisted in non-naturally occurring environments. Specific examples of isolated *Metschnikowia* species include a partially pure microbial organism, a substantially pure microbial organism and a microbial organism cultured in a medium that is non-naturally occurring.

As used herein, the term "medium," "culture medium," "growth medium" or grammatical equivalents thereof refers to a liquid or solid (e.g., gelatinous) substance containing nutrients that supports the growth of a cell, including any microbial organism such as the *Metschnikowia* species described herein. Nutrients that support growth include: a substrate that supplies carbon, such as, but are not limited to, xylose, cellobiose, galactose, glucose, ethanol, acetate, arabinose, arabitol, sorbitol and glycerol; salts that provide essential elements including magnesium, nitrogen, phosphorus, and sulfur; a source for amino acids, such as peptone or tryptone; and a source for vitamin content, such as yeast extract. Specific examples of medium useful in the methods and in characterizing the *Metschnikowia* species described herein include yeast extract peptone (YEP) medium and yeast nitrogen base (YNB) medium having a carbon source such as, but not limited to xylose, glucose, cellobiose, galactose, or glycerol, or a combination thereof. The formulations of YEP and YNB medium are well known in the art. For example, YEP medium having 4% xylose includes, but is not limited to, yeast extract 1.0 g, peptone 2.0 g, xylose 4.0 g, and 100 ml water. As another example, YNB medium having 2% glucose and 2% xylose includes, but is not limited to, biotin 2 µg, calcium pantothenate 400 µg, folic acid 2 µg, inositol 2000 µg, niacin 400 µg, p-aminobenzoic acid 200 µg, pyridoxine hydrochloride 400 µg, riboflavin 200 µg, thiamine hydrochloride 400 µg, boric acid 500 µg, copper sulfate 40 µg, potassium iodide 100 µg, ferric chloride 200 µg, manganese sulfate 400 µg, sodium molybdate 200 µg, zinc sulfate 400 µg, potassium phosphate monobasic 1 g, magnesium sulfate 500 mg, sodium chloride 100 mg, calcium chloride 100 mg, 20 g glucose, 20 g, xylose and 1 L water. The amount of the carbon source in the medium can be readily determined by a person skilled in the art. When more than one substrate that supplies carbon is present in the medium, these are referred to as "co-substrates." Medium can also include substances other than nutrients needed for growth, such as a substance that only allows select cells to grow (e.g., antibiotic or antifungal), which are generally found in selective medium, or a substance that allows for differentiation of one microbial organism over another when grown on the same medium, which are generally found in differential or indicator medium. Such substances are well known to a person skilled in the art.

As used herein, the term "*Metschnikowia* species" refers to any species of yeast that falls within the *Metschnikowia* genus. Exemplary *Metschnikowia* species include, but are not limited to, *Metschnikowia pulcherrima, Metschnikowia fructicola, Metschnikowia chrysoperlae, Metschnikowia reukaufii, Metschnikowia andauensis, Metschnikowia shanxiensis, Metschnikowia sinensis, Metschnikowia zizyphicola, Metschnikowia bicuspidata, Metschnikowia lunata, Metschnikowia zobellii, Metschnikowia australis, Metschnikowia agaveae, Metschnikowia gruessii, Metschnikowia hawaiiensis, Metschnikowia krissii, Metschnikowia* sp. strain NS-O-85, *Metschnikowia* sp. strain NS-O-89 and the unique *Metschnikowia* species described herein *Metschnikowia* sp. H0, alternatively known "H0 *Metschnikowia* sp." The *Metschnikowia* species described herein, i.e., the "H0 *Metschnikowia* sp.", is a newly discovered species, which is designated Accession No. 081116-01, and was deposited at International Depositary Authority of Canada ("IDAC"), an International Depositary Authority, at the address of 1015 Arlington Street, Winnipeg, Manitoba, Canada R3E 3R2, on Nov. 8, 2016, under the terms of the Budapest Treaty. The proposed scientific name for the H0 *Metschnikowia* sp. is *Metschnikowia vinificola* (vinifi: from *vinifera* (species of wine grape vine); cola: from Latin word "incola" meaning inhabitant). Thus, the species name of *vinificola* (inhabitant of *vinifera*) refers to the isolation of the type strain from wine grapes.

Additionally, a *Metschnikowia* species referred to herein can include a "non-naturally occurring" or "recombinant" *Metschnikowia* species. Such an organism is intended to mean a *Metschnikowia* species that has at least one genetic alteration not normally found in the naturally occurring *Metschnikowia* species, including wild-type strains of the referenced species. Genetic alterations include, for example, modifications introducing expressible nucleic acids encoding metabolic polypeptides, other nucleic acid additions, nucleic acid deletions and/or other gene disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a metabolic pathway (e.g., xylitol pathway) described herein.

A metabolic modification refers to a biochemical reaction that is altered from its naturally occurring state. Therefore, the *Metschnikowia* species described herein can have genetic modifications to one or more nucleic acid sequences encoding metabolic polypeptides, or functional fragments thereof, which alter the biochemical reaction that the metabolic polypeptide catalyzes, including catabolic or anabolic reactions and basal metabolism. Exemplary metabolic modifications are disclosed herein.

As used herein, the term "overexpression" or grammatical equivalents thereof, is intended to mean the expression of a gene product (e.g., ribonucleic acids (RNA), protein or enzyme) in an amount that is greater than is normal for a host *Metschnikowia* species, or at a time or location within the host *Metschnikowia* species that is different from that of wild-type expression.

As used herein, the terms "sequence identity" or "sequence homology," when used in reference to a nucleic acid sequence or an amino acid sequence, refers to the similarity between two or more nucleic acid molecules or between two or more polypeptides. Identity can be determined by comparing a position in each sequence, which may be aligned for purposes of comparison. When a position in the compared sequence is occupied by the same base or amino acid, then the molecules are identical at that position. A degree of identity between sequences is a function of the number of matching or homologous positions shared by the sequences. The alignment of two sequences to determine their percent sequence identity can be done using software programs known in the art, such as, for example, those described in Ausubel et al., Current Protocols in Molecular Biology, John Wiley and Sons, Baltimore, Md. (1999). Preferably, default parameters are used for the alignment. One alignment program well known in the art that can be used is BLAST set to default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information.

As used herein, the term "substantially anaerobic" when used in reference to a culture or growth condition is intended to mean that the amount of dissolved oxygen in a liquid medium is less than about 10% of saturation. The term also is intended to include sealed chambers maintained with an atmosphere of less than about 1% oxygen that include liquid or solid medium.

As used herein, the term "sugar alcohol" refers to an alcohol produced by the reduction of an aldehyde or ketone of a sugar. Thus a "C7 sugar alcohol" refers to an alcohol produced by the reduction of an aldehyde or ketone of a sugar having seven carbon atoms, such as volemitol or an isomer thereof.

As used herein, the term "xylitol" refers to a pentose sugar alcohol having the chemical formula of $C_5H_{12}O_5$, a Molar mass of 152.15 g/mol, and one IUPAC name of (2R,3r,4S)-pentane-1,2,3,4,5-pentol [(2S,4R)-pentane-1,2,3,4,5-pentol]. Xylitol is commonly used as a low-calorie, low-carbohydrate alternative to sugar, which does not affect insulin levels of people with diabetes and individuals with hyperglycemia.

As used herein, the term "xylitol dehydrogenase" refers to an enzyme that catalyzes the oxidation of xylitol to produce xylulose. Such oxidation of xylitol includes an enzyme that uses the cofactor NAD. An exemplary xylitol dehydrogenase includes an enzyme that is classified under E.C. 1.1.1.9 or E.C. 1.1.1.B19. The term "*Metschnikowia* xylitol dehydrogenase" or grammatical equivalent thereof refers to a xylitol dehydrogenase from a *Metschnikowia* species. Table 1 provides both amino acid and nucleic acid sequences of exemplary xylitol dehydrogenases.

TABLE 1

| SEQ ID NO: | Description | Sequence |
|---|---|---|
| 1. | Amino acid sequence of Xyl2 protein from H0 *Metschnikowia* sp. | MPANPSLVLNKVNDITFENYEVPLLTDPNDVLVQVKKTGICGS DIHYYTHGRIGDFVLTKPMVLGHESAGVVVEVGKGVTDLKV GDKVAIEPGVPSRTSDEYKSGHYNLCPHMCFAATPNSNPDEPN PPGTLCKYYKSPADFLVKLPEHVSLELGAMVEPLTVGVHASR LGRVTFGDHVVVFGAGPVGILAAAVARKFGAASVTIVDIFDSK LELAKSIGAATHTFNSMTEGVLSEALPAGVRPDVVLECTGAEI CVQQGVLALKAGGRHVQVGNAGSYLKFPITEFVTKELTLFGS FRYGYNDYKTSVAILDENYKNGKENALVDFEALITHRFPFKN AIEAYDAVRAGDGAVKCIIDGPE* |
| 2. | Amino acid sequence of exemplary xylitol dehydrogenase from *Metschnikowia fructicola* 277 | MPANPSLVLNKVNDISFENYEVPLLTDPNDVLVQVKKTGICGS DIHYYTHGRIGDFVLTKPMVLGHESAGVVVEVGKGVTDLKV GDKVAIEPGVPSRTSDEYKSGHYNLCPHMCFAATPNSNPDEPN PPGTLCKYYKSPADFLVKLPEHVSLELGAMVEPLTVGVHASR LGRVTFGDHVVVFGAGPVGILAAAVARKFGAASVTIVDIFDSK LELAKSIGAATHTFNSMTEGVLSEALPAGVRPDVVLECTGAEI CVQQGVLALKAGGRHVQVGNAGSYLKFPITEFVTKELTLFGS FRYGYNDYKTSVAILDENYKNGKENALVDFEALITHRFPFKN AIEAYDAVRAGDGAVKCIIDGPE |
| 3. | Amino acid sequence of exemplary xylitol dehydrogenase from *Metschnikowia pulcherrima* flavia (identical to H0 Xyl2p) | MPANPSLVLNKVNDITFENYEVPLLTDPNDVLVQVKKTGICGS DIHYYTHGRIGDFVLTKPMVLGHESAGVVVEVGKGVTDLKV GDKVAIEPGVPSRTSDEYKSGHYNLCPHMCFAATPNSNPDEPN PPGTLCKYYKSPADFLVKLPEHVSLELGAMVEPLTVGVHASR LGRVTFGDHVVVFGAGPVGILAAAVARKFGAASVTIVDIFDSK LELAKSIGAATHTFNSMTEGVLSEALPAGVRPDVVLECTGAEI CVQQGVLALKAGGRHVQVGNAGSYLKFPITEFVTKELTLFGS FRYGYNDYKTSVAILDENYKNGKENALVDFEALITHRFPFKN AIEAYDAVRAGDGAVKCIIDGPE |
| 4. | Amino acid sequence of exemplary xylitol dehydrogenase from *Metschnikowia bicuspidata* var. *bicuspidata* NRRL YB-4993 | MTTNPSLVLNKVDDISFENYQIPRITEPNEVLVQVKKTGICGSD IHYYAHGKIGDFVLTKPMVLGHESSGIVVEVGDAVSHLKAGD KVAIEPGVPSRFSDEYKSGHYNLCPHMKFAATPNSKEGEPNPP GTLCKYYKSPADFLVKLPDHVSLELGAMVEPLTVGVHASRLG KITFGDHVVVFGAGPVGILAAAVARKFGAASVTVVDIFDNKL KLAKDMGAATHVFNSRTSDSLGDNLPAGVNPDVVLECTGAE VCIQQGVLALKAGGRFVQVGNAGSYVKFPITELVTKELILFGS FRYGYNDYKTSVDILDENYKNGKDNAMIDFEALITHRFSFDD AIKAYDKVRSGDGAAKCIIDGPE |
| 5. | Amino acid sequence of exemplary xylitol dehydrogenase from *Pichia stipitis* (no more Xyl2p sequence available in *Metschnikowia* spp.) | MTANPSLVLNKIDDISFETYDAPEISEPTDVLVQVKKTGICGSDI HFYAHGRIGNFVLTKPMVLGHESAGTVVQVGKGVTSLKVGD NVAIEPGIPSRFSDEYKSGHYNLCPHMAFAATPNSKEGEPNPPG TLCKYFKSPEDFLVKLPDHVSLELGALVEPLSVGVHASKLGSV AFGDYVAVFGAGPVGLLAAAVAKTFGAKGVIVVDIFDNKLK MAKDIGAATHTFNSKTGGSEELIKAFGGNVPNVVLECTGAEPC IKLGVDAIAPGGRFVQVGNAAGPVSFPITVFAMKELTLFGSFR YGFNDYKTAVGIFDTNYQNGRENAPIDFEQLITHRYKFKDAIE AYDLVRAGKGAVKCLIDGPE |

TABLE 1-continued

| SEQ ID NO: | Description | Sequence |
|---|---|---|
| 6. | Nucleic acid sequence of XYL2 from H0 *Metschnikowia* sp. | ATGCCTGCTAACCCATCCTTGGTTTTGAACAAAGTGAACGA<br>CATCACGTTCGAGAACTACGAGGTTCCGTTACTCACAGACC<br>CCAACGATGTATTGGTTCAGGTGAAAAAGACTGGAATCTGT<br>GGATCTGACATCCACTACTACACCCACGGCAGAATTGGCGA<br>CTTCGTGTTGACAAAGCCAATGGTTTTGGGCCACGAATCCG<br>CCGGTGTGGTCGTGGAGGTCGGCAAAGGTGTCACTGACTTG<br>AAGGTTGGTGATAAGGTTGCCATTGAGCCCGGAGTGCCTTC<br>TCGCACCAGTGACGAGTACAAGAGTGGCCACTACAACTTGT<br>GCCCACACATGTGTTTTGCCGCCACGCCCAACTCTAACCCC<br>GACGAGCCAAACCCGCCAGGGACTTTGTGCAAATATTACAA<br>GTCCCCAGCGGACTTCTTGGTGAAATTGCCTGAGCACGTCT<br>CCCTTGAGTTGGGCGCTATGGTCGAGCCTTTGACTGTCGGT<br>GTGCACGCCTCGCGTTTGGGCCGTGTCACTTTTGGTGACCA<br>CGTTGTGGTTTTCGGTGCTGGCCCAGTCGGTATCCTTGCGGC<br>TGCCGTGGCCAGAAAGTTTGGCGCTGCCAGCGTGACTATCG<br>TCGACATCTTCGACAGCAAATTGGAATTGGCCAAGTCCATT<br>GGCGCGGCCACTCACACATTCAACTCAATGACTGAGGGTGT<br>TCTTTCGGAGGCTTTGCCCGCGGGCGTGAGACCTGACGTTG<br>TATTGGAGTGCACTGGAGCAGAGATCTGTGTGCAGCAAGGT<br>GTACTTGCGTTGAAGGCTGGTGGCCGCCACGTGCAAGTTGG<br>AAATGCCGGCTCCTATCTCAAATTCCCCATCACCGAATTTGT<br>TACCAAGGAGTTGACTCTCTTTGGATCCTTCCGTTACGGTTA<br>CAACGACTACAAGACGTCGGTCGCCATCTTGGACGAGAATT<br>ACAAGAACGGGAAGGAGAATGCGTTGGTGGACTTTGAAGC<br>CTTGATTACTCACCGTTTCCCCTTCAAGAATGCCATTGAGGC<br>TTACGACGCGGTGCGCGCTGGCGACGGAGCTGTCAAGTGTA<br>TCATTGACGGCCCAGAGTAA |
| 7. | Nucleic acid sequence of exemplary xylitol dehydrogenase from *Metschnikowia fructicola* 277 | ATGCCTGCTAACCCATCCTTGGTTTTGAACAAAGTGAACGA<br>CATCTCGTTCGAGAACTACGAGGTTCCGTTACTCACAGACC<br>CCAACGATGTATTGGTTCAGGTGAAAAAGACTGGAATCTGT<br>GGATCTGACATCCACTACTACACCCACGGCAGAATTGGCGA<br>CTTTGTATTGACAAAGCCAATGGTTTTGGGCCACGAGTCCG<br>CCGGTGTGGTCGTGGAGGTCGGCAAAGGCGTCACTGACTTG<br>AAGGTTGGCGATAAGGTTGCCATTGAGCCCGGAGTGCCTTC<br>TCGCACCAGTGACGAGTACAAGAGTGGTCACTACAACTTGT<br>GCCCACACATGTGTTTTGCCGCCACGCCCAACTCTAACCCC<br>GACGAGCCAAACCCGCCAGGGACTTTGTGCAAATACTACA<br>AGTCCCCCGCGGACTTCTTGGTGAAATTGCCTGAGCACGTC<br>TCCCTTGAGTTGGGCGCTATGGTCGAGCCTTTGACTGTCGGT<br>GTGCACGCCTCGCGTTTGGGCCGTGTCACTTTTGGTGACCA<br>CGTTGTGGTTTTCGGTGCTGGCCCAGTCGGTATTCTTGCGGC<br>TGCCGTGGCCAGAAAGTTTGGCGCTGCCAGTGTGACTATCG<br>TCGACATCTTCGACAGCAAATTGGAATTGGCCAAGTCCATT<br>GGCGCGGCCACTCACACATTCAACTCAATGACTGAGGGTGT<br>TCTTTCTGAGGCTTTGCCCGCGGGCGTGAGACCTGACGTTG<br>TATTGGAGTGCACTGGAGCAGAGATCTGTGTGCAGCAAGGT<br>GTACTTGCGTTGAAGGCTGGTGGCCGCCACGTGCAAGTTGG<br>AAATGCCGGCTCCTATCTCAAATTCCCCATCACCGAGTTCG<br>TCACCAAGGAGTTGACTCTCTTTGGGTCCTTCCGTTACGGCT<br>ACAACGACTACAAGACGTCGGTCGCCATCTTGGACGAGAAT<br>TACAAGAACGGGAAAGAGAATGCGTTGGTGGACTTTGAAG<br>CCTTGATTACTCACCGTTTCCCCTTCAAGAATGCCATTGAGG<br>CTTACGACGCGGTGCGCGCTGGCGACGGAGCTGTCAAGTGT<br>ATCATTGACGGCCCAGAGTAA |
| 8. | Nucleic acid sequence of exemplary xylitol dehydrogenase from *Metschnikowia pulcherrima* flavia | ATGCCTGCTAACCCATCCTTGGTTTTGAACAAAGTGAACGA<br>CATCACGTTCGAGAACTACGAGGTTCCGTTACTCACAGACC<br>CCAACGATGTATTGGTTCAGGTGAAAAAGACTGGAATCTGT<br>GGATCTGACATTCACTACTACACCCACGGCAGAATTGGCGA<br>CTTTGTATTGACAAAGCCGATGGTTTTGGGCCACGAATCCG<br>CCGGTGTGGTCGTGGAGGTCGGCAAAGGCGTCACTGACTTG<br>AAGGTTGGTGATAAGGTTGCCATTGAGCCTGGAGTGCCTTC<br>TCGCACCAGTGACGAGTACAAGAGTGGTCACTACAACTTGT<br>GCCCACACATGTGTTTTGCCGCCACGCCCAACTCTAACCCC<br>GACGAGCCAAACCCGCCAGGGACTTTGTGCAAATACTACA<br>AGTCCCCCGCGGACTTCTTGGTGAAATTGCCTGAGCACGTC<br>TCCCTTGAGTTGGGCGCTATGGTCGAGCCTTTGACTGTCGGT<br>GTGCACGCCTCGCGTTTGGGCCGTGTCACTTTTGGTGACCA<br>CGTTGTGGTTTTCGGTGCTGGCCCAGTCGGTATCCTTGCGGC<br>TGCCGTGGCCAGAAAGTTTGGCGCTGCCAGTGTGACTATCG<br>TCGACATCTTCGACAGCAAATTGGAATTGGCCAAGTCCATT<br>GGCGCGGCCACTCACACATTCAACTCAATGACTGAGGGTGT<br>TCTTTCGGAGGCTTTGCCCGCGGGCGTGAGACCTGACGTTG<br>TATTGGAGTGCACTGGAGCAGAGATCTGTGTGCAGCAAGGT<br>GTACTTGCGTTGAAGGCTGGTGGCCGCCACGTGCAAGTTGG |

TABLE 1-continued

| SEQ ID NO: | Description | Sequence |
|---|---|---|
| | | AAATGCCGGCTCCTATCTCAAATTCCCCATCACCGAGTTCG<br>TCACCAAGGAGTTGACTCTCTTTGGGTCCTTCCGTTACGGCT<br>ACAACGACTACAAGACGTCGGTCGCCATCTTGGACGAGAAT<br>TACAAGAACGGGAAAGAGAATGCGTTGGTGGATTTTGAAG<br>CCTTGATTACTCACCGTTTCCCCTTCAAGAATGCCATTGAGG<br>CTTACGACGCGGTGCGCGCTGGCGACGGAGCTGTCAAGTGT<br>ATCATTGACGGCCCAGAGTAA |
| 9. | Nucleic acid sequence of exemplary xylitol dehydrogenase from *Metschnikowia bicuspidata* var. *bicuspidata* NRRL YB-4993 | ATGACTACAAACCCATCGTTGGTATTGAACAAAGTGGACGA<br>TATTTCGTTCGAAAACTACCAGATCCCTAGAATCACTGAGC<br>CTAATGAAGTATTAGTCCAGGTAAAGAAGACGGGAATCTG<br>CGGCTCTGATATTCACTACTACGCACATGGAAAAATCGGAG<br>ACTTCGTTTTGACAAAGCCAATGGTCTTAGGCCATGAATCC<br>TCGGGAATTGTTGTTGAGGTGGGTGATGCTGTATCCCATTT<br>GAAAGCTGGGGACAAGGTTGCCATTGAGCCTGGAGTGCCTT<br>CTCGTTTTAGCGATGAGTACAAGAGCGGTCACTATAACTTA<br>TGCCCGCATATGAAATTTGCTGCTACCCCCAACTCGAAAGA<br>GGGTGAACCAAACCCTCCGGGCACTTTGTGCAAGTATTATA<br>AGTCGCCCGCAGACTTCTTGGTTAAATTGCCTGATCACGTG<br>TCGCTCGAATTGGGAGCAATGGTCGAGCCATTGACCGTGGG<br>TGTGCATGCTTCTCGGTTGGGTAAGATCACTTTTGGTGATCA<br>TGTGGTTGTATTTGGCGCTGGTCCAGTTGGAATTCTTGCAGC<br>CGCTGTTGCAAGAAAATTTGGCGCCGCCTCCGTCACCGTTG<br>TTGATATCTTCGACAACAAATTAAAGCTAGCGAAGGACATG<br>GGTGCTGCCACCCATGTCTTTAACTCGAGGACTTCCGACTCT<br>TTGGGGGATAATTTGCCCGCAGGTGTGAATCCAGATGTTGT<br>TTTGGAGTGTACCGGAGCTGAAGTTTGTATCCAGCAAGGTG<br>TTTTGGCTTTAAAAGCGGGTGGTCGCTTTGTGCAAGTGGGC<br>AATGCCGGTTCATATGTCAAGTTCCCAATTACTGAGCTTGT<br>GACCAAAGAGTTGATTCTTTTTGGGTCCTTCCGGTATGGAT<br>ACAATGACTACAAGACCTCTGTGGATATCTTGGATGAAAAT<br>TACAAAAACGGAAAAGACAATGCAATGATAGACTTCGAGG<br>CTTTGATTACTCACCGGTTCTCATTCGACGATGCCATCAAGG<br>CATACGACAAAGTGCGTTCTGGTGACGGCGCTGCAAAATGT<br>ATCATTGATGGGCCAGAATAA |
| 10 | Nucleic acid sequence of exemplary xylitol dehydrogenase from *Pichia stipitis* (No more XYL2 gene sequence available in *Metschnikowia* spp.) | ATGACTGCTAACCCTTCCTTGGTGTTGAACAAGATCGACGA<br>CATTTCGTTCGAAACTTACGATGCCCCAGAAATCTCTGAAC<br>CTACCGATGTCCTCGTCCAGGTCAAGAAAACCGGTATCTGT<br>GGTTCCGACATCCACTTCTACGCCCATGGTAGAATCGGTAA<br>CTTCGTTTTGACCAAGCCAATGGTCTTGGGTCACGAATCCG<br>CCGGTACTGTTGTCCAGGTTGGTAAGGGTGTCACCTCTCTTA<br>AGGTTGGTGACAACGTCGCTATCGAACCAGGTATTCCATCC<br>AGATTCTCCGACGAATACAAGAGCGGTCACTACAACTTGTG<br>TCCTCACATGGCCTTCGCCGCTACTCCTAACTCCAAGGAAG<br>GCGAACCAAACCCACCAGGTACCTTATGTAAGTACTTCAAG<br>TCGCCAGAAGACTTCTTGGTCAAGTTGCCAGACCACGTCAG<br>CTTGGAACTCGGTGCTCTTGTTGAGCCATTGTCTGTTGGTGT<br>CCACGCCTCCAAGTTGGGTTCCGTTGCTTTCGGCGACTACGT<br>TGCCGTCTTTGGTGCTGGTCCTGTTGGTCTTTTGGCTGCTGC<br>TGTCGCCAAGACCTTCGGTGCTAAGGGTGTCATCGTCGTTG<br>ACATTTTCGACAACAAGTTGAAGATGGCCAAGGACATTGGT<br>GCTGCTACTCACACCTTCAACTCCAAGACCGGTGGTTCTGA<br>AGAATTGATCAAGGCTTTCGGTGGTAACGTGCCAAACGTCG<br>TTTTGGAATGTACTGGTGCTGAACCTTGTATCAAGTTGGGT<br>GTTGACGCCATTGCCCCAGGTGGTCGTTTCGTTCAAGTTGGT<br>AACGCTGCTGGTCCAGTCAGCTTCCCAATCACCGTTTTCGCC<br>ATGAAGGAATTGACTTTGTTCGGTTCTTTCAGATACGGATTC<br>AACGACTACAAGACTGCTGTTGGAATCTTTGACACTAACTA<br>CCAAAACGGTAGAGAAAATGCTCCAATTGACTTTGAACAAT<br>TGATCACCCACAGATACAAGTTCAAGGACGCTATTGAAGCC<br>TACGACTTGGTCAGAGCCGGTAAGGGTGCTGTCAAGTGTCT<br>CATTGACGGCCCTGAGTAA |

As used herein, the term "xylose" refers to a five carbon monosaccharide with a formyl functional group having the chemical formula of $C_5H_{10}O_5$, a Molar mass of 150.13 g/mol, and one IUPAC name of (3R,4S,5R)-oxane-2,3,4,5-tetrol. Xylose is also known in the art as D-xylose, D-xylopyranose, xyloside, d-(+)-xylose, xylopyranose, wood sugar, xylomed and D-xylopentose.

As used herein, the term "xylose reductase" refers to an enzyme that catalyzes the reduction of xylose to produce xylitol. Such reduction of xylose includes an enzyme that uses NADH or NADPH as a cofactor. An exemplary xylose reductase includes an enzyme that is classified under E.C. 1.1.1.307. The term "*Metschnikowia* xylose reductase" or grammatical equivalent thereof refers to a xylose reductase from a *Metschnikowia* species. Table 2 provides both amino acid and nucleic acid sequences of exemplary xylose reductases.

TABLE 2

| SEQ ID NO: | Description | Sequence |
|---|---|---|
| 11. | Amino acid sequence of XYL1 protein from H0 Metschnikowia sp. | MATIKLNSGYDMPQVGFGCWKVTNSTCADTIYNAIKVGYRLF DGAEDYGNEKEVGEGINRAIDEGLVARDELFVVSKLWNNFHH PDNVEKALDKTLGDLNVEYLDLFLIHFPIAFKFVPFEEKYPPGF YCGEGDKFIYEDVPLLDTWRALEKFVKKGKIRSIGISNFSGALI QDLLRGAEIPPAVLQIEHHPYLQQPRLIEYVQSKGIAITAYSSFG PQSFVELDHPKVKECVTLFEHEDIVSIAKAHDKSAGQVLLRWA TQRGLAVIPKSNKTERLLLNLNVNDFDLSEAELEQIAKLDVGL RFNNPWDWDKIPIFH* |
| 12. | Amino acid sequence of exemplary xylose reductase from Spathaspora passalidarum CBS 10155; Xyl1.1p | MATIKLSSGHLMPLVGFGCWKVDNATAADQIYNAIKAGYRLF DGAEDYGNEKEVGDGLKRAIDEGLVKREELFITSKLWNNYHD PKNVETALNRTLSDLQLDYVDLFLIHFPIAFKFVPLEEKYPPGF YCGDGNNFHYENVPLLDTWKALEKLVQAGKIKSIGISNFPGAL IYDLVRGATIKPAVLQIEHHPYLQQPKLIEYVQKGIAITAYSSF GPQSFLELNQNRALNTPTLFEHDTIKSISTRLNKTPAQVLLRWA TQRNIAVIPKSNNPARLAQNLDVTSFDLTEEDFNAISALDINLR FNDPWDWDNIPIFV |
| 13. | Amino acid sequence of exemplary xylose reductase from Spathaspora passalidarum UFMGCMY469; Xyl1.2p | MSFKLSSGYEMPKIGFGTWKMDKATIPQQIYDAIKGGIRSFDG AEDYGNEKEVGLGYKKAIEDGLVKRGDLFITSKLWNNFHDPK NVEKALDRTLADLQLDYVDLFLIHFPIAFKFVPLEERYPPCFYC GDGDNFHYEDVPLLETWKALEALVKKGKIRSLGVSNFTGALL LDLLRGATIKPAVLQVEHHPYLQQPRLIEFAQKQGIVVTAYSSF GPQSFTELNQNRANNTPRLFDHEVIKKIAARRGRTPAQVILRW ATQRNVVIIPKSDTPERLVENLAVFDFDLTEEDFKEIAALDANL RFNDPWDWDHIPIFV* |
| 14. | Amino acid sequence of exemplary xylose reductase from Metschnikowia bicuspidata var. bicuspidate NRRL YB-4993 | MSTIKLNSGYEMPQVGFGCWKVTNDTCADTIYNAIKVGYRLF DGAQDYGNEKEVGQGLNRAIDEGLVARDELFVVSKLWNNFH HPDNVEKALDKTLGDLNVEYLDLFLIHFPIAFKFVPFEEKYPPG FYCGDGDKFHYEDVPLLDTWRALEKMVKKGKIRSIGISNFSG ALIQDLLRGAEIAPAVLQIEHHPYLQQPRLVEYVKSKGIAITAY SSFGPQSFIELDHPKVKECVTLFDHDTILSVARAHNKSAGQVLL RWATQRGLAVIPKSNKTERLVQNLEVNDFDLSDAELKSISKLD VGLRFNNPWDWDKIPIFH |
| 15. | Amino acid sequence of exemplary xylose reductase from Clavispora lusitaniae ATCC 42720 | MATIKLNSGYEMPQVGFGCWKVDNKTCADQIYNAIKVGYRL FDGAEDYGNEKEVGEGINRAIADGLVARDELFVVSKLWNNFH HPDNVEKALDKTLSDLNLEYLDLFLIHFPIAFKFVPFEEKYPPG FYCGDTNKFIYEDVPIIDTWRALEKLVEKGKIRSIGVSNFNGSL LLDLLRAAKIKPAVLQIEHHPYLQQPLIKWVKSKGIAVTAYS SFGPQSFVELNHPKVGSCTTLFEHEDIVSIAKKHGKSPGQVLLR WATQNGLAVIPKSNKTERLVQNLNVNDFDLSASDLSAIAKLDI GLRFNDPWDWDEIPIFH |
| 16. | Amino acid sequence of exemplary xylose reductase from Meyerozyma guilliermondii | MSIKLNSGYDMPSVGFGCWKVDNATCADTIYNAIKVGYRLFD GAEDYGNEKEVGDGINRALDEGLVARDELFVVSKLWNSFHDP KNVEKALDKTLSDLKVDYLDLFLIHFPIAFKFVPFEEKYPPGFY CGDGDKFHYEDVPLIDTWRALEKLVEKGKIRSIGISNFSGALIQ DLLRSAKIKPAVLQIEHHPYLQQPRLVEYVQSQGIAITAYSSFG PQSFVELDHPRVDVKPLFEHDVIKSVAGKVKKTPAQVLLRW ATQRGLAVIPKSNNPDRLLSNLKVNDFDLSQEDFQEISKLDIEL RFNNPWDWDKIPTFI |
| 17. | Amino acid sequence of exemplary xylose reductase from Candida tropicalis | MSTTVNTPTIKLNSGYEMPLVGFGCWKVTNATAADQIYNAIK TGYRLFDGAEDYGNEKEVGEGINRAIKDGLVKREELFITSKLW NNFHDPKNVETALNKTLSDLNLDYVDLFLIHFPIAFKFVPIEEK YPPGFYCGDGDNFHYEDVPLLDTWKALEKLVEAGKIKSIGISN FTGALIYDLIRGATIKPAVLQIEHHPYLQQPKLIEYVQKAGIAIT GYSSFGPQSFLELESKRALNTPTLFEHETIKSIADKHGKSPAQV LLRWATQRNIAVIPKSNNPERLAQNLDVSVVDFDLTKDDLDNIAK LDIGLRFNDPWDWDNIPIFV |
| 18. | Amino acid sequence of exemplary xylose reductase from Scheffersomyces stipitis CBS 6054 | MPSIKLNSGYDMPAVGFGCWKVDVDTCSEQIYRAIKTGYRLF DGAEDYANEKLVGAGVKKAIDEGIVKREDLFLTSKLWNNYH HPDNVEKALNRTLSDLQVDYVDLFLIHFPVTFKFVPLEEKYPP GFYCGKGDNFDYEDVPILETWKALEKLVKAGKIRSIGVSNFPG ALLLDLLRGATIKPSVLQVEHHPYLQQPRLIEFAQSRGIAVTAY SSFGPQSFVELNQGRALNTSPLFENETIKAIAAKHGKSPAQVLL RWSSQRGIAIIPKSNTVPRLLENKDVNSFDLDEQDFADIAKLDI NLRFNDPWDWDKIPIFV |
| 19. | Nucleic acid sequence of XYL1 gene from H0 Metschnikowia sp. | ATGGCTACTATCAAATTGAACTCTGGATACGACATGCCCCA AGTGGGTTTTGGGTGCTGGAAAGTAACAACAGTACATGTG CTGATACGATCTACAACGCGATCAAAGTTGGCTACAGATTA TTTGATGGCGCTGAAGATTACGGGAACGAGAAAGAGGTGG GCGAAGGAATCAACAGGGCCATTGACGAAGGCTTGGTGGC |

TABLE 2-continued

| SEQ ID NO: | Description | Sequence |
|---|---|---|
| | | ACGTGACGAGTTGTTCGTGGTGTCCAAGCTCTGGAACAACT<br>TCCATCATCCAGACAACGTCGAGAAGGCGTTGGACAAGACT<br>TTGGGCGACTTGAATGTCGAGTACTTGGACTTGTTCTTGATC<br>CATTTCCCAATTGCGTTCAAATTCGTGCCCTTTGAGGAGAA<br>ATACCCGCCCGGCTTCTACTGTGGAGAAGGCGATAAGTTTA<br>TCTACGAGGATGTGCCTTTGCTTGACACGTGGCGGGCATTG<br>GAGAAGTTTGTGAAGAAGGGTAAGATCAGATCCATCGGAA<br>TCTCGAACTTTTCCGGCGCGTTGATCCAGGACTTGCTCAGG<br>GGCGCCGAGATCCCCCCTGCCGTGTTGCAGATTGAGCACCA<br>CCCATACTTGCAGCAGCCCAGATTGATTGAGTATGTGCAGT<br>CCAAGGGTATTGCCATCACAGCCTACTCCTCTTTTGGCCCAC<br>AGTCGTTTGTGGAGTTGGACCACCCCAAGGTCAAGGAGTGT<br>GTCACGCTTTTCGAGCACGAAGACATTGTTTCCATCGCTAA<br>AGCTCACGACAAGTCCGCGGGCCAGGTATTATTGAGGTGGG<br>CCACGCAAAGGGGTCTTGCCGTGATTCCAAAGTCAAACAAA<br>ACCGAGCGTTTGTTGCTGAATTTGAATGTGAACGATTTTGA<br>TCTCTCTGAAGCAGAATTGGAGCAAATCGCAAAGTTGGACG<br>TGGGCTTGCGCTTCAACAACCCTTGGGACTGGGACAAGATT<br>CCAATCTTCCATTAA |
| 20. | Nucleic acid sequence of exemplary xylose reductase from Spathaspora passalidarum CBS 10155; XYL1.1 | ATGGCTACTATTAAATTATCCTCAGGTCACTTGATGCCTTTA<br>GTTGGTTTCGGTTGTTGGAAGGTCGACAACGCTACCGCTGC<br>TGACCAAATCTACAACGCTATCAAGGCTGGTTACAGATTAT<br>TCGACGGTGCTGAAGATTACGGTAACGAAAAGGAAGTCGG<br>TGACGGTTTAAAGAGAGCCATTGATGAAGGTCTCGTCAAGA<br>GAGAAGAATTATTCATCACCTCTAAGTTATGGAACAACTAC<br>CACGACCCAAAGAACGTTGAAACTGCTTTAAACAGAACCTT<br>ATCCGATTTACAATTGGACTACGTTGATTATTCTTGATCCA<br>CTTCCCAATTGCTTTCAAGTTCGTTCCATTAGAAGAAAAT<br>ACCCACCAGGTTTCTACTGTGGTGACGGTAACAACTTCCAC<br>TATGAAAATGTTCCATTATTGGACACTTGGAAGGCCTTGGA<br>AAAGTTAGTTCAAGCTGGTAAGATCAAGTCTATCGGTATCT<br>CTAACTTCCCTGGTGCTTTAATCTACGACTTGGTCAGAGGTG<br>CTACCATCAAGCCAGCTGTTTTACAAATTGAACACCACCCA<br>TACTTACAACAACCAAAGTTGATTGAATACGTCCAAAAGCA<br>AGGTATTGCTATTACCGCTTACTCTTCTTTCGGTCCTCAATC<br>TTTCTTGGAATTGAACCAAAACAGAGCTTTAAACACCCCAA<br>CCTTGTTTGAACACGACACCATCAAGTCTATCTCTACCAGA<br>TTAAACAAGACCCCAGCTCAAGTCTTATTAAGATGGGCCAC<br>CCAAAGAAACATTGCTGTTATTCCAAAGTCTAACAACCCAG<br>CTAGATTAGCTCAAAACTTGGACGTCACCTCTTTCGACTTG<br>ACCGAAGAAGACTTCAACGCTATCTCTGCTTTGGACATCAA<br>CTTGAGATTCAACGACCCATGGGACTGGGACAACATTCCAA<br>TCTTCGTTTAA |
| 21. | Nucleic acid sequence of exemplary xylose reductase from Spathaspora passalidarum UFMGCMY469; XYL1.2 | ATGTCTTTTAAATTATCTTCAGGTTATGAAATGCCAAAAATC<br>GGTTTTGGTACTTGGAAGATGGACAAGGCCACCATTCCTCA<br>GCAAATTTACGATGCTATCAAGGGTGGTATCAGATCATTCG<br>ATGGTGCTGAAGATTATGGTAACGAAAAGGAAGTTGGTCTT<br>GGTTACAAGAAGGCTATTGAAGACGGTCTTGTTAAGAGAG<br>GAGATCTTTTTATTACCTCCAAGTTATGGAATAACTTCCATG<br>ACCCAAAGAATGTGGAAAAGGCTTTAGACAGAACTTTAGCT<br>GATTTGCAATTGGATTACGTCGACTTATTTTTAATTCATTTC<br>CCAATTGCTTTCAAGTTTGTTCCATTGGAAGAAAGATACCC<br>ACCTTGCTTCTACTGTGGTGATGGTGACAACTTCCATTATGA<br>AGATGTCCCATTATTGGAAACCTGGAAGGCTTTAGAAGCCT<br>TGGTTAAGAAGGGTAAGATTAGATCACTTGGTGTTTCTAAC<br>TTCACTGGTGCTTTGTTGTTAGATTTACTTAGAGGTGCTACC<br>ATTAAGCCAGCTGTTTTGCAAGTCGAACATCATCCATACTT<br>GCAACAACCAAGATTAATTGAATTTGCTCAAAAGCAAGGTA<br>TTGTTGTCACTGCTTACTCTTCATTTGGTCCTCAATCTTTCAC<br>TGAATTGAACCAAAACAGAGCTAACAACACTCCAAGATTGT<br>TTGACCACGAAGTCATAAAGAAGATTGCTGCTAGAAGGGG<br>CAGAACTCCAGCTCAAGTTATCTTAAGATGGGCCACCCAAA<br>GAAATGTCGTGATTATTCCAAAATCCGATACTCCAGAAAGA<br>TTGGTCGAAAACTTGGCTGTCTTTGACTTTGACTTAACTGAA<br>GAAGATTTCAAAGAAATTGCTGCCTTGGATGCTAATTTGAG<br>ATTTAATGACCCATGGGACTGGGACCATATTCCAATCTTTG<br>TTTAA |
| 22. | Nucleic acid sequence of exemplary xylose reductase from *Metschnikowia bicuspidata* var. *bicuspidate* NRRL YB-4993 | ATGAGCACTATCAAATTGAACTCGGGCTACGAAATGCCCCA<br>AGTGGGCTTTGGCTGCTGGAAGGTGACAAACGACACTTGCG<br>CGGATACTATCTACAATGCCATCAAAGTGGGGTACAGATTG<br>TTCGATGGTGCCCAAGACTACGGAAATGAAAAAGAAGTTG<br>GCCAGGGACTCAACAGAGCGATCGATGAAGGATTGGTGGC<br>ACGTGATGAGTTATTGTGGTATCCAAGCTTTGGAACAATT<br>TCCATCACCCAGACAATGTTGAAAAGGCCCTAGACAAGAC |

TABLE 2-continued

| SEQ ID NO: | Description | Sequence |
|---|---|---|
| | | ATTGGGTGACTTGAACGTCGAATACTTGGACTTATTTCTCAT<br>CCACTTTCCCATTGCTTTCAAATTTGTTCCCTTTGAGGAAAA<br>GTACCCACCTGGGTTCTACTGCGGTGACGGCGACAAATTCC<br>ATTACGAGGACGTGCCTTTGCTCGACACGTGGCGGGCTTTG<br>GAGAAAATGGTCAAGAAAGGTAAAATCAGATCCATTGGTA<br>TTTCGAACTTTTCTGGAGCTTTGATCCAAGACTTGCTTAGGG<br>GCGCTGAAATTGCTCCCGCTGTTCTACAAATTGAACACCAC<br>CCATACTTGCAACAGCCCCGGTTGGTTGAGTATGTGAAATC<br>AAAGGGCATTGCTATTACTGCCTACTCGTCTTTTGGCCCACA<br>GTCTTTTATCGAGTTAGATCACCCTAAAGTAAAGGAATGCG<br>TCACTTTGTTTGACCATGACACAATTTTGTCCGTTGCCAGAG<br>CACACAATAAGTCTGCCGGCCAAGTTTTGTTGAGATGGGCC<br>ACTCAAAGAGGTCTTGCAGTTATTCCCAAATCTAACAAGAC<br>AGAACGCTTGGTGCAAAACTTGGAGGTAAACGACTTTGACC<br>TTTCTGACGCTGAGTTGAAGTCCATCTCCAAGCTAGATGTG<br>GGGTTGCGTTTCAACAACCCTTGGGACTGGGACAAGATTCC<br>TATCTTCCACTGA |
| 23. | Nucleic acid sequence of exemplary xylose reductase from *Clavispora lusitaniae* ATCC 42720 | ATGGCCACTATTAAGTTGAACTCAGGATACGAGATGCCTCA<br>GGTTGGTTTCGGCTGCTGGAAAGTCGACAACAAAACCTGTG<br>CTGACCAAATCTACAATGCCATCAAAGTCGGTTACAGATTG<br>TTTGACGGCGCTGAAGATTATGGTAACGAAAAAGAAGTTG<br>GCGAAGGTATCAACAGAGCCATTGCTGATGGCTTGGTTGCT<br>CGTGACGAGTTATTCGTTGTCTCGAAGCTCTGGAACAACTT<br>CCATCACCCTGACAATGTGGAAAAAGCTTTGGACAAGACAT<br>TGAGCGACTTGAACCTCGAGTACCTTGACTTGTTTTTGATCC<br>ATTTCCCAATTGCTTTCAAGTTTGTTCCTTTCGAAGAAAAGT<br>ACCCTCCAGGATTCTACTGTGGAGACACCAACAAGTTCATT<br>TACGAAGACGTTCCAATCATTGACACTTGGAGAGCTTTGGA<br>AAAGTTGGTGGAAAAGGGAAAGATTAGATCCATTGGTGTTT<br>CCAACTTCAATGGCTCCTTGCTTCTCGACTTGCTTAGAGCTG<br>CTAAGATCAAGCCTGCTGTTTTGCAAATCGAGCACCACCCA<br>TACTTGCAACAACCACAGTTGATCAAATGGGTCAAGAGCAA<br>AGGAATTGCTGTGACTGCGTACTCTTCGTTTGGTCCTCAATC<br>ATTCGTTGAGTTGAACCACCCTAAGGTCGGTAGCTGCACCA<br>CATTGTTCGAACACGAAGACATTGTCTCCATCGCCAAAAAG<br>CATGGAAAGAGCCCTGGCCAAGTCTTGTTGAGATGGCTAC<br>TCAGAACGGTCTTGCTGTTATTCCAAAGTCCAACAAAACCG<br>AACGTTTGGTTCAGAACTTGAATGTCAACGATTTTGACCTTT<br>CTGCTCTGGACTTGAGTGCCATTGCTAAATTGGACATTGGC<br>TTGCGTTTCAATGATCCATGGGACTGGGATGAAATCCCAAT<br>CTTCCACTAG |
| 24. | Nucleic acid sequence of exemplary xylose reductase from *Meyerozyma guilliermondii* | ATGTCTATCAAGTTAAACTCTGGATATGACATGCCCTCGGT<br>GGGTTTTGGCTGCTGGAAGGTCGACAATGCCACCTGTGCCG<br>ACACCATCTACAATGCCATCAAGGTGGGATACAGATTATTT<br>GACGGAGCCGAGGATTACGGTAACGAAAAGGAAGTGGGAG<br>ATGGTATTAATAGAGCACTCGATGAGGGCTTGGTTGCCAGA<br>GATGAGCTTTTCGTTGTTTCCAAGCTCTGGAACTCGTTCCAT<br>GACCCCAAAAACGTGGAAAAGGCGTTGGACAAACATTGA<br>GCGACTTGAAGGTGGACTACCTTGACTTGTTCTTGATCCACT<br>TTCCAATTGCTTTCAAGTTTGTTCCCTTCGAGGAGAAATATC<br>CTCCAGGATTCTACTGTGGAGATGGGGACAAGTTCCACTAC<br>GAGGACGTGCCACTCATCGACACCTGGAGAGCATTGGAGA<br>AGTTGGTGGAGAAGGGTAAAATCAGATCCATTGGTATTTCC<br>AACTTTAGTGGTGCGTTGATCCAGGACTTGTTGAGAAGTGC<br>CAAAATCAAGCCAGCAGTGTTGCAGATCGAACACCACCCTT<br>ACTTGCAGCAACCAAGATTGGTTGAGTACGTTCAATCTCAA<br>GGCATCGCCATCACCGCATACTCGTCTTTCGGACCCCAATC<br>TTTCGTGGAATTGGACCACCCTCGTGTCAAGGATGTCAAGC<br>CATTGTTCGAGCACGACGTCATCAAGTCCGTTGCTGGCAAA<br>GTCAAGAAGACCCCAGCACAGGTGTTGTTGAGATGGCCA<br>CTCAAAGAGGACTTGCCGTGATTCCCAAGTCGAACAATCCC<br>GATAGGTTGTTGAGCAACTTGAAGGTGAACGACTTTGATTT<br>GTCGCAAGAAGACTTCCAAGAAATCTCCAAGTTGGACATTG<br>AATTGAGATTCAACAATCCTTGGGACTGGGACAAGATTCCA<br>ACTTTCATCTAA |
| 25. | Nucleic acid sequence of exemplary xylose reductase from *Candida tropicalis* | ATGTCTACTACTGTTAATACTCCTACTATTAAATTAAACTCC<br>GGTTATGAAATGCCATTAGTTGGTTTCGGATGTTGGAAAGT<br>CACCAATGCCACTGCCGCTGACCAAATCTACAATGCCATTA<br>AAACTGGTTACAGATTATTTGATGGTGCTGAAGATTACGGT<br>AACGAAAAAGAAGTTGGTGAAGGTATCAACAGAGCCATTA<br>AAGATGGATTAGTTAAAAGAGAAGAATTATTCATCACTTCT<br>AAATTATGGAACAATTTCCATGATCCAAAGAATGTTGAAAC<br>TGCTTTAAACAAACTTTAAGTGACTTGAACTTGGACTATG<br>TTGATTTATTCTTGATTCATTTCCCAATTGCTTTTAAATTTGT |

TABLE 2-continued

| SEQ ID NO: | Description | Sequence |
|---|---|---|
| | | TCCAATTGAAGAAAAATACCCACCTGGTTTCTACTGTGGTG<br>ATGGTGATAACTTCCACTATGAAGATGTTCCATTATTAGAT<br>ACTTGGAAAGCTTTGGAAAAATTGGTTGAAGCTGGTAAGAT<br>CAAATCTATTGGTATTTCCAATTTCACTGGTGCTTTGATTTA<br>CGATTTGATCAGAGGTGCTACTATCAAACCAGCTGTTTTAC<br>AAATTGAACATCACCCATACTTGCAACAACCAAAATTGATT<br>GAATATGTTCAAAAAGCTGGTATTGCCATTACTGGTTACTC<br>TTCATTTGGTCCACAATCATTCTTGGAATTAGAATCCAAGA<br>GAGCTTTGAATACCCCAACTTTATTTGAACATGAAACTATT<br>AAATCAATTGCTGATAAACATGGTAAATCTCCAGCTCAAGT<br>TTTATTAAGATGGGCTACTCAAAGAAATATTGCTGTTATTCC<br>AAAATCAAACAATCCAGAAAGATTAGCTCAAAACTTGTCTG<br>TTGTTGACTTTGACTTGACTAAGGATGATTTGGACAATATTG<br>CTAAATTGGACATTGGTTTGAGATTCAATGATCCATGGGAC<br>TGGGACAACATTCCAATCTTTGTTTAA |
| 26. | Nucleic acid sequence of exemplary xylose reductase from *Scheffersomyces stipitis* CBS 6054 | ATGCCTTCTATTAAGTTGAACTCTGGTTACGACATGCCAGC<br>CGTCGGTTTCGGCTGTTGGAAAGTCGACGTCGACACCTGTT<br>CTGAACAGATCTACCGTGCTATCAAGACCGGTTACAGATTG<br>TTCGACGGTGCCGAAGATTACGCCAACGAAAAGTTAGTTGG<br>TGCCGGTGTCAAGAAGGCCATTGACGAAGGTATCGTCAAGC<br>GTGAAGACTTGTTCCTTACCTCCAAGTTGTGGAACAACTAC<br>CACCACCCAGACAACGTCGAAAAGGCCTTGAACAGAACCC<br>TTTCTGACTTGCAAGTTGACTACGTTGACTGTTCTTGATCC<br>ACTTCCCAGTCACCTTCAAGTTCGTTCCATTAGAAGAAAAG<br>TACCCACCAGGATTCTACTGTGGTAAGGGTGACAACTTCGA<br>CTACGAAGATGTTCCAATTTTAGAGACCTGGAAGGCTCTTG<br>AAAAGTTGGTCAAGGCCGGTAAGATCAGATCTATCGGTGTT<br>TCTAACTTCCCAGGTGCTTTGCTCTTGGACTTGTTGAGAGGT<br>GCTACCATCAAGCCATCTGTCTTGCAAGTTGAACACCACCC<br>ATACTTGCAACAACCAAGATTGATCGAATTCGCTCAATCCC<br>GTGGTATTGCTGTCACCGCTTACTCTTCGTTCGGTCCTCAAT<br>CTTTCGTTGAATTGAACCAAGGTAGAGCTTTGAACACTTCT<br>CCATTGTTCGAGAACGAAACTATCAAGGCTATCGCTGCTAA<br>GCACGGTAAGTCTCCAGCTCAAGTCTTGTTGAGATGGTCTT<br>CCCAAAGAGGCATTGCCATCATTCCAAAGTCCAACACTGTC<br>CCAAGATTGTTGGAAAACAAGGACGTCAACAGCTTCGACTT<br>GGACGAACAAGATTTCGCTGACATTGCCAAGTTGGACATCA<br>ACTTGAGATTCAACGACCCATGGGACTGGGACAAGATTCCT<br>ATCTTCGTCTAA |

As used herein, the term "xylose transporter" refers to a membrane protein that facilitates the movement of xylose across a cell membrane. The term "*Metschnikowia* xylose transporter" or grammatical equivalent thereof refers to a xylose transporter from a *Metschnikowia* species. Table 3 provides both amino acid and nucleic acid sequences of exemplary xylose transporters.

TABLE 3

| SEQ ID NO: | Description | Sequence |
|---|---|---|
| 27. | Amino acid sequence of Xyt1p for H0 *Metschnikowia* sp. | MGYEEKLVAPALKFKNFLDKTPNIHNVYVIAAISCTSGMMFGF<br>DISSMSVFVDQQPYLKMFDNPSSVIQGFITASMSLGSFFGSLTS<br>TFISEPFGRRASLFICGILWVIGAAVQSSSQNRAQLICGRIIAGW<br>GIGFGSSVAPVYGSEMAPRKIRGTIGGIFQPFSVTVGIFIMPLIGY<br>GCSFIQGKASFRIPWGVQMVPGLILLIGLFFIPESPRWLAKQGY<br>WEDAEIIVANVQAKGNRNDANVQIEMSEIKDQLMLDEHLKEF<br>TYADLFTKKYRQRTITAIFAQIWQQLTGMNVMMYYIVYIFQM<br>AGYSGNTNLVPSLIQYIINMAVTVPALFCLDLLGRRTILLAGAA<br>FMMAWQFGVAGILATYSEPAYISDTVRITIPDDHKSAAKGVIA<br>CCYLFVCSFAFSWGVGIWVYCSEVVVGDSQSRQRGAALATSA<br>NWIFNFAIAMFTPSSFKNITWKTYIIYATFCACMFIHVFFFFP<br>ETKGKRLEEIGQLWDEGVPAWRSAKWQPTVPLASDAELAHKMD<br>VAHAEHADLLATHSPSSDEKTGTV |
| 28. | Amino acid sequence of Gxf1p from H0 *Metschnikowia* sp. | MSQDELHTKSGVETPINDSLLEEKHDVTPLAALPEKSFKDYISI<br>SIFCLFVAFGGFVFGFDTGTISGFVNMSDFKTRFGEMNAQGEY<br>YLSNVRTGLMVSIFNVGCAVGGIFLCKIADVYGRRIGLMFSMV<br>VYVVGIIIQIASTTKWYQYFIGRLIAGLAVGTVSVISPLFISEVAP<br>KQLRGTLVCCFQLCITLGIFLGYCTTYGTKTYTDSRQWRIPLGI<br>CFAWALFLVAGMLNMPESPRYLVEKSRIDDARKSIARSNKVS<br>EEDPAVYTEVQLIQAGIDREALAGSATWMELVTGKPKIFRRVI<br>MGVMLQSLQQLTGDNYFFYYGTTIFKAVGLQDSFQTSIILGIV<br>NFASTFVGIYAIERMGRRLCLLTGSACMFVCFIIYSLIGTQHLY<br>KNGFSNEPSNTYKPSGNAMIFITCLYIFFFASTWAGGVYCIVSE |

TABLE 3-continued

| SEQ ID NO: | Description | Sequence |
|---|---|---|
| | | SYPLRIRSKAMSVATAANWMVVGFLISFFTPFITSAIHFYYGFVF<br>TGCLAFSFFYVYFFVVETKGLSLEEVDILYASGTLPWKSSGWVP |
| 29. | Amino acid sequence of ΔGxf1p (variant of Gxf1p with shorter N-terminus) from H0 *Metschnikowia* sp. | MSDFKTRFGEMNAQGEYYLSNVRTGLMVSIFNVGCAVGGIFL<br>CKIADVYGRRIGLMFSMVVYVGIIIQIASTTKWYQYFIGRLIA<br>GLAVGTVSVISPLFISEVAPKQLRGTLVCCFQLCITLGIFLGYCT<br>TYGTKTYTDSRQWRIPLGICFAWALFLVAGMLNMPESPRYLV<br>EKSRIDDARKSIARSNKVSEEDPAVYIEVQLIQAGIDREALAGS<br>ATWMELVTGKPKIFRRVIMGVMLQSLQQLTGDNYFFYYGTTI<br>FKAVGLQDSFQTSIILGIVNFASTFVGIYAIERMGRRLCLLTGSA<br>CMFVCFIIYSLIGTQHLYKNGFSNEPSNTYKPSGNAMIFITCLYI<br>FFFASTWAGGVYCIVSESYPLRIRSKAMSVATAANWMWGFLI<br>SFFTPFITSAIHFYYGFVFTGCLAFSFFYVYFFVVETKGLSLEEV<br>DILYASGTLPWKSSGWVP |
| 30. | Amino acid sequence of Gxf2p from H0 *Metschnikowia* sp. | MSAEQEQQVSGTSATIDGLASLKQEKTAEEEDAFKPKPATAYF<br>FISFLCGLVAFGGYVFGFDTGTISGFVNMDDYLMRFGQQHAD<br>GTYYLSNVRTGLIVSIFNIGCAVGGLALSKVGDIWGRRIGIMV<br>AMIIYMVGIIIQIASQDKWYQYFIGRLITGLGVGTTSVLSFISE<br>SAPKHLRGTLVCCFQLMVTLGIFLGYCTTYGTKNYTDSRQWR<br>IPLGLCFAWALLLISGMVFMPESPRFLIERQRFDEAKASVAKSN<br>QVSTEDPAVYTEVELIQAGIDREALAGSAGWKELITGKPKMLQ<br>RVILGMMLQSIQQLTGNNYFFYYGTTIFKAVGMSDSFQTSIVL<br>GIVNFASTFVGIWAIERMGRRSCLLVGSACMSVCFLIYSILGSV<br>NLYIDGYENTPSNTRKPTGNAMIFITCLFIFFFASTWAGGVYSI<br>VSETYPLRIRSKGMAVATAANWMWGFLISFFTPFITSAIHFYY<br>GFVFTGCLIFSFFYVFFFVRETKGLSLEEVDELYATDLPPWKTA<br>GWTPPSAEDMAHTTGFAEAAKPTNKHV |
| 31. | Amino acid sequence of Gxs1p from H0 *Metschnikowia* sp. | MGLESNKLIRKYINVGEKRAGSSGMGIFVGVFAALGGVLFGY<br>DTGTISGVMAMPWVKEHFPKDRVAFSASESSLIVSILSAGTFFG<br>AILAPLLTDTLGRRWCIIISSLVVFNLGAALQTAATDIPLLIVGR<br>VIAGLGVGLISSTIPLYQSEALPKWIRGAVVSCYQWAITIGIFLA<br>AVINQGTHKINSPASYRIPLGIQMAWGLILGVGMFFLPETPRFY<br>ISKGQNAKAAVSLARLRKLPQDHPELLEELEDIQAAYEFETVH<br>GKSSWSQVFTNKNKQLKKLATGVCLQAFQQLTGVNFIFYFGT<br>TFFNSVGLDGFTTSLATNIVNVGSTIPGILGVEIFGRRKVLLTGA<br>AGMCLSQFIVAIVGVATDSKAANQVLIAFCCIFIAFFAATWGPT<br>AWVVCGEIFPLRTRAKSIAMCAASNWLLNWAIAYATPYLVDS<br>DKGNLGTNVFFIWGSCNFFCLVFAYFMIYETKGLSLEQVDELY<br>EKVASARKSPGFVPSEHAFREHADVETAMPDNFNLKAEAISVE<br>DASV |
| 32. | Amino acid sequence of Hgt12p from H0 *Metschnikowia* sp. | MGLESNKLIRKYINVGEKRAGSSGMGIFVGVFAALGGVLFGY<br>DTGTISGVMAMPWVKEHFPKDRVAFSASESSLIVSILSAGTFFG<br>AILAPLLTDTLGRRWCIIISSLVVFNLGAALQTAATDIPLLIVGR<br>VIAGLGVGLISSTIPLYQSEALPKWIRGAVVSCYQWAITIGIFLA<br>AVINQGTHKINSPASYRIPLGIQMAWGLILGVGMFFLPETPRFY<br>ISKGQNAKAAVSLARLRKLPQDHPELLEELEDIQAAYEFETVH<br>GKSSWSQVFTNKNKQLKKLATGVCLQAFQQLTGVNFIFYFGT<br>TFFNSVGLDGFTTSLATNIVNVGSTIPGILGVEIFGRRKVLLTGA<br>AGMCLSQFIVAIVGVATDSKAANQVLIAFCCIFIAFFAATWGPT<br>AWVVCGEIFPLRTRAKSIAMCAASNWLLNWAIAYATPYLVDS<br>DKGNLGTNVFFIWGSCNFFCLVFAYFMIYETKGLSLEQVDELY<br>EKVASARKSPGFVPSEHAFREHADVETAMPDNFNLKAEAISVE<br>DASV |
| 33. | Amino acid sequence of Hxt5p from H0 *Metschnikowia* sp. | MSIFEGKDGKGVSSIESLSNDVRYDNMEKVDQDVLRHNFNFD<br>KEFEELEIEAAQVNDKPSFVDRILSLEYKLHFENKNHMVVVLLG<br>AFAAAAGLLSGLDQSIISGASIGMNKALNLTEREASLVSSLMPL<br>GAMAGSMIMTPLNEWFGRKSSLITSCIWYTIGSALCAGARDHH<br>MMYAGRPILGVGVGIEGGCVGIYISESVPANVRGSIVSMYQFN<br>IALGEVLGYAVAAIFYTVHGGWRFMVGSSLVFSTILFAGLFFL<br>PESPRWLVHKGRNGMAYDVWKRLRDINDESAKLEFLEMRQA<br>AYQERERRSQESLFSSWGELFTIARNRRALTYSVIMITLGQLTG<br>VNAVMYYMSTLMGAIGFNEKDSVFMSLVGGGSLLIGTIPAIL<br>WMDRFGRRVVVGYNLVGFFVGLVLVGVGYRFNPVTQKAASE<br>GVYLTGLIVYFLFFGSYSTLTWVIPSESFDLRTRSLGMTICSTFL<br>YLWSFTVTYNFTKMSAAFTYTGLTLGFYGGIAFLGLIYQVCFM<br>PETKDKTLEEIDDIFNRSAFSIARENISNLKKGIW |
| 34. | Amino acid sequence of Hxt2.6p from H0 *Metschnikowia* sp. | MSSTTDTLEKRDIEPFTSDAPVTVHDYIAEERPWWKVPHLRV<br>LTWSVFVITLTSTNNGYDGSMLNGLQSLDIWQEDLGPAGQK<br>LGALANGVLFGNLAAVPFASYFCDRFGRRPVICFGQILTIVGA<br>VLQGLSNSYGFFLGSRIVLGFGAMIATIPSPTLISEIAYPTHRETS<br>TFAYNVCWYLGAIIASWVTYGTRDLQSKACWSIPSYLQAALP<br>FFQVCMIWFVPESPRFLVAKGKIDQARAVLSKYHTGDSTDPRD<br>VALVDFELHEIESALEQEKLNTRSSYFDFFKKRNFRKRGFLCV |

TABLE 3-continued

| SEQ ID NO: | Description | Sequence |
|---|---|---|
| | | MVGVAMQLSGNGLVSYYLSKVLDSIGITETKRQLEINGCLMIY NFVICVSLMSVCRMFKRRVLFLTCFSGMTVCYTIWTILSALNE QRHFEDKGLANGVLAMIFFYYFFYNVGINGLPFLYITEILPYSH RAKGLNLFQFSQFLTQIYNGYVNPIAMDAISWKYYIVYCCILF VELVIVFFTFPETSGYTLEEVAQVFGDEAPGLHNRQLDVAKES LEHVEHV |
| 35. | Amino acid sequence of Qup2p from H0 Metschnikowia sp. | MGFRNLKRRLSNVGDSMSVHSVKEEEDFSRVEIPDEIYNYKIV LVALTAASAAIIIGYDAGFIGGTVSLTAFKSEFGLDKMSATAAS AIEANVVSVFQAGAYFGCLFFYPIGEIWGRKIGLLLSGFLLTFG AAISLISNSSRGLGAIYAGRVLTGLGIGGCSSLAPIYVSEIAPAAI RGKLVGCWEVSWQVGGIVGYWINYGVLQTLPISSQQWIIPFA VQLIPSGLFWGLCLLIPESPRFLVSKGKIDKARKNLAYLRGLSE DHPYSVFELENISKAIEENFEQTGRGFFDPLKALFFSKKMLYRL LLSTSMFMMQNGYGINAVTYYSPTIFKSLGVQGSNAGLLSTGI FGLLKGAASVFWVFFLVDTFGRRFCLCYLSLPCSICMWYIGAY IKIANPSAKLAAGDTATTPAGTAAKAMLYIWTIFYGITWNGTT WVICAEIFPQSVRTAAQAVNASSNWFWAFMIGHFTGQALENI GYGYYFLFAACSAIFPVVVVVFVYPETKGVPLEAVEYLFEVRP WKAHSYALEKYQIEYNEGEFHQHKPEVLLQGSENSD |
| 36. | Amino acid sequence of Aps1p/Hgt19p from H0 Metschnikowia sp. | MGYEEKLVAPALKFKNFLDKTPNIHNVYVIAAISCTSGMMFGF DISSMSVFVDQQPYLKMFDNPSSVIQGFITASMSLGSFFGSLTS TFISEPFGRRASLFICGILWVIGAAVQSSSQNRAQLICGRIIAGW GIGFGSSVAPVYGSEMAPRKIRGTIGGIFQFSVTVGIFIMPLIGY GCSFIQGKASFRIPWGVQMVPGLILLIGLFFIPESPRWLAKQGY WEDAEIIVANVQAKGNRNDANVQIEMSEIKDQLMLDEHLKEF TYADLFTKKYRQRTITAIFAQIWQQLTGMNVMMYYIVYIFQM AGYSGNTNLVPSLIQYIINMAVTVPALFCLDLLGRRTILLAGAA FMMAWQFGVAGILATYSEPAYISDTVRITIPDDHKSAAKGVIA CCYLFVCSFAFSWGVGIWVYCSEVWGDSQSRQRGAALATSA NWIFNFAIAMFTPSSFKNITWKTYIIYATFCACMFIHVFFFFPET KGKRLEEIGQLWDEGVPAWRSAKWQPTVPLASDAELAHKMD VAHAEHADLLATHSPSSDEKTGTV |
| 37. | Amino acid sequence of exemplary xylose transporter from Pichia gulliermondii; Axt1p | MAYEDKLVAPALKFRNFLDKTPNIYNPYIISIISCIAGMMFGFDI SSMSAFVSLPAYVNYFDTPSAVIQGFITSAMALGSFFGSIASAF VSEPFGRRASLLTCSWFWMIGAAIQASSQNRAQLIIGRIISGFG VGFGSSVAPVYGSEMAPRKIRGRIGGIFQLSVTLGIMIMFFISYG TSHIKTAAAFRLAWALQIIPGLLMCIGVFFIPESPRWLAKQGH WDEAEIIVAKIQAKGDRENPDVLIEISEIKDQLMVDENAKAFT YADLFSKKYLPRTITAMFAQIWQQLTGMNVMMYYIVYIFEMA GYGGNGVLVSSTIQYVIFVVVTFVSLFFLDKFGRRKILLVGAAS MMTWQFAVAGILARYSVPYDLSDTVKIKIPDNHKSAAKGVIA CCYLFVASFGFSWGVGIWLYCSEVWGDSQSRQRGAAVSTASN WIFNFALAMFTPSSFKNITWKTYCIYATFCACMFIHVFFFFPET KGKRLEEIAQIWEEKIPAWKTTNWQPHVPLLSDHELAEKINAE HVENVNSREQSDDEKSQV |
| 38. | Amino acid sequence of exemplary xylose transporter from Candida intermedia PYCC 4715; Gxf1p | MSQDSHSSGAATPVNGSILEKEKEDSPVLQVDAPQKGFKDYIV ISIFCFMVAFGGFVFGFDTGTISGFVNMSDFKDRFGQHHADGT PYLSDVRVGLMISIFNVGCAVGGIFLCKVADVWGRRIGLMFS MAVYVVGIIIQISSSTKWYQFFIGRLIAGLAVGTVSVVSPLFISE VSPKQIRGTLVCCFQLCITLGIFLGYCTTYGTKTYTDSRQWRIP LGLCFAWAILLVVGMLNMPESPRYLVEKHRIDEAKRSIARSNK IPEEDPFVYIEVQLIQAGIEREALAGQASWKELITGKPKIFRRVI MGIMLQSLQQLTGDNYFFYYGTTIFQAVGLKDSFQTSIILGIVN FASTFVGIYVIERLGRRLCLLTGSAAMFICFIIYSLIGTQHLYKQ GYSNETSNTYKASGNAMIFITCLYIFFFASTWAGGVYCIISESYP LRIRSKAMSIATAANWLWGFLISFFTPFITSAIHFYYGFVFTGCL AFSFFYVYFFVYETKGLSLEEVDEMYASGVLPLKSASWVPPNL EHMAHSAGYAGADKATDEQV |
| 39. | Amino acid sequence of exemplary glucose/xylose symporter from Candida intermedia; Gxs1p | MGLEDNRMVKRFVNVGEKKAGSTAMAIIVGLFAASGGVLFG YDTGTISGVMTMDYVLARYPSNKHSFTADESSLIVSILSVGTFF GALCAPFLNDTLGRRWCLILSALIVFNIGAILQVISTAIPLLCAG RVIAGFGVGLISATIPLYQSETAPKWIRGAIVSCYQWAITIGLFL ASCVNKGTEHMTNSGSYRIPLAIQCLWGLILGIGMIFLPETPRF WISKGNQEKAAESLARLRKLPIDHPDSLEELRDITAAYEFETVY GKSSWSQVFSHKNHQLKRLFTGVAIQAFQQLTGVNFIFYYGTT FFKRAGVNGFTISLATNIVNVGSTIPGILLMEVLGRRNMLMGG ATGMSLSQLIVAIVGVATSENNKSSQSVLVAFSCIFIAFFAATW GPCAWVVVGELFPLRTRAKSVSLCTASNWLWNWGIAYATPY MVDEDKGNLGSNVFFIWGGFNLACVFFAWYFIYETKGLSLEQ VDELYEHVSKAWKSKGFVPSKHSFREQVDQQMDSKTEAIMSE EASV |

TABLE 3-continued

| SEQ ID NO: | Description | Sequence |
|---|---|---|
| 40. | Amino acid sequence of exemplary xylose transporter from *Saccharomyces cerevisiae*; Gxf2p/Gal2p | MAVEENNMPVVSQQPQAGEDVISSLSKDSHLSAQSQKYSNDE LKAGESGSEGSQSVPIEIPKKPMSEYVTVSLLCLCVAFGGFMFG WDTGTISGFVVQTDFLRRFGMKHKDGTHYLSNVRTGLIVAIFN IGCAFGGIILSKGGDMYGRKKGLSIVVSVYIVGIIIQIASINKWY QYFIGRIISGLGVGGIAVLCPMLISEIAPKHLRGTLVSCYQLMIT AGIFLGYCTNYGTKSYSNSVQWRVPLGLCFAWSLFMIGALTL VPESPRYLCEVNKVEDAKRSIAKSNKVSPEDPAVQAELDLIMA GIEAEKLAGNASWGELFSTKTKVFQRLLMGVFVQMFQQLTGN NYFFYYGTVIFKSVGLDDSFETSIVIGVVNFASTFFSLWTVENL GHRKCLLLGAATMMACMVIYASVGVTRLYPHGKSQPSSKGA GNCMIVFTCFYIFCYATTWAPVAWVITAESFPLRVKSKCMAL ASASNWVWGFLIAFFTPFITSAINFYYGYVFMGCLVAMFFYVF FFVPETKGLSLEEIQELWEEGVLPWKSEGWIPSSRRGNNYDLE DLQHDDKPWYKAMLE |
| 41. | Nucleic acid sequence of XYT1 from H0 *Metschnikowia* sp. | ATGGGTTACGAGGAAAAGCTTGTAGCGCCCGCGTTGAAATT CAAAAACTTTCTTGACAAAACCCCCAATATTCACAATGTCT ATGTCATTGCCGCCATCTCCTGTACATCAGGTATGATGTTTG GATTTGATATCTCGTCGATGTCTGTCTTTGTCGACCAGCAGC CATACTTGAAGATGTTTGACAACCCTAGTTCCGTGATTCAA GGTTTCATTACCGCGCTGATGAGTTTGGGCTCGTTTTTCGGC TCGCTCACATCCACGTTCATCTCTGAGCCTTTTGGTCGTCGT GCATCGTTGTTCATTTGTGGTATTCTTTGGGTAATTGGAGCA GCGGTTCAAAGTTCGTCGCAGAACAGGGCCCAATTGATTTG TGGGCGTATCATTGCAGGATGGGGCATTGGCTTTGGGTCAT CGGTGGCTCCTGTTTACGGGTCCGAGATGGCTCCGAGAAAG ATCAGAGGCACGATTGGTGGAATCTTCCAGTTCTCCGTCAC CGTGGGTATCTTTATCATGTTCTTGATTGGGTACGGATGCTC TTTCATTCAAGGAAAGGCCTCTTTCCGGATCCCCTGGGGTG TGCAAATGGTTCCCGGCCTTATCCTCTTGATTGGACTTTTCT TTATTCCTGAATCTCCCCGTTGGTTGGCCAAACAGGGCTACT GGGAAGACGCCGAAATCATTGTGGCCAATGTGCAGGCCAA GGGTAACCGTAACGACGCCAACGTGCAGATTGAAATGTCG GAGATTAAGGATCAATTGATGCTTGACGAGCACTTGAAGGA GTTTACGTACGCTGACCTTTTCACGAAGAAGTACCGCCAGC GCACGATCACGGCGATCTTTGCCCAGATCTGGCAACAGTTG ACCGGTATGAATGTGATGATGTACTACATTGTGTACATTTTC CAGATGGCAGGCTACAGCGGCAACACGAACTTGGTGCCCA GTTTGATCCAGTACATCATCAACATGGCGGTCACGGTGCCG GCGCTTTTCTGCTTGGATCTCTTGGGCCGTCGTACCATTTTG CTCGCGGGTGCCGCGTTCATGATGGCGTGGCAATTCGGCGT GGCGGGCATTTTGGCCACTTACTCAGAACCGGCATATATCT CTGACACTGTGCGTATCACGATCCCCGACGACCACAAGTCT GCTGCAAAAGGTGTGATTGCATGCTGCTATTTGTTTGTGTGC TCGTTTGCATTCTCGTGGGGTGTCGGTATTTGGGTGTACTGT TCCGAGGTTTGGGGTGACTCCCAGTCGAGACAAAGAGGCG CCGCTCTTGCGACGTCGGCCAACTGGATCTTCAACTTCGCC ATTGCCATGTTCACGCCGTCCTCATTCAAGAATATCACGTG GAAGACGTATATCATCTACGCCACGTTCTGTGCGTGCATGT TCATACACGTGTTTTTCTTTTTCCCAGAAACAAAGGGCAAG CGTTTGGAGGAGATAGGCCAGCTTTGGGACGAAGGAGTCC CAGCATGGAGGTCAGCCAAGTGGCAGCCAACAGTGCCGCT CGCGTCCGACGCAGAGCTTGCACACAAGATGGATGTTGCGC ACGCGGAGCACGCGGACTTATTGGCCACGCACTCGCCATCT TCAGACGAGAAGACGGGCACGGTCTAA |
| 42. | Nucleic acid sequence of GXF1 from H0 *Metschnikowia* sp. | ATGTCTCAAGACGAACTTCATACAAAGTCTGGTGTTGAAAC ACCAATCAACGATTCGCTTCTCGAGGAGAAGCACGATGTCA CCCCACTCGCGGCATTGCCCGAGAAGTCCTTCAAGGACTAC ATTTCCATTTCCATTTTCTGTTTGTTTGTGGCATTTGGTGGTT TTGTTTTCGGTTTCGACACCGGTACGATTTCCGGTTTCGTCA ACATGTCCGACTTCAAGACCAGATTTGGTGAGATGAATGCC CAGGGCGAATACTACTTGTCCAATGTTAGAACTGGTTTGAT GGTTTCTATTTTCAACGTCGGTTGCGCCGTTGGTGGTATCTT CCTTTGTAAGATTGCCGATGTTTATGGCAGAAGAATTGGTC TTATGTTTTCCATGGTGGTTTATGTCGTTGGTATCATTATTC AGATTGCCTCCACCACCAAATGGTACCAATACTTCATTGGC CGTCTTATTGCTGGCTTGGCTGTGGGTACTGTTTCCGTCATC TCGCCACTTTTCATTTCCGAGGTTGCTCCTAAACAGCTCAGA GGTACGCTTGTGTGCTGCTTCCAGTTGTGTATCACCTTGGGT ATCTTTTGGGTTACTGCACGACCTACGGTACAAAGACTTA CACTGACTCCAGACAGTGGAGAATCCATTGGGTATCTGTT TCGCGTGGGCTTTGTTTTTGGTGGCCGGTATGTTGAACATGC CCGAGTCTCCTAGATACTTGGTTGAGAAATCGAGAATCGAC GATGCCAGAAAGTCCATTGCCAGATCCAACAAGGTTTCCGA GGAAGACCCCGCCGTGTACACCGAGGTGCAGCTTATCCAGG CTGGTATTGACAGAGAGGCCCTTGCCGGCAGCGCCACATGG – continued

| SEQ ID NO: | Description | Sequence |
|---|---|---|
| | | ATGGAGCTTGTGACTGGTAAGCCCAAAATCTTCAGAAGAGT<br>CATCATGGGTGTCATGCTTCAGTCCTTGCAACAATTGACTG<br>GTGACAACTACTTTTTCTACTACGGAACCACGATTTTCAAG<br>GCTGTTGGCTTGCAGGACTCTTTCCAGACGTCGATTATCTTG<br>GGTATTGTCAACTTTGCCTCGACTTTTGTCGGTATTTACGCC<br>ATTGAGAGAATGGGCAGAAGATTGTGTTTGTTGACCGGATC<br>TGCGTGCATGTTTGTGTGTTTCATCATCTACTCGCTCATTGG<br>TACGCAGCACTTGTACAAGAACGGCTTCTCTAACGAACCTT<br>CCAACACATACAAGCCTTCCGGTAACGCCATGATCTTCATC<br>ACGTGTCTTTACATTTTCTTCTTTGCCTCGACCTGGGCCGGT<br>GGTGTTTACTGTATCGTGTCCGAGTCTTACCCATTGAGAATC<br>AGATCCAAGGCCATGTCTGTCGCCACCGCCGCCAACTGGAT<br>GTGGGGTTTCTTGATCTCGTTCTTCACGCCTTTCATCACCTC<br>CGCCATCCACTTTTACTACGGTTTTGTTTTCACTGGCTGCTT<br>GGCGTTCTCCTTCTTCTACGTCTACTTCTTTGTCGTGGAGAC<br>CAAGGGTCTTTCCTTGGAGGAGGTTGACATTTTGTACGCTTC<br>CGGTACGCTTCCATGGAAGTCCTCTGGCTGGGTGCCTCCTA<br>CCGCGGACGAAATGGCCCACAACGCCTTCGACAACAAGCC<br>AACTGACGAACAAGTCTAA |
| 43. | Nucleic acid sequence of ΔGXF1 (variant of GXF1 with shorter N-terminus) from H0 Metschnikowia sp. | ATGTCCGACTTCAAGACCAGATTTGGTGAGATGAATGCCCA<br>GGGCGAATACTACTTGTCCAATGTTAGAACTGGTTTGATGG<br>TTTCTATTTTCAACGTCGGTTGCGCCGTTGGTGGTATCTTCC<br>TTTGTAAGATTGCCGATGTTTATGGCAGAAGAATTGGTCTT<br>ATGTTTTCCATGGTGGTTTATGTCGTTGGTATCATTATTCAG<br>ATTGCCTCCACCACCAAATGGTACCAATACTTCATTGGCCG<br>TCTTATTGCTGGCTTGGCTGTGGGTACTGTTTCCGTCATCTC<br>GCCACTTTTCATTTCCGAGGTTGCTCCTAAACAGCTCAGAG<br>GTACGCTTGTGTGCTGCTTCCAGTTGTGTATCACCTTGGGTA<br>TCTTTTTGGGTTACTGCACGACCTACGGTACAAAGACTTAC<br>ACTGACTCCAGACAGTGGAGAATCCCATTGGGTATCTGTTT<br>CGCGTGGGCTTTGTTTTTGGTGGCCGGTATGTTGAACATGCC<br>CGAGTCTCCTAGATACTTGGTTGAGAAATCGAGAATCGACG<br>ATGCCAGAAAGTCCATTGCCAGATCCAACAAGGTTTCCGAG<br>GAAGACCCCGCCGTGTACACCGAGGTGCAGCTTATCCAGGC<br>TGGTATTGACAGAGAGGCCCTTGCCGGCAGCGCCACATGGA<br>TGGAGCTTGTGACTGGTAAGCCCAAAATCTTCAGAAGAGTC<br>ATCATGGGTGTCATGCTTCAGTCCTTGCAACAATTGACTGG<br>TGACAACTACTTTTTCTACTACGGAACCACGATTTTCAAGG<br>CTGTTGGCTTGCAGGACTCTTTCCAGACGTCGATTATCTTGG<br>GTATTGTCAACTTTGCCTCGACTTTTGTCGGTATTTACGCCA<br>TTGAGAGAATGGGCAGAAGATTGTGTTTGTTGACCGGATCT<br>GCGTGCATGTTTGTGTGTTTCATCATCTACTCGCTCATTGGT<br>ACGCAGCACTTGTACAAGAACGGCTTCTCTAACGAACCTTC<br>CAACACATACAAGCCTTCCGGTAACGCCATGATCTTCATCA<br>CGTGTCTTTACATTTTCTTCTTTGCCTCGACCTGGGCCGGTG<br>GTGTTTACTGTATCGTGTCCGAGTCTTACCCATTGAGAATCA<br>GATCCAAGGCCATGTCTGTCGCCACCGCCGCCAACTGGATG<br>TGGGGTTTCTTGATCTCGTTCTTCACGCCTTTCATCACCTCC<br>GCCATCCACTTTTACTACGGTTTTGTTTTCACTGGCTGCTTG<br>GCGTTCTCCTTCTTCTACGTCTACTTCTTTGTCGTGGAGACC<br>AAGGGTCTTTCCTTGGAGGAGGTTGACATTTTGTACGCTTCC<br>GGTACGCTTCCATGGAAGTCCTCTGGCTGGGTGCCTCCTAC<br>CGCGGACGAAATGGCCCACAACGCCTTCGACAACAAGCCA<br>ACTGACGAACAAGTCTAA |
| 44. | Nucleic acid sequence of GXF2/GAL2 from H0 Metschnikowia sp. | ATGAGTGCCGAACAGGAACAACAAGTATCGGGCACATCTG<br>CCACGATAGATGGGCTGGCGTCCTTGAAGCAAGAAAAAAC<br>CGCCGAGGAGGAAGACGCCTTCAAGCCTAAGCCCGCCACG<br>GCGTACTTTTTCATTTCGTTCCTCTGTGGCTTGGTCGCCTTTG<br>GCGGCTACGTTTTCGGTTTCGATACCGGTACGATTTCCGGGT<br>TTGTTAACATGGACGACTATTTGATGAGATTCGGCCAGCAG<br>CACGCTGATGGCACGTATTACCTTTCCAACGTGAGAACCGG<br>TTTGATCGTGTCGATCTTCAACATTGGCTGTGCCGTTGGTGG<br>TCTTTGCGCTTTCGAAAGTCGGTGACATTTGGGGCAGAAGAA<br>TTGGTATTATGGTTGCTATGATCATCTACATGGTGGGAATC<br>ATCATCCAGATCGCTTCACAGGATAAATGGTACCAGTACTT<br>CATTGGCCGTTTGATCACCGGATTGGGTGTCGGCACCACGT<br>CCGTGCTTAGTCCTCTTTTCATCTCCGAGTCGGCTCCGAAGC<br>ATTTGAGAGGCACCCTTGTGTGTTGTTTCCAGCTCATGGTCA<br>CCTTGGGTATCTTTTTGGGCTACTGCACGACCTACGGTACCA<br>AGAACTACACTGACTCGCGCCAGTGGCGGATTCCCTTGGGT<br>CTTTGCTTCGCATGGGCTCTTTTGTTGATCTCGGGAATGGTT<br>TTCATGCCTGAATCCCCACGTTTCTTGATTGAGCGCCAGAG<br>ATTCGACGAGGCCAAGGCTTCCGTGGCCAAATCGAACCAG<br>GTTTCGACCGAGGACCCCGCCGTGTACACTGAAGTCGAGTT<br>GATCCAGGCCGGTATTGACCGTGAGGCATTGGCCGGATCCG<br>CTGGCTGGAAAGAGCTTATCACGGGTAAGCCCAAGATGTTG |

TABLE 3-continued

| SEQ ID NO: | Description | Sequence |
|---|---|---|
| | | CAGCGTGTGATTTTGGGAATGATGCTCCAGTCGATCCAGCA<br>GCTTACCGGTAACAACTACTTTTTCTACTATGGTACCACGAT<br>CTTCAAGGCCGTGGGCATGTCGGACTCGTTCCAGACCTCGA<br>TTGTTTTGGGTATTGTCAACTTCGCCTCCACTTTTGTCGGAA<br>TCTGGGCCATCGAACGCATGGGCCGCAGATCTTGTTTGCTT<br>GTTGGTTCCGCGTGCATGAGTGTGTGTTTCTTGATCTACTCC<br>ATCTTGGGTTCCGTCAACCTTTACATCGACGGCTACGAGAA<br>CACGCCTTCCAACACGCGTAAGCCTACCGGTAACGCCATGA<br>TTTTCATCACGTGTTTGTTCATCTTCTTCTTCGCCTCCACCTG<br>GGCCGGTGGTGTGTACAGTATTGTGTCTGAAACATACCCAT<br>TGAGAATCCGCTCTAAAGGTATGGCCGTGGCCACCGCTGCC<br>AACTGGATGTGGGGTTTCTTGATTTCGTTCTTCACGCCTTTC<br>ATCACCTCGGCCATCCACTTCTACTACGGGTTTGTGTTCACA<br>GGGTGTCTTATTTTCTCCTTCTTCTACGTGTTCTTCTTTGTTA<br>GGGAAACCAAGGGTCTCTCGTTGGAAGAGGTGGATGAGTT<br>ATATGCCACTGACCTCCCACCATGGAAGACCGCGGGCTGGA<br>CGCCTCCTTCTGCTGAGGATATGGCCCACACCACCGGGTTT<br>GCCGAGGCCGCAAAGCCTACGAACAAACACGTTTAA |
| 45. | Nucleic acid sequence of GXS1 from H0 Metschnikowia sp. | ATGGGCATTTTCGTTGGCGTTTTCGCCGCGCTTGGCGGTGTT<br>CTCTTTGGCTACGATACCGGTACCATCTCTGGTGTGATGGCC<br>ATGCCTTGGGTCAAGGAACATTTCCCAAAAGACCGTGTTGC<br>ATTTAGTGCTTCCGAGTCGTCGTTGATTGTGTCTATTTTATC<br>TGCAGGAACTTTCTTTGGAGCCATTCTTGCTCCGCTCTTGAC<br>CGATACATTGGGTAGACGCTGGTGTATTATCATCTCTTCGCT<br>CGTTGTGTTCAATTTGGGTGCTGCTTTGCAGACGGCTGCCAC<br>GGATATCCCGCTCTTGATTGTTGGTCGTGTCATTGCCGGTTT<br>AGGGGTTGGTTTGATTTCGCTGACGATTCCATTGTACCAGTC<br>CGAAGCGCTTCCCAAATGGATTAGAGGTGCTGTTGTCTCGT<br>GCTACCAATGGGCCATTACTATTGGTATCTTTTTGGCTGCCG<br>TGATCAACCAGGGCACTCACAAGATCAACAGCCCTGCGTCG<br>TACAGAATTCCATTGGGTATTCAGATGGCATGGGGTCTTAT<br>CTTGGGTGTCGGCATGTTCTTCTTGCCCGAGACGCCTCGTTT<br>CTACATTTCCAAGGGCCAGAATGCGAAGGCTGCTGTTTCAT<br>TGGCGCGTTTGAGAAAGCTTCCGCAAGATCACCCGGAGTTG<br>TTGGAGGAATTGGAAGATATCCAGGCGGCATACGAGTTTGA<br>GACTGTCCATGGCAAGTCTTCATGGCTGCAGGTTTTCACCA<br>ACAAGAACAAACAATTGAAGAAGTTGGCCACGGGCGTGTG<br>CTTGCAGGCGTTCCAACAATTGACTGGTGTGAACTTCATTTT<br>CTACTTTGGCACGACTTTCTTCAACAGTGTTGGGCTTGACGG<br>ATTCACCACCTCCTTGGCCACCAACATTGTCAATGTTGGCTC<br>GACGATCCCTGGTATTTTGGGTGTTGAGATTTTCGGCAGAA<br>GAAAAGTGTTGTTGACCGGCGCTGCTGGTATGTGTCTTTCG<br>CAATTCATTGTTGCCATTGTTGGTGTAGCCACCGACTCCAA<br>GGCTGCGAACCAAGTTCTTATTGCCTTCTGCTGCATTTTCAT<br>TGCGTTCTTTGCAGCCACCTGGGGCCCCACCGCATGGGTTG<br>TTTGTGGCGAGATTTTCCCCTTGAGAACCAGAGCCAAGTCG<br>ATTGCCATGTGCGCTGCTTCGAACTGGTTGTTGAACTGGGC<br>AATTGCATACGCCACGCCATACTTGGTTGACTCCGATAAGG<br>GTAACTTGGGCACCAATGTGTTTTTCATTTGGGGAAGCTGT<br>AACTTCTTCTGCCTTGTGTTTGCCTACTTCATGATTTACGAG<br>ACCAAGGGTCTTTCCTTGGAGCAGGTTGATGAGCTTTACGA<br>GAAGGTTGCCAGCGCCAGAAAGTCGCCTGGCTTCGTGCCAA<br>GCGAGCACGCTTTCAGAGAGCACGCCGATGTGGAGACCGC<br>CATGCCAGACAACTTCAACTTGAAGGCGGAGGCGATTTCTG<br>TCGAGGATGCCTCTGTTTAA |
| 46. | Nucleic acid sequence of HGT12 from H0 Metschnikowia sp. | ATGAGCATCTTTGAAGGCAAAGACGGGAAGGGGGTATCCT<br>CCACCGAGTCGCTTTCCAATGACGTCAGATATGACAACATG<br>GAGAAAGTTGATCAGGATGTTCTTAGACACAACTTCAACTT<br>TGACAAAGAATTCGAGGAGCTCGAAATCGAGGCGGCGCAA<br>GTCAACGACAAACCTTCTTTTGTCGACAGGATTTTATCCCTC<br>GAATACAAGCTTCATTTCGAAAACAAGAACCACATGGTGTG<br>GCTCTTGGGCGCTTTCGCAGCCGCCGCAGGCTTATTGTCTG<br>GCTTGGATCAGTCCATTATTTCTGGTGCATCCATTGGAATGA<br>ACAAAGCATTGAACTTGACTGAACGTGAAGCCTCATTGGTG<br>TCTTCGCTTATGCCTTTAGGCGCCATGGCAGGCTCCATGATT<br>ATGACACCTCTTAATGAGTGGTTCGGAAGAAAATCATCGTT<br>GATTATTTCTTGTATTTGGTATACCATCGGATCCGCTTTGTG<br>CGCTGGCGCCAGAGATCACCACATGATGTACGCTGGCAGAT<br>TTATTCTTGGTGTCGGTGTGGGTATAGAAGGTGGGTGTGTG<br>GGCATTTACATTTCCGAGTCTGTCCCAGCCAATGTGCGTGG<br>TAGTATCGTGTCGATGTACCAGTTCAATATTGCTTTGGGTGA<br>AGTTCTAGGGTATGCTGTTGCTGCCATTTTCTACACTGTTCA<br>TGGTGGATGGAGGTTCATGGTGGGTCTTCTTTAGTATTCTC<br>TACTATATTGTTTGCCGGATTGTTTTTCTTGCCCGAGTCACC<br>TCGTTGGTTGGTGCACAAAGGCAGAAACGGAATGGCATAC<br>GATGTGTGGAAGAGATTGAGAGACATAAACGATGAAAGCG |

TABLE 3-continued

| SEQ ID NO: | Description | Sequence |
|---|---|---|
| | | CAAAGTTGGAATTTTTGGAGATGAGACAGGCTGCTTATCAA<br>GAGAGAGAAAGACGCTCGCAAGAGTCTTTGTTCTCCAGCTG<br>GGGCGAATTATTCACCATCGCTAGAAACAGAAGAGCACTTA<br>CTTACTCTGTCATAATGATCACTTTGGGTCAATTGACTGGTG<br>TCAATGCCGTCATGTACTACATGTCGACTTTGATGGGTGCA<br>ATTGGTTTCAACGAGAAAGACTCTGTGTTCATGTCCCTTGTG<br>GGAGGCGGTTCTTTGCTTATAGGTACCATTCCTGCCATTTTG<br>TGGATGGACCGTTTCGGCAGAAGAGTTTGGGGTTATAATCT<br>TGTTGGTTTCTTCGTTGGTTTGGTGCTCGTTGGTGTTGGCTA<br>CCGTTTCAATCCCGTCACTCAAAAGGCGGCTTCAGAAGGTG<br>TGTACTTGACGGGTCTCATTGTCTATTTCTTGTTCTTTGGTTC<br>CTACTCGACCTTAACTTGGGTCATTCCATCCGAGTCTTTTGA<br>TTTGAGAACAAGATCTTTGGGTATGACAATCTGTTCCACTTT<br>CCTTTACTTGTGGTCTTTCACCGTCACCTACAACTTCACCAA<br>GATGTCCGCCGCCTTCACATACACTGGGTTGACACTTGGTTT<br>CTACGGTGGCATTGCGTTCCTTGGTTTGATTTACCAGGTCTG<br>CTTCATGCCCGAGACGAAGGACAAGACTTTGGAAGAAATT<br>GACGATATCTTCAATCGTTCTGCGTTCTCTATCGCGCGCGAG<br>AACATCTCCAACTTGAAGAAGGGTATTTGGTAA |
| 47. | Nucleic acid sequence of HXT5 from H0 *Metschnikowia* sp. | ATGAGCATCTTTGAAGGCAAAGACGGGAAGGGGGTATCCT<br>CCACCGAGTCGCTTTCCAATGACGTCAGATATGACAACATG<br>GAGAAAGTTGATCAGGATGTTCTTAGACACAACTTCAACTT<br>TGACAAAGAATTCGAGGAGCTCGAAATCGAGGCGGCGCAA<br>GTCAACGACAAACCTTCTTTTGTCGACAGGATTTTATCCCTC<br>GAATACAAGCTTCATTTCGAAAACAAGAACCACATGGTGTG<br>GCTCTTGGGCGCTTTCGCAGCCGCCGCAGGCTTATTGTCTG<br>GCTTGGATCAGTCCATTATTTCTGGTGCATCCATTGGAATGA<br>ACAAAGCATTGAACTTGACTGAACGTGAAGCCTCATTGGTG<br>TCTTCGCTTATGCCTTTAGGCGCCATGGCAGGCTCCATGATT<br>ATGACACCTCTTAATGAGTGGTTCGGAAGAAAATCATCGTT<br>GATTATTTCTTGTATTTGGTATACCATCGGATCCGCTTTGTG<br>CGCTGGCGCCAGAGATCACCACATGATGTACGCTGGCAGAT<br>TTATTCTTGGTGTCGGTGTGGGTATAGAAGGTGGGTGTGTG<br>GGCATTTACATTTCCGAGTCTGTCCCAGCCAATGTGCGTGG<br>TAGTATCGTGTCGATGTACCAGTTCAATATTGCTTTGGGTGA<br>AGTTCTAGGGTATGCTGTTGCTGCCATTTTCTACACTGTTCA<br>TGGTGGATGGAGGTTCATGGTGGGTCTTCTTTAGTATTCTC<br>TACTATATTGTTTGCCGGATTGTTTTTCTTGCCCGAGTCACC<br>TCGTTGGTTGGTGCACAAAGGCAGAAACGGAATGGCATAC<br>GATGTGTGGAAGAGATTGAGAGACATAAACGATGAAAGCG<br>CAAAGTTGGAATTTTTGGAGATGAGACAGGCTGCTTATCAA<br>GAGAGAGAAAGACGCTCGCAAGAGTCTTTGTTCTCCAGCTG<br>GGGCGAATTATTCACCATCGCTAGAAACAGAAGAGCACTTA<br>CTTACTCTGTCATAATGATCACTTTGGGTCAATTGACTGGTG<br>TCAATGCCGTCATGTACTACATGTCGACTTTGATGGGTGCA<br>ATTGGTTTCAACGAGAAAGACTCTGTGTTCATGTCCCTTGTG<br>GGAGGCGGTTCTTTGCTTATAGGTACCATTCCTGCCATTTTG<br>TGGATGGACCGTTTCGGCAGAAGAGTTTGGGGTTATAATCT<br>TGTTGGTTTCTTCGTTGGTTTGGTGCTCGTTGGTGTTGGCTA<br>CCGTTTCAATCCCGTCACTCAAAAGGCGGCTTCAGAAGGTG<br>TGTACTTGACGGGTCTCATTGTCTATTTCTTGTTCTTTGGTTC<br>CTACTCGACCTTAACTTGGGTCATTCCATCCGAGTCTTTTGA<br>TTTGAGAACAAGATCTTTGGGTATGACAATCTGTTCCACTTT<br>CCTTTACTTGTGGTCTTTCACCGTCACCTACAACTTCACCAA<br>GATGTCCGCCGCCTTCACATACACTGGGTTGACACTTGGTTT<br>CTACGGTGGCATTGCGTTCCTTGGTTTGATTTACCAGGTCTG<br>CTTCATGCCCGAGACGAAGGACAAGACTTTGGAAGAAATT<br>GACGATATCTTCAATCGTTCTGCGTTCTCTATCGCGCGCGAG<br>AACATCTCCAACTTGAAGAAGGGTATTTGGTAA |
| 48. | Nucleic acid sequence of HXT2.6 from H0 *Metschnikowia* sp. | ATGCTGAGCACTACCGATACCCTCGAAAAAAGGGACACCG<br>AGCCTTTCACTTCAGATGCTCCTGTCACAGTCCATGACTATA<br>TCGCAGAGGAGCGTCCGTGGTGGAAAGTGCCGCATTTGCGT<br>GTATTGACTTGGTCTGTTTTCGTGATCACCCTCACCTCCACC<br>AACAACGGGTATGATGGCTGATGTTGAATGGATTGCAATC<br>CTTGGACATTTGGCAGGAGGATTTGGGTCACCCTGCGGGCC<br>AGAAATTGGGTGCCTTGGCCAACGGTGTTTTGTTTGGTAAC<br>CTTGCTGCTGTGCCTTTTGCTTCGTATTTCTGCGATCGTTTTG<br>GTAGAAGGCCGGTCATTTGTTTCGGACAGATCTTGACAATT<br>GTTGGTGCTGTATTACAAGGTTTGTCCAACAGCTATGGATTT<br>TTTTTGGGTTCGAGAATTGTGTTGGGTTTTGGTGCTATGATA<br>GCCACTATTCCGCTGCCAACATTGATTTCCGAAATCGCCTA<br>CCCTACGCATAGAGAAACTTCCACTTTCGCCTACAACGTGT<br>GCTGGTATTTGGGAGCCATTATCGCCTCCTGGGTCACATAC<br>GGCACCAGAGATTTACAGAGCAAGGCTTGCTGGTCAATTCC<br>TTCTTATCTCCAGGCCGCCTTACCTTTCTTTCAAGTGTGCAT<br>GATTTGGTTTGTGCCAGAGTCTCCCAGATTCCTCGTTGCCAA |

TABLE 3-continued

| SEQ ID NO: | Description | Sequence |
|---|---|---|
| | | GGGCAAGATCGACCAAGCAAGGGCTGTTTTGTCTAAATACC ATACAGGAGACTCGACTGACCCCAGAGACGTTGCGTTGGTT GACTTTGAGCTCCATGAGATTGAGAGTGCATTGGAGCAGGA AAAATTGAACACTCGCTCGTCATACTTTGACTTTTTCAAGA AGAGAAACTTTAGAAAGAGAGGCTTCTTGTGTGTCATGGTC GGTGTTGCAATGCAGCTTTCTGGAAACGGCTTAGTGTCCTA TTACTTGTCGAAAGTGCTAGACTCGATTGGAATCACTGAAA CCAAGAGACAGCTCGAGATCAATGGCTGCTTGATGATCTAT AACTTTGTCATCTGCGTCTCGTTGATGAGTGTTTGCCGTATG TTCAAAAGAAGAGTATTATTTCTCACGTGTTTCTCAGGAAT GACGGTTTGCTACACGATATGGACGATTTTGTCAGCGCTTA ATGAACAGAGACACTTTGAGGATAAAGGCTTGGCCAATGG CGTGTTGGCAATGATCTTCTTCTACTATTTTTCTACAACGT TGGCATCAATGGATTGCCATTCCTATACATCACCGAGATCT TGCCTTACTCACACAGAGCAAAAGGCTTGAATTTATTCCAA TTCTCGCAATTTCTCACGCAAATCTACAATGGCTATGTGAA CCCAATCGCCATGGACGCAATCAGCTGGAAGTATTACATTG TGTACTGCTGTATTCTCTTCGTGGAGTTGGTGATTGTGTTTT TCACGTTCCCAGAAACTTCGGGATACACTTTGGAGGAGGTC GCCCAGGTATTTGGTGATGAGGCTCCCGGGCTCCACAACAG ACAATTGGATGTTGCGAAAGAATCACTCGAGCATGTTGAGC ATGTTTGA |
| 49. | Nucleic acid sequence of QUP2 from H0 Metschnikowia sp. | ATGGGCTTTCGCAACTTAAAGCGCAGGCTCTCAAATGTTGG CGACTCCATGTCAGTGCACTCTGTGAAAGAGGAGGAAGACT TCTCCCGCGTGGAAATCCCGGATGAAATCTACAACTATAAG ATCGTCCTTGTGGCTTTAACAGCGGCGTCGGCTGCCATCAT CATCGGCTACGATGCAGGCTTCATTGGTGGCACGGTTTCGT TGACGGCGTTCAAACTGGAATTTGGCTTGGACAAAATGTCT GCGACGGCGGCTTCTGCTATCGAAGCCAACGTTGTTTCCGT GTTCCAGGCCGGCGCCTACTTTGGGTGTCTTTTCTTCTATCC GATTGGCGAGATTTGGGGCCGTAAAATCGGTCTTCTTCTTTC CGGCTTTCTTTTGACGTTTGGTGCTGCTATTCTTTGATTTCG AACTCGTCTCGTGGCCTTGGTGCCATATATGCTGGAAGAGT ACTAACAGGTTTGGGGATTGGCGGATGTCTGAGTTTGGCCC CAATCTACGTTTCTGAAATCGCGCCTGCAGCAATCAGAGGC AAGCTTGTGGGCTGCTGGGAAGTGTCATGGCAGGTGGGCG GCATTGTTGGCTACTGGATCAATTACGGAGTCTTGCAGACT CTTCCGATTAGCTCACAACAATGGATCATCCCGTTTGCTGTA CAATTGATCCCATCGGGGCTTTTCTGGGGCCTTTGTCTTTTG ATTCCAGAGCTGCCACGTTTTCTTGTATCGAAGGGAAAGAT CGATAAGGCGCGCAAAAACTTAGCGTACTTGCGTGGACTTA GCGAGGACCACCCCTATTCTGTTTTTGAGTTGGAGAACATT AGTAAGGCCATTGAAGAGAACTTCGAGCAAACAGGAAGGG GTTTTTTCGACCCATTGAAAGCTTTGTTTTTCAGCAAAAAAA TGCTTTACCGCCTTCTCTTGTCCACGTCAATGTTCATGATGC AGAATGGCTATGGAATCAATGCTGTGACATACTACTCGCCC ACGATCTTCAAATCCTTAGGCGTTCAGGGCTCAAACGCCGG TTTGCTCTCAACAGGAATTTTCGGTCTTCTTAAAGGTGCCGC TTCGGTGTTCTGGGTCTTTTTCTTGGTTGACACATTCGGCCG CCGGTTTTGTCTTTGCTACCTCTCTCTCCCCTGCTCGATCTGC ATGTGGTATATTGGCGCATACATCAAGATTGCCAACCCTTC AGCGAAGCTTGCTGCAGGAGACACAGCCACCACCCCAGCA GGAACTGCAGCGAAAGCGATGCTTTACATATGGACGATTTT CTACGGCATTACGTGGAATGGTACGACCTGGGTGATCTGCG CGGAGATTTTCCCCCAGTCGGTGAGAACAGCCGCGCAGGCC GTCAACGCTTCTTCTAATTGGTTCTGGGCTTTCATGATCGGC CACTTCACTGGCCAGGCGCTCGAGAATATTGGGTACGGATA CTACTTCTTGTTTGCGGCGTGCTCTGCAATCTTCCCTGTGGT AGTCTGGTTTGTGTACCCCGAAACAAAGGGTGTGCCTTTGG AGGCCGTGGAGTATTTGTTCGAGGTGCGTCCTTGGAAAGCG CACTCATATGCTTTGGAGAAGTACCAGATTGAGTACAACGA GGGTGAATTCCACCAACATAAGCCCGAAGTACTCTTACAAG GGTCTGAAAACTCGGACACGAGCGAGAAAAGCCTCGCCTG A |
| 50. | Nucleic acid sequence of APS1/HGT19 from H0 Metschnikowia sp. | ATGTCAGAAAAGCCTGTTGTCGCACAGCATCGACACGAC GCTGTCTACGTCATCGAAACAAGTCTATGACGGTAACTCGC TTCTTAAGACCCTGAATGAGCGCGATGGCGAACGCGGCAAT ATCTTGTCGCAGTACACTGAGGAACAGGCCATGCAAATGGG CCGCAACTATGCGTTGAAGCACAATTTAGATGCGACACTCT TTGGAAAGGCGGCCGCGGTCGCAAGAAACCCATACGAGTT CAATTCGATGAGTTTTTTGACCGAAGAGGAAAAAGTCGCGC TTAACACGGAGCAGACCAAGAAATGGCACATCCCAAGAAA GTTGGTGGAGGTGATTGCATTGGGGTCCATGGCCGCTGCGG TGCAGGGTATGGATGAGTCGGTGGTGAATGGTGCAACGCTT TTCTACCCCACGGCAATGGGTATCACAGATATCAAGAATGC CGATTTGATTGAAGGTTTGATCAACGGTGCGCCCTATCTTTG |

TABLE 3-continued

| SEQ ID NO: | Description | Sequence |
|---|---|---|
| | | CTGCGCCATCATGTGCTGGACATCTGATTACTGGAACAGGA<br>AGTTGGGCCGTAAGTGGACCATTTTCTGGACATGTGCCATT<br>TCTGCAATCACATGTATCTGGCAAGGTCTCGTCAATTTGAA<br>ATGGTACCATTTGTTCATTGCGCGTTTCTGCTTGGGTTTCGG<br>TATCGGTGTCAAGTCTGCCACCGTGCCTGCGTATGCTGCCG<br>AAACCACCCCGGCCAAAATCAGAGGCTCGTTGGTCATGCTT<br>TGGCAGTTCTTCACCGCTGTCGGAATCATGCTTGGTTACGTG<br>GCGTCTTTGGCATTCTATTACATTGGTGACAATGGCATTTCT<br>GGCGGCTTGAACTGGAGATTGATGCTAGGATCTGCATGTCT<br>TCCAGCTATCGTTGTGTTAGTCCAAGTTCCGTTTGTTCCAGA<br>ATCCCCTCGTTGGCTCATGGGTAAGGAAAGACACGCTGAAG<br>CATATGATTCGCTCCGGCAATTGCGGTTCAGTGAAATCGAG<br>GCGGCCCGTGACTGTTTCTACCAGTACGTGTTGTTGAAAGA<br>GGAGGGCTCTTATGGAACGCAGCCATTCTTCAGCAGAATCA<br>AGGAGATGTTCACCGTGAGAAGAAACAGAAATGGTGCATT<br>GGGCGCGTGGATCGTCATGTTCATGCAGCAGTTCTGTGGAA<br>TCAACGTCATTGCTTACTACTCGTCGTCGATCTTCGTGGAGT<br>CGAATCTTTCTGAGATCAAGGCCATGTTGGCGTCTTGGGGG<br>TTCGGTATGATCAATTTCTTGTTTGCAATTCCAGCGTTCTAC<br>ACCATTGACACGTTTGGCCGACGCAACTTGTTGCTCACTAC<br>TTTCCCTCTTATGGCGGTATTCTTACTCATGGCCGGATTCGG<br>GTTCTGGATCCCGTTCGAGACAAACCCACACGGCCGTTTGG<br>CGGTGATCACTATTGGTATCTATTTGTTTGCATGTGTCTACT<br>CTGCGGGCGAGGGACCAGTTCCCTTCACATACTCTGCCGAA<br>GCATTCCCGTTGTATATCCGTGACTTGGGTATGGGCTTTGCC<br>ACGGCCACGTGTTGGTTCTTCAACTTCATTTTGGCATTTTCC<br>TGGCCTAGAATGAAGAATGCATTCAAGCCTCAAGGTGCCTT<br>TGGCTGGTATGCCGCCTGGAACATTGTTGGCTTCTTCTTAGT<br>GTTATGGTTCTTGCCCGAGACAAAGGGCTTGACGTTGGAGG<br>AATTGGACGAAGTGTTTGATGTGCCTTTGAGAAAACACGCG<br>CACTACCGTACCAAAGAATTAGTATACAACTTGCGCAAATA<br>CTTCTTGAGGCAGAACCCTAAGCCATTGCCGCCACTTTATG<br>CACACCAAAGAATGGCTGTTACCAACCCAGAATGGTTGGA<br>AAAGACCGAGGTCACGCACGAGGAGAATATCTAG |
| 51. | Nucleic acid sequence of exemplary xylose transporter from *Pichia gulliermondii*; AXT1 | ATGGCTTACGAGGACAAACTAGTGGCTCCGGCCTTGAAGTT<br>TAGAAACTTTCTTGACAAAACTCCCAATATCTACAATCCAT<br>ATATCATTTCTATAATCTCGTGCATTGCGGGTATGATGTTCG<br>GTTTTGATATTTCTTCAATGTCAGCGTTTGTCAGTTTACCAG<br>CATACGTGAATTATTTCGATACACCTTCAGCAGTGATTCAA<br>GGATTTATCACATCTGCCATGGCTTTGGGTTCATTTTTCGGG<br>TCAATTGCTTCTGCGTTTGTGTCTGAGCCATTTGGAAGACGA<br>GCTTCCTTACTAACTTGTTCGTGGTTTTGGATGATAGGAGCA<br>GCCATCCAAGCGTCTTCGCAGAACCGAGCTCAATTGATTAT<br>TGGTCGGATTATATCTGGATTTGGGGTTGGTTTCGGGTCGTC<br>TGTGGCTCCCGTATATGGCTCCGAGATGGCACCTAGAAAAA<br>TTAGAGGAAGAATTGGTGGAATTTTTCAATTATCTGTCACC<br>CTCGGTATCATGATTATGTTCTTCATAAGTTACGGAACTTCT<br>CATATTAAGACTGCGGCAGCTTTTCAGGTTAGCCTGGGCACT<br>CCAGATCATTCCTGGACTCCTCATGTGTATTGGTGTCTTCTT<br>TATTCCAGAATCTCCTAGATGGTTGGCCAAACAAGGTCACT<br>GGGACGAAGCCGAAATCATTGTAGCCAAAATTCAAGCCAA<br>AGGAGATCGAGAAAATCCCGATGTTTTGATTGAAATTTCGG<br>AAATAAAAGACCAATTGATGGTTGACGAGAATGCCAAAGC<br>CTTTACCTATGCTGACTTGTTTTCGAAAAAATATCTTCCCAG<br>AACCATCACAGCCATGTTCGCTCAAATCTGGCAACAATTGA<br>CAGGAATGAATGTCATGATGTACTATATCGTTTACATTTTCG<br>AAATGGCTGGCTACGGTGGAAATGGAGTGTTGGTATCATCG<br>ACAATTCAGTACGTTATCTTTGTCGTTGTTACATTTGTCTCA<br>TTATTCTTTTTGGACAAATTTGGAAGAAGAAAAATTTTACTT<br>GTCGGAGCAGCTTCCATGATGACCTGGCAGTTTGCAGTGGC<br>AGGGATCTTGGCCAGGTACTCGGTCCCGTACGATCTCAGCG<br>ATACTGTCAAAATTAAAATTCCTGACAATCACAAATCGGCT<br>GCAAAAGGTGTCATTGCATGCTGCTATCTTTTCGTAGCATC<br>GTTCGGATTTTCCTGGGGAGTTGGTATCTGGTTATACTGCTC<br>TGAAGTCTGGGGAGACTCACAATGAGACAGAGAGGAGCC<br>GCTGTGTCAACTGCTTCAAATTGGATTTTCAATTTTGCGCTC<br>GCCATGTTCACACCATCTTCGTTTAAAAATATCACCTGGAA<br>GACATACTGTATTTATGCCACTTTCTGCGCATGTATGTTCAT<br>CCATGTGTTCTTCTTCTTCCCAGAAACCAAGGGGAAGCGCT<br>TGGAAGAAATTGCTCAAATTTGGGAAGAAAAAATTCCAGCT<br>TGGAAAACCACCAACTGGCAACCTCATGTTCCTTTGTTGTC<br>GGACCACGAACTTGCGGAAAAGATCAATGCCGAACATGTG<br>GAGAACGTGAATTCTAGGGAACAATCGGATGACGAGAAGT<br>CGCAGGTATAA |

TABLE 3-continued

| SEQ ID NO: | Description | Sequence |
|---|---|---|
| 52. | Nucleic acid sequence of exemplary xylose transporter from *Candida intermedia* PYCC 4715; GXF1 | ATGTCACAAGATTCGCATTCTTCTGGTGCCGCTACACCAGT<br>CAATGGTTCCATCCTTGAAAAGGAAAAAGAAGACTCTCCAG<br>TTCTTCAAGTTGATGCCCCACAAAAGGGTTTCAAGGACTAC<br>ATTGTCATTTCTATCTTCTGTTTTATGGTTGCCTTCGGTGGTT<br>TCGTCTTCGGTTTCGACACTGGTACCATTTCCGGTTTCGTGA<br>ACATGTCTGACTTTAAAGACAGATTCGGTCAACACCACGT<br>GATGGTACTCCTTACTTGTCCGACGTTAGAGTTGGTTTGATG<br>ATTTCTATTTTCAACGTTGGTTGCGCTGTCGGTGGTATTTTC<br>CTCTGCAAGGTCGCTGATGTCTGGGGTAGAAGAATTGGTCT<br>TATGTTCTCCATGGCTGTCTACGTTGTTGGTATTATTATTCA<br>GATCTCTTCATCCACCAAGTGGTACCAGTTCTTCATTGGTCG<br>TCTTATTGCTGGTTTGGCTGTTGGTACCGTTTCTGTCGTTTCC<br>CCACTTTTCATCTCTGAGGTTTCTCCAAAGCAAATTAGAGGT<br>ACTTTAGTGTGCTGCTTCCAGTTGTGTATCACCTTGGGTATC<br>TTCTTGGGTTACTGTACTACTTACGGTACTAAGACCTACACT<br>GACTCTAGACAGTGGAGAATTCCTTTGGGTTTGTGTTTCGCT<br>TGGGCTATCTTGTTGGTTGTCGGTATGTTGAACATGCCAGA<br>GTCTCCAAGATACTTGGTTGAGAAGCACAGAATTGATGAGG<br>CCAAGAGATCCATTGCCAGATCCAACAAGATCCCTGAGGA<br>GGACCCATTCGTCTACACTGAGGTTCAGCTTATTCAGGCCG<br>GTATTGAGAGAGAAGCTTTGGCTGGTCAGGCATCTTGGAAG<br>GAGTTGATCACTGGTAAGCCAAAGATCTTCAGAAGAGTTAT<br>CATGGGTATTATGCTTCAGTCCTTGCAACAGTTGACCGGTG<br>ACAACTACTTCTTCTACTACGGTACTACCATTTTCCAGGCTG<br>TCGGTTTGAAGGATTCTTTCCAGACTTCTATCATTTTGGGTA<br>TTGTCAACTTTGCTTCCACCTTCGTTGGTATCTATGTCATTG<br>AGAGATTGGGTAGAAGATTGTGTCTTTTGACCGGTTCCGCT<br>GCTATGTTCATCTGTTTCATCATCTACTCTTTGATTGGTACT<br>CAGCACTTGTACAAGCAAGGTTACTCCAACGAGACCTCCAA<br>CACTTACAAGGCTTCTGGTAACGCTATGATCTTCATCACTTG<br>TCTTTACATTTTCTTCTTTGCTTCTACCTGGGCTGGTGGTGTT<br>TACTGTATCATTTCCGAGTCCTACCCATTGAGAATTAGATCC<br>AAGGCCATGTCTATTGCTACCGCTGCTAACTGGTTGTGGGG<br>TTTCTTGATTTCCTTCTTCACTCCATTCATCACCAGTGCCATC<br>CACTTCTACTACGGTTTCGTTTTCACTGGTTGTTTGGCTTTCT<br>CTTTCTTCTACGTCTACTTCTTCGTCTACGAAACCAAGGGTC<br>TTTCTTTGGAGGAGGTTGATGAGATGTACGCTTCCGGTGTTC<br>TTCCACTCAAGTCTGCCAGCTGGGTTCCACCAAATCTTGAG<br>CACATGGCTCACTCTGCCGGTTACGCTGGTGCTGACAAGGC<br>CACCGACGAACAGGTTTAA |
| 53. | Nucleic acid sequence of exemplary glucose/xylose symporter from *Candida intermedia*; GXS1 | ATGTCACAAGATTCGCATTCTTCTGGTGCCGCTACACCAGT<br>CAATGGTTCCATCCTTGAAAAGGAAAAAGAAGACTCTCCAG<br>TTCTTCAAGTTGATGCCCCACAAAAGGGTTTCAAGGACTAC<br>ATTGTCATTTCTATCTTCTGTTTTATGGTTGCCTTCGGTGGTT<br>TCGTCTTCGGTTTCGACACTGGTACCATTTCCGGTTTCGTGA<br>ACATGTCTGACTTTAAAGACAGATTCGGTCAACACCACGT<br>GATGGTACTCCTTACTTGTCCGACGTTAGAGTTGGTTTGATG<br>ATTTCTATTTTCAACGTTGGTTGCGCTGTCGGTGGTATTTTC<br>CTCTGCAAGGTCGCTGATGTCTGGGGTAGAAGAATTGGTCT<br>TATGTTCTCCATGGCTGTCTACGTTGTTGGTATTATTATTCA<br>GATCTCTTCATCCACCAAGTGGTACCAGTTCTTCATTGGTCG<br>TCTTATTGCTGGTTTGGCTGTTGGTACCGTTTCTGTCGTTTCC<br>CCACTTTTCATCTCTGAGGTTTCTCCAAAGCAAATTAGAGGT<br>ACTTTAGTGTGCTGCTTCCAGTTGTGTATCACCTTGGGTATC<br>TTCTTGGGTTACTGTACTACTTACGGTACTAAGACCTACACT<br>GACTCTAGACAGTGGAGAATTCCTTTGGGTTTGTGTTTCGCT<br>TGGGCTATCTTGTTGGTTGTCGGTATGTTGAACATGCCAGA<br>GTCTCCAAGATACTTGGTTGAGAAGCACAGAATTGATGAGG<br>CCAAGAGATCCATTGCCAGATCCAACAAGATCCCTGAGGA<br>GGACCCATTCGTCTACACTGAGGTTCAGCTTATTCAGGCCG<br>GTATTGAGAGAGAAGCTTTGGCTGGTCAGGCATCTTGGAAG<br>GAGTTGATCACTGGTAAGCCAAAGATCTTCAGAAGAGTTAT<br>CATGGGTATTATGCTTCAGTCCTTGCAACAGTTGACCGGTG<br>ACAACTACTTCTTCTACTACGGTACTACCATTTTCCAGGCTG<br>TCGGTTTGAAGGATTCTTTCCAGACTTCTATCATTTTGGGTA<br>TTGTCAACTTTGCTTCCACCTTCGTTGGTATCTATGTCATTG<br>AGAGATTGGGTAGAAGATTGTGTCTTTTGACCGGTTCCGCT<br>GCTATGTTCATCTGTTTCATCATCTACTCTTTGATTGGTACT<br>CAGCACTTGTACAAGCAAGGTTACTCCAACGAGACCTCCAA<br>CACTTACAAGGCTTCTGGTAACGCTATGATCTTCATCACTTG<br>TCTTTACATTTTCTTCTTTGCTTCTACCTGGGCTGGTGGTGTT<br>TACTGTATCATTTCCGAGTCCTACCCATTGAGAATTAGATCC<br>AAGGCCATGTCTATTGCTACCGCTGCTAACTGGTTGTGGGG<br>TTTCTTGATTTCCTTCTTCACTCCATTCATCACCAGTGCCATC<br>CACTTCTACTACGGTTTCGTTTTCACTGGTTGTTTGGCTTTCT<br>CTTTCTTCTACGTCTACTTCTTCGTCTACGAAACCAAGGGTC |

TABLE 3-continued

| SEQ ID NO: | Description | Sequence |
|---|---|---|
| | | TTTCTTTGGAGGAGGTTGATGAGATGTACGCTTCCGGTGTTC<br>TTCCACTCAAGTCTGCCAGCTGGGTTCCACCAAATCTTGAG<br>CACATGGCTCACTCTGCCGGTTACGCTGGTGCTGACAAGGC<br>CACCGACGAACAGGTTTAA |
| 54. | Nucleic acid sequence of exemplaiy xylose transporter from *Saccharomyces cerevisiae*; GAL2/GXF2 | ATGGCAGTTGAGGAGAACAATATGCCTGTTGTTTCACAGCA<br>ACCCCAAGCTGGTGAAGACGTGATCTCTTCACTCAGTAAAG<br>ATTCCCATTTAAGCGCACAATCTCAAAAGTATTCTAATGAT<br>GAATTGAAAGCCGGTGAGTCAGGGTCTGAAGGCTCCCAAA<br>GTGTTCCTATAGAGATACCCAAGAAGCCCATGTCTGAATAT<br>GTTACCGTTTCCTTGCTTTGTTTGTGTGTTGCCTTCGGCGGC<br>TTCATGTTTGGCTGGGATACCGGTACTATTTCTGGGTTTGTT<br>GTCCAAACAGACTTTTTGAGAAGGTTTGGTATGAAACATAA<br>GGATGGTACCCACTATTTGTCAAACGTCAGAACAGGTTTAA<br>TCGTCGCCATTTTCAATATTGGCTGTGCCTTTGGTGGTATTA<br>TACTTTCCAAAGGTGGAGATATGTATGGCCGTAAAAAGGGT<br>CTTTCGATTGTCGTCTCGGTTTATATAGTTGGTATTATCATT<br>CAAATTGCCTCTATCAACAAGTGGTACCAATATTTCATTGG<br>TAGAATCATATCTGGTTTGGGTGTCGGCGGCATCGCCGTCT<br>TATGTCCTATGTTGATCTCTGAAATTGCTCCAAAGCACTTGA<br>GAGGCACACTAGTTTCTTGTTATCAGCTGATGATTACTGCA<br>GGTATCTTTTTGGGCTACTGTACTAATTACGGTACAAAGAG<br>CTATTCGAACTCAGTTCAATGGAGAGTTCCATTAGGGCTAT<br>GTTTCGCTTGGTCATTATTTATGATTGGCGCTTTGACGTTAG<br>TTCCTGAATCCCCACGTTATTTATGTGAGGTGAATAAGGTA<br>GAAGACGCCAAGCGTTCCATTGCTAAGTCTAACAAGGTGTC<br>ACCAGAGGATCCTGCCGTCCAGGCAGAGTTAGATCTGATCA<br>TGGCCGGTATAGAAGCTGAAAAACTGGCTGGCAATGCGTCC<br>TGGGGGGAATTATTTTCCACCAAGACCAAAGTATTTCAACG<br>TTTGTTGATGGGTGTGTTTGTTCAAATGTTCCAACAATTAAC<br>CGGTAACAATTATTTTTTCTACTACGGTACCGTTATTTTCAA<br>GTCAGTTGGCCTGGATGATTCCTTTGAAACATCCATTGTCAT<br>TGGTGTAGTCAACTTTGCCTCCACTTTCTTTAGTTTGTGGAC<br>TGTCGAAAACTTGGGACATCGTAAATGTTTACTTTTGGGCG<br>CTGCCACTATGATGGCTTGTATGGTCATCTACGCCTCTGTTG<br>GTGTTACTAGATTATATCCTCACGGTAAAAGCCAGCCATCT<br>TCTAAAGGTGCCGGTAACTGTATGATTGTCTTTACCTGTTTT<br>TATATTTTCTGTTATGCCACAACCTGGGCGCCAGTTGCCTGG<br>GTCATCACAGCAGAATCATTCCCACTGAGAGTCAAGTCGAA<br>ATGTATGGCGTTGGCCTCTGCTTCCAATTGGGTATGGGGGT<br>TCTTGATTGCATTTTTCACCCCATTCATCACATCTGCCATTA<br>ACTTCTACTACGGTTATGTCTTCATGGGCTGTTTGGTTGCCA<br>TGTTTTTTTATGTCTTTTTCTTTGTTCCAGAAACTAAAGGCCT<br>ATCGTTAGAAGAAATTCAAGAATTATGGGAAGAAGGTGTTT<br>TACCTTGGAAATCTGAAGGCTGGATTCCTTCATCCAGAAGA<br>GGTAATAATTACGATTTAGAGGATTTACAACATGACGACAA<br>ACCGTGGTACAAGGCCATGCTAGAATAA |

Provided herein are novel isolated *Metschnikowia* species having a xylitol pathway. Such *Metschnikowia* species can produce xylitol from xylose when cultured in medium having xylose. In some embodiments, a xylitol pathway described herein includes a xylose reductase, which converts xylose to xylitol. Additionally, in some embodiments, the isolated *Metschnikowia* species includes a genetic modification to a xylitol dehydrogenase, which would normally convert xylitol to xylulose. Accordingly, in some embodiments, provided herein is an isolated *Metschnikowia* species having at least one exogenous nucleic acid encoding a xylose reductase or, alternatively or additionally, at least one exogenous nucleic acid that results in overexpression of a xylose reductase of the isolated *Metschnikowia* species. In some embodiments, also provided herein is an isolated *Metschnikowia* species having a genetic modification that attenuates or inactivates a xylitol dehydrogenase of the isolated *Metschnikowia* species. In some embodiments, provided herein is an isolated *Metschnikowia* species having: (a) at least one exogenous nucleic acid encoding a xylose reductase or that results in overexpression of a xylose reductase of the isolated *Metschnikowia* species; and (b) a genetic modification that attenuates or inactivates a xylitol dehydrogenase of the isolated *Metschnikowia* species.

The isolated *Metschnikowia* species provided here can produce xylitol from xylose at a specific rate. For example, in some embodiments, the isolated *Metschnikowia* species provided herein produces at least 0.50 g/L/h, at least 0.60 g/L/h, at least 0.70 g/L/h, at least 0.80 g/L/h, at least 0.90 g/L/h, at least 1.00 g/L/h, at least 1.50 g/L/h, at least 2.00 g/L/h, at least 2.50 g/L/h, at least 3.00 g/L/h, at least 3.50 g/L/h, at least 4.00 g/L/h, at least 5.00 g/L/h, at least 6.00 g/L/h, at least 7.00 g/L/h, at least 8.00 g/L/h, at least 9.00 g/L/h, or at least 10.00 g/L/h of xylitol from xylose when cultured. Accordingly, in some embodiments, the isolated *Metschnikowia* species provided herein produces at least 0.50 g/L/h of xylitol from xylose when cultured. In some embodiments, the isolated *Metschnikowia* species provided herein produces at least at least 0.60 g/L/h of xylitol from xylose when cultured. In some embodiments, the isolated *Metschnikowia* species provided herein produces at least 0.70 g/L/h of xylitol from xylose when cultured. In some embodiments, the isolated *Metschnikowia* species provided herein produces at least 0.80 g/L/h of xylitol from xylose when cultured. In some embodiments, the isolated *Metschnikowia* species provided herein produces at least at least 0.90 g/L/h of xylitol from xylose when cultured. In some embodiments, the isolated *Metschnikowia* species provided herein produces at least 1.00 g/L/h of xylitol from xylose when cultured. In some embodiments, the isolated *Metschnikowia* species provided herein produces at least 1.50 g/L/h of xylitol from xylose when cultured. In some embodiments, the isolated *Metschnikowia* species provided herein produces at least 2.00 g/L/h of xylitol from xylose when cultured. In some embodiments, the isolated *Metschnikowia* species provided herein produces at least 2.50 g/L/h of xylitol from xylose when cultured. In some embodiments, the isolated *Metschnikowia* species provided herein produces at least 3.00 g/L/h of xylitol from xylose when cultured. In some embodiments, the isolated *Metschnikowia* species provided herein produces at least 3.50 g/L/h of xylitol from xylose when cultured. In some embodiments, the isolated *Metschnikowia* species provided herein produces at least 4.00 g/L/h of xylitol from xylose when cultured. In some embodiments, the isolated *Metschnikowia* species provided herein produces at least 5.00 g/L/h of xylitol from xylose when cultured. In some embodiments, the isolated *Metschnikowia* species provided herein produces at least 6.00 g/L/h of xylitol from xylose when cultured. In some embodiments, the isolated *Metschnikowia* species provided herein produces at least 7.00 g/L/h of xylitol from xylose when cultured. In some embodiments, the isolated *Metschnikowia* species provided herein produces at least 8.00 g/L/h of xylitol from xylose when cultured. In some embodiments, the isolated *Metschnikowia* species provided herein produces at least 9.00 g/L/h of xylitol from xylose when cultured. In some embodiments, the isolated *Metschnikowia* species provided herein produces at least 10.00 g/L/h of xylitol from xylose when cultured.

The isolated *Metschnikowia* species provided here can produce xylitol from xylose at a specific concentration. For example, in some embodiments, the isolated *Metschnikowia* species provided herein produces at least 75 g/L, at least 80 g/L, at least 85 g/L, at least 90 g/L, at least 95 g/L, at least 100 g/L, at least 110 g/L, at least 120 g/L, at least 130 g/L, at least 140 g/L, at least 150 g/L, at least 160 g/L, at least 170 g/L, at least 180 g/L, at least 190 g/L, at least 200 g/L, at least 250 g/L, or at least 300 g/L of xylitol from xylose when cultured. According, in some embodiments, the isolated *Metschnikowia* species provided herein produces at least 75 g/L of xylitol from xylose when cultured. In some embodiments, the isolated *Metschnikowia* species provided herein produces at least 80 g/L of xylitol from xylose when cultured. In some embodiments, the isolated *Metschnikowia* species provided herein produces at least 90 g/L of xylitol from xylose when cultured. In some embodiments, the isolated *Metschnikowia* species provided herein produces at least 95 g/L of xylitol from xylose when cultured. In some embodiments, the isolated *Metschnikowia* species provided herein produces at least 100 g/L of xylitol from xylose when cultured. In some embodiments, the isolated *Metschnikowia* species provided herein produces at least 110 g/L of xylitol from xylose when cultured. In some embodiments, the isolated *Metschnikowia* species provided herein produces at least 120 g/L of xylitol from xylose when cultured. In some embodiments, the isolated *Metschnikowia* species provided herein produces at least 130 g/L of xylitol from xylose when cultured. In some embodiments, the isolated *Metschnikowia* species provided herein produces at least 140 g/L of xylitol from xylose when cultured. In some embodiments, the isolated *Metschnikowia* species provided herein produces at least 150 g/L of xylitol from xylose when cultured. In some embodiments, the isolated *Metschnikowia* species provided herein produces at least 160 g/L of xylitol from xylose when cultured. In some embodiments, the isolated *Metschnikowia* species provided herein produces at least 170 g/L of xylitol from xylose when cultured. In some embodiments, the isolated *Metschnikowia* species provided herein produces at least 180 g/L of xylitol from xylose when cultured. In some embodiments, the isolated *Metschnikowia* species provided herein produces at least 190 g/L of xylitol from xylose when cultured. In some embodiments, the isolated *Metschnikowia* species provided herein produces at least 200 g/L of xylitol from xylose when cultured. In some embodiments, the isolated *Metschnikowia* species provided herein produces at least 250 g/L of xylitol from xylose when cultured. In some embodiments, the isolated *Metschnikowia* species provided herein produces at least 300 g/L of xylitol from xylose when cultured.

The xylitol pathway described herein can be introduced into any *Metschnikowia* species known in the art. Exemplary, non-limiting, *Metschnikowia* species that can have the xylitol pathway described herein include *Metschnikowia pulcherrima, Metschnikowia fructicola, Metschnikowia chrysoperlae, Metschnikowia reukaufii, Metschnikowia andauensis, Metschnikowia shanxiensis, Metschnikowia sinensis, Metschnikowia zizyphicola, Metschnikowia bicuspidata, Metschnikowia lunata, Metschnikowia zobellii, Metschnikowia australis, Metschnikowia agaveae, Metschnikowia gruessii, Metschnikowia hawaiiensis, Metschnikowia krissii, Metschnikowia* sp. strain NS-O-85, and *Metschnikowia* sp. strain NS-O-89. In a particular embodiment, the xylitol pathway described herein can be introduced into the *Metschnikowia* species designated Accession No. 081116-01, deposited at the International Depositary Authority of Canada, an International Depositary Authority, on Nov. 8, 2016, under the terms of the Budapest Treaty.

As can be appreciated by a person skilled in the art, because the *Metschnikowia* species provided herein can be any *Metschnikowia* species known in the art, the exogenous nucleic acid encoding a xylose reductase described herein is, in some embodiments, a heterologous nucleic acid as compared to the host *Metschnikowia* species to which the exogenous nucleic acid was introduced. In other words, in some embodiments, at least one exogenous nucleic acid encoding a xylose reductase is a heterologous nucleic acid.

In some embodiments, the exogenous nucleic acid encoding a xylose reductase or the xylose reductase that is overexpressed by the introduction of the exogenous nucleic acid is one of the exemplary xylose reductases described herein. For example, in some embodiments, the xylose reductase has an amino acid sequence selected from any one of SEQ ID NOS: 11-18. Accordingly, in some embodiments, the xylose reductase has an amino acid sequence of SEQ ID NO: 11. In some embodiments, the xylose reductase has an amino acid sequence of SEQ ID NO: 12. In some embodiments, the xylose reductase has an amino acid sequence of SEQ ID NO: 13. In some embodiments, the xylose reductase has an amino acid sequence of SEQ ID NO: 14. In some embodiments, the xylose reductase has an amino acid sequence of SEQ ID NO: 15. In some embodiments, the xylose reductase has an amino acid sequence of SEQ ID NO: 16. In some embodiments, the xylose reductase has an amino acid sequence of SEQ ID NO: 17. In some embodiments, the xylose reductase has an amino acid sequence of SEQ ID NO: 18.

In some embodiments, the xylose reductase introduced into the isolated *Metschnikowia* species described herein is a variant of a xylose reductase described herein. Such a variant still retains the functional activity of the xylose reductase. For example, in some embodiments, the xylose reductase has an amino acid sequence of any one of SEQ ID NOS: 11-18, wherein the amino acid sequence includes 1, 2, 3, 4, 5, 6, 7, 8, 9, 10, 11, 12, 13, 14, 15, 16, 17, 18, 19, 20, 21, 22, 23, 24, or 25 amino acid substitutions, deletions or insertions. Variants of a xylose reductase provided herein also include, for example, deletions, fusions, or truncations when compared to the reference polypeptide sequence. Accordingly, in some embodiments, the xylose reductase provided herein has an amino acid sequence that is at least 95.0%, at least 95.1%, at least 95.2%, at least 95.3%, at least 95.4%, at least 95.5%, at least 95.6%, at least 95.7%, at least 95.8%, at least 95.9%, at least 96.0%, at least 96.1%, at least 96.2%, at least 96.3%, at least 96.4%, at least 96.5%, at least 96.6%, at least 96.7%, at least 96.8%, at least 96.9%, at least 97.0%, at least 97.1%, at least 97.2%, at least 97.3%, at least 97.4%, at least 97.5%, at least 97.6%, at least 97.7%, at least 97.8%, at least 97.9%, at least 98.0%, at least 98.1%, at least 98.2%, at least 98.3%, at least 98.4%, at least 98.5%, at least 98.6%, at least 98.7%, at least 98.8%, at least 98.9%, at least 99.0%, at least 99.1%, at least 99.2%, at least 99.3%, at least 99.4%, at least 99.5%, at least 99.6%, at least 99.7%, or at least 99.8% identical to any one of SEQ ID NOS: 11-18. In a specific embodiment, the xylose reductase has the amino acid sequence of SEQ ID NO: 11 or an amino acid sequence with at least 95% sequence identity to SEQ ID NO: 11.

Also provided herein is an isolated *Metschnikowia* species described herein, wherein the genetic modification that attenuates or inactivates a xylitol dehydrogenase of the isolated *Metschnikowia* species includes the deletion of one or both alleles encoding the xylitol dehydrogenase or a portion thereof of the isolated *Metschnikowia* species. Accordingly, in some embodiments, the isolated *Metschnikowia* species provided herein includes the deletion of at least one allele encoding the xylitol dehydrogenase or a portion thereof of the isolated *Metschnikowia* species. In some embodiments, the isolated *Metschnikowia* species provided herein includes the deletion of both alleles encoding the xylitol dehydrogenase or a portion thereof of the isolated *Metschnikowia* species.

Also provided herein is an isolated *Metschnikowia* species having a xylitol pathway that includes overexpression of a xylose transporter. Such *Metschnikowia* species can have increased production of xylitol from xylose when cultured in medium having xylose as compared to the *Metschnikowia* species without the xylose transporter. Accordingly, in some embodiments, provided herein is an isolated *Metschnikowia* species having at least one exogenous nucleic acid encoding a xylose transporter or, alternatively or additionally, at least one exogenous nucleic acid that results in overexpression of a xylose transporter of the isolated *Metschnikowia* species. In some embodiments, provided herein is an isolated *Metschnikowia* species having: (a) at least one exogenous nucleic acid encoding a xylose reductase or that results in overexpression of a xylose reductase of the isolated *Metschnikowia* species; (b) a genetic modification that attenuates or inactivates a xylitol dehydrogenase of the isolated *Metschnikowia* species; and (c) at least one exogenous nucleic acid encoding a xylose transporter or that results in overexpression of a xylose transporter of the isolated *Metschnikowia* species.

In some embodiments, the exogenous nucleic acid encoding a xylose transporter or the xylose transporter that is overexpressed by the introduction of the exogenous nucleic acid is one of the exemplary xylose transporters described herein. For example, in some embodiments, the xylose transporter has an amino acid sequence selected from any one of SEQ ID NOS: 27-40. Accordingly, in some embodiments, the xylose reductase has an amino acid sequence of SEQ ID NO: 27. In some embodiments, the xylose reductase has an amino acid sequence of SEQ ID NO: 28. In some embodiments, the xylose reductase has an amino acid sequence of SEQ ID NO: 29. In some embodiments, the xylose reductase has an amino acid sequence of SEQ ID NO: 30. In some embodiments, the xylose reductase has an amino acid sequence of SEQ ID NO: 31. In some embodiments, the xylose reductase has an amino acid sequence of SEQ ID NO: 32. In some embodiments, the xylose reductase has an amino acid sequence of SEQ ID NO: 33. In some embodiments, the xylose reductase has an amino acid sequence of SEQ ID NO: 34. In some embodiments, the xylose reductase has an amino acid sequence of SEQ ID NO: 35. In some embodiments, the xylose reductase has an amino acid sequence of SEQ ID NO: 36. In some embodiments, the xylose reductase has an amino acid sequence of SEQ ID NO: 37. In some embodiments, the xylose reductase has an amino acid sequence of SEQ ID NO: 38. In some embodiments, the xylose reductase has an amino acid sequence of SEQ ID NO: 39. In some embodiments, the xylose reductase has an amino acid sequence of SEQ ID NO: 40.

In some embodiments, the xylose transporter introduced into the isolated *Metschnikowia* species described herein is a variant of a xylose transporter described herein. Such a variant still retains the functional activity of the xylose transporter. For example, in some embodiments, the xylose transporter has an amino acid sequence of any one of SEQ ID NOS: 27-40, wherein the amino acid sequence includes 1, 2, 3, 4, 5, 6, 7, 8, 9, 10, 11, 12, 13, 14, 15, 16, 17, 18, 19, 20, 21, 22, 23, 24, or 25 amino acid substitutions, deletions or insertions. Variants of a xylose transporter provided herein also include, for example, deletions, fusions, or truncations when compared to the reference polypeptide sequence. Accordingly, in some embodiments, the xylose transporter provided herein has an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of SEQ ID NOS: 27-40. In a specific embodiment, the xylose transporter has the amino acid sequence of any one of SEQ ID NOS: 27-36 or an amino acid sequence that is at least 30%, at least 35%, at least 40%, at least 45%, at least 50%, at least 55%, at least 60%, at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of SEQ ID NOS: 27-36.

The xylose reductases and the xylose transporters provided herein can be a *Metschnikowia* xylose reductase or *Metschnikowia* transporter, respectively, including those from the H0 *Metschnikowia* sp. having amino acid sequences as shown herein, as well as their variants that retain their respective function (e.g., conversion of xylose to xylitol or xylose transport). For example, provided herein is Xyl1 from the H0 *Metschnikowia* sp. that has an amino acid sequence of SEQ ID NO: 11, as well as variants thereof that retain the enzymatic function of Xyl1. The enzymatic function of Xyl1 includes, but is not limited to, catalyzing the conversion of xylose to xylitol, which can be determined, for example, by subjecting the variant to an assay as described herein or otherwise known in the art. As another example, provided herein is Xyt1 from the H0 *Metschnikowia* sp. that has an amino acid sequence of SEQ ID NO: 27, as well as variants thereof that retain the transporter function of Xyt1. The transporter function of Xyt1 includes, but is not limited to, transport of xylose across cell wall and/or cell membrane, which can be determined, for example, by subjecting the variant to a transporter assay as described herein or otherwise known in the art.

The xylose reductase function can be determined, for example, by expressing the xylose reductase in a *Metschnikowia* species and measuring the increase in xylitol production by the *Metschnikowia* species. Likewise, the xylose transporter function can be determined, for example, by expressing the transporter in a *Metschnikowia* species and measuring the increase in xylose uptake by the *Metschnikowia* species. In an exemplary assay, a *Metschnikowia* species overexpressing an endogenous nucleic acid encoding a xylose reductase and/or a xylose transporter can be cultured in a xylose-containing medium and the decrease of xylose in the culture medium and/or the increase of xylitol in the medium can be measured by high performance liquid chromatography (HPLC). In another exemplary assay, starter cultures for wild type and recombinant *Metschnikowia* species expressing a xylose reductase and/or a xylose transporter can be grown in YEP base medium with controlled amounts of glucose and xylose (%; w/v). Uninoculated medium is used as a reference for a given sampling time; the medium indicates 100% of the starting xylose or xylose at time 0 h. At 24 h intervals, samples at volumes of 300-1000 μL can be removed from the culture aseptically and filtered through a 0.2 μm syringe filter, physically separating medium and yeast. The medium can be transferred to glass vials and the xylose and xylitol content can be examined by HPLC. The recombinant *Metschnikowia* species expressing a xylose reductase and/or a xylose transporter can consume xylose and produce xylitol at a higher rate than its wild type counterpart, and the differences between wild type and recombinant *Metschnikowia* species can indicate the xylose reductase and/or xylose transporter function of the variant.

As described herein, the recombinant *Metschnikowia* species provided can be modified to include a xylitol pathway capable of producing xylitol from xylose. When that modification includes the introduction of a heterologous exogenous nucleic acid sequence encoding at least one enzyme of the xylitol pathway, the coding sequence of the enzyme can be modified in accordance with the codon usage of the host. The standard genetic code is well known in the art, as reviewed in, for example, Osawa et al., *Microbiol Rev.* 56(1):229-64 (1992). Yeast species, including but not limited to *Saccharomyces cerevisiae, Candida azyma, Candida diversa, Candida magnoliae, Candida rugopelliculosa, Yarrowia lipolytica*, and *Zygoascus hellenicus*, use the standard code. Certain yeast species use alternative codes. For example, "CUG," standard codon for "Leu," encodes "Ser" in "CUG" clade species such as *Candida albicans, Candida cylindracea, Candida melibiosica, Candida parapsilosis, Candida rugose, Pichia stipitis*, and *Metschnikowia* species. The DNA codon table for the H0 *Metschnikowia* sp. is provided herein. The DNA codon CTG in a foreign gene from a non "CUG" clade species needs to be changed to TTG, CTT, CTC, TTA or CTA for a functional expression of a protein in the *Metschnikowia* species. Other codon optimization can result in increase of protein expression of a foreign gene in the *Metschnikowia* species. Methods of Codon optimization are well known in the art (e.g. Chung et al., *BMC Syst Biol.* 6:134 (2012); Chin et al., *Bioinformatics* 30(15):2210-12 (2014)), and various tools are available (e.g. DNA2.0 at https://www.dna20.com/services/genegps; and OPTIMIZER at http://genomes.urv.es/OPTIMIZER).

In some embodiments, the isolated *Metschnikowia* species can have one or more copies of an exogenous nucleic acid described herein. In some embodiments, the *Metschnikowia* species has two, three, four, five, six, seven, eight, nine, ten, eleven, twelve, thirteen, fourteen, fifteen, sixteen, seventeen, eighteen, nineteen, twenty, or more copies of the exogenous nucleic acid. Expression of more than one exogenous nucleic acid described herein can further improve xylose uptake into the *Metschnikowia* species and/or conversion of xylose to xylitol. As such, the *Metschnikowia* species can have at least one, at least two, at least three, at least four, at least five, at least six, at least seven, at least eight, at least nine, or at least ten exogenous nucleic acids each encoding a xylose transporter and/or a xylose reductase. In some embodiments, the *Metschnikowia* species have at least two exogenous nucleic acids each encoding a xylose transporter and/or a xylose reductase. In some embodiments, the *Metschnikowia* species have at least three exogenous nucleic acids each encoding a xylose transporter and/or a xylose reductase. In some embodiments, the *Metschnikowia* species have at least four exogenous nucleic acids each encoding a xylose transporter and/or a xylose reductase. In some embodiments, the *Metschnikowia* species have at least five exogenous nucleic acids each encoding a xylose transporter and/or a xylose reductase. In some embodiments, the *Metschnikowia* species have at least six exogenous nucleic acids each encoding a xylose transporter and/or a xylose reductase. In some embodiments, the *Metschnikowia* species have at least seven exogenous nucleic acids each encoding a xylose transporter and/or a xylose reductase. In some embodiments, the *Metschnikowia* species have at least eight exogenous nucleic acids each encoding a xylose transporter. In some embodiments, the *Metschnikowia* species have at least nine exogenous nucleic acids each encoding a xylose transporter and/or a xylose reductase. In some embodiments, the *Metschnikowia* species have at least ten exogenous nucleic acids each encoding a xylose transporter and/or a xylose reductase.

In some embodiments, the isolated *Metschnikowia* species provided herein can have one or more xylitol pathway to produce xylitol from xylose. The xylitol pathway can be an endogenous pathway or an exogenous pathway. The *Metschnikowia* species provided herein can further have expressible nucleic acids encoding one or more of the enzymes or proteins participating in one or more xylitol pathway for production of xylitol. The nucleic acids for some or all of a particular xylitol pathway can be expressed, depending upon what enzymes or proteins are endogenous to the *Metschnikowia* species. In some embodiments, the *Metschnikowia* species can have endogenous expression of all enzymes of a xylitol pathway to produce xylitol from xylose and naturally produce the xylitol, which can be improved by further modifying or increasing expression of an enzyme or protein of the xylitol pathway (e.g., a xylose transporter or xylose reductase). In some embodiments, the *Metschnikowia* species can be deficient in one or more enzymes or proteins for a desired xylitol pathway, then expressible nucleic acids for the deficient enzyme(s) or protein(s) are introduced into the *Metschnikowia* species for subsequent exogenous expression. Alternatively, if the *Metschnikowia* species exhibits endogenous expression of some pathway genes, but is deficient in others, then an encoding nucleic acid is needed for the deficient enzyme(s) or protein(s) to achieve biosynthesis of xylitol. Thus, a recombinant *Metschnikowia* species can further include exogenous enzyme or protein activities to obtain a desired xylitol pathway or a desired xylitol pathway can be obtained by introducing one or more exogenous enzyme or protein activities that, together with one or more endogenous enzymes or proteins, produces xylitol.

The *Metschnikowia* species provided herein can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

In the case of genetic modifications that attenuate or inactive an enzyme or protein, a particularly useful stable genetic alteration is a gene deletion. The use of a gene deletion to introduce a stable genetic alteration is particularly useful to reduce the likelihood of a reversion to a phenotype prior to the genetic alteration. For example, stable growth-coupled production of xylitol can be achieved, for example, by deletion of a gene encoding a xylitol dehydrogenase. The stability of growth-coupled production of xylitol can be further enhanced through multiple deletions (e.g., deletion of both alleles of given gene), significantly reducing the likelihood of multiple compensatory reversions occurring for each disrupted activity.

Those skilled in the art will understand that the genetic alterations, including metabolic modifications exemplified herein, are described with reference to a suitable host organism such as a *Metschnikowia* species provided herein and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical compound, those skilled in the art will understand that the orthologous gene harboring the metabolic activity to be introduced or disrupted is to be chosen for construction of the *Metschnikowia* species provided herein. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the *Metschnikowia* species provided herein having biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes. Similarly for a gene disruption, evolutionarily related genes can also be disrupted or deleted in a host microbial organism to reduce or eliminate functional redundancy of enzymatic activities targeted for disruption.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 2099) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

Provided herein are methods of producing xylitol using an isolated *Metschnikowia* species described herein. Such methods can include culturing the isolated *Metschnikowia* species having a xylitol pathway for producing xylitol under conditions and for a sufficient period of time to produce xylitol from xylose. Accordingly, in some embodiments, provided herein is a method for producing xylitol comprising culturing an isolated *Metschnikowia* species having: (a) at least one exogenous nucleic acid encoding a xylose reductase or that results in overexpression of a xylose reductase of the isolated *Metschnikowia* species; and (b) a genetic modification that attenuates or inactivates a xylitol dehydrogenase of the isolated *Metschnikowia* species, under conditions and for a sufficient period of time to produce xylitol from xylose.

The methods provided herein include the production of xylitol at a specified rate and/or concentration. Accordingly, in some embodiments, the method provided herein produces the xylitol from xylose at a rate of at least 0.50 g/L/h. In some embodiments, the method provided herein produces xylitol from xylose at a rate of at least 0.60 g/L/h. In some embodiments, the method provided herein produces xylitol from xylose at a rate of at least 0.70 g/L/h. In some embodiments, the method provided herein produces xylitol from xylose at a rate of at least 0.80 g/L/h. In some embodiments, the method provided herein produces xylitol from xylose at a rate of at least 0.90 g/L/h. In some embodiments, the method provided herein produces xylitol from xylose at a rate of at least 1.00 g/L/h. In some embodiments, the method provided herein produces xylitol from xylose at a rate of at least 1.50 g/L/h. In some embodiments, the method provided herein produces xylitol from xylose at a rate of at least 2.00 g/L/h. In some embodiments, the method provided herein produces xylitol from xylose at a rate of at least 2.50 g/L/h. In some embodiments, the method provided herein produces xylitol from xylose at a rate of at least 3.00 g/L/h. In some embodiments, the method provided herein produces xylitol from xylose at a rate of at least 3.50 g/L/h. In some embodiments, the method provided herein produces xylitol from xylose at a rate of at least 4.00 g/L/h. In some embodiments, the method provided herein produces xylitol from xylose at a rate of at least 5.00 g/L/h. In some embodiments, the method provided herein produces xylitol from xylose at a rate of at least 6.00 g/L/h. In some embodiments, the method provided herein produces xylitol from xylose at a rate of at least 7.00 g/L/h. In some embodiments, the method provided herein produces xylitol from xylose at a rate of at least 8.00 g/L/h. In some embodiments, the method provided herein produces xylitol from xylose at a rate of at least 9.00 g/L/h. In some embodiments, the method provided herein produces xylitol from xylose at a rate of or at least 10.00 g/L/h.

In some embodiments, the method provided herein produces xylitol from xylose at a concentration of at least 75 g/L In some embodiments, the method provided herein produces xylitol from xylose at a concentration of at least 80 g/L. In some embodiments, the method provided herein produces xylitol from xylose at a concentration of at least 85 g/L. In some embodiments, the method provided herein produces xylitol from xylose at a concentration of at least 90 g/L. In some embodiments, the method provided herein produces xylitol from xylose at a concentration of at least 95 g/L. In some embodiments, the method provided herein produces xylitol from xylose at a concentration of at least 100 g/L. In some embodiments, the method provided herein produces xylitol from xylose at a concentration of at least 110 g/L. In some embodiments, the method provided herein produces xylitol from xylose at a concentration of at least 120 g/L. In some embodiments, the method provided herein produces xylitol from xylose at a concentration of at least 130 g/L. In some embodiments, the method provided herein produces xylitol from xylose at a concentration of at least 140 g/L. In some embodiments, the method provided herein produces xylitol from xylose at a concentration of at least 150 g/L. In some embodiments, the method provided herein produces xylitol from xylose at a concentration of at least 160 g/L. In some embodiments, the method provided herein produces xylitol from xylose at a concentration of at least 170 g/L. In some embodiments, the method provided herein produces xylitol from xylose at a concentration of at least 180 g/L. In some embodiments, the method provided herein produces xylitol from xylose at a concentration of at least 190 g/L. In some embodiments, the method provided herein produces xylitol from xylose at a concentration of at least 200 g/L. In some embodiments, the method provided herein produces xylitol from xylose at a concentration of at least 250 g/L. In some embodiments, the method provided herein produces xylitol from xylose at a concentration of at least 300 g/L.

Any of the *Metschnikowia* species described herein can be cultured to produce and/or secrete xylitol. For example, the *Metschnikowia* species provided herein can be cultured for the biosynthetic production of xylitol. Accordingly, in some embodiments, provided herein are culture media containing xylitol. In some aspects, the culture medium can also be separated from the *Metschnikowia* species that produced the xylitol. Methods for separating a microbial organism from culture medium are well known in the art. Exemplary methods include filtration, flocculation, precipitation, centrifugation, sedimentation, and the like.

For the production of xylitol, the *Metschnikowia* species provided herein are cultured in a medium with a carbon source and other essential nutrients. In some embodiments, the *Metschnikowia* species provided herein are cultured in an aerobic culture medium. The aerobic culturing can be batch, fed-batch or continuous culturing, wherein the dissolved oxygen in the medium is above 50% of saturation. In some embodiments, the *Metschnikowia* species provided herein are cultured in a substantially anaerobic culture medium. As described herein, one exemplary growth condition for achieving biosynthesis of xylitol includes anaerobic culture or fermentation conditions. In certain embodiments, the *Metschnikowia* species provided herein can be sustained, cultured or fermented under anaerobic or substantially anaerobic conditions. Briefly, an anaerobic condition refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also include growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

It is sometimes desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United States publication 2009/0047719, filed Aug. 10, 2007. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high yields.

If desired, the pH of the medium can be maintained at a desired pH, such as a pH of around 5.5-6.5 by addition of a base, such as NaOH or other bases, or acid, as needed to maintain the culture medium at a desirable pH. The growth rate can be determined by measuring optical density using a spectrophotometer (600 nm), and the xylose uptake rate by monitoring carbon source depletion over time.

The culture medium for the *Metschnikowia* species provided herein can include xylose, either as the sole source of carbon or in combination with one or more co-substrates described herein or known in the art. The culture medium can further include other supplements, such as yeast extract, and/or peptone. The culture medium can further include, for example, any other carbohydrate source which can supply a source of carbon to the *Metschnikowia* species. Such sources include, for example: other sugars such as cellobiose, galactose, glucose, ethanol, acetate, arabitol, sorbitol and glycerol. Thus, the culture medium can include xylose and the co-substrate glucose. The culture medium can include xylose and the co-substrate cellobiose. The culture medium can include xylose and the co-substrate galactose. The culture medium can include xylose and the co-substrate glycerol. The culture medium can include a combination of glucose, xylose and cellobiose. The culture medium can include a combination of glucose, xylose, and galactose. The culture medium can include a combination of glucose, xylose, and glycerol. The culture medium can include a combination of xylose, cellobiose, galactose and glycerol.

The culture medium can have 1%, 2%, 3%, 4%, 5%, 6%, 7%, 8%, 9%, 10%, 11%, 12%, 13%, 14%, 15%, 16%, 17%, 18%, 19%, 20%, or higher amount of a carbon source (w/v). In some embodiments, the culture medium can have 2% carbon source. In some embodiments, the culture medium can have 4% carbon source. In some embodiments, the culture medium can have 10% carbon source. In some embodiments, the culture medium can have 1%, 2%, 3%, 4%, 5%, 6%, 7%, 8%, 9%, 10%, 11%, 12%, 13%, 14%, 15%, 16%, 17%, 18%, 19%, 20%, or higher amount of xylose (w/v). The culture medium can have 1% xylose. The culture medium can have 2% xylose. The culture medium can have 3% xylose. The culture medium can have 4% xylose. The culture medium can have 5% xylose. The culture medium can have 6% xylose. The culture medium can have 7% xylose. The culture medium can have 8% xylose. The culture medium can have 9% xylose. The culture medium can have 10% xylose. The culture medium can have 11% xylose. The culture medium can have 12% xylose. The culture medium can have 13% xylose. The culture medium can have 14% xylose. The culture medium can have 15% xylose. The culture medium can have 16% xylose. The culture medium can have 17% xylose. The culture medium can have 18% xylose. The culture medium can have 19% xylose. The culture medium can have 20% xylose.

In some embodiments, xylose is not the only carbon source. For example, in some embodiments, the medium includes xylose and a C3 carbon source, a C4 carbon source, a C5 carbon source, a C6 carbon source, or a combination thereof. Accordingly, in some embodiments, the medium includes xylose and a C3 carbon source (e.g., glycerol). In some embodiments, the medium includes xylose and a C4 carbon source (e.g., erythrose or threose). In some embodiments, the medium includes xylose and a C5 carbon source (e.g., arabitol, ribose or lyxose). In some embodiments, the medium includes xylose and a C6 carbon source (e.g., glucose, galactose, mannose, allose, altrose, gulose, and idose). Alternatively or additionally, in some embodiments, the medium includes xylose and cellobiose, galactose, glucose, arabitol, sorbitol and glycerol, or a combination thereof. In a specific embodiment, the medium includes xylose and glucose. The amount of the two or more carbon sources in the medium can range independently from 1% to 20% (e.g., 1% to 20% xylose and 1% to 20% glucose), or alternatively 2% to 14% (e.g., 2% to 14% xylose and 2% to 14% glucose), or alternatively 4% to 10% (e.g., 4% to 10% xylose and 4% to 10%). In a specific embodiment, the amount of each of the carbon sources is 2% (e.g., 2% xylose and 2% glucose)

The culture medium can be a C5-rich medium, with a five carbon sugar (such as xylose) as the primary carbon source. The culture medium can also have a C6 sugar (six-carbon sugar). In some embodiments, the culture medium can have a C6 sugar as the primary carbon source. In some embodiments, the C6 sugar is glucose. The culture can have both a C6 sugar and a C5 sugar as the carbon source, and can have the C6 sugar and the C5 sugar present at different ratios. In some embodiment, the ratio of the amount of C6 sugar to that of the C5 sugar (the C6:C5 ratio) in the culture medium is between about 10:1 and about 1:20. For example, the C6:C5 ratio in the culture medium can be about 10:1, 9:1, 8:1, 7:1, 6:1, 5:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19 or 1:20. In some embodiments, the C6:C5 ratio in the culture medium is about 3:1. In some embodiments, the C6:C5 ratio in the culture medium is about 1:1. In some embodiments, the C6:C5 ratio in the culture medium is about 1:5. In some embodiments, the C6:C5 ratio in the culture medium is about 1:10. The C5 sugar can be xylose, and the C6 sugar can be glucose. In some embodiments, the ratio of the amount of glucose to that of xylose (the glucose:xylose ratio) in the culture medium is between about 20:1 and about 1:10. For example, the glucose:xylose ratio in the culture medium can be about 20:1, 19:1, 18:1, 17:1, 16:1, 15:1, 14:1, 13:1, 12:1, 11:1, 10:1, 9:1, 8:1, 7:1, 6:1, 5:1, 3:1, 2:1, 1:1, 1:2, 1:3, 1:4, 1:5, 1:6, 1:7, 1:8, 1:9 or 1:10. In some embodiments, the glucose:xylose ratio in the culture medium is about 3:1. In some embodiments, the glucose:xylose ratio in the culture medium is about 1:1. In some embodiments, the glucose:xylose ratio in the culture medium is about 1:5. In some embodiments, the glucose:xylose ratio in the culture medium is about 1:10.

Other sources of carbohydrate include, for example, renewable feedstocks and biomass. Exemplary types of biomasses that can be used as feedstocks in the methods provided herein include cellulosic biomass and hemicellulosic biomass feedstocks or portions of feedstocks. Such biomass feedstocks contain, for example, carbohydrate substrates useful as carbon sources such as xylose, glucose, arabinose, galactose, mannose, fructose and starch. Given the teachings and guidance provided herein, those skilled in the art will understand that renewable feedstocks and biomass other than those exemplified above also can be used for culturing the microbial organisms provided herein for the production of xylitol.

Accordingly, given the teachings and guidance provided herein, those skilled in the art will understand that a *Metschnikowia* species can be produced that secretes xylitol when grown on xylose as a carbon source. All that is required is to engineer in one or more of the required enzyme or protein activities to achieve biosynthesis of xylitol including, for example, inclusion of some or all of the biosynthetic pathway for producing xylitol. Additionally, a genetic modification can be engineered into the *Metschnikowia* species that attenuate or inactivates an enzyme that further catalyzes the conversion of xylitol into another compound, such as a xylitol dehydrogenase. Accordingly, provided herein is a *Metschnikowia* species that produces and/or secretes xylitol when grown on a carbohydrate, such as xylose, or other carbon source.

The *Metschnikowia* species provided herein can be constructed using methods well known in the art as exemplified herein to exogenously express at least one nucleic acid encoding an enzyme or protein of a xylitol pathway described herein in sufficient amounts to produce xylitol from xylose. It is understood that the *Metschnikowia* species provided herein are cultured under conditions sufficient to produce xylitol. Following the teachings and guidance provided herein, the *Metschnikowia* species provided herein can achieve biosynthesis of the desired compound resulting in intracellular concentrations between about 0.1-200 mM or more. Generally, the intracellular concentration of the desired compound between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the *Metschnikowia* species provided herein.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719. Any of these conditions can be employed with the *Metschnikowia* species as well as other anaerobic conditions well known in the art. Under such anaerobic or substantially anaerobic conditions, the producer strains can synthesize the desired compound at intracellular concentrations of 5-10 mM or more as well as all other concentrations exemplified herein. It is understood that, even though the above description refers to intracellular concentrations, the producing microbial organisms can produce the desired compound intracellularly and/or secrete the compound into the culture medium.

The methods provided herein can include any culturing process well known in the art, such as batch cultivation, fed-batch cultivation or continuous cultivation. Such process can include fermentation. Exemplary fermentation processes include, but are not limited to, fed-batch fermentation and batch separation; fed-batch fermentation and continuous separation; and continuous fermentation and continuous separation. In an exemplary batch fermentation protocol, the production organism is grown in a suitably sized bioreactor sparged with an appropriate gas. Under anaerobic conditions, the culture is sparged with an inert gas or combination of gases, for example, nitrogen, $N_2/CO_2$ mixture, argon, helium, and the like. As the cells grow and utilize the carbon source, additional carbon source(s) and/or other nutrients are fed into the bioreactor at a rate approximately balancing consumption of the carbon source and/or nutrients. The temperature of the bioreactor is maintained at a desired temperature, generally in the range of 22-37 degrees C., but the temperature can be maintained at a higher or lower temperature depending on the growth characteristics of the production organism and/or desired conditions for the fermentation process. Growth continues for a desired period of time to achieve desired characteristics of the culture in the fermenter, for example, cell density, compound concentration, and the like. In a batch fermentation process, the time period for the fermentation is generally in the range of several hours to several days, for example, 8 to 24 hours, or 1, 2, 3, 4 or 5 days, or up to a week, depending on the desired culture conditions. The pH can be controlled or not, as desired, in which case a culture in which pH is not controlled will typically decrease or increase to pH 5-6 by the end of the run. Upon completion of the cultivation period, the fermenter contents can be passed through a cell separation unit, for example, a centrifuge, filtration unit, and the like, to remove cells and cell debris. In the case where the desired compound is expressed intracellularly, the cells can be lysed or disrupted enzymatically or chemically prior to or after separation of cells from the fermentation broth, as desired, in order to release additional compound. The fermentation broth can be transferred to a compound separations unit. Isolation of compound occurs by standard separations procedures employed in the art to separate a desired compound from dilute aqueous solutions. Such methods include, but are not limited to, liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the compound, if appropriate, standard distillation methods, and the like, depending on the chemical characteristics of the compound of the fermentation process.

In an exemplary fully continuous fermentation protocol, the production organism is generally first grown up in batch mode in order to achieve a desired cell density. When the carbon source and/or other nutrients are exhausted, feed medium of the same composition is supplied continuously at a desired rate, and fermentation liquid is withdrawn at the same rate. Under such conditions, the compound concentration in the bioreactor generally remains constant, as well as the cell density. The temperature of the fermenter is maintained at a desired temperature, as discussed above. During the continuous fermentation phase, it is generally desirable to maintain a suitable pH range for optimized production. The pH can be monitored and maintained using routine methods, including the addition of suitable acids or bases to maintain a desired pH range. The bioreactor is operated continuously for extended periods of time, generally at least one week to several weeks and up to one month, or longer, as appropriate and desired. The fermentation liquid and/or culture is monitored periodically, including sampling up to every day, as desired, to assure consistency of compound concentration and/or cell density. In continuous mode, fermenter contents are constantly removed as new feed medium is supplied. The exit stream, containing cells, medium, and product, are generally subjected to a continuous compound separations procedure, with or without removing cells and cell debris, as desired. Continuous separations methods employed in the art can be used to separate the compound from dilute aqueous solutions, including but not limited to continuous liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like), standard continuous distillation methods, and the like, or other methods well known in the art.

In addition to the culturing and fermentation conditions disclosed herein, growth condition for achieving biosynthesis of the desired compound can include the addition of an osmoprotectant to the culturing conditions. In certain embodiments, the *Metschnikowia* species provided herein can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfonioproprionate, 3-dimethyl sulfonio-2-methylproprionate, pipecolic acid, dimethyl sulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

The culture conditions can include, for example, liquid culture procedures as well as fermentation and other large scale culture procedures. As described herein, particularly useful yields of the biosynthetic products can be obtained under aerobic, anaerobic or substantially anaerobic culture conditions.

The culture conditions described herein can be scaled up and grown continuously for manufacturing of a desired compound. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of a desired product. Generally, and as with non-continuous culture procedures, the continuous and/or near-continuous production includes culturing the microbial organisms provided herein in sufficient nutrients and medium to sustain and/or nearly sustain growth in an exponential phase. Continuous culture under such conditions can include, for example, growth or culturing for 1 day, 2, 3, 4, 5, 6 or 7 days or more. Additionally, continuous culture can include longer time periods of 1 week, 2, 3, 4 or 5 or more weeks and up to several months. Alternatively, organisms provided herein can be cultured for hours, if suitable for a particular application. It is to be understood that the continuous and/or near-continuous culture conditions also can include all time intervals in between these exemplary periods. It is further understood that the time of culturing the microbial organism provided herein is for a sufficient period of time to produce a sufficient amount of compound for a desired purpose.

In addition to the above fermentation procedures using *Metschnikowia* species provided herein using continuous production of substantial quantities of xylitol, the bioderived compound also can be, for example, simultaneously subjected to chemical synthesis and/or enzymatic procedures to convert the xylitol to other compounds, or the bioderived xylitol can be separated from the fermentation culture and sequentially subjected to chemical and/or enzymatic conversion to convert the xylitol to other compounds, if desired.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of a desired product.

In some embodiments, the methods provided herein to produce bioderived xylitol further include separating the bioderived xylitol from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, ultrafiltration, activated charcoal adsorption, pH adjustment and precipitation, or a combination of one or more methods enumerated above. All of the above methods are well known in the art.

Provided herein is bioderived xylitol as described herein. Such bioderived xylitol is, in some embodiments, are produced by the *Metschnikowia* species described herein. Also provided herein are compositions having bioderived xylitol produced by the *Metschnikowia* species described herein, and an additional component. The component other than the bioderived xylitol can be a cellular portion, for example, a trace amount of a cellular portion of the culture medium, or can be fermentation broth or culture medium or a purified or partially purified fraction thereof produced in the presence of, a *Metschnikowia* species provided herein.

Thus, in some embodiments, the composition is culture medium. In some embodiments, the culture medium can be culture medium from which the isolated *Metschnikowia* species provided herein has been removed. The composition can have, for example, a reduced level of a byproduct when produced by the *Metschnikowia* species provided herein. The composition can have, for example, bioderived xylitol, and a cell lysate or culture supernatant of a *Metschnikowia* species provided herein. The additional component can be a byproduct, or an impurity, such as glycerol, arabitol, a C7 sugar alcohol, or a combination thereof. The byproduct can be glycerol. The byproduct can be arabitol. The byproduct can be a C7 sugar alcohol (e.g., volemitol or an isomer thereof). In some embodiments, the byproduct or impurity (e.g., glycerol or arabitol, or both) is at least 10%, 20%, 30% or 40% greater than the amount of the respective byproduct or impurity produced by a microbial organism other than the isolated *Metschnikowia* species provided herein.

In some embodiments, the compositions provided herein can have bioderived xylitol and an additional component. The additional component can be fermentation broth or culture medium. The additional component can be the supernatant of fermentation broth or culture medium. The additional component can be a cellular portion of fermentation broth or culture medium. The additional component can be the *Metschnikowia* species provided herein. The additional component can be the cell lysate of the *Metschnikowia* species provided herein. The additional component can be a byproduct, such as glycerol, arabitol, a C7 sugar alcohol, or a combination thereof.

In some embodiments, the carbon feedstock and other cellular uptake sources such as phosphate, ammonia, sulfate, chloride and other halogens can be chosen to alter the isotopic distribution of the atoms present in the bioderived xylitol produced by microbial organisms provided herein. The various carbon feedstock and other uptake sources enumerated above will be referred to herein, collectively, as "uptake sources." Uptake sources can provide isotopic enrichment for any atom present in the bioderived xylitol produced by microbial organisms provided herein, or in the byproducts or impurities. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=−19 per mil (Olsson, *The use of Oxalic acid as a Standard.* in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}$=−19 per mil. This is equivalent to an absolute (AD 1950) $^{14}C/^{12}C$ ratio of 1.176±0.010×10$^{12}$ (Karlen et al., *Arkiv Geofisik*, 4:465-471 (1968)). The standard calculations take into account the differential uptake of one isotope with respect to another, for example, the preferential uptake in biological systems of $^{12}C$ over $^{13}C$ over $^{14}C$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mil. ASTM D6866-11 suggests use of the available Oxalic Acid II standard SRM 4990 C (Hox2) for the modern standard (see discussion of original vs. currently available oxalic acid standards in Mann, Radiocarbon, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products that utilize provided herein having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, provided herein bio-derived xylitol that has a carbon-12, carbon-13, and carbon-14 ratio that reflects an atmospheric carbon, also referred to as environmental carbon, uptake source. For example, in some aspects the bioderived xylitol can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, provided herein is bioderived xylitol that has a carbon-12, carbon-13, and carbon-14 ratio that reflects petroleum-based carbon uptake source. In this aspect, the bioderived xylitol provided herein can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, bioderived xylitol provided herein can have a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, provided herein are also the products derived the bioderived xylitol, wherein the bioderived xylitol has a carbon-12, carbon-13, and carbon-14 isotope ratio of about the same value as the $CO_2$ that occurs in the environment. For example, in some aspects, provided herein is a biobased product having the bioderived xylitol described herein with a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived xylitol as disclosed herein, wherein the bioderived xylitol is chemically modified to generate a final product. Methods of chemically modifying bioderived xylitol to generate a desired product are well known to those skilled in the art, as described herein.

Provided herein are also biobased products having bioderived xylitol produced by a *Metschnikowia* species described herein or produced using a method described herein. In some embodiments, provided herein are biobased products produced using bioderived xylitol. Such manufacturing can include chemically reacting the bioderived compound (e.g. chemical conversion, chemical functionalization, chemical coupling, oxidation, reduction, polymerization, copolymerization and the like) into the final product. In some embodiments, provided herein are biobased products having bioderived xylitol described herein. In some embodiments, provided herein are biobased products having at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived xylitol as disclosed herein.

Provided herein is an isolated polypeptide directed to the xylose reductase (Xyl1 protein) of the H0 *Metschnikowia* sp. and an isolated nucleic acid directed to the XYL1 gene of the H0 *Metschnikowia* sp., as well as host cells comprising such nucleic acids. The presence of this nucleic acid in a *Metschnikowia* species can result in the *Metschnikowia* species being able to produce xylitol from xylose as described herein. Thus, provided herein is an isolated polypeptide that has the amino acid sequence of the Xyl1 protein or a variant thereof; an isolated nucleic acid that has a nucleic acid sequence that encodes the Xyl1 protein or a variant thereof; an isolated nucleic acid that has the nucleic acid sequence of the gene for XYL1; as well as a host cell having such nucleic acid sequences and/or expressing such proteins.

In some embodiments, provided herein is an isolated polypeptide having the amino acid sequence of SEQ ID NO: 11. Also provided herein an isolated polypeptide having an amino acid sequence that is a variant to the Xyl1 protein of the H0 *Metschnikowia* sp. described herein, but still retains the functional activity of the polypeptide. For example, in some embodiments, the isolated polypeptide has an amino acid sequence of SEQ ID NO: 11, wherein the amino acid sequence includes 1, 2, 3, 4, 5, 6, 7, 8, 9, 10, 11, 12, 13, 14, 15, 16, 17, 18, 19, 20, 21, 22, 23, 24, or 25 amino acid substitutions, deletions or insertions. Variants of a protein provided herein also include, for example, deletions, fusions, or truncations when compared to the reference polypeptide sequence. Accordingly, in some embodiments, the isolated polypeptide provided herein has an amino acid sequence that is at least 95.0%, at least 95.1%, at least 95.2%, at least 95.3%, at least 95.4%, at least 95.5%, at least 95.6%, at least 95.7%, at least 95.8%, at least 95.9%, at least 96.0%, at least 96.1%, at least 96.2%, at least 96.3%, at least 96.4%, at least 96.5%, at least 96.6%, at least 96.7%, at least 96.8%, at least 96.9%, at least 97.0%, at least 97.1%, at least 97.2%, at least 97.3%, at least 97.4%, at least 97.5%, at least 97.6%, at least 97.7%, at least 97.8%, at least 97.9%, at least 98.0%, at least 98.1%, at least 98.2%, at least 98.3%, at least 98.4%, at least 98.5%, at least 98.6%, at least 98.7%, at least 98.8%, at least 98.9%, at least 99.0%, at least 99.1%, at least 99.2%, at least 99.3%, at least 99.4%, at least 99.5%, at least 99.6%, at least 99.7%, or at least 99.8% identical to SEQ ID NO: 11.

Variants of the Xyl1 protein described herein can also contain conservatively amino acids substitution, meaning that one or more amino acid can be replaced by an amino acid that does not alter the secondary and/or tertiary stricture of the protein. Such substitutions can include the replacement of an amino acid, by a residue having similar physicochemical properties, such as substituting one aliphatic residue (Ile, Val, Leu, or Ala) for another, or substitutions between basic residues Lys and Arg, acidic residues Glu and Asp, amide residues Gln and Asn, hydroxyl residues Ser and Tyr, or aromatic residues Phe and Tyr. Phenotypically silent amino acid exchanges are described more fully in Bowie et al., *Science* 247:1306-10 (1990). In addition, variants of a protein described herein include those having amino acid substitutions, deletions, or additions to the amino acid sequence outside functional regions of the protein so long as the substitution, deletion, or addition does not affect the function of the resulting polypeptide. Techniques for making these substitutions and deletions are well known in the art and include, for example, site-directed mutagenesis.

The isolated polypeptides provided herein also include functional fragments of the Xyl1 protein described herein, which retains its function. In some embodiments, provided herein is an isolated polypeptide that is a functional fragment of the Xyl1 protein described herein. In some embodiments, provided herein is an isolated nucleic acid that encodes a polypeptide that is a functional fragment of the Xyl1 protein described herein. In some embodiments, the isolated polypeptide can be fragments of Xyl1 (SEQ ID NO: 11), which retains the function of the protein.

In some embodiments, variants of the Xyl1 protein described herein include covalent modification or aggregative conjugation with other chemical moieties, such as glycosyl groups, polyethylene glycol (PEG) groups, lipids, phosphate, acetyl groups, and the like. In some embodiments, variants of the Xyl1 protein described herein further include, for example, fusion proteins formed of the protein described herein and another polypeptide. The added polypeptides for constructing the fusion protein include those that facilitate purification or oligomerization of the protein described herein, or those that enhance stability and/or function of the Xyl1 protein described herein.

The Xyl1 protein described herein can be fused to heterologous polypeptides to facilitate purification. Many available heterologous peptides (peptide tags) allow selective binding of the fusion protein to a binding partner. Non-limiting examples of peptide tags include 6-His, thioredoxin, hemaglutinin, GST, and the OmpA signal sequence tag. A binding partner that recognizes and binds to the heterologous peptide tags can be any molecule or compound, including metal ions (for example, metal affinity columns), antibodies, antibody fragments, or any protein or peptide that selectively or specifically binds the heterologous peptide to permit purification of the fusion protein.

The Xyl1 protein described herein can also be modified to facilitate formation of oligomers. For example, the protein described herein can be fused to peptide moieties that promote oligomerization, such as leucine zippers and certain antibody fragment polypeptides, such as Fc polypeptides. Techniques for preparing these fusion proteins are known, and are described, for example, in WO 99/31241 and in Cosman et al., *Immunity* 14:123-133 (2001). Fusion to an Fc polypeptide offers the additional advantage of facilitating purification by affinity chromatography over Protein A or Protein G columns. Fusion to a leucine-zipper (LZ), for example, a repetitive heptad repeat, often with four or five leucine residues interspersed with other amino acids, is described in Landschulz et al., *Science* 240:1759-64 (1988).

The Xyl1 protein described herein can be provided in an isolated form, or in a substantially purified form. The polypeptides can be recovered and purified from recombinant cell cultures by known methods, including, for example, ammonium sulfate or ethanol precipitation, anion or cation exchange chromatography, phosphocellulose chromatography, hydrophobic interaction chromatography, affinity chromatography, hydroxylapatite chromatography, and lectin chromatography. In some embodiments, protein chromatography is employed for purification.

In some embodiments, provided herein are recombinant microbial organisms having an exogenous nucleic acid encoding a Xyl1 protein described herein. In some embodiments, the recombinant microbial organism has an exogenous nucleic acid encoding the Xyl1 protein described herein, wherein the protein has 1 to 25, 1 to 20, 1 to 15, 1 to 10, or 1 to 5, amino acid substitutions, deletions or insertions. In some embodiments, the Xyl1 protein has the amino acid sequence of SEQ ID NO: 11. In some embodiments, the Xyl1 protein has 1 to 10 amino acid substitutions, deletions or insertions of SEQ ID NO: 11 and retains the function of the protein. In some embodiments, the Xyl1 protein has 1 to 5 amino acid substitutions, deletions or insertions of SEQ ID NO: 11 and retains the function of the protein. The recombinant microbial organism can be a *Metschnikowia* species, including, but not limited to, the H0 *Metschnikowia* sp. described herein.

The Xyl1 protein described herein can be recombinantly expressed by suitable hosts. When heterologous expression of the protein is desired, the coding sequences of specific genes can be modified in accordance with the codon usage of the host. The standard genetic code is well known in the art, as reviewed in, for example, Osawa et al., *Microbiol Rev.* 56(1):229-64 (1992). Yeast species, including but not limited to *Saccharomyces cerevisiae, Candida azyma, Candida diversa, Candida magnoliae, Candida rugopelliculosa, Yarrowia lipolytica,* and *Zygoascus hellenicus,* use the standard code. Certain yeast species use alternative codes. For example, "CUG," standard codon for "Leu," encodes "Ser" in species such as *Candida albicans, Candida cylindracea, Candida melibiosica, Candida parapsilosis, Candida rugose, Pichia stipitis,* and *Metschnikowia* species. The codon table for the H0 *Metschnikowia* sp. is provided herein.

Furthermore, the hosts can simultaneously produce other forms of the same category of proteins such that multiple forms of the same type of protein are expressed in the same cell. For example, the hosts can simultaneously produce different xylose reductases.

Variants of the Xyl1 protein described herein can be generated by conventional methods known in the art, such as by introducing mutations at particular locations by oligonucleotide-directed site-directed mutagenesis. Site-directed-mutagenesis is considered an informational approach to protein engineering and can rely on high-resolution crystallographic structures of target proteins for specific amino acid changes (Van Den Burg et al., *PNAS* 95:2056-60 (1998)). Computational methods for identifying site-specific changes for a variety of protein engineering objectives are also known in the art (Hellinga, *Nature Structural Biology* 5:525-27 (1998)).

Other techniques known in the art include, but are not limited to, non-informational mutagenesis techniques (referred to generically as "directed evolution"). Directed evolution, in conjunction with high-throughput screening, allows testing of statistically meaningful variations in protein conformation (Arnold, 1998). Directed evolution technology can include diversification methods similar to that described by Crameri et al., *Nature* 391:288-91 (1998), site-saturation mutagenesis, staggered extension process (StEP) (Zhao et al., *Nature Biotechnology* 16:258-61 (1998)), and DNA synthesis/reassembly (U.S. Pat. No. 5,965,408).

As disclosed herein, a nucleic acid encoding an Xyl1 protein described herein can be introduced into a host organism. In some cases, it can also be desirable to modify an activity of the protein to increase production of a desired product. For example, known mutations that increase the activity of a protein can be introduced into an encoding nucleic acid molecule. Additionally, optimization methods can be applied to increase the activity of a protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >$10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Often and Quax. *Biomol. Eng* 22:1-9 (2005); and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux;

oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a protein described herein. Such methods include, but are not limited to EpPCR, which introduces random point mutations by reducing the fidelity of DNA polymerase in PCR reactions (Pritchard et al., *J Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc Natl Acad Sci USA* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol* 352:191-204 (2007); Bergquist et al., *Biomol. Eng* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. USA* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res* 29:E16 (2001)); SCRATCHY, which combines two methods for recombining genes, ITCHY and DNA shuffling (Lutz et al., *Proc. Natl. Acad. Sci. USA* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional is mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. USA* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. USA* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego Calif.), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein or otherwise known in the art.

Provided herein is an isolated nucleic acid having nucleic acid sequences encoding the Xyl1 protein described herein as well as the specific encoding nucleic acid sequences of the XYL1 gene described herein. Nucleic acids provided herein include those having the nucleic acid sequence provided in the sequence listing; those that hybridize to the nucleic acid sequences provided in the sequence listing, under high stringency hybridization conditions (for example, 42°, 2.5 hr., 6×SCC, 0.1% SDS); and those having substantial nucleic acid sequence identity with the nucleic acid sequence provided in the sequence listing. The nucleic acids provided herein also encompass equivalent substitutions of codons that can be translated to produce the same amino acid sequences. Provided herein are also vectors including the nucleic acids described herein. The vector can be an expression vector suitable for expression in a host microbial organism. The vector can be a viral vector.

The nucleic acids provided herein include those encoding proteins having an amino acid sequence as described herein, as well as their variants that retain their function. The nucleic acids provided herein can be cDNA, chemically synthesized DNA, DNA amplified by PCR, RNA, or combinations thereof. Due to the degeneracy of the genetic code, two DNA sequences can differ and yet encode identical amino acid sequences.

Provided herein are also useful fragments of nucleic acids encoding the proteins described herein, include probes and primers. Such probes and primers can be used, for example, in PCR methods to amplify or detect the presence of nucleic acids encoding the proteins described herein in vitro, as well as in Southern and Northern blots for analysis. Cells expressing the proteins described herein can also be identified by the use of such probes. Methods for the production and use of such primers and probes are well known.

Provided herein are also fragments of nucleic acids encoding the proteins described herein that are antisense or sense oligonucleotides having a single-stranded nucleic acid capable of binding to a target mRNA or DNA sequence of the protein or nucleic acid sequence described herein.

A nucleic acid encoding a protein described herein can include nucleic acids that hybridize to a nucleic acid disclosed herein by SEQ ID NO or a nucleic acid molecule that hybridizes to a nucleic acid molecule that encodes an amino acid sequence disclosed herein by SEQ ID NO. Hybridization conditions can include highly stringent, moderately stringent, or low stringency hybridization conditions that are well known to one of skill in the art such as those described herein.

Stringent hybridization refers to conditions under which hybridized polynucleotides are stable. As known to those of skill in the art, the stability of hybridized polynucleotides is reflected in the melting temperature ($T_m$) of the hybrids. In general, the stability of hybridized polynucleotides is a function of the salt concentration, for example, the sodium ion concentration and temperature. A hybridization reaction can be performed under conditions of lower stringency, followed by washes of varying, but higher, stringency. Reference to hybridization stringency relates to such washing conditions. Highly stringent hybridization includes conditions that permit hybridization of only those nucleic acid sequences that form stable hybridized polynucleotides in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C. Hybridization conditions other than highly stringent hybridization conditions can also be used to describe the nucleic acid sequences disclosed herein. For example, the phrase moderately stringent hybridization refers to conditions equivalent to hybridization in 50% formamide, 5×Denhart's solution, 5×SSPE, 0.2% SDS at 42° C., followed by washing in 0.2×SSPE, 0.2% SDS, at 42° C. The phrase low stringency hybridization refers to conditions equivalent to hybridization in 10% formamide, 5×Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable low, moderate and high stringency hybridization buffers and conditions are well known to those of skill in the art and are described, for example, in Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Nucleic acids encoding a protein provided herein include those having a certain percent sequence identity to a nucleic acid sequence disclosed herein by SEQ ID NO. For example, a nucleic acid molecule can have at least 95.0%, at least 95.1%, at least 95.2%, at least 95.3%, at least 95.4%, at least 95.5%, at least 95.6%, at least 95.7%, at least 95.8%, at least 95.9%, at least 96.0%, at least 96.1%, at least 96.2%, at least 96.3%, at least 96.4%, at least 96.5%, at least 96.6%, at least 96.7%, at least 96.8%, at least 96.9%, at least 97.0%, at least 97.1%, at least 97.2%, at least 97.3%, at least 97.4%, at least 97.5%, at least 97.6%, at least 97.7%, at least 97.8%, at least 97.9%, at least 98.0%, at least 98.1%, at least 98.2%, at least 98.3%, at least 98.4%, at least 98.5%, at least 98.6%, at least 98.7%, at least 98.8%, at least 98.9%, at least 99.0%, at least 99.1%, at least 99.2%, at least 99.3%, at least 99.4%, at least 99.5%, at least 99.6%, at least 99.7%, or at least 99.8% sequence identity, or be identical, to a sequence selected from SEQ ID NO: 11.

Accordingly, in some embodiments, the isolated nucleic acid provided herein has a nucleic acid sequence of the XYL1 gene of the H0 *Metschnikowia* sp. disclosed herein. Accordingly, in some embodiments, provided herein is an isolated nucleic acid having a nucleic acid sequence of XYL1 (SEQ ID NO: 11).

Also provided herein is a method of expressing a polypeptide in a *Metschnikowia* species (e.g., H0 *Metschnikowia* sp.), wherein the polypeptide comprises a leucine (Leu; L). Such a method includes introducing an exogenous nucleic acid sequence encoding the polypeptide into the Metschnikowia species under conditions that allow expression of the polypeptide, wherein the exogenous nucleic acid sequence has a CTT, CTG, CTA, TTA or TTG codon in place of a CTG codon for the leucine, as exemplified herein. In a particular embodiment, the codon in place of the CTG codon is TTG. Methods for making such modifications to encoding nucleic acid sequences are well known in the art.

Also provided herein is a method for introducing exogenous nucleic acids into a Metschnikowia species (e.g., H0 Metschnikowia sp.). Such a method is a modified lithium acetate protocol or electroporation protocol as exemplified in Example I.

It is understood that modifications which do not substantially affect the activity of the various embodiments of this invention are also provided within the definition of the invention provided herein. Accordingly, the following examples are intended to illustrate but not limit the present invention. Throughout this application various publications have been referenced. The disclosures of these publications in their entireties, including GenBank and GI number publications, are hereby incorporated by reference in this application in order to more fully describe the state of the art to which this invention pertains.

Example I

Production of Xylitol from Xylose of H0 *Metschnikowia* sp.

This example demonstrates that the H0 *Metschnikowia* sp. produces xylitol from xylose when cultured in YEP medium containing xylose.

The production of xylitol from xylose was assayed for the H0 *Metschnikowia* sp. in yeast extract peptone (YEP) medium supplemented with 4% w/v or 10% w/v xylose. As a control, *S. cerevisiae* wine yeast M2 was also assayed.

H0 *Metschnikowia* sp. cells were inoculated into 50 ml of YEP+4% w/v or 10% w/v xylose medium in a 125 ml flask and grown at 30° C. incubator with shaking at 120 rpm. A 1 ml sample was taken from the culture and cells were removed by centrifugation. The supernatant was filtrated through a 0.22 μm nylon syringe filter into a HPLC sample vial. The xylitol content in the supernatant was analyzed by HPLC on Rezex RPM-monosaccharide Pb+2 column (Phenomenex) at 80° C. using water as a mobile phase at a rate of 0.6 ml/min. The peaks were detected with an Agilent G1362A refractive index detector (Agilent).

The H0 *Metschnikowia* sp. produced xylitol via a xylose dependent pathway. For example, in 4% xylose medium, the H0 *Metschnikowia* sp. produced approximately 13.8 g/L of xylitol from 40 g/L of xylose in 5 days, whereas in 10% xylose it produced approximately 23 g/L of xylitol from 100 g/L of xylose in 10 days (FIG. 1). When xylose was used up, the H0 *Metschnikowia* sp. started to consume the xylitol in the medium (FIG. 1). In both mediums, the *S. cerevisiae* M2 species produced no xylitol (FIG. 1).

Example II

Construction of Recombinant *Metschnikowia* Species Having Xylitol Pathway

Figure 2:
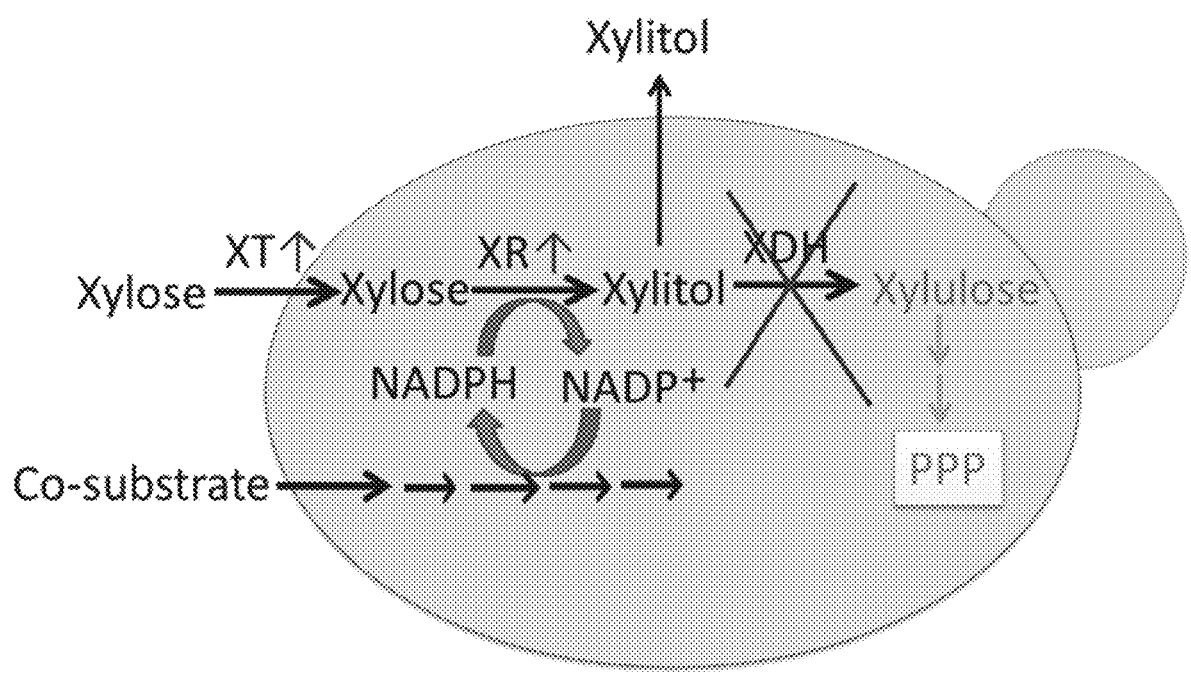
FIG. 2 shows an exemplary xylitol pathway for production from xylose. Reduction of xylose to xylitol occurs by xylose reductase (XR) and conversion of xylitol to xylulose is prevented by the deletion of the XYL2 gene that encodes a xylitol dehydrogenase (XDH). Overexpression of the xylose transporter (XT) and xylose reductase (XR) enhance the production of xylitol. Use of a co-substrate supports the cell's metabolism and supplies redox balance for xylose reductase.

In order to increase the yield and productivity of xylitol by the H0 *Metschnikowia* sp. as exemplified in Example I, a xylitol production pathway was modified in the H0 *Metschnikowia* sp. genome. The modification included deleting the XYL2 gene (SEQ ID NO: 6), which encoded a xylitol dehydrogenase (XDH; SEQ ID NO: 1), and overexpressing the XYL1 gene (SEQ ID NO: 19), which encoded a xylose reductase (XR; SEQ ID NO: 11) and, in some experiments, overexpressing a xylose transporter (GXF1; SEQ ID NO: 42, or GXF2 SEQ ID NO: 44) (FIG. 2). A co-substrate was supplied to support the cell's metabolism and supply redox balance for xylose reductase (FIG. 2).

Usable antifungal resistance genes, as selection markers for gene manipulation, needed to be identified in order to engineer the xylitol pathway in the H0 *Metschnikowia* sp. First, the sensitivity of the H0 *Metschnikowia* sp. to various known antifungals was tested. A single yeast colony was inoculated into 5 ml YPD broth containing different concentrations of antibiotics (50 ug/mL, 100 ug/mL, 150 ug/mL, 200 ug/mL, 250 ug/mL, 300 ug/mL, 350 ug/mL, 400 ug/mL, 450 ug/mL). Cultures were aerobically grown at 30° C. for 2 days, and the growth was monitored by assaying optical density of culture at 600 nm. H0 *Metschnikowia* sp. was determined to be sensitive to 100 ug/mL nourseothricin (cloNAT), 300 ug/mL hygromycin, 200 ug/mL phleomycin, and 400 ug/ml geneticin, respectively.

Based on this sensitivity profile, genes that are known to provide resistance in *S. cerevisiae* were introduced into the H0 *Metschnikowia* sp.—natMX and hphMX genes, which generally provide resistance to nourseothricin and hygromycin, respectively. However, introduction of the natMX and hphMX genes resulted in no viable colonies. It was hypothesized that H0 *Metschnikowia* sp. might belong to the fungal CTG clade species, in which the universal leucine CUG codon is predominantly translated as serine and rarely as leucine (Santos et al., 2011, *C. R. Bio.*, 334:607-611), just like the closely related species, *C. lusitaniae* (Young et al., 2000, *Genetics*, 155:17-29). The CTG codon was changed to TTG for leucine encoding (see Table 4) and other codons were optimized based on a codon preference calculated from multiple H0 *Metschnikowia* sp. open reading frames as the total genome annotation for the H0 *Metschnikowia* sp. is not available.

TABLE 4

| Codons for H0 *Metschnikowia* sp. | | |
|---|---|---|
| Amino Acid | SLC | DNA codons |
| Isoleucine | I | ATT ATC ATA |
| Leucine | L | CTT CTC CTA TTA TTG |
| Valine | V | GTT GTC GTA GTG |
| Phenylalanine | F | TTT TTC |
| Methionine | M | ATG |
| Cysteine | C | TGT TGC |
| Alanine | A | GCT GCC GCA GCG |
| Glycine | G | GGT GGC GGA GGG |
| Proline | P | CCT CCC CCA CCG |
| Threonine | T | ACT ACC ACA ACG |
| Serine | S | TCT TCC TCA TCG AGT AGC CTG |
| Tyrosine | Y | TAT TAC |
| Tryptophan | W | TGG |
| Glutamine | O | CAA CAG |

TABLE 4-continued

Codons for H0 *Metschnikowia* sp.

| Amino Acid | SLC | DNA codons |
|---|---|---|
| Asparagine | N | AAT AAC |
| Histidine | H | CAT CAC |
| Glutamic acid | E | GAA GAG |
| Aspartic acid | D | GAT GAC |
| Lysine | K | AAA AAG |
| Arginine | R | CGT CGC CGA CGG AGA AGG |
| Stop codons | Stop | TAA TAG TGA |

Codon optimized antibiotics gene sequence were as follows:

MeNAT:
(SEQ ID NO: 55)
ATGGGTACCACCTTGGACGACACCGCCTACAGATACAGAACCTCCGTCCC

AGGTGACGCCGAGGCCATCGAGGCCTTGGACGGTTCCTTCACCACCGACA

CCGTCTTCAGAGTCACCGCCACCGGTGACGGTTTCACCTTGAGAGAGGTC

CCAGTGGACCCACCATTGACCAAGGTCTTCCCAGACGACGAGTCCGACGA

CGAGTCCGACGACGGTGAGGACGGTGACCCAGACTCCAGAACCTTCGTCG

CCTACGGTGACGACGGTGACTTGGCCGGTTTCGTGGTCGTCTCCTACTCC

GGTTGGAACAGAAGATTGACCGTCGAGGACATCGAGGTCGCCCCAGAGCA

CAGAGGTCACGGTGTCGGTAGAGCCTTGATGGGTTTGGCCACCGAGTTCG

CCAGAGAGAGAGGTGCCGGTCACTTGTGGTTGGAGGTCACCAACGTCAAC

GCCCCAGCCATCCACGCCTACAGAAGAATGGGTTTCACCTTGTGCGGTTT

GGACACTGCCTTGTACGACGGCACCGCCTCTGACGGTGAGCAGGCTTTGT

ACATGTCCATGCCATGTCCATAA

MeHPH:
(SEQ ID NO: 56)
ATGGGTACCAAGAAGCCTGAGTTGACCACTACTTCTGTTGAGAAGTTCTT

GATCGAAAAGTTCGACTCTGTTTCTGACTTGATGCAGTTGTCCGAGGGTG

AGGAGTCCAGAGCTTTCTCCTTCGACGTTGGTGGTAGAGGTTACGTCTTG

AGAGTCAACTCCTGTGCCGACGGTTTCTACAAGGACAGATACGTCTACAG

ACACTTCGCCTCCGCTGCTTTGCCAATCCCAGAGGTCTTGGACATCGGTG

AGTTCTCTGAGTCTTTGACCTACTGTATCTCCAGAAGAGCCCAGGGTGTC

ACCTTGCAGGACTTGCCAGAGACCGAGTTGCCAGCCGTCTTGCAGCCAGT

CGCTGAGGCTATGGACGCTATCGCTGCTGCCGACTTGTCTCAGACTTCTG

GTTTCGGTCAATTCGGTCCACAGGGTATCGGTCAGTACACCACTTGGAGA

GACTTCATCTGTGCCATCGCCGACCCACACGTCTACCACTGGCAGACCGT

TATGGACGACACCGTTTCTGCCTCTGTTGCCCAGGCTTTGGACGAGTTGA

TGTTGTGGGCTGAGGACTGTCCAGAGGTTAGACACTTGGTTCACGCTGAC

TTCGGTTCCAACAACGTCTTGACCGACAACGGTAGAATCACCGCTGTCAT

CGACTGGTCTGAGGCTATGTTCGGTGACTCCCAGTACGAGGTCGCCAACA

TCTTCTTCTGGAGACCTTGGTTGGCCTGTATGGAGCAGCAGACCAGATAC

TTCGAGAGAAGACACCCAGAGTTGGCTGGTTCTCCAAGATTGAGAGCTTA

CATGTTGAGAATCGGTTTGGACCAGTTGTACCAGTCCTTGGTTGACGGTA

ACTTCGACGACGCTGCCTGGGCTCAGGGTAGATGTGACGCTATCGTCAGA

TCTGGTGCTGGCACCGTTGGTAGAACCCAGATCGCTAGAAGATCCGCTGC

TGTCTGGACCGACGGTTGTGTCGAGGTTTTGGCTGACTCTGGTAACAGAA

GACCATCCACCAGACCAAGAGCCAAGGAGTAA

MeKAN:
(SEQ ID NO: 57)
ATGGGTACCAAGGAAAAGACTCACGTTTCGAGACCAAGATTGAACTCCAA

CATGGATGCTGATTTGTACGGTTACAAATGGGCTAGAGATAACGTCGGTC

AATCTGGTGCGACTATCTACAGACTTTACGGCAAGCCCGATGCGCCAGAG

TTGTTCTTGAAGCATGGCAAAGGTTCCGTTGCCAACGACGTTACCGATGA

GATGGTCAGACTTAACTGGTTGACGGAATTTATGCCTCTTCCTACCATCA

AGCACTTCATCCGTACTCCTGATGACGCCTGGTTGCTCACCACTGCGATC

CCAGGCAAAACCGCTTTCCAGGTCTTGGAGGAATACCCTGATTCTGGTGA

GAACATTGTTGACGCGTTGGCCGTGTTCTTGCGTAGATTGCACTCGATTC

CTGTTTGTAACTGTCCTTTCAACTCCGACCGTGTGTTCAGACTCGCTCAG

GCCCAATCCAGAATGAACAACGGTTTGGTTGACGCGTCTGACTTTGATGA

CGAGCGTAACGGCTGGCCTGTTGAGCAGGTCTGGAAAGAGATGCACAAGC

TCTTGCCATTCTCTCCAGATTCCGTCGTTACTCACGGTGATTTCTCTCTT

GACAACCTTATTTTCGACGAGGGTAAGTTGATCGGTTGTATTGATGTTGG

TAGAGTCGGTATCGCTGACAGATACCAGGATCTTGCCATCCTCTGGAACT

GCCTCGGTGAGTTCTCTCCTTCCTTGCAGAAGAGACTTTTCCAGAAGTAC

GGTATTGATAACCCTGATATGAACAAGTTGCAGTTCCACTTGATGCTCGA

CGAGTTCTTTTGA

MeBLE:
(SEQ ID NO: 58)
ATGGGTACCGCCGACCAAGCGACGCCCAACTTGCCATCCAGAGATTTCGA

TTCCACGGCTGCCTTCTACGAAAGATTGGGCTTCGGTATCGTTTTCAGAG

ACGCCGGTTGGATGATCCTCCAGAGAGGTGATCTCAAGTTGGAGTTCTTC

GCCCACCCAGGTCTCGATCCACTCGCTTCCTGGTTCAGCTGCTGTTTGAG

ATTGGACGACCTCGCGGAGTTCTACAGACAGTGCAAATCCGTCGGCATCC

AGGAAACCAGCAGCGGTTACCCAAGAATCCACGCTCCAGAGTTGCAGGAG

TGGGGTGGCACGATGGCCGCTTTGGTTGACCCAGACGGTACGCTCTTGCG

TTTGATCCAGAACGAGTTGCTTGCTGGCATCTCCTGA

Figure 3:
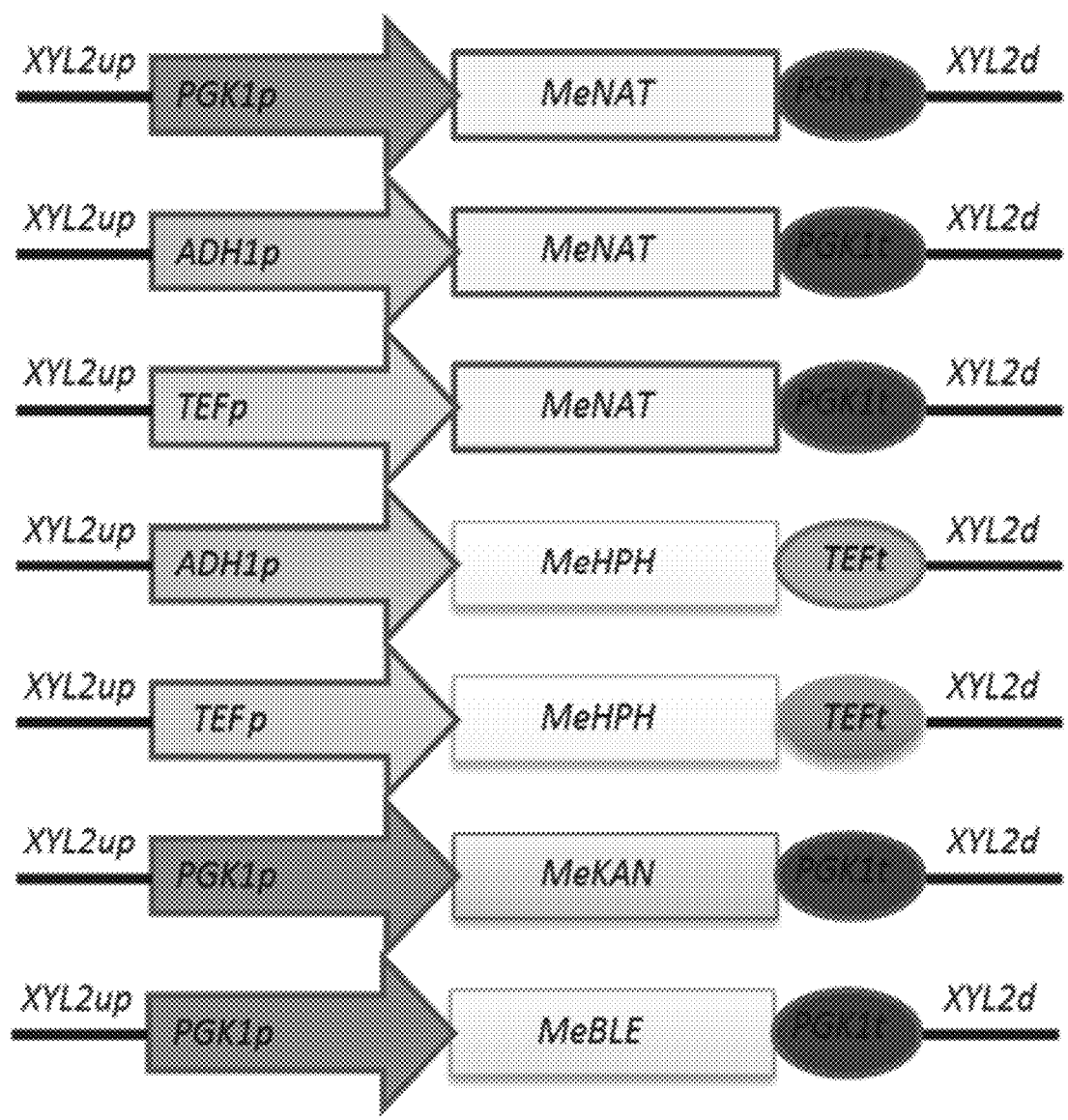
FIG. 3 shows a diagram of resistance marker gene expression cassettes for H0 *Metschnikowia* sp. genome integration.

Using a modified lithium acetate protocol (discussed below), the new anti-nourseothricin gene (named MeNAT, representing *Metschnikowia* natMX4) under the control of PGK1, ADH1 and TEF promoters and PGK1 terminator (FIG. 3) was successfully transformed into the H0 *Metschnikowia* sp. with high efficiency and resulted in nourseothricin resistant colonies. With the same protocol, the codon optimized anti-hygromycin gene (MeHPH), anti-geneticin gene (MeKAN), and anti-phleomycin gene (MeBLE) under the control of different promoters and terminators (FIG. 3) were also successfully generated and transformed into the H0 *Metschnikowia* sp. and resulted in corresponding resistant colonies. The marker gene expression cassettes were flanked by H0 *Metschnikowia* sp. gene sequences for specific genome integration by homologous recombination (FIG. 3). The length of flanking sequence affected the integration efficiency. At least 200 base nucleotides are required for homologous recombination in the H0 *Metschnikowia* sp.

In order to transform the H0 *Metschnikowia* sp., a modified lithium acetate protocol and electroporation protocol were developed. The modified lithium acetate protocol includes the following steps:

1. Inoculate a single colony to YPD broth, grow overnight at 30° C.
2. Dilute yeast cells to $OD_{600}$=0.4 in YPD and grow for another two generations till $OD_{600}$=1.5-1.8 (5 to 6 hours).
3. For each transformation, collect 5 to 10 OD cells and resuspend them in 200 µl of pre-treatment solution (0.1 M lithium acetate, 1×TE pH7.5, and 10 mM DTT). Incubate cells at 30° C. for 1 h with shaking.
4. Collect cells by centrifugation @ 13000 rpm for 1.5 min. Wash cells in 500 µl cold sterile water and collect cells by centrifugation @ 13000 rpm for 1.5 min. Cells are now ready for transformation and can be stored at 4° C. for a few hours.
5. For each transformation, prepare following mix and add to the cells:
   50% PEG: 240 µl
   1 M lithium acetate: 36 µl
   To be transformed DNA: 1-4 µg
   10 mg/ml sperm DNA 10 µl
   Add sterile $H_2O$ to: 360 µl
6. Mix cells vigorously by vortexing for 1 min.
7. Incubate cells at 30° C. for 30 min without shaking.
8. Heat shock cells at 42° C. for 20-25 min.
9. Collect cells and resuspend them in 1 ml YPD broth.
10. Incubate cells at 30° C. for 1 h with shaking (followed by step 11 to 14) or incubate cells at 30° C. for 6 h with shaking, collect cells, resuspend them in 200 µl $dH_2O$, and plate 100 µl of cells directly in selective plates and incubate at 30° C. for 2 to 3 days.
11. Collect cells and resuspend in 200 µl $dH_2O$.
12. Plate 100 µl of cells in YPD plate, and incubate overnight at 30° C. (Save the remaining 100 µl of cells at 4° C. for the second time plating if necessary)
13. Replica plate cells onto selective plates.
14. Incubate at 30° C. for 2 to 3 days.
15. The selective plates can be YPD+100 ug/mL nourseothricin (cloNAT), or 300 ug/mL hygromycin, or 200 ug/mL phleomycin, or 400 ug/ml geneticin, or the combination of these antibiotics if multiple antibiotics gene cassettes were transformed.

The electroporation protocol includes the following steps:
1. Inoculate a single colony to YPD broth, grow overnight at 30° C.
2. Dilute yeast cells to $OD_{600}$=0.4 in YPD and grow for another two generations till $OD_{600}$=1.5-1.8 (5 to 6 hours).
3. Collect 5 to 10 OD cells, wash with water and treat cells with 200 µl of LiAC-TE-DTT solution (0.1 M lithium acetate, 1×TE pH7.5, and 10 mM DTT). Incubate cells at 30° C. for 1 h with shaking.
4. Wash cells with 200 µl of 1M cold sorbitol and resuspend them in 50 µl of 1M cold sorbitol.
5. Mix cells with 5 µl DNA (1-3 µg)
6. Add the mixture to the bottom of 0.2 cm chilled electroporation cuvette. Electroporate cells at 1.8 kV, 25 µF, 200Ω.
7. Immediately add 1 ml of cold YPD broth containing 1 M sorbitol. Recover 1 h at 30° C.
8. Collect cells and resuspend them in 200 µl 1 M sorbitol.
9. Plate 100 µl of cells in YPD agar plate, and incubate the plate overnight at 30° C. (Save the remaining 100 µl of cells at 4° C. for the second time plating if necessary)
10. Replica cells to selective plates and incubate at 30° C. for 2 to 3 days.

Figure 4:
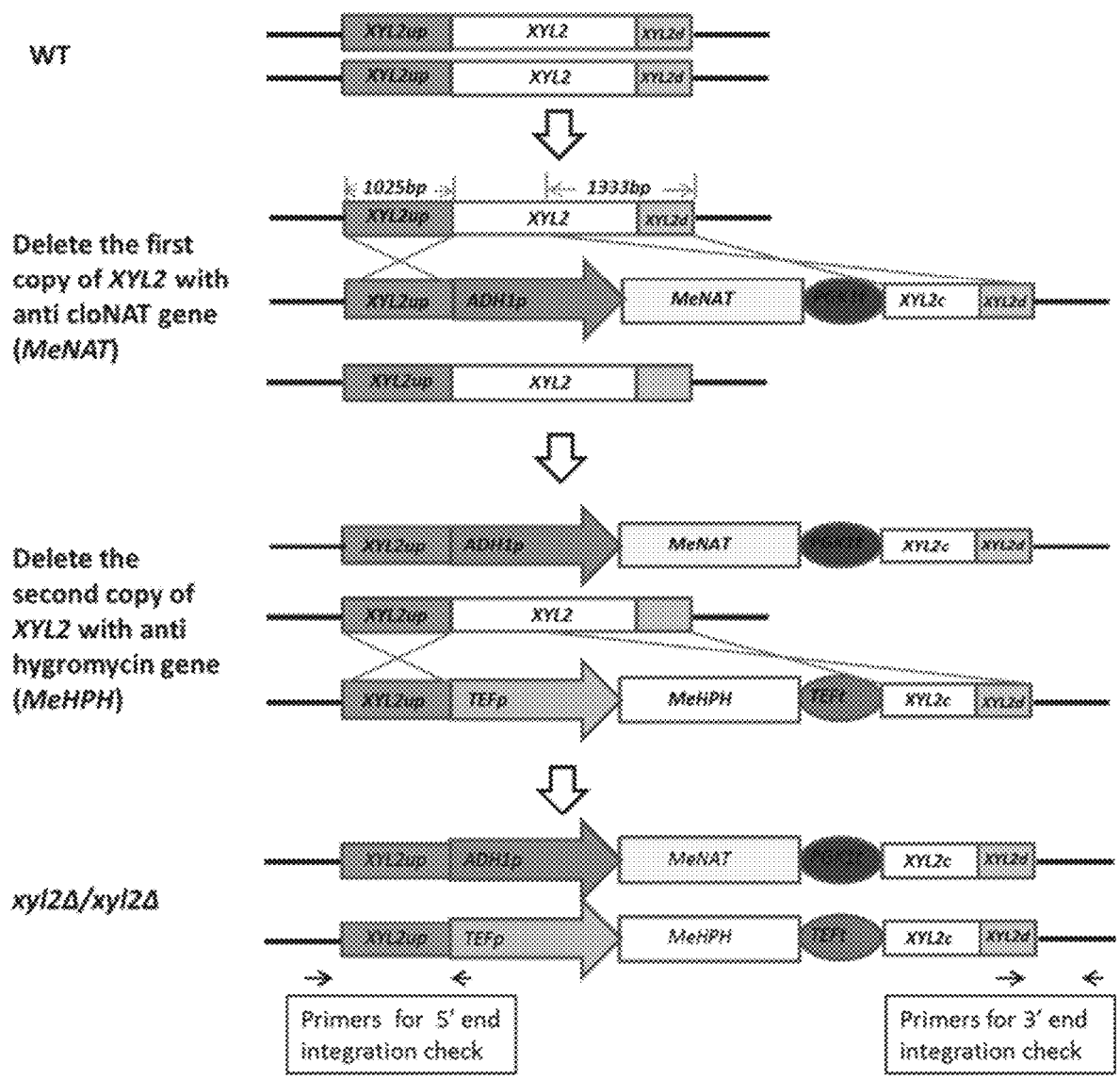
FIG. 4 shows an exemplary strategy for deletion of the XYL2 gene.

Next, deletion of the XYL2 gene was performed. An exemplary deletion strategy is shown in FIG. 4. Briefly, the first 309 nt of the XYL2 open readying frame (ORF) was replaced by an antifungal resistance gene cassette flanked by sequences homologous to the XYL2 upstream and downstream sequences.

Figure 5:
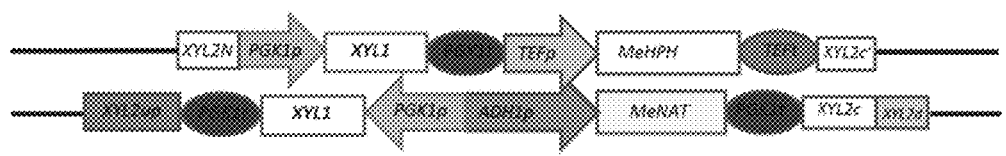
FIG. 5 shows an exemplary construction strategy of XYL1 overexpression in an XYL2 deletion strain of H0 *Metschnikowia* sp.

Then, overexpression of the XYL1 gene was introduced into the xyl2 deletion strain. The xylose reductase gene (XYL1) ORF from H0 *Metschnikowia* sp. (SEQ ID NO: 19) was linked to the PGK1 promoter and terminator. This XYL1 expression cassette was inserted into XYL2 deletion cassette discussed above (FIG. 5).

All the H0 *Metschnikowia* sp. gene sequences were amplified from the H0 *Metschnikowia* sp. yeast genome DNA by PCR using Q5 high fidelity DNA polymerase from New England Biolabs. The primers were designed by sequence homology search with the whole-genome shotgun contigs of *M. fructicola* 277 (ANFW01000000) and the whole-genome shotgun contigs of H0 *Metschnikowia* sp. Sequences amplified from the genome of the H0 *Metschnikowia* sp. and used for deletion and overexpression cassette construction discussed above and shown in FIGS. 3-5 were as follows:

XYL2up:

(SEQ ID NO: 59)
ACCGGATGCACACGAAAGGAGTATGTGCCAGCGAAGCAACAACGCCAAGT

GTCACGGATGACGAGTATGACGATGAAACAGACGTGGAGAACTGTAATGG

AGGGGAACCTGAATCAAGAGTGAGACAATACAGAACATGTGCAGATGATA

TTTTAAGTGTTCAGAGCCTTGACTAAAGCAGTTGATTCAAGACGTATAGT

ACCTTTGAAGTACCTATATAAAAGTAATAAGAGGTACTCGGCACACGTTG

ACCAATCTTATGTTTTGGCATGACTACGATGTACCGTAGAGTGTTCAATT

TGATGTTTAGATCAATCTATTAGCGACTGCGGAAAGTAAGGGAGAGCCCT

AAGAACTGAATCCCCGCATTGCCGGCGTCGACCGCAGTGAAACCAACGTA

AGTCTATTATGTCGAATGTGAACAACGAGCCAAGTGCATAGATTGGGTCT

CCCCGCGACGCACAAGCGGAGACTCCGGAGAGTCACACATGTGGCTGAGA

CGGCAAAAGTGGGCTGATTCAAGAGCAACGCATTCCAAAACATCAGATT

TTCACAAGCTTTGAATAAATTTTTATTCGCCTGACAATTACGAGCGTACT

GCGGCGATGTAAGTGAATCGGATGCCCCCATTTGTTTCATGCGCAGCCG

CAATATAATAAAAAAAAGGGGCCGATCTATGACGTAATGGCTATTTCAG

CGCTTTTATTCGAGATCTGAAGCTCGTCACTTGCTGAAGTTCGTAATATA

TTCTAACACAAATAAATTCCGACGTGGCGCATGAAACTGAGTTTATGAGG

GTCAAGCAGGATAAGAATTTACGAAAGGCTTAACGCGTGCGTTATGAACT

GAATAACCTTCGTGTCAACAACAAACTGGGGTTTCCCCGCGCTGAGTTTT

CCCGAGAATCATTGCTGCGCGAAGACTCCGACACTCTGCAGTATGCGTGG

GATGCTATAAATTATGGACGACGACGTATTCCACTTTTTTTCCTTTTCTT

TAATCAGCCGACACCATATCCGAAA

XYL2N:
(SEQ ID NO: 60)
ATGCCTGCTAACCCATCCTTGGTTTTGAACAAAGTGAACGACATCACGTT

CGAGAACTACGAGGTTCCGTTACTCACAGACCCCAACGATGTATTGGTTC

AGGTGAAAAAGACTGGAATCTGTGGATCTGACATCCACTACTACACCCAC

GGCAGAATTGGCGACTTCGTGTTGACAAAGCCAATGGTTTTGGGCCACGA

XYL2 C:
(SEQ ID NO: 61)
AGTGGCCACTACAACTTGTGCCCACACATGTGTTTTGCCGCCACGCCCAA

CTCTAACCCCGACGAGCCAAACCCGCCAGGGACTTTGTGCAAATATTACA

AGTCCCCAGCGGACTTCTTGGTGAAATTGCCTGAGCACGTCTCCCTTGAG

TTGGGCGCTATGGTCGAGCCTTTGACTGTCGGTGTGCACGCCTCGCGTTT

GGGCCGTGTCACTTTTGGTGACCACGTTGTGGTTTTCGGTGCTGGCCCAG

TCGGTATCCTTGCGGCTGCCGTGGCCAGAAAGTTTGGCGCTGCCAGCGTG

ACTATCGTCGACATCTTCGACAGCAAATTGGAATTGGCCAAGTCCATTGG

CGCGGCCACTCACACATTCAACTCAATGACTGAGGGTGTTCTTTCGGAGG

CTTTGCCCGCGGGCGTGAGACCTGACGTTGTATTGGAGTGCACTGGAGCA

GAGATCTGTGTGCAGCAAGGTGTACTTGCGTTGAAGGCTGGTGGCCGCCA

CGTGCAAGTTGGAAATGCCGGCTCCTATCTCAAATTCCCCATCACCGAAT

TTGTTACCAAGGAGTTGACTCTCTTTGGATCCTTCCGTTACGGTTACAAC

GACTACAAGACGTCGGTCGCCATCTTGGACGAGAATTACAAGAACGGGAA

GGAGAATGCGTTGGTGGACTTTGAAGCCTTGATTACTCACCGTTTCCCCT

TCAAGAATGCCATTGAGGCTTACGACGCGGTGCGCGCTGGCGACGGAGCT

GTCAAGTGTATCATTGACGGCCCAGAGTAA

XYL2C':
(SEQ ID NO: 62)
CCTTCCGTTACGGTTACAACGACTACAAGACGTCGGTCGCCATCTTGGAC

GAGAATTACAAGAACGGGAAGGAGAATGCGTTGGTGGACTTTGAAGCCTT

GATTACTCACCGTTTCCCCTTCAAGAATGCCATTGAGGCTTACGACGCGG

TGCGCGCTGGCGACGGAGCTGTCAAGTGTATCATTGACGGCCCAGAGTAA

XYL2 d:
(SEQ ID NO: 63)
CGATGAAATAAAAAGATAATACTTGCTCTTACTCCATTTATAGACTAATG

TACGCTGCTTCACGATAGTTTTCCTCACGATAGTTTATTTAGGCTCGTCG

AGTCTCGCCGTCTCGCATGCTCATGAGATCGTTGGCGAGCTCTCTTTCTT

GTCTGCTCCGGCCATTCATGGTGGAGGCTATTGAATTTTCAAACTTTGAC

AGTGATGAGTGCCTACCGAAGGTTGCATATTGGTAAGGCACATCGTGCGT

GTATGAGCTTGCCGGATACTGCATGAGAAATGATGCTGGGACCGCAGAAT

TCAGCAAGTTTGCCAGCGATGTGCTTGTCAGTTTCGCCTCCATCACGTCA

TTCGTAGTGGACGCAATAGCGCTTGAAGACTGCGTTGGCCGAACCAGTCT

GCTTCCATCAGCGTGAATCTTGTTCAGCATACCCGACAACATCTTCGTCT

TGTATTTGATGTACTTCAAAATTCTGAGATACTTCAAGTCCTCGTCTAGA

TTCTCGTCATCCCAATCGATATCGGTACTCTCTGCATCTTCGACATCGGA

CTC

XYL1:
(SEQ ID NO: 64)
ATGCCCCAAGTGGGGTTTGGGTGCTGGAAAGTAACTAACAGTACATGTGC

TGATACGATCTACAACGCGATCAAAGTTGGCTACAGATTATTTGATGGCG

CTGAAGATTACGGGAACGAGAAAGAGGTGGGCGAAGGAATCAACAGGGCC

ATTGACGAAGGCTTGGTGGCACGTGACGAGTTGTTCGTGGTGTCCAAGCT

CTGGAACAACTTCCATCATCCAGACAACGTCGAGAAGGCGTTGGACAAGA

CTTTGGGCGACTTGAATGTCGAGTACTTGGACTTGTTCTTGATCCATTTC

CCAATTGCGTTCAAATTCGTGCCCTTTGAGGAGAAATACCCGCCCGGCTT

CTACTGTGGAGAAGGCGATAAGTTTATCTACGAGGATGTGCCTTTGCTTG

ACACGTGGCGGGCATTGGAGAAGTTTGTGAAGAAGGGTAAGATCAGATCC

ATCGGAATCTGAACTTTTCCGGCGCGTTGATCCAGGACTTGCTCAGGGG

CGCCGAGATCCCCCCTGCCGTGTTGCAGATTGAGCACCACCCATACTTGC

AGCAGCCCAGATTGATTGAGTATGTGCAGTCCAAGGGTATTGCCATCACA

GCCTACTCCTCTTTTGGCCCACAGTCGTTTGTGGAGTTGGACCACCCCAA

GGTCAAGGAGTGTGTCACGCTTTTCGAGCACGAAGACATTGTTTCCATCG

CTAAAGCTCACGACAAGTCCGCGGGCCAGGTATTATTGAGGTGGGCCACG

CAAAGGGGTCTTGCCGTGATTCCAAAGTCAAACAAAACCGAGCGTTTGTT

GCTGAATTTGAATGTGAACGATTTTGATCTCTCTGAAGCAGAATTGGAGC

AAATCGCAAAGTTGGACGTGGGCTTGCGCTTCAACAACCCTTGGGACTGG

GACAAGATTCCAATCTTCCACTAA

ADH1 promotor:
(SEQ ID NO: 65)
TTGTCTTGTAAAGAGTCTTCGGTCATTTTTACGCCGAATCGGCCTCTGGT

GTACAGGTGTAATGTAAGCAGAAAGATGTAGATAATACATAGCGTCAACG

GTTCTATCGAGTCAGGATTGACTGCGGGCCAAATGTGGGGTATCACGTG

TCGATGGAAACTGTCAACAAAAGATGAATTTTTTTTTGATCGTCAACGCT

GCTCTAAGCGTGAATCAAGGATATGCGCTTATGGGGACGTGCGATCCGCG

CCGCATTCACCCGAAGAACGTGCTCTCGATCGATCACCCGGCGCCGCGCA

CGGCCCAATCGAGAAAGAGGGACCTCGGAGATAAGCACCCCCTTTCTCGA

AGTATGTACATATTATTTACAGCGAAATCACAAAGGCCAAGTCTACTCTC

TATCACAATGATTATTTGCACGCTAGAAGTTTGCCGCCCCTCTTTCCTCA

TTCAAAGCTGTTTCAGAAATGCACTCGTAAGCGCATGTTCGTATCGGCAT

CGCAGGCTCAAATGCCCAGGAGCCGCCCGCGCAGCCCCATAAACCCATTT

CAGGCATATGCGCCTAGTGGCCCGCAGCGTGCGCGAGCACCGAACATCAC

CCCACAGCAATGTATAAAACCCGAACAATATAAAAGCGATCCACATCGCT

CGGTAATGCGTCCGTTCTTTCGTTCATCAGTATCACTTGCATTCACTTCA

CGAATCCGAGCTACAAACATCATCGCAATCAGAAA

-continued

PGK1 promoter:
(SEQ ID NO: 66)
ATGTTCTGGGTGTTTCTGGTTTGGAGACTGGCTCAGAGATAAAGCAACCG

GGTGAATAGAGATACAGTTTATTTGAGGCGGAAAGAGATCATCAGGCATA

CAAAATGCGTTTCGAGAATAAAGTTTTGTTGGAATGCCTTTATGCGTGAT

GTTGATGTGGGGATCTGTAAAGCAACTTGACCTGCAATTGCATTGCATGG

GCCCGGTCGTGCTCATTTGTTGGTATGCGCTTATCCGGGCAACCACGTTG

TTGAAAAGCGCGGATGGGCCGGAGTACTCACAGCAAGGGCAATCGACCAC

ATTTATTCTTAGCGCCCATAGTTCAGGCGTCCGGAGTCATCAGCGGATGG

TATCTGTTGAAAATAAAGTCTCCTAGAGTTTTTAATGTAATTACTTGCGT

TTTCGATTTTTGTAGAAAGTTTTGGAGTTTGTGGGACTGAACTCAGGCCC

AATGCGATTTCCGAATCTGGAGAAACGTAGTCGATATGCGATTAGGGGTA

ACAAAAAGATTTCATAGTCACACAAAGATCAATTCGACAGTATTTTGCAG

TGATTGCATTGAAGGCCATAATATCATTGCAAATAGTGTCTATTTGGGCC

CATTGGTGAATTCTGTCTGTGTTGAGTCATTCAAGACACAGCAATCAATT

CGATTGCAGTCTCGCAGGTGGTGTGGTTGTGGTGCGACTTGAAAAACCCG

GAGGATGGTAATCCGCCGAGAATGAACTCCGAGCGAAAACCCGTCAGACA

TATATAAACCCTCACAGTGCGCACTACTCGCCTGGAAAAATTAGAATTCG

TTTCTATCAATTCATCTCCATTTGATATCAATTGATTCGCATACTAAAAT

CTATAACTA

PGK1 terminator:
(SEQ ID NO: 67)
GTAGTTCGATAAGTTTGACACTTACCGATTGAATACACATTTTAATCTAT

GACTTTCATGTTTATTATGTATATTGAGGTCCAAAGCGTGTAAAAGGGCG

GAGACATGTTCACAACTTAGCGGCTCCACTCATGATTTTGGTCCACGACT

CTTCAGTCAATTCTTCATACCTGTTCTTGTTCAACCAGTAGATCAACTCT

TTGCCGTCATCGCCCTTTGGTAACTTTTGATTCTTGAACTGATTTTTTGG

CACCTTGTGATTGTGAGATGCTTGTATGTATTG

The TEF promoter and terminator sequence was amplified from the plasmid pUG6 (Güldener et al., 1996, Nucleic Acids res., 24:2519-2524).

Example III

Production of Xylitol from Xylose by Recombinant Metschnikowia Species Using Cellobiose as a Co-Substrate This example demonstrates that recombinant Metschnikowia species having a xylitol pathway increases production of xylitol from xylose when cultured with xylose and cellobiose.

The xylitol dehydrogenase inactivated strain cannot grow in the media with xylose as the sole carbon source (data not shown). Therefore several different co-substrates were screened and cellobiose was found to work well as a co-substrate (data not shown).

The wild-type H0 Metschnikowia sp., xyl2 deletion strain, and xyl2 deletion plus XYL1 overexpression strain were pre-grown in YPD at 30° C. until $OD_{600}$=~10. Cells (120 OD) were collected and re-inoculated in 6 ml of xylose plus cellobiose media solution in a 15 ml test tube and incubated at 30° C. on a rotator with a speed of 150 rpm/min. The medium contained 4%, 6%, 8% and 10% (w/v) xylose plus half the amount of cellubiose, respectively. A 600 µL of sample was taken each time for analyses and yeast cells were removed by centrifugation. The supernatant was filtered using a 2 µm syringe filter and 4 µl was analyzed by HPLC to quantify xylose, cellobiose and xylitol.

Figures 6A, 6B, 6C:
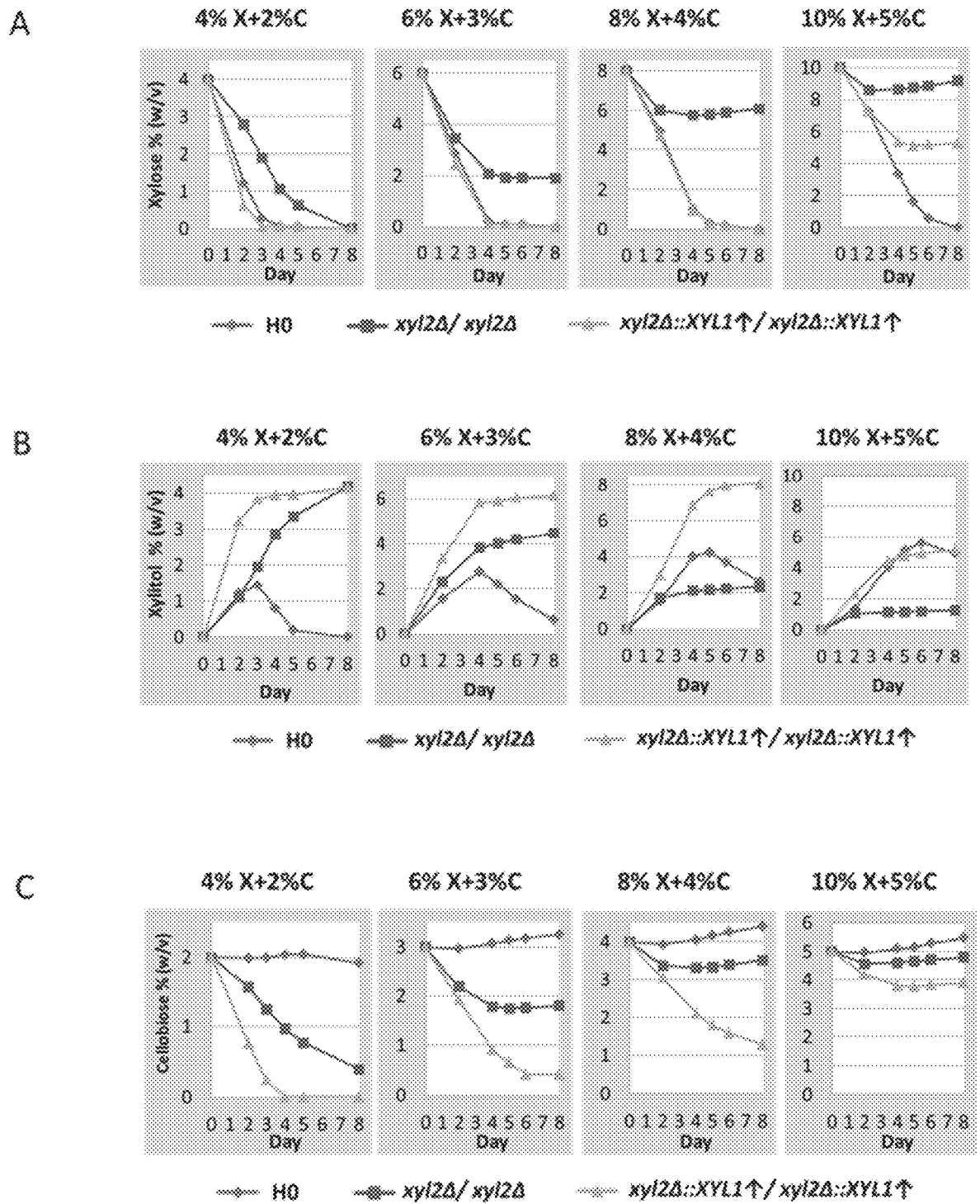
FIGS. 6A-6C show the consumption of xylose (FIG. 6A), production of xylitol from xylose (FIG. 6B), and utilization of cellobiose (FIG. 6C) for wild-type H0 *Metschnikowia* sp. (H0), xyl2 deletion H0 *Metschnikowia* sp. strain (xyl2Δ/xyl2Δ) and overexpression of XYL1 together with xyl2 deletion H0 *Metschnikowia* sp. strain (xyl2Δ::XYL1↑/xyl2Δ::XYL1↑) when cultured in different concentrations of xylose (X, ≤10%) and cellobiose (C).

All three strains consumed some xylose, but the xyl2 deletion strain (xyl2Δ/xyl2Δ) consumed the least amount of xylose and overexpression of XYL1 together with xyl2 deletion (xyl2Δ::XYL1↑/xyl2Δ::XYL1↑) made the H0 Metschnikowia sp. consume xylose most efficiently in 8% xylose and 4% cellobiose (FIG. 6A).

For the wild type H0 Metschnikowia sp., the xylitol concentration increased and then decreased along the time course, which is evidence that it converted xylose to xylitol by xylose reductase, and simultaneously dehydrogenated xylitol to xylulose by xylitol dehydrogenase (FIG. 6B). The maximum amount of xylitol produced by the H0 Metschnikowia sp. wild type yeast was 1.45% from 4% xylose in 3 days, 2.76% from 6% xylose in 4 days, 4.23% from 8% xylose in 5 days and 5.63% from 10% in 6 days (FIGS. 6A and 6B). The maximum amount of xylitol produced by xyl2 deletion strain in 8 days was 4% from 4% xylose, 4.4% from 6% xylose, 2.35% from 8% xylose and 1.25% from 10% xylose, while the maximum amount of xylitol produced by overexpression of XYL1 together with xyl2 deletion strain in 8 days was 4% from 4% xylose, 6% from 6% xylose, 8% from 8% xylose and 5.1% from 10% xylose.

Without being bound by theory, too high of a concentration of xylose appeared to inhibit the production of xylitol from xylose. For example, the xyl2 deletion strain converted all of the xylose to xylitol in 4% xylose media, but only converted 4.4% from 6% xylose, 2.35% from 8% xylose and 1.25% from 10% xylose into xylitol (FIGS. 6A and 6B). Also, overexpression of XYL1 together with xyl2 deletion produced 79.5 g/L xylitol from 80 g/L xylose in 6 days, so the conversion rate was 0.99 g xylitol/g xylose and the volumetric productivity was 0.55 g/L/h (FIG. 6B). However, in 10% xylose media, the same strain only converted half amount of xylose into xylitol (5.1%) in 6 days. Thus, overexpression of XYL1 together with xyl2 deletion made the H0 Metschnikowia sp. work well in xylitol production in up to 8% xylose using cellobiose as a co-substrate (FIG. 6B).

Cellobiose metabolism was suppressed in the wild type H0 Metschnikowia sp., but was utilized by the other recombinant H0 Metschnikowia sp. strains to support the activity of xylose reductase (FIG. 6C). The leftover cellobiose in the media indicates the cellobiose that was added was too much.

Figure 7:
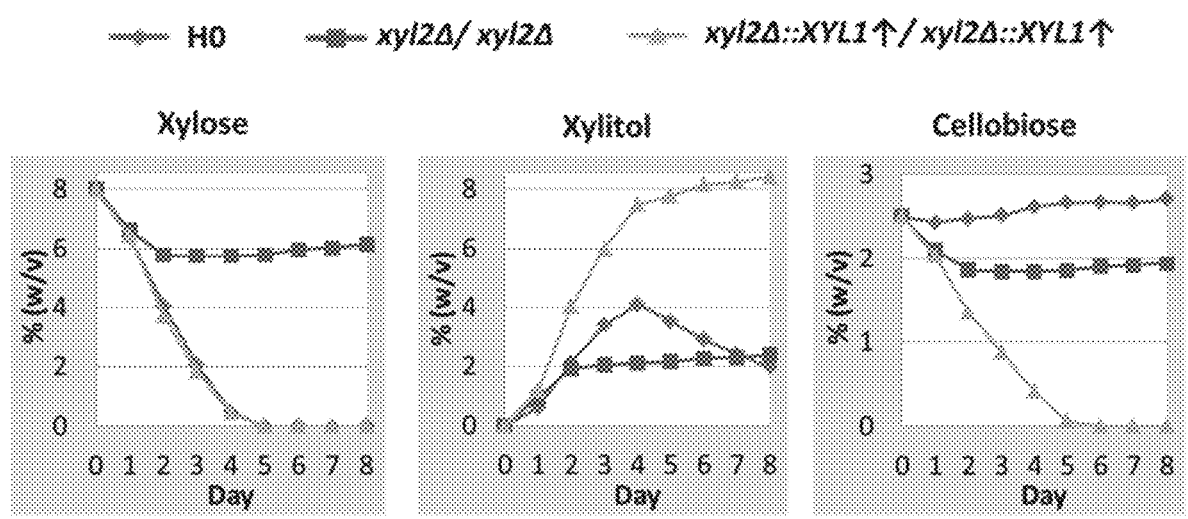
FIG. 7 shows the consumption of xylose, production of xylitol from xylose, and utilization of cellobiose for wild-type H0 *Metschnikowia* sp. (H0), xyl2 deletion H0 *Metschnikowia* sp. strain (xyl2Δ/xyl2Δ) and overexpression of XYL1 together with xyl2 deletion H0 *Metschnikowia* sp. strain (xyl2Δ::XYL1↑/xyl2Δ::XYL1↑) when cultured in 8% (w/v) xylose and 2.5% (w/v) cellobiose.

The cellobiose to xylose ratio was reduce from 1:2 to 1:3 and 1:4 and found that 1:3 (2.4% cellobiose in 8% xylose) worked better. These experiments were repeated in 8% xylose plus 2.4% cellobiose in 50 ml culture. The H0 Metschnikowia sp. strain with overexpression of XYL1 together with xyl2 deletion produced 77.7 g/L xylitol from 80 g/L of xylose in 5 days with xylitol yield of 0.97 g/g xylose and productivity of 0.65 g/L/h (FIG. 7).

Thus, deletion of the XYL2 gene and overexpression of the XYL1 gene in the H0 Metschnikowia sp. increased the production of xylitol to a yield of 0.97-0.99 g/g of xylose and productivity of 0.55-0.65 g/L/h using cellobiose as a co-substrate. One additional advantage of using the recombinant H0 Metschnikowia sp. having a deletion of the XYL2 gene and overexpression of the XYL1 gene is that the production medium consisted of only xylose, cellobiose and water, which allows for easy purification and cost effective production.

Example IV

Production of Xylitol from Xylose by Recombinant *Metschnikowia* Species Using Galactose as a Co-Substrate This example demonstrates that use of galactose as a co-substrate significantly enhanced production of xylitol in recombinant *Metschnikowia* species having a xylitol pathway.

The wild-type H0 *Metschnikowia* sp., the xyl2 deletion strain, and the xyl2 deletion plus XYL1 overexpression strain were pre-grown in YPD at 30° C. till $OD_{600}$=~10. Cells (120 OD) were collected and re-inoculated in 6 ml of media in a 15 ml test tube and grown at 30° C. on a rotator with a speed of 150 rpm/min. The media contained 10%, 12%, 14%, 16%, 18% and 20% (w/v) xylose plus one-fifth amount of galactose, respectively. 600 μL of sample was taken each day and cells were removed by centrifugation. The supernatant was filtered by a 2 μm syringe filter and 4 μl was applied to an HPLC to quantify xylose, cellobiose and xylitol.

Figure 8:
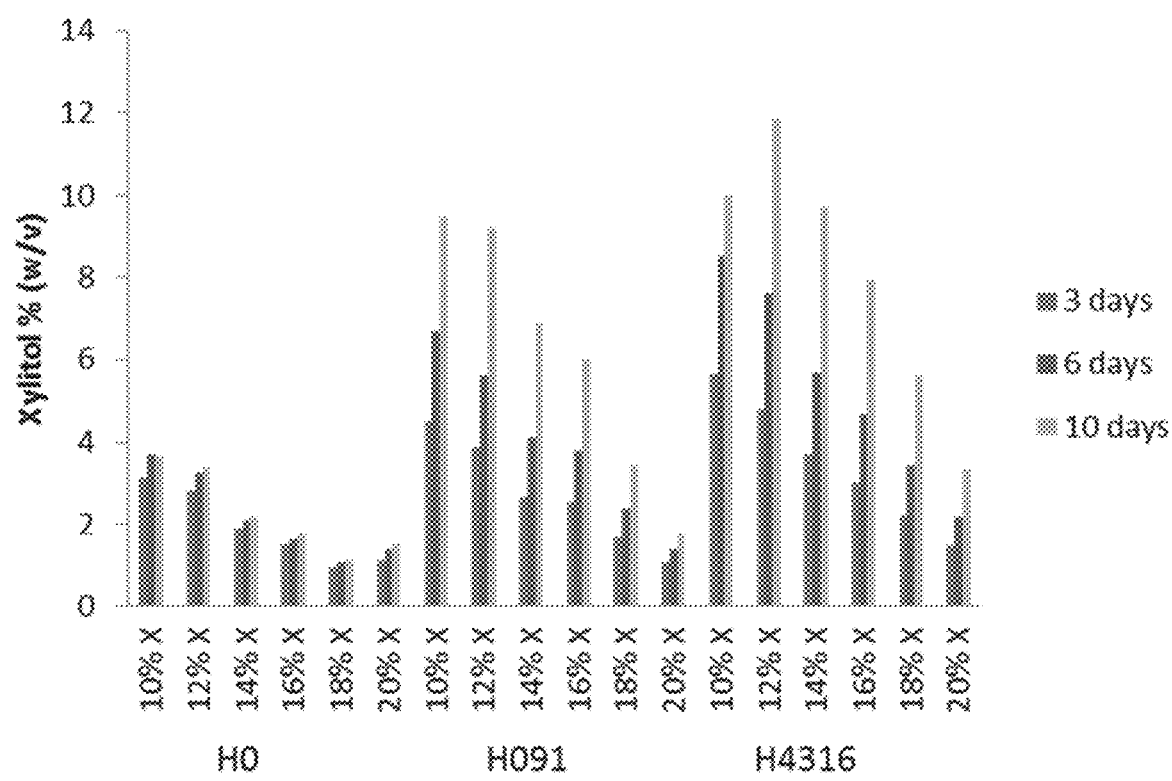
FIG. 8 shows the production of xylitol from xylose for wild-type H0 *Metschnikowia* sp. (H0), deletion H0 *Metschnikowia* sp. strain (H091: xyl2Δ/xyl2Δ) and overexpression of XYL1 together with xyl2 deletion (H4316: xyl2Δ::XYL1↑/xyl2:XYL1↑) when cultures in different concentration of xylose (10%≤X≤20%)) and galactose.

By using galactose as a co-substrate, within 10 days, the maximum amount of xylitol produced was from 12% xylose media by xyl2 deletion plus XYL1 overexpression (FIG. 8, H0=wild type; H091=xyl2Δ/xyl2Δ; H4316=xyl2Δ::XYL1↑/xyl2Δ::XYL1↑). The xyl2 deletion plus XYL1 overexpression strain (H4316) produced over 200 g/L xylitol with a yield of 0.98 g/g and productivity of 0.53 g/L/h.

Figure 9:
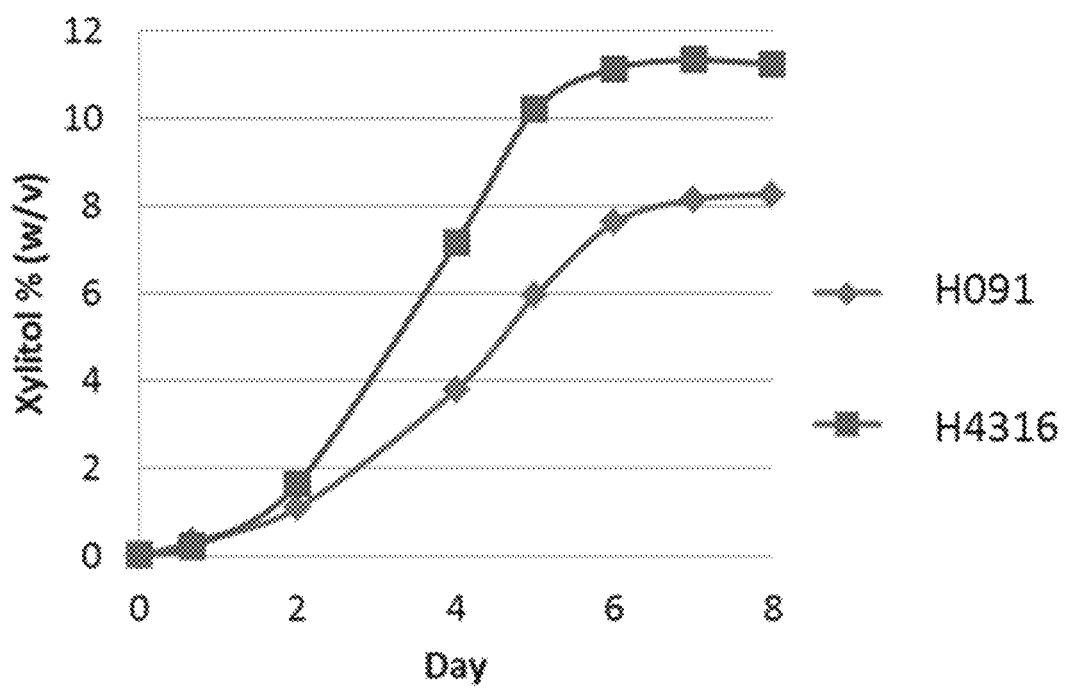
FIG. 9 shows xylitol production by recombinant H0 *Metschnikowia* sp. from 12% (w/v) xylose using galactose as co-substrate. H091=xyl2 deletion strain; H4316=xyl2 deletion plus XYL1 overexpression strain.

Further experiments using 12% xylose plus 4% galactose showed that the xyl2 deletion strain (H091) produced 7.6% xylitol in 6 days, while the xyl2 deletion plus XYL1 overexpression strain (H4316) produced 113 g xylitol from 120 g xylose in 6 days (FIG. 9), which exceeded the previously reported 93 g/L xylitol production by an engineered *S. cerevisiae* strain using cellobiose as a co-substrate (Oh et al., 2013, *Metab. Eng.*, 15:226-234).

Production of xylitol from xylose was further increased by use of modified medium in a fed-batch method. The wild-type H0 *Metschnikowia* sp., the xyl2 deletion strain, and the xyl2 deletion plus XYL1 overexpression strain were pre-cultured in YPD overnight at 30° C. and cells (30 OD) were collected and suspended in 4 ml $H_2O$ in a 15 ml test tube. 2 ml of medium (24% xylose, 8% galactose, 0.5% yeast extract, 1% peptone, 0.05% $KH_2PO_4$, 0.05% $MgSO_4$, 0.05% $(NH_4)_2SO_4$ and 1% glucose) were added and the test tube was incubated at 30° C. on a rotating drum with speed of 150 rpm. A 500 μl of sample was taken for HPLC analysis. Starting from day 2 to day 10, 500 μl of production media was added every day after sampling. In accordance with the previous results, 8% xylose was used as an initial concentration in the medium and 0.5 ml of medium was added every day from day 2 to day 10 (fed-batch) to keep xylose levels above 3% and below 8%.

Figures 10A, 10B, 10C:
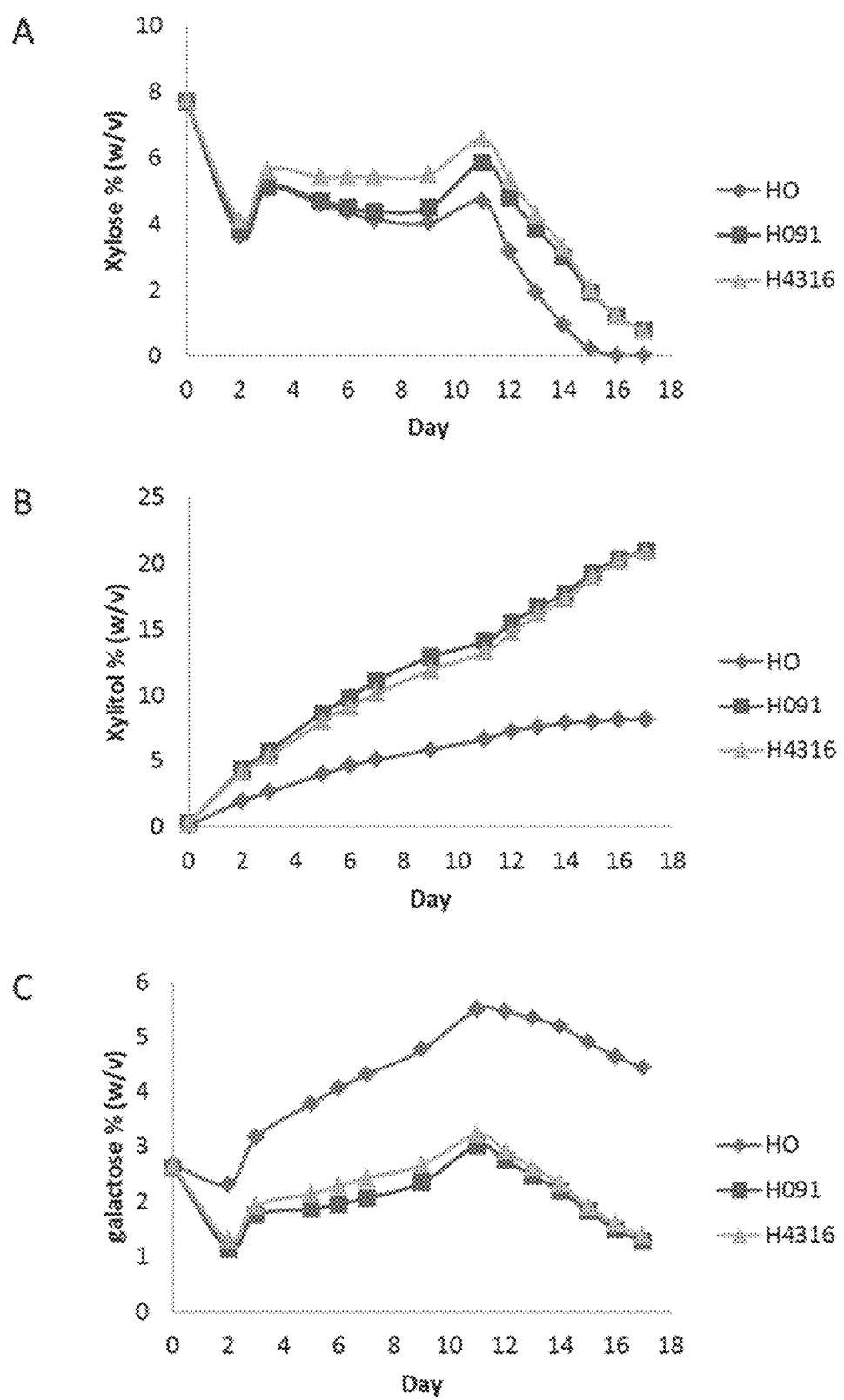
FIGS. 10A-10C show xylose consumption (FIG. 10A), xylitol production (FIG. 10B) and galactose utilization (FIG. 10C) by the recombinant H0 *Metschnikowia* sp. H0=wild type; H091=xyl2 deletion strain; H4316=xyl2 deletion plus XYL1 overexpression strain.

The above experiment showed that with the addition of a low amount of glucose and other nutrients, wild-type H0 *Metschnikowia* sp. and both recombinant H0 *Metschnikowia* sp. strains can continuously consume xylose and produce xylitol (FIGS. 10A-10C). The wild-type H0 *Metschnikowia* sp. produced 8.1% xylitol in 16 days, while the xyl2 deletion mutant (H091) produced 20.3% xylitol in 16 days with a yield of 0.98 g/g and productivity of 0.53 g/L/h. Overexpression of XYL1 plus xyl2 deletion (H4316) showed similar xylitol production as xyl2 deletion mutant. After 17 days, about 0.8% xylose and 1.3% galactose was left in the media by xyl2 deletion strain, indicating that galactose can be further reduced.

Production of xylitol from xylose was further increased by re-feeding with solid xylose. The wild-type H0 *Metschnikowia* sp., and the xyl2 deletion strain were pre-cultured in YPD overnight at 30° C. and cells (30 OD) were collected and suspended in 20 ml water in a 125 ml flask. 10 ml of medium (24% xylose, 8% galactose, 0.5% yeast extract, 1% peptone, 0.05% $KH_2PO_4$, 0.05% $MgSO_4$, 0.05% $(NH_4)_2SO_4$ and 1% glucose) was added and the flask was incubated at 30° C. incubator shaking at 120 rpm. A 600 μl of sample was taken for HPLC analysis to monitor xylose content in the medium. Xylose powder and other nutrients with the same ratio as the above medium were added 5 times to the flask to maintain the xylose concentration between 2% and 10%.

Figure 11:
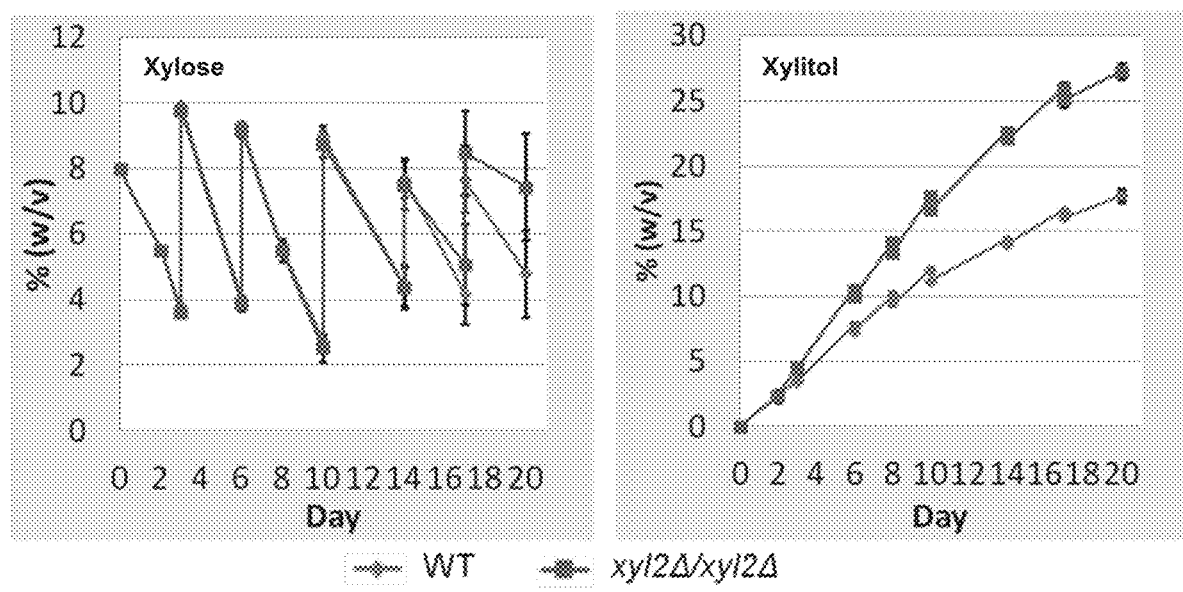
FIG. 11 shows xylose consumption and xylitol production in a 5× re-feeding with solid xylose.

The above experiment showed that with the addition of solid xylose into the medium, wild-type H0 *Metschnikowia* sp. and the xyl2 deletion strain can continuously consume xylose and produce over 17% (w/v) and 27% (w/v) of xylitol in 20 days, respectively (FIG. 11).

Based on the above, using galactose as a co-substrate, and the addition of nutrients including additional xylose, more than 27% of xylitol was obtained by using the XYL2 deleted H0 *Metschnikowia* sp. with a productivity of 0.56 g/L/h.

Galactose is one of the most abundant sugars in marine biomass, especially in red seaweed. Hence, marine biomass is an attractive renewable source for the production of xylitol. As such, using the method described in this example, marine biomass can be utilized to produce xylitol by a recombinant *Metschnikowia* species having a xylitol pathway that converts xylose to xylitol.

Example V

Increasing Production of Xylitol from Xylose by Overexpressing a Xylose Transporter This example demonstrates that increasing the transport of xylose into a recombinant *Metschnikowia* species having a xylitol pathway can speed up production of xylitol.

The strain was constructed by replacing one copy XYL2 in the H0 *Metschnikowia* sp. wild type strain with a GXF1-XYl1 overexpression cassette (XYL2p-MeHPH-TEF1t-TPIp-GXF1-DIT1t-UBI4p-XYL1-XYL2t) or a GXF2-XYL1 overexpression cassette ((XYL2p-MeHPH-TEF1t-TPIp-GXF1-DIT1t-UBI4p-XYL1-XYL2t). The other copy of XYL2 was kept wild type or replaced by ADH1p-MeNAT-PGK1t cassette.

The H0 *Metschnikowia* sp. wild type strain, xyl2 deletion strain, and transporter-xylose reductase overexpression along with xyl2 deletion strains were pre-grown in YPD medium. Yeast cells were collected and resuspended in 6 ml YP xylose (8%) medium plus 4% galactose, or 4% cellobiose, or 4% glycerol as a co-substrate. 600 μl of sample was taken for HPLC analysis to measure the consumption of xylose and production of xylitol.

Figure 12A:
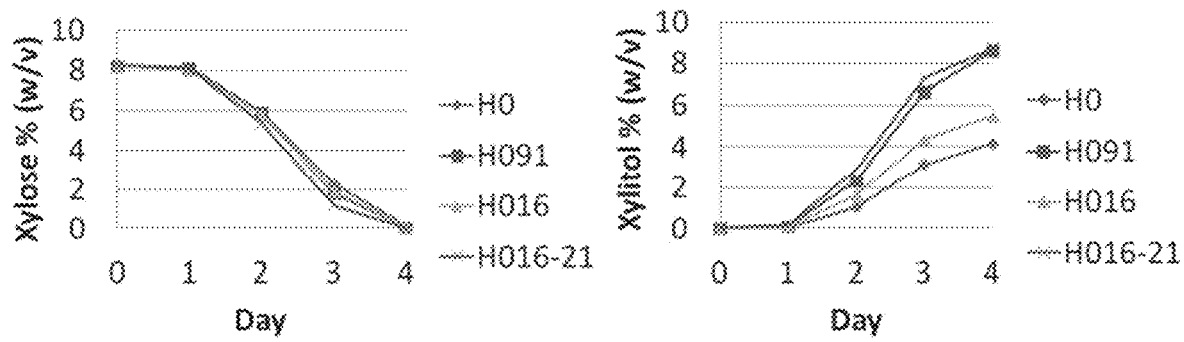
FIGS. 12A-12C show xylose consumption and xylitol production by H0 *Metschnikowia* sp. having a xylitol pathway and overexpression of a xylose transporter in a method using galactose as a co-substrate (FIG. 12A), cellobiose as a co-substrate (FIG. 12B), or glycerol as a co-substrate (FIG. 12C). H0=wild type; H091=xyl2 deletion strain; H016=strain with one copy of XYL2 replaced with GXF1 and XYL1 overexpression cassette; H016-21=xyl2 deletion plus GXF1 and XYL1 overexpression strain.
Figure 12B:
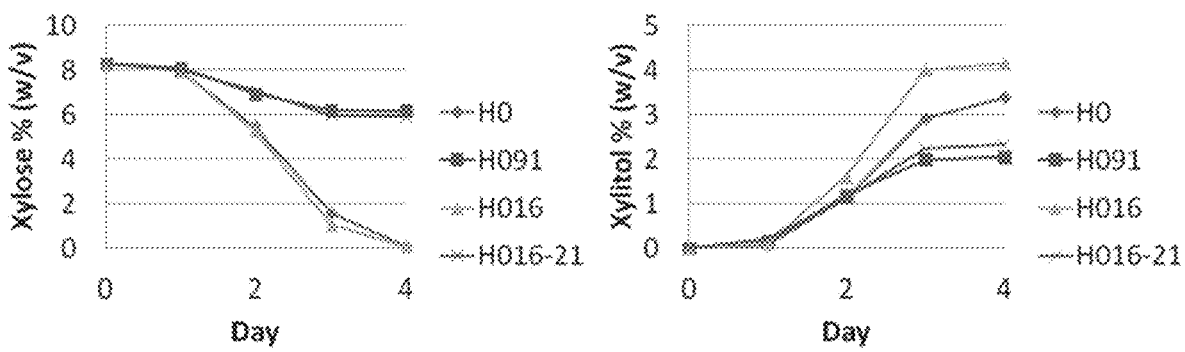
Figure 12C:
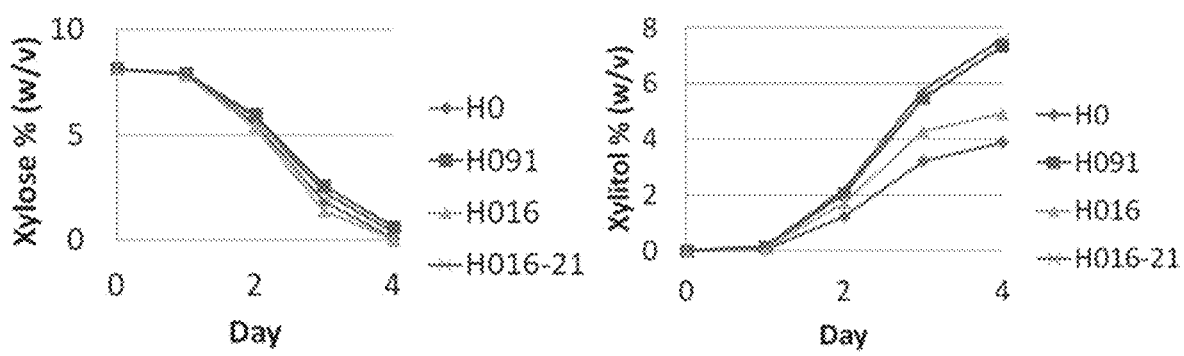
Figure 13:
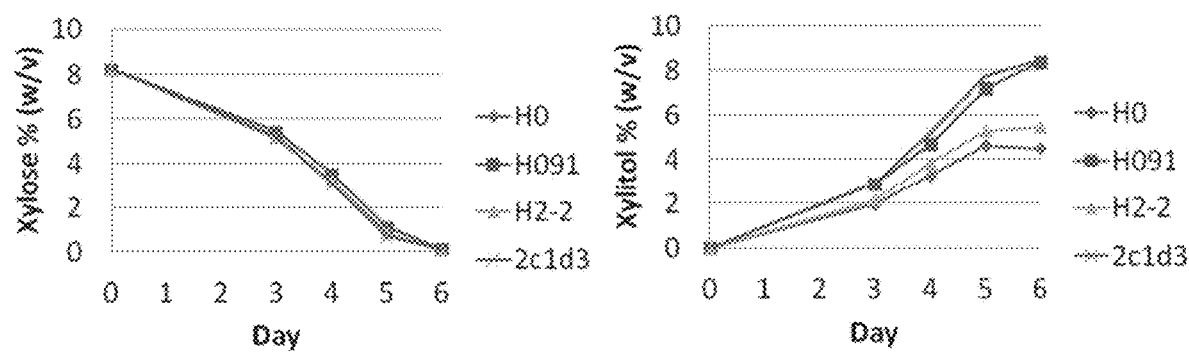
FIG. 13 shows xylose consumption and xylitol production by H0 *Metschnikowia* sp. having a xylitol pathway and overexpression of a xylose transporter in a method using galactose as a co-substrate. H0=wild type; H091=xyl2 deletion strain; H2-2=strain with one copy of XYL2 replaced by GXF2 and XYL1 overexpression cassette; 2c1d3=xyl2 deletion plus GXF2 and XYL1 overexpression strain.

The above experiment showed that with the overexpression of the GXF1 xylose transporter in the xyl2 deletion plus XYL1 overexpression strain resulted in about 5% to 10% faster production of xylitol when cultured in medium having xylose and the co-substrate galactose (FIG. 12A) or cellobiose (FIG. 12B) or glycerol (FIG. 12C) compared to xyl2 deletion strain, although use of the co-substrate cellobiose did not improve xylitol production in the engineered strains (FIGS. 12A-12C, H0=wild type; H091=xyl2 deletion strain; H016=one copy of XYL2 replaced by GXF1 and XYL1 overexpression strain; H016-21=xyl2 deletion plus GXF1 and XYL1 overexpression strain). Moreover, overexpression of the GXF2 xylose transporter in the xyl2 deletion plus XYL1 overexpression strain also resulted in about 5% to 10% faster production of xylitol when cultured in medium having xylose and galactose as the co-substrate (FIG. 13, H0=wild type; H091=xyl2 deletion strain; H2-2=one copy of XYL2 replaced by GXF2 and XYL1 overexpression strain; 2c1D3=xyl2 deletion plus GXF2 and XYL1 overexpression strain).

Based on the above, over expression of a xylose transporter can improve the speed at which xylitol can be produced by a recombinant *Metschnikowia* species having a xylitol pathway.

Example VI

Fed-Batch Fermentation in 3 L Bioreactor

This example demonstrates that using a fed-batch fermentation methodology production of xylitol from xylose can be increased to at least 30% xylitol.

Using the recombinant *Metschnikowia* species strain H016-21 (1 copy of TPI1p-GXF1-DIT1t-UBI4p-XYL1 in xyl2 deletion strain), 2 L fed-batch fermentation was conducted in the 3 L bioreactors (Applikon Biotechnology). Two independent experiments were performed.

Figure 14A:
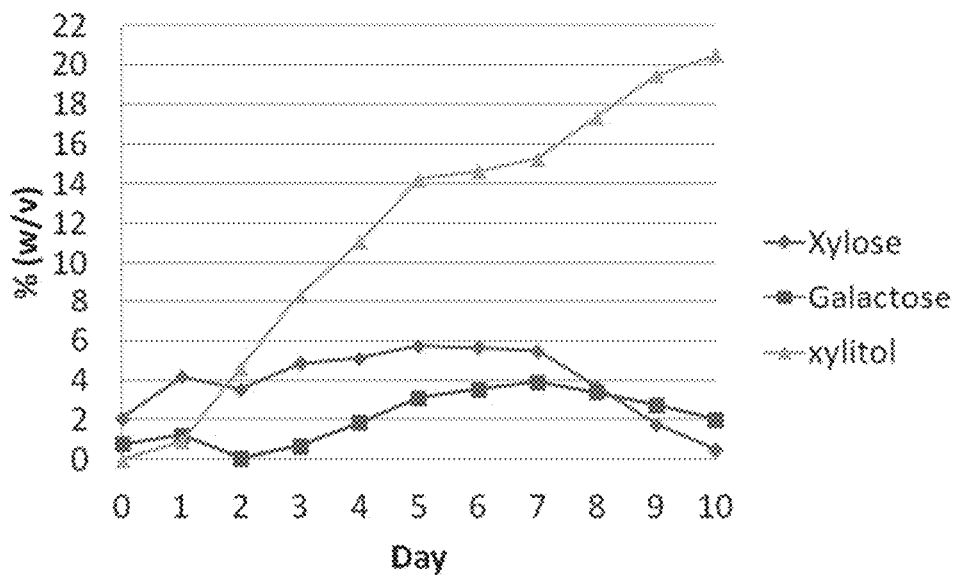
FIGS. 14A and 14B show xylose and galactose consumption and production of xylitol by xyl2 deletion plus GXF1 and XYL1 overexpression strain using fed-batch fermentation using different feeding medium and aeration rate.

The procedures for the first fed-batch fermentation are: yeast cells were grown in 50 ml of YPD overnight at 30° C., and transferred to 500 ml of YPD. 167 ml of the culture was then mixed with 50 ml of 40% xylose and 33 ml of 20% galactose and transferred to 750 ml YPD in the 3 L vessel with the final inoculum at $OD_{600}$=2.0. The vessel was sparged in the medium with air or oxygen. The minimum agitation rate was 300 rpm, and was automatically adjusted to maintain the dissolved oxygen (DO) level at 50% saturation. The pH was kept at 5.5-6.0. The feeding stock contains 36% xylose, 12% galactose, 1.5% glucose, 1.5% peptone, 0.75% yeast extract, 0.075% $KH_2PO_4$, 0.075% $MgSO_4.7H_2O$, 0.075% $(NH_4)_2SO_4$. The feeding speed was adjusted to maintain the xylose level lower than 6%. 1 L of stock media was added in 7 days, and the fermentation was continued for another 3 days to consume the remaining xylose in the medium. Total fermentation lasted for 10 days and 20% xylitol was produced in 2 L volume (FIG. 14A), 3 days shorter than the previous best result.

Figure 14B:
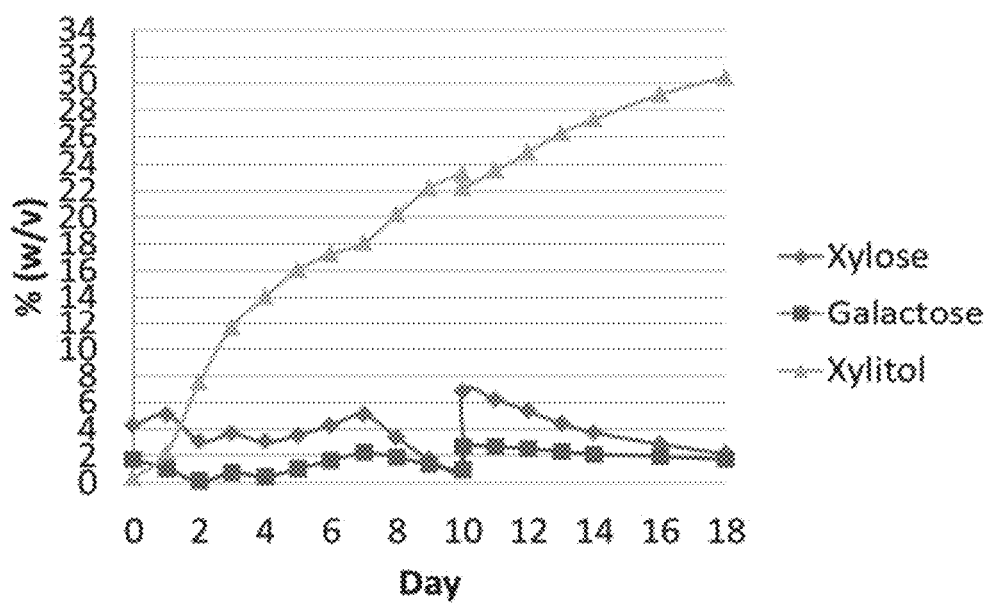

In the second fed-batch fermentation, the process was modified to improve the productivity: The cells were grown in 10 ml of YPD for 20 hr at 30° C. and transferred to 400 ml of YPD plus 4% xylose and 2% galactose. The culture was grown at 30° C. for 24 hr with shaking at 150 rpm. The pre-culture was pumped into the 3 L bioreactor vessel containing 680 ml of media (YPD+4% xylose+2% galactose) with the final inoculum at $OD_{600}$=3.0. The feeding stock contained 36% xylose, 12% galactose, 3% glucose, 3% peptone, 1.5% yeast extract, 0.075% $KH_2PO_4$, 0.075% $MgSO_4.7H_2O$, 0.075% $(NH_4)_2SO_4$. The feeding speed was at 6 ml/hr. The aeration rate was automatically adjusted to keep the DO at 70% saturation. 1 L of stock media was added in 7 days, and the fermentation was continued till the xylose was almost used up. More solid medium compounds were added at day 10 to increase the xylose concentration to 7%. Total fermentation lasted for 18 days. The xylitol yield reached 20% at day 8, 2 days faster than the previous fed-batch fermentation. By addition of more xylose, 30.5% xylitol was produced at day 18, the highest amount we have ever achieved (FIG. 14B).

Based on the above, use of a fed-batch fermentation method can improve the rate and overall concentration of xylitol produced by a recombinant *Metschnikowia* species having a xylitol pathway.

Example VII

Growth and Production of Metabolites Specific to the H0 *Metschnikowia* sp.

This example demonstrates that the H0 *Metschnikowia* sp. grows differently and produces different metabolites when compared to a closely related *Metschnikowia* species (*Metschnikowia pulcherrima flavia*).

Three single colonies of H0 *Metschnikowia* sp. and *Metschnikowia pulcherrima flavia* (FL) were inoculated into 5 ml yeast extract peptone dextrose (YEPD) media respectively, grown at 30° C. overnight. Cultures were shifted to 100 ml YEPD and grown at 30° C. for 4 hours. Cells were collected and inoculated into 200 ml medium in a 500 ml flask with OD600=1.0. Four different medium types were used: 1) YNBG: yeast nitrogen base with 4% glucose, 2) YNBX: yeast nitrogen base with 4% xylose, 3) YNBGX: yeast nitrogen base with 2% glucose and 2% xylose, and 4) YPDX: YEP with 2% dextrose and 2% xylose. Cultures were grown at 30° C. with shaking at 180 rpm. Samples were taken daily to monitor growth, which was measured by $OD_{600}$, and the metabolite content, which was measured by High Performance Liquid Chromatography (HPLC). The volatile compounds produced by H0 *Metschnikowia* sp. and FL were measured by headspace GC-MS. The $OD_{600}$ and HPLC data are the averages of three biological replicates. Standard deviations were also calculated. GC-MS data was compared roughly by the peak height.

Figures 15A, 15B, 15C, 15D:
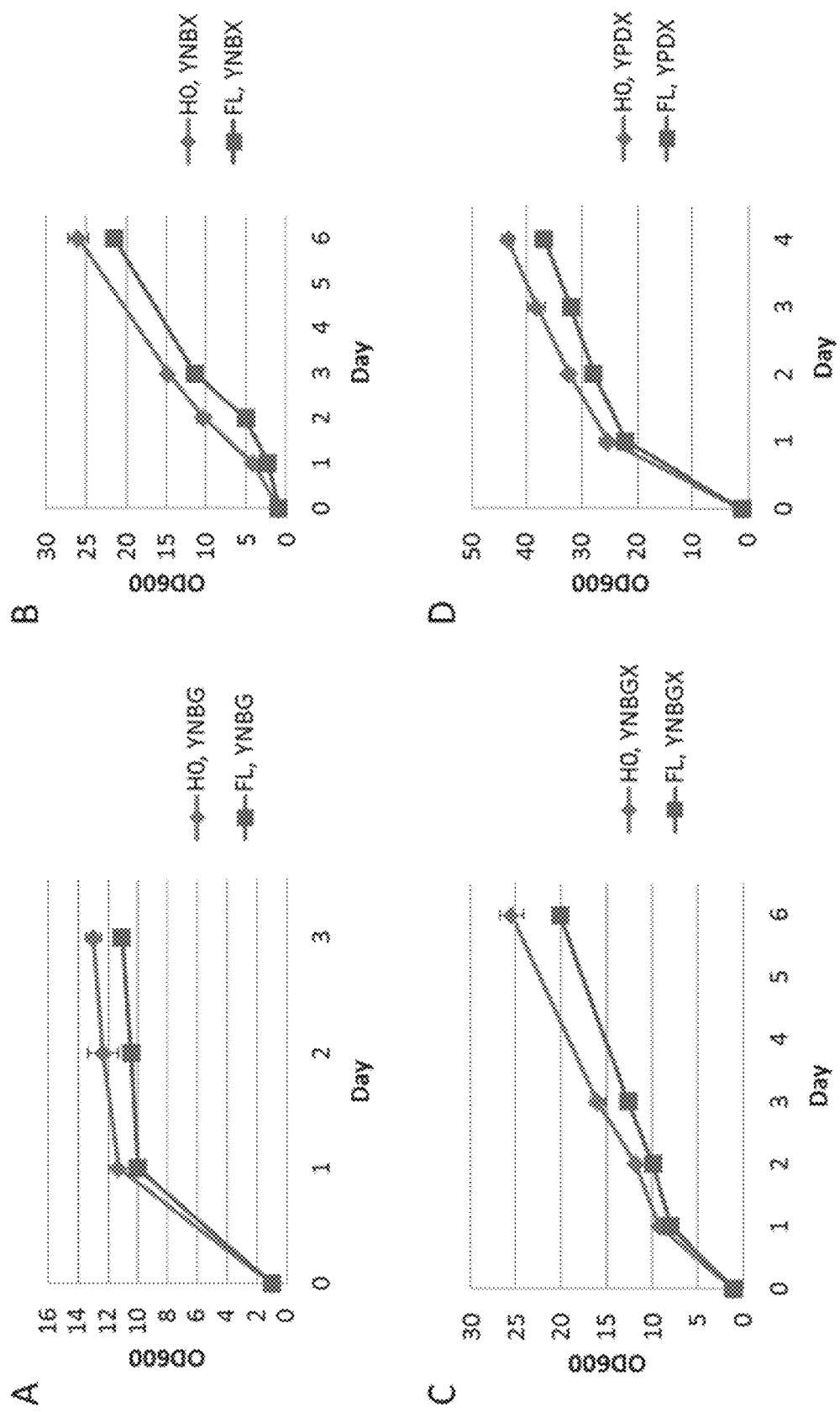
FIGS. 15A-15D show cell growth curves for H0 *Metschnikowia* sp. and FL strain cultured in different media.

Differences were observed in the growth rate between H0 *Metschnikowia* sp. and FL strains in all media tested. Specifically, H0 *Metschnikowia* sp. grows faster than FL (FIGS. 15A-15D). For example, on day 3 the ratio of $OD_{600}$ with H0 *Metschnikowia* sp. versus FL was 1.17 in YNBG (FIG. 15A), 1.30 in YNBX (FIG. 15B), 1.26 in YNBGX (FIG. 15C), and 1.19 in YPDX (FIG. 15D).

Figures 16A, 16B:
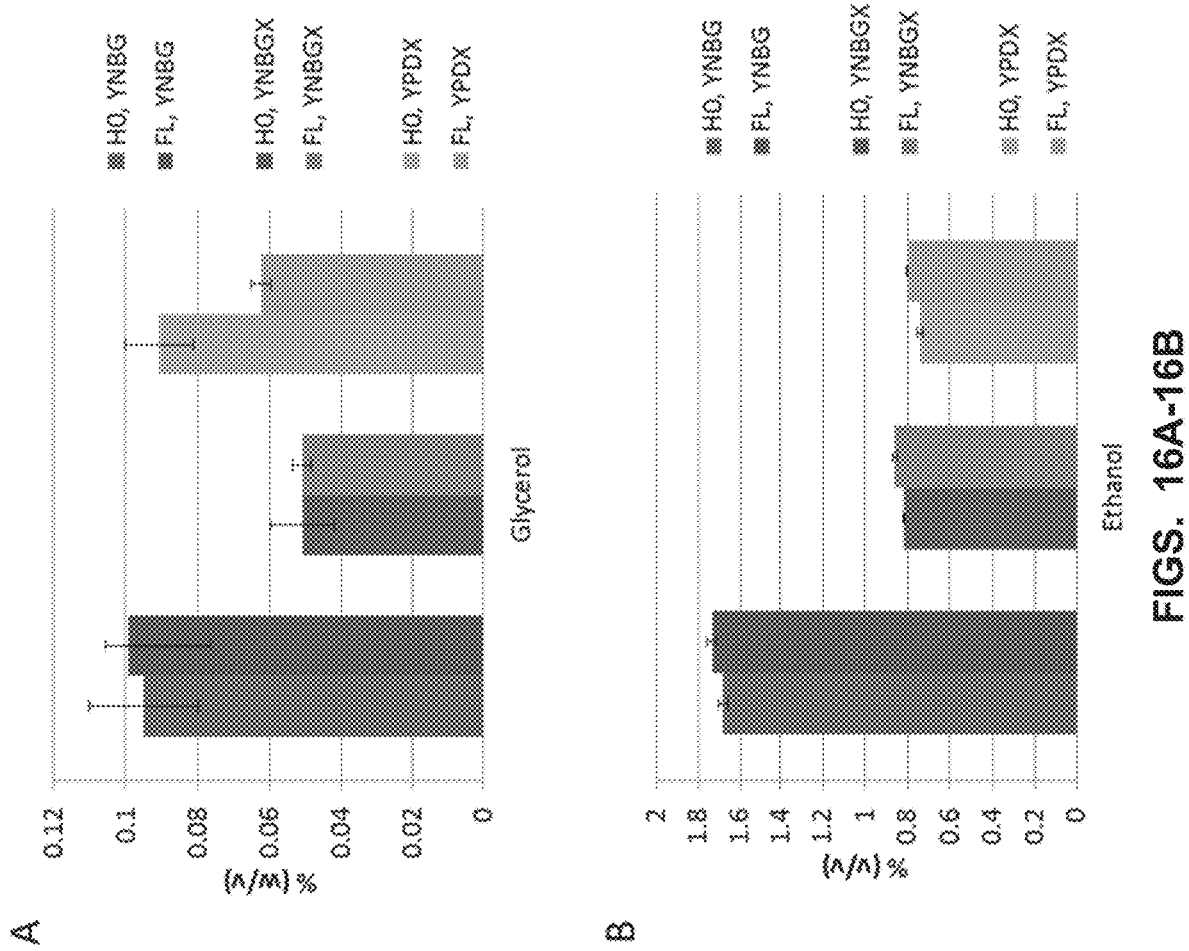
FIGS. 16A and 16B show glycerol and ethanol produced by H0 *Metschnikowia* sp. and FL strain in YNBG, YNBGX and YPDX media.

Glycerol and ethanol were detected on day 1 in the YNBG, YNBGX and YPDX media. The concentrations were similar between both strains in YNBG and YNBGX media (FIGS. 16A and 16B). However, in YPDX medium, H0 *Metschnikowia* sp. produced 45% more glycerol than FL (905 mg/L vs. 624 mg/L; FIG. 16A).

Figures 17A, 17B, 17C, 17D:
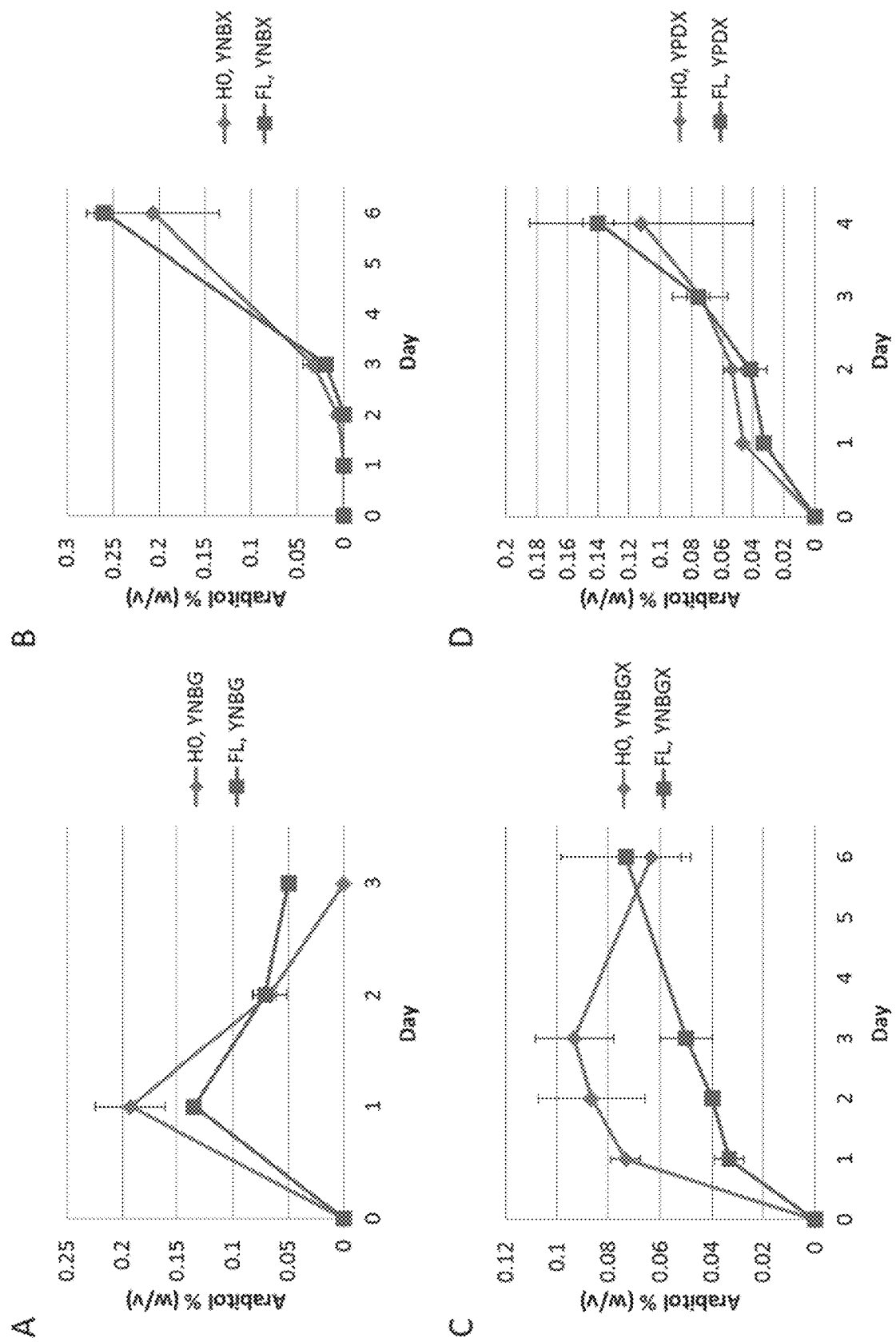
FIGS. 17A-17D show arabitol levels produced during the growth of H0 *Metschnikowia* sp. and *Metschnikowia pulcherrima flavia* (FL) strain in YNBG (FIG. 17A), YNBX (FIG. 17B), YNBGX (FIG. 17C) and YPDX (FIG. 17D) media.

Both H0 *Metschnikowia* sp. and FL produced arabitol in all growth media (FIGS. 17A-17D). However, in YNBG medium, H0 *Metschnikowia* sp. produced a different amount of arabitol on day 1—H0 *Metschnikowia* sp. produced 60 mg/L more arabitol than FL (FIG. 17A). Most dramatically, in YNBGX medium, H0 *Metschnikowia* sp. produced a significantly higher amount of arabitol on day 1, day 2 and day 3—with H0 *Metschnikowia* sp. producing about 40 mg/L more arabitol than FL (FIG. 17C). In YNBX and YPDX media, the arabitol levels were similar between the two species (FIGS. 17B and 17D).

Figures 18A, 18B, 18C:
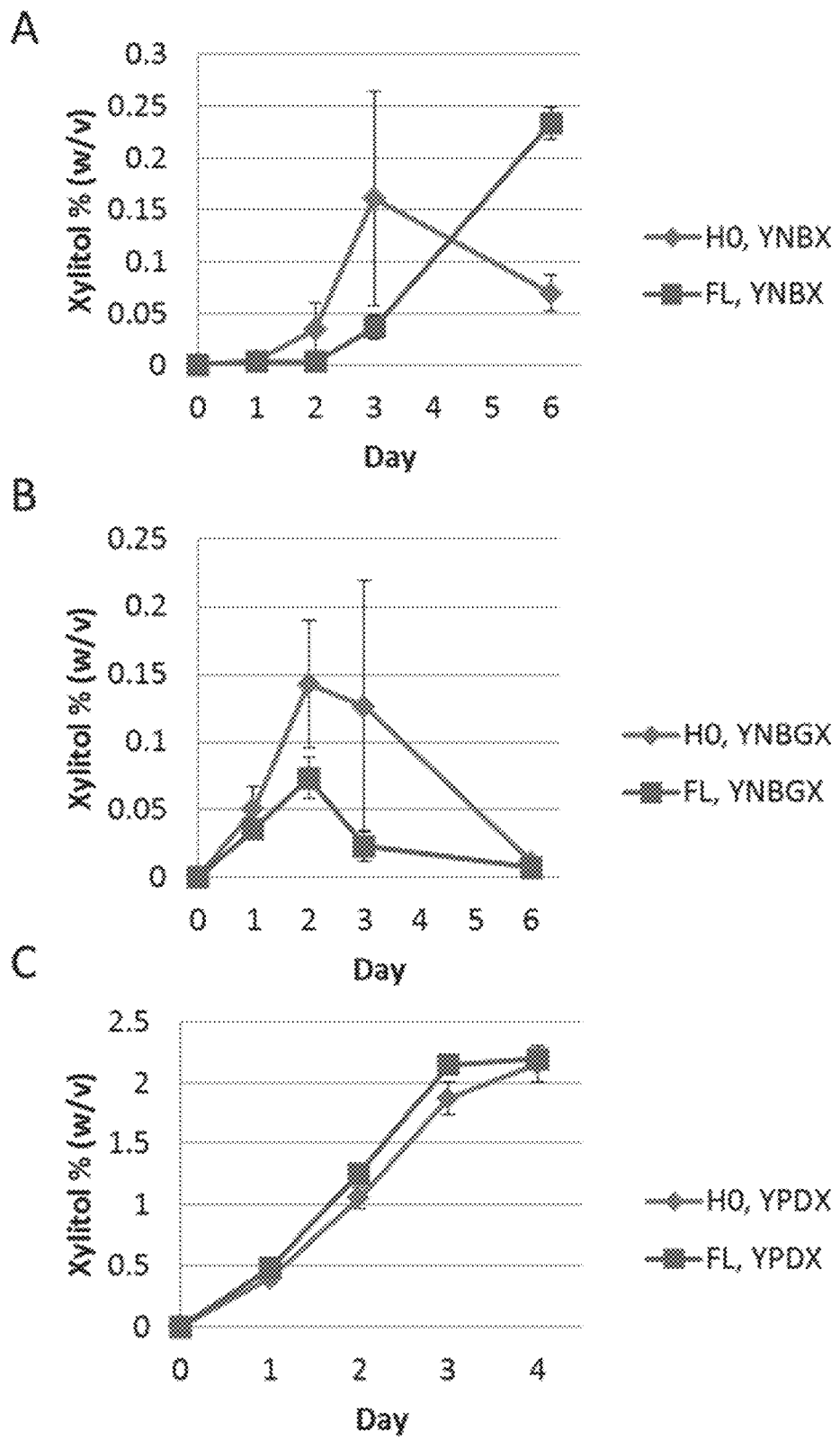
FIGS. 18A-18C show xylitol levels produced during the growth of H0 *Metschnikowia* sp. and FL strain in YNBX (FIG. 18A), YNBGX (FIG. 18B) and YPDX (FIG. 18C) media.

The H0 *Metschnikowia* sp. produced the maximum amount of xylitol on day 3 in YNBX (1.61 g/L), day 2 in YNBGX (1.43 g/L) and day 4 in YPDX (21.5 g/L) media, while FL produced maximum xylitol on day 6 in YNBX (2.33 g/L), day 2 in YNBGX (0.73 g/L) and day 4 in YPDX (21.9 g/L) (FIGS. 18A-18C). The ratio of xylitol content on day 3 between H0 *Metschnikowia* sp. and FL was 4.39 in YNBX, 5.43 in YNBGX and 0.87 in YPDX.

Figures 19A, 19B, 19C, 19D:
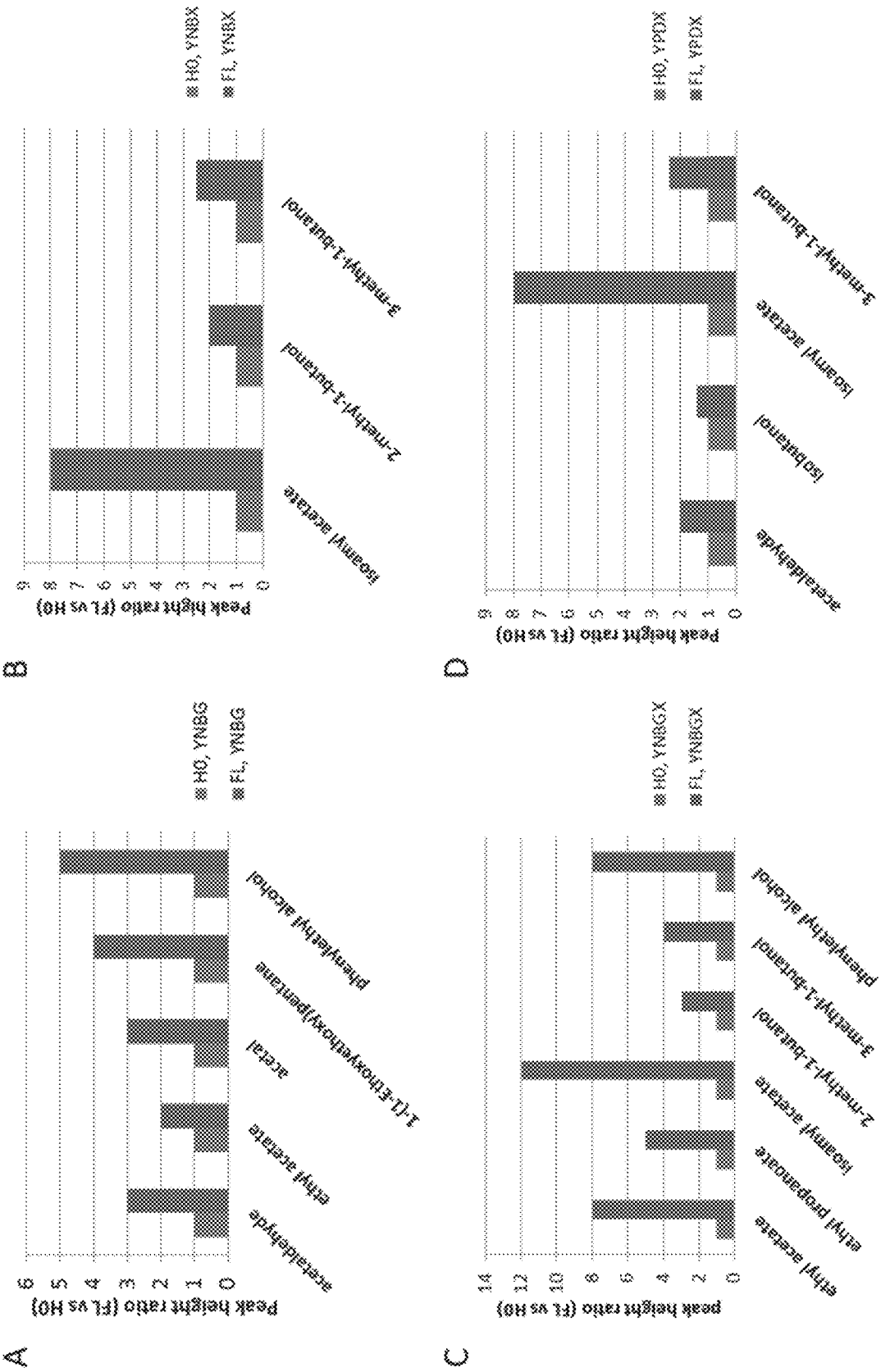
FIGS. 19A-19D show peak ratios production of various volatile compounds produced by H0 *Metschnikowia* sp. and FL strain in YNBG (FIG. 19A), YNBX (FIG. 19B), YNBGX (FIG. 19C) and YPDX (FIG. 19D) media.

The volatile compounds in the media after growing for 1 day in YNBG and 3 days in YNBX, YNBGX, and YPDX, respectively, were measured by head space GC-MS. The peak height ratio was calculated and compared between the FL and H0 *Metschnikowia* sp. This analysis showed that FL produced more volatile compounds than H0 *Metschnikowia* sp. (FIGS. 19A-19D). Specifically, FL produced more acetaldehyde, ethyl acetate, acetal, 1-(1-Ethoxyethoxy) pentane, and phenylethyl alcohol in YNBG medium (FIG. 19A); more isoamyl acetate, 2-methyl-1-butanol, and 3-methyl-1-butanol in YNBX medium (FIG. 19B); more ethyl acetate, ethyl propanoate, isoamyl acetate, 2-methyl-1-butanol, 3-methyl-1-butanol, and phenylethyl alcohol in YNBGX medium (FIG. 19C) and more acetaldehyde, isobutanol, isoamyl acetate, 3-methyl-1-butanol, ethyl nonanoate, and phenylethyl alcohol in YPDX medium (FIG. 19D).

Based on the above results, the profile of growth and the secreted metabolites between H0 *Metschnikowia* sp. and *Metschnikowia pulcherrima flavia* species show differences in the growth rate and the content as well as the dynamics of some metabolites during the growth in different media.

Example VIII

Metabolization of Xylose by *Metschnikowia* Species

This example demonstrates that *Metschnikowia* species consume and metabolize xylose as a carbon source and that the H0 *Metschnikowia* sp. and *Metschnikowia zizyphicola* are particularly useful host species for production of xylitol from xylose using a xylitol pathway.

Several known *Metschnikowia pulcherrima* clade species (*Metschnikowia pulcherrima*, *Metschnikowia andauensis*, *Metschnikowia chrysoperlae*, *Metschnikowia sinensis*, *Metschnikowia shanxiensis*, and *Metschnikowia zizyphicola*) as well as the new H0 *Metschnikowia* sp. described herein were grown on YP medium having 2% xylose for an extend period of time, wherein the growth of the cell cultures were monitored by assaying the $OD_{600}$ at hours 10, 13, 16, 19, 34 and 41.

Figure 20:
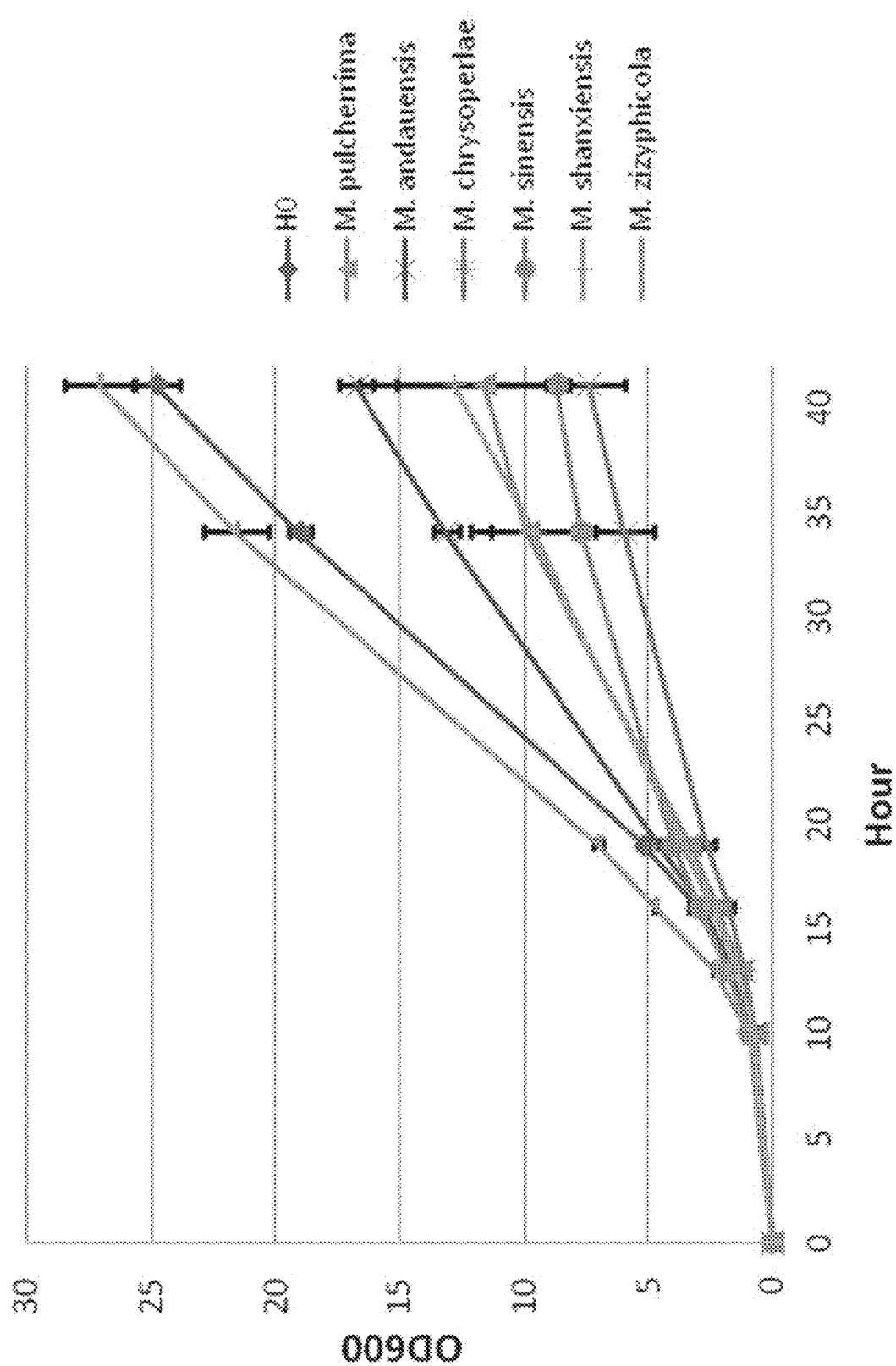
FIG. 20 shows exemplary growth curves for the H0 *Metschnikowia* sp. as compared to members of the *Metschnikowia pulcherrima* clade.

These experiments showed that all assayed species consumed xylose for growth (FIG. 20). The H0 *Metschnikowia* sp. was distinguished from most of the *Metschnikowia pulcherrima* clade species by its growth, which at the late stages (41 hours) from an initial $OD_{600}$ at 0.03 reached an $OD_{600}$ of about 25 (FIG. 20). The $OD_{600}$ of the *Metschnikowia zizyphicola* culture and the H0 *Metschnikowia* sp. culture were also similar, and were both much higher than that of the other species assayed (FIG. 20).

We claim:

1. A culture medium comprising xylose, an isolated *Metschnikowia* species and bioderived xylitol produced by the isolated *Metschnikowia* species, wherein the isolated *Metschnikowia* species comprises: (a) at least one exogenous nucleic acid encoding a xylose reductase or that results in overexpression of a xylose reductase of the isolated *Metschnikowia* species; and (b) a genetic modification that attenuates or inactivates a xylitol dehydrogenase of the isolated *Metschnikowia* species, wherein the isolated *Metschnikowia* species is the *Metschnikowia* species designated Accession No. 081116-01, deposited at the International Depositary Authority of Canada, an International Depositary Authority, on Nov. 8, 2016, under the terms of the Budapest Treaty.

2. The culture medium of claim 1 comprising glycerol, arabitol, a C7 sugar alcohol, or a combination thereof, as impurities.

3. The culture medium of claim 2, wherein the C7 sugar alcohol is volemitol or an isomer thereof.

4. The culture medium of claim 2, wherein the amount of glycerol or arabitol, or both, is at least 10%, 20%, 30% or 40% greater than the amount of the respective glycerol or arabitol, or both, produced by a microbial organism other than the isolated *Metschnikowia* species.

5. The culture medium of claim 1, wherein the isolated *Metschnikowia* species comprising parts (a) and (b) of claim 1 produces at least 0.50 g/L/h, at least 0,60 g/L/h, at least 0.70 g/L/h, at least 0.80 g/L/h, at least 0.90 g/L/h, at least 1.00 g/L/h, at least 1.50 g/L/h, at least 2.00 g/L/h, at least 2.50 g/L/h, at least 3.00 g/L/h, at least 3.50 g/L/h, at least 4.00 g/L/h, at least 5,00 g/L/h, at least 6.00 g/L/h, at least 7.00 g/L/h, at least 8.00 g/L/h, at least 9.00 g/L/h, or at least 10.00 g/L/h of xylitol from xylose when cultured.

6. The culture medium of claim 1, wherein the isolated *Metschnikowia* species comprising parts (a) and (b) of claim 1 produces at least 75 g/L, at least 80 g/L, at least 85 g/L, at least 90 g/L, at least 95 g/L, at least 100 g/L, at least 110 g/L, at least 120 g/L, at least 130 g/L, at least 140 g/L, at least 150 g/L, at least 160 g/L, at least 170 g/L, at least 180 g/L, at least 190 g/L, at least 200 g/L, at least 250 g/L, at least 300 g/L of xylitol from xylose when cultured.

7. The culture medium of claim 1, wherein the at least one exogenous nucleic acid encoding a xylose reductase is a heterologous nucleic acid.

8. The culture medium of claim 1, wherein the xylose reductase comprises the amino acid sequence selected from the group consisting of SEQ ID NOS: 11-18.

9. The culture medium of claim 1, wherein the xylose reductase comprises the amino acid sequence of SEQ ID NO: 11 or an amino acid sequence with at least 95% sequence identity to SEQ ID NO: 11.

10. The culture medium of claim 1, wherein the genetic modification comprises the deletion of one allele encoding the xylitol dehydrogenase or a portion thereof of the isolated *Metschnikowia* species.

11. The culture medium of claim 1, wherein the genetic modification comprises the deletion of both alleles encoding the xylitol dehydrogenase or a portion thereof of the isolated *Metschnikowia* species.

12. The culture medium of claim 1, wherein the isolated *Metschnikowia* species further comprises at least one exogenous nucleic acid encoding a xylose transporter or that results in overexpression of a xylose transporter of the isolated *Metschnikowia* species.

13. The culture medium of claim 12, wherein the xylose transporter comprises the amino acid sequence selected from the group consisting of SEQ ID NO: 27-40.

14. The culture medium of claim 12, wherein the xylose transporter comprises the amino acid sequence of any one of SEQ ID NOS: 27-36 or an amino acid sequence with at least 30% sequence identity to any one of SEQ ID NOS: 27-36.

15. The culture medium of claim 1, wherein the isolated *Metschnikowia* species comprises multiple copies of the exogenous nucleic acid encoding the xylose reductase.

16. The culture medium of claim 1, wherein the isolated *Metschnikowia* species comprises two, three, four, five, six, seven, eight, nine, ten, eleven, twelve, thirteen, fourteen, fifteen, sixteen, seventeen, eighteen, nineteen, twenty, or more copies of the exogenous nucleic acid encoding the xylose reductase.

17. The culture medium of claim 1, wherein the culture medium comprises xylose in combination with a co-substrate.

18. The culture medium of claim 17, wherein the co-substrate is glucose.

19. The culture medium of claim 18, wherein the medium is a xylose-rich medium comprising a glucose to xylose ratio of about 1:2, 1:3, 1:4, 1:5, 1:6, 1:7, 1:8, 1:9 or 1:10.

* * * * *

SEQUENCE LISTING

```
<160> NUMBER OF SEQ ID NOS: 67

<210> SEQ ID NO 1
<211> LENGTH: 362
<212> TYPE: PRT
<213> ORGANISM: Metschnikowia
<220> FEATURE:
<223> OTHER INFORMATION: Xyl2 protein from H0 Metschnikowia sp

<400> SEQUENCE: 1

Met Pro Ala Asn Pro Ser Leu Val Leu Asn Lys Val Asn Asp Ile Thr
1               5                   10                  15

Phe Glu Asn Tyr Glu Val Pro Leu Leu Thr Asp Pro Asn Asp Val Leu
            20                  25                  30

Val Gln Val Lys Lys Thr Gly Ile Cys Gly Ser Asp Ile His Tyr Tyr
        35                  40                  45

Thr His Gly Arg Ile Gly Asp Phe Val Leu Thr Lys Pro Met Val Leu
    50                  55                  60

Gly His Glu Ser Ala Gly Val Val Val Glu Val Gly Lys Gly Val Thr
65                  70                  75                  80

Asp Leu Lys Val Gly Asp Lys Val Ala Ile Glu Pro Gly Val Pro Ser
                85                  90                  95

Arg Thr Ser Asp Glu Tyr Lys Ser Gly His Tyr Asn Leu Cys Pro His
            100                 105                 110

Met Cys Phe Ala Ala Thr Pro Asn Ser Asn Pro Asp Glu Pro Asn Pro
        115                 120                 125
```

```
Pro Gly Thr Leu Cys Lys Tyr Tyr Lys Ser Pro Ala Asp Phe Leu Val
        130                 135                 140

Lys Leu Pro Glu His Val Ser Leu Glu Leu Gly Ala Met Val Glu Pro
145                 150                 155                 160

Leu Thr Val Gly Val His Ala Ser Arg Leu Gly Arg Val Thr Phe Gly
                165                 170                 175

Asp His Val Val Val Phe Gly Ala Gly Pro Val Gly Ile Leu Ala Ala
                180                 185                 190

Ala Val Ala Arg Lys Phe Gly Ala Ala Ser Val Thr Ile Val Asp Ile
            195                 200                 205

Phe Asp Ser Lys Leu Glu Leu Ala Lys Ser Ile Gly Ala Ala Thr His
        210                 215                 220

Thr Phe Asn Ser Met Thr Glu Gly Val Leu Ser Glu Ala Leu Pro Ala
225                 230                 235                 240

Gly Val Arg Pro Asp Val Val Leu Glu Cys Thr Gly Ala Glu Ile Cys
                245                 250                 255

Val Gln Gln Gly Val Leu Ala Leu Lys Ala Gly Gly Arg His Val Gln
                260                 265                 270

Val Gly Asn Ala Gly Ser Tyr Leu Lys Phe Pro Ile Thr Glu Phe Val
            275                 280                 285

Thr Lys Glu Leu Thr Leu Phe Gly Ser Phe Arg Tyr Gly Tyr Asn Asp
        290                 295                 300

Tyr Lys Thr Ser Val Ala Ile Leu Asp Glu Asn Tyr Lys Asn Gly Lys
305                 310                 315                 320

Glu Asn Ala Leu Val Asp Phe Glu Ala Leu Ile Thr His Arg Phe Pro
                325                 330                 335

Phe Lys Asn Ala Ile Glu Ala Tyr Asp Ala Val Arg Ala Gly Asp Gly
                340                 345                 350

Ala Val Lys Cys Ile Ile Asp Gly Pro Glu
            355                 360

<210> SEQ ID NO 2
<211> LENGTH: 362
<212> TYPE: PRT
<213> ORGANISM: Metschnikowia
<220> FEATURE:
<223> OTHER INFORMATION: Xyl2 protein from H0 Metschnikowia sp

<400> SEQUENCE: 2

Met Pro Ala Asn Pro Ser Leu Val Leu Asn Lys Val Asn Asp Ile Ser
1               5                   10                  15

Phe Glu Asn Tyr Glu Val Pro Leu Leu Thr Asp Pro Asn Asp Val Leu
                20                  25                  30

Val Gln Val Lys Lys Thr Gly Ile Cys Gly Ser Asp Ile His Tyr Tyr
            35                  40                  45

Thr His Gly Arg Ile Gly Asp Phe Val Leu Thr Lys Pro Met Val Leu
        50                  55                  60

Gly His Glu Ser Ala Gly Val Val Val Glu Val Gly Lys Gly Val Thr
65                  70                  75                  80

Asp Leu Lys Val Gly Asp Lys Val Ala Ile Glu Pro Gly Val Pro Ser
                85                  90                  95

Arg Thr Ser Asp Glu Tyr Lys Ser Gly His Tyr Asn Leu Cys Pro His
                100                 105                 110

Met Cys Phe Ala Ala Thr Pro Asn Ser Asn Pro Asp Glu Pro Asn Pro
            115                 120                 125
```

Pro Gly Thr Leu Cys Lys Tyr Tyr Lys Ser Pro Ala Asp Phe Leu Val
    130                 135                 140

Lys Leu Pro Glu His Val Ser Leu Glu Leu Gly Ala Met Val Glu Pro
145                 150                 155                 160

Leu Thr Val Gly Val His Ala Ser Arg Leu Gly Arg Val Thr Phe Gly
                165                 170                 175

Asp His Val Val Val Phe Gly Ala Gly Pro Val Gly Ile Leu Ala Ala
                180                 185                 190

Ala Val Ala Arg Lys Phe Gly Ala Ser Val Thr Ile Val Asp Ile
            195                 200                 205

Phe Asp Ser Lys Leu Glu Leu Ala Lys Ser Ile Gly Ala Ala Thr His
210                 215                 220

Thr Phe Asn Ser Met Thr Glu Gly Val Leu Ser Glu Ala Leu Pro Ala
225                 230                 235                 240

Gly Val Arg Pro Asp Val Val Leu Glu Cys Thr Gly Ala Glu Ile Cys
                245                 250                 255

Val Gln Gln Gly Val Leu Ala Leu Lys Ala Gly Gly Arg His Val Gln
            260                 265                 270

Val Gly Asn Ala Gly Ser Tyr Leu Lys Phe Pro Ile Thr Glu Phe Val
            275                 280                 285

Thr Lys Glu Leu Thr Leu Phe Gly Ser Phe Arg Tyr Gly Tyr Asn Asp
290                 295                 300

Tyr Lys Thr Ser Val Ala Ile Leu Asp Glu Asn Tyr Lys Asn Gly Lys
305                 310                 315                 320

Glu Asn Ala Leu Val Asp Phe Glu Ala Leu Ile Thr His Arg Phe Pro
                325                 330                 335

Phe Lys Asn Ala Ile Glu Ala Tyr Asp Ala Val Arg Ala Gly Asp Gly
            340                 345                 350

Ala Val Lys Cys Ile Ile Asp Gly Pro Glu
            355                 360

<210> SEQ ID NO 3
<211> LENGTH: 362
<212> TYPE: PRT
<213> ORGANISM: Metschnikowia
<220> FEATURE:
<223> OTHER INFORMATION: exemplary xylitol dehydrogenase from
      Metschnikowia pulcherrima flavia (identical to H0 Xyl2p)

<400> SEQUENCE: 3

Met Pro Ala Asn Pro Ser Leu Val Leu Asn Lys Val Asn Asp Ile Thr
1               5                   10                  15

Phe Glu Asn Tyr Glu Val Pro Leu Leu Thr Asp Pro Asn Asp Val Leu
                20                  25                  30

Val Gln Val Lys Lys Thr Gly Ile Cys Gly Ser Asp Ile His Tyr Tyr
            35                  40                  45

Thr His Gly Arg Ile Gly Asp Phe Val Leu Thr Lys Pro Met Val Leu
        50                  55                  60

Gly His Glu Ser Ala Gly Val Val Glu Val Gly Lys Gly Val Thr
65                  70                  75              80

Asp Leu Lys Val Gly Asp Lys Val Ala Ile Glu Pro Gly Val Pro Ser
                85                  90                  95

Arg Thr Ser Asp Glu Tyr Lys Ser Gly His Tyr Asn Leu Cys Pro His
            100                 105                 110

Met Cys Phe Ala Ala Thr Pro Asn Ser Asn Pro Asp Glu Pro Asn Pro
        115                 120                 125

```
Pro Gly Thr Leu Cys Lys Tyr Lys Ser Pro Ala Asp Phe Leu Val
        130                 135                 140

Lys Leu Pro Glu His Val Ser Leu Glu Leu Gly Ala Met Val Glu Pro
145                 150                 155                 160

Leu Thr Val Gly Val His Ala Ser Arg Leu Gly Arg Val Thr Phe Gly
                165                 170                 175

Asp His Val Val Val Phe Gly Ala Gly Pro Val Gly Ile Leu Ala Ala
                180                 185                 190

Ala Val Ala Arg Lys Phe Gly Ala Ala Ser Val Thr Ile Val Asp Ile
                195                 200                 205

Phe Asp Ser Lys Leu Glu Leu Ala Lys Ser Ile Gly Ala Ala Thr His
    210                 215                 220

Thr Phe Asn Ser Met Thr Glu Gly Val Leu Ser Glu Ala Leu Pro Ala
225                 230                 235                 240

Gly Val Arg Pro Asp Val Val Leu Glu Cys Thr Gly Ala Glu Ile Cys
                245                 250                 255

Val Gln Gln Gly Val Leu Ala Leu Lys Ala Gly Gly Arg His Val Gln
                260                 265                 270

Val Gly Asn Ala Gly Ser Tyr Leu Lys Phe Pro Ile Thr Glu Phe Val
                275                 280                 285

Thr Lys Glu Leu Thr Leu Phe Gly Ser Phe Arg Tyr Gly Tyr Asn Asp
    290                 295                 300

Tyr Lys Thr Ser Val Ala Ile Leu Asp Glu Asn Tyr Lys Asn Gly Lys
305                 310                 315                 320

Glu Asn Ala Leu Val Asp Phe Glu Ala Leu Ile Thr His Arg Phe Pro
                325                 330                 335

Phe Lys Asn Ala Ile Glu Ala Tyr Asp Ala Val Arg Ala Gly Asp Gly
                340                 345                 350

Ala Val Lys Cys Ile Ile Asp Gly Pro Glu
            355                 360

<210> SEQ ID NO 4
<211> LENGTH: 362
<212> TYPE: PRT
<213> ORGANISM: Metschnikowia
<220> FEATURE:
<223> OTHER INFORMATION: exemplary xylitol dehydrogenase from
      Metschnikowia bicuspidata var. bicuspidata NRRL YB-4993

<400> SEQUENCE: 4

Met Thr Thr Asn Pro Ser Leu Val Leu Asn Lys Val Asp Asp Ile Ser
1               5                   10                  15

Phe Glu Asn Tyr Gln Ile Pro Arg Ile Thr Glu Pro Asn Glu Val Leu
            20                  25                  30

Val Gln Val Lys Lys Thr Gly Ile Cys Gly Ser Asp Ile His Tyr Tyr
        35                  40                  45

Ala His Gly Lys Ile Gly Asp Phe Val Leu Thr Lys Pro Met Val Leu
    50                  55                  60

Gly His Glu Ser Ser Gly Ile Val Val Glu Val Gly Asp Ala Val Ser
65                  70                  75                  80

His Leu Lys Ala Gly Asp Lys Val Ala Ile Glu Pro Gly Val Pro Ser
                85                  90                  95

Arg Phe Ser Asp Glu Tyr Lys Ser Gly His Tyr Asn Leu Cys Pro His
            100                 105                 110

Met Lys Phe Ala Ala Thr Pro Asn Ser Lys Glu Gly Glu Pro Asn Pro
```

```
            115                 120                 125
Pro Gly Thr Leu Cys Lys Tyr Tyr Lys Ser Pro Ala Asp Phe Leu Val
        130                 135                 140
Lys Leu Pro Asp His Val Ser Leu Glu Leu Gly Ala Met Val Glu Pro
145                 150                 155                 160
Leu Thr Val Gly Val His Ala Ser Arg Leu Gly Lys Ile Thr Phe Gly
                165                 170                 175
Asp His Val Val Val Phe Gly Ala Gly Pro Val Gly Ile Leu Ala Ala
                180                 185                 190
Ala Val Ala Arg Lys Phe Gly Ala Ala Ser Val Thr Val Val Asp Ile
                195                 200                 205
Phe Asp Asn Lys Leu Lys Leu Ala Lys Asp Met Gly Ala Ala Thr His
        210                 215                 220
Val Phe Asn Ser Arg Thr Ser Asp Ser Leu Gly Asp Asn Leu Pro Ala
225                 230                 235                 240
Gly Val Asn Pro Asp Val Val Leu Glu Cys Thr Gly Ala Glu Val Cys
                245                 250                 255
Ile Gln Gln Gly Val Leu Ala Leu Lys Ala Gly Gly Arg Phe Val Gln
                260                 265                 270
Val Gly Asn Ala Gly Ser Tyr Val Lys Phe Pro Ile Thr Glu Leu Val
                275                 280                 285
Thr Lys Glu Leu Ile Leu Phe Gly Ser Phe Arg Tyr Gly Tyr Asn Asp
        290                 295                 300
Tyr Lys Thr Ser Val Asp Ile Leu Asp Glu Asn Tyr Lys Asn Gly Lys
305                 310                 315                 320
Asp Asn Ala Met Ile Asp Phe Glu Ala Leu Ile Thr His Arg Phe Ser
                325                 330                 335
Phe Asp Asp Ala Ile Lys Ala Tyr Asp Lys Val Arg Ser Gly Asp Gly
                340                 345                 350
Ala Ala Lys Cys Ile Ile Asp Gly Pro Glu
                355                 360

<210> SEQ ID NO 5
<211> LENGTH: 363
<212> TYPE: PRT
<213> ORGANISM: Pichia stipitis
<220> FEATURE:
<223> OTHER INFORMATION: exemplary xylitol dehydrogenase from Pichia
      stipites (no more Xyl2p sequence available in Metschnikowia spp.)

<400> SEQUENCE: 5

Met Thr Ala Asn Pro Ser Leu Val Leu Asn Lys Ile Asp Asp Ile Ser
1               5                   10                  15
Phe Glu Thr Tyr Asp Ala Pro Glu Ile Ser Glu Pro Thr Asp Val Leu
                20                  25                  30
Val Gln Val Lys Lys Thr Gly Ile Cys Gly Ser Asp Ile His Phe Tyr
            35                  40                  45
Ala His Gly Arg Ile Gly Asn Phe Val Leu Thr Lys Pro Met Val Leu
        50                  55                  60
Gly His Glu Ser Ala Gly Thr Val Val Gln Val Gly Lys Gly Val Thr
65                  70                  75                  80
Ser Leu Lys Val Gly Asp Asn Val Ala Ile Glu Pro Gly Ile Pro Ser
                85                  90                  95
Arg Phe Ser Asp Glu Tyr Lys Ser Gly His Tyr Asn Leu Cys Pro His
                100                 105                 110
```

```
Met Ala Phe Ala Ala Thr Pro Asn Ser Lys Glu Gly Glu Pro Asn Pro
             115                 120                 125

Pro Gly Thr Leu Cys Lys Tyr Phe Lys Ser Pro Glu Asp Phe Leu Val
        130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Val Asp Ile
        195                 200                 205

Phe Asp Asn Lys Leu Lys Met Ala Lys Asp Ile Gly Ala Ala Thr His
    210                 215                 220

Thr Phe Asn Ser Lys Thr Gly Gly Ser Glu Glu Leu Ile Lys Ala Phe
225                 230                 235                 240

Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
        275                 280                 285

Ala Met Lys Glu Leu Thr Leu Phe Gly Ser Phe Arg Tyr Gly Phe Asn
    290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Lys Asp Ala Ile Glu Ala Tyr Asp Leu Val Arg Ala Gly Lys
            340                 345                 350

Gly Ala Val Lys Cys Leu Ile Asp Gly Pro Glu
        355                 360

<210> SEQ ID NO 6
<211> LENGTH: 1089
<212> TYPE: DNA
<213> ORGANISM: Metschnikowia
<220> FEATURE:
<223> OTHER INFORMATION: XYL2 from H0 Metschnikowia sp.

<400> SEQUENCE: 6
atgcctgcta acccatcctt ggttttgaac aaagtgaacg acatcacgtt cgagaactac      60
gaggttccgt tactcacaga ccccaacgat gtattggttc aggtgaaaaa gactggaatc     120
tgtggatctg acatccacta ctacacccac ggcagaattg gcgacttcgt gttgacaaag     180
ccaatggttt tgggccacga atccgccggt gtggtcgtgg aggtcggcaa aggtgtcact     240
gacttgaagg ttggtgataa ggttgccatt gagcccggag tgccttctcg caccagtgac     300
gagtacaaga gtggccacta caacttgtgc ccacacatgt gttttgccgc acgcccaac     360 tctaaccccg acgagccaaa cccgccaggg actttgtgca atattacaa gtccccagcg     420 gacttcttgg tgaaattgcc tgagcacgtc tcccttgagt gggcgctat ggtcgagcct     480 ttgactgtcg gtgtgcacgc ctcgcgtttg ggccgtgtca cttttggtga ccacgttgtg     540
gttttcggtg ctggcccagt cggtatcctt gcggctgccg tggccagaaa gtttggcgct     600
gccagcgtga ctatcgtcga catcttcgac agcaaattgg aattggccaa gtccattggc     660
```

```
gcggccactc acacattcaa ctcaatgact gagggtgttc tttcggaggc tttgcccgcg      720
ggcgtgagac ctgacgttgt attggagtgc actggagcag atctgtgt gcagcaaggt       780 gtacttgcgt tgaaggctgg tggccgccac gtgcaagttg gaaatgccgg ctcctatctc     840
aaattcccca tcaccgaatt tgttaccaag gagttgactc tctttggatc cttccgttac    900
ggttacaacg actacaagac gtcggtcgcc atcttggacg agaattacaa gaacgggaag    960
gagaatgcgt tggtggactt tgaagccttg attactcacc gtttccccctt caagaatgcc  1020 attgaggctt acgacgcggt gcgcgctggc gacggagctg tcaagtgtat cattgacggc  1080
ccagagtaa                                                             1089

<210> SEQ ID NO 7
<211> LENGTH: 1089
<212> TYPE: DNA
<213> ORGANISM: Metschnikowia
<220> FEATURE:
<223> OTHER INFORMATION: exemplary xylitol dehydrogenase from
      Metschnikowia fructicola 277

<400> SEQUENCE: 7
atgcctgcta acccatcctt ggttttgaac aaagtgaacg catctcgtt cgagaactac     60 gaggttccgt tactcacaga ccccaacgat gtattggttc aggtgaaaaa gactggaatc   120
tgtggatctg acatccacta ctacacccac ggcagaattg gcgactttgt attgacaaag   180
ccaatggttt tgggccacga gtccgccggt gtggtcgtgg aggtcggcaa aggcgtcact   240
gacttgaagg ttggcgataa ggttgccatt gagcccggag tgccttctcg caccagtgac   300
gagtacaaga gtggtcacta caacttgtgc ccacacatgt gttttgccgc cacgcccaac   360
tctaaccccg acgagccaaa cccgccaggg actttgtgca atactacaa gtcccccgcg    420 gacttcttgg tgaaattgcc tgagcacgtc tcccttgagt tgggcgctat ggtcgagcct   480
ttgactgtcg gtgtgcacgc ctcgcgtttg ggccgtgtca cttttggtga ccacgttgtg   540
gttttcggtg ctggcccagt cggtattctt gcggctgccg tggccagaaa gtttggcgct   600
gccagtgtga ctatcgtcga catcttcgac agcaaattgg aattggccaa gtccattggc   660
gcggccactc acacattcaa ctcaatgact gagggtgttc tttctgaggc tttgcccgcg   720
ggcgtgagac ctgacgttgt attggagtgc actggagcag atctgtgt gcagcaaggt     780 gtacttgcgt tgaaggctgg tggccgccac gtgcaagttg gaaatgccgg ctcctatctc   840
aaattcccca tcaccgagtt cgtcaccaag gagttgactc tctttgggtc cttccgttac   900
ggctacaacg actacaagac gtcggtcgcc atcttggacg agaattacaa gaacgggaaa   960
gagaatgcgt tggtggactt tgaagccttg attactcacc gtttccccctt caagaatgcc  1020 attgaggctt acgacgcggt gcgcgctggc gacggagctg tcaagtgtat cattgacggc  1080
ccagagtaa                                                             1089

<210> SEQ ID NO 8
<211> LENGTH: 1089
<212> TYPE: DNA
<213> ORGANISM: Metschnikowia
<220> FEATURE:
<223> OTHER INFORMATION: exemplary xylitol dehydrogenase from
      Metschnikowia pulcherrima flavia

<400> SEQUENCE: 8
atgcctgcta acccatcctt ggttttgaac aaagtgaacg catcacgtt cgagaactac     60
```

```
gaggttccgt tactcacaga ccccaacgat gtattggttc aggtgaaaaa gactggaatc    120
tgcggatctg acattcacta ctacacccac ggcagaattg gcgactttgt attgacaaag    180
ccgatggttt tgggccacga atccgccggt gtggtcgtgg aggtcggcaa aggcgtcact    240
gacttgaagg ttggtgataa ggttgccatt gagcctggag tgccttctcg caccagtgac    300
gagtacaaga gtggtcacta caacttgtgc ccacacatgt gttttgccgc cacgcccaac    360
tctaaccccg acgagccaaa cccgccaggg actttgtgca atactacaa gtcccccgcg     420 gacttcttgg tgaaattgcc tgagcacgtc tcccttgagt tgggcgctat ggtcgagcct    480
ttgactgtcg gtgtgcacgc ctcgcgtttg ggccgtgtca cttttggtga ccacgttgtg    540
gttttcggtg ctggcccagt cggtatcctt gcggctgccg tggccagaaa gtttggcgct    600
gccagtgtga ctatcgtcga catcttcgac agcaaattgg aattggccaa gtccattggc    660
gcggccactc acacattcaa ctcaatgact gagggtgttc tttcggaggc tttgcccgcg    720
ggcgtgagac ctgacgttgt attggagtgc actggagcag agatctgtgt gcagcaaggt    780
gtacttgcgt tgaaggctgg tggccgccac gtgcaagttg aaatgccgg ctcctatctc     840 aaattcccca tcaccgagtt cgtcaccaag gagttgactc tctttgggtc cttccgttac    900
ggctacaacg actacaagac gtcggtcgcc atcttgacg agaattacaa gaacgggaaa     960
gagaatgcgt tggtggattt tgaagccttg attactcacc gtttccccct caagaatgcc   1020
attgaggctt acgacgcggt gcgcgctggc gacggagctg tcaagtgtat cattgacggc   1080
ccagagtaa                                                          1089

<210> SEQ ID NO 9
<211> LENGTH: 1089
<212> TYPE: DNA
<213> ORGANISM: Metschnikowia
<220> FEATURE:
<223> OTHER INFORMATION: exemplary xylitol dehydrogenase from
      Metschnikowia bicuspidata var. bicuspidata NRRL YB-4993

<400> SEQUENCE: 9
atgactacaa acccatcgtt ggtattgaac aaagtggacg atatttcgtt cgaaaactac     60
cagatcccta gaatcactga gcctaatgaa gtattagtcc aggtaaagaa gacgggaatc    120
tgcggctctg atattcacta ctacgcacat ggaaaaatcg gagacttcgt tttgacaaag    180
ccaatggtct taggccatga atcctcggga attgttgttg aggtgggtga tgctgtatcc    240
catttgaaag ctggggacaa ggttgccatt gagcctggag tgccttctcg ttttagcgat    300
gagtacaaga gcggtcacta taacttatgc ccgcatatga aatttgctgc tacccccaac    360
tcgaaagagg gtgaaccaaa ccctccgggc actttgtgca agtattataa gtcgcccgca    420
gacttcttgg ttaaattgcc tgatcacgtg tcgctcgaat tgggagcaat ggtcgagcca    480
ttgaccgtgg gtgtgcatgc ttctcggttg ggtaagatca cttttggtga tcatgtggtt    540
gtatttggcg ctggtccagt tggaattctt gcagccgctg ttgcaagaaa atttggcgcc    600
gcctccgtca ccgttgttga tatcttcgac aacaaattaa agctagcgaa ggacatgggt    660
gctgccaccc atgtctttaa ctcgaggact tccgactctt tggggataa tttgcccgca     720 ggtgtgaatc cagatgttgt tttggagtgt accggagctg aagtttgtat ccagcaaggt    780
gttttggctt taaaagcggg tggtcgcttt gtgcaagtgg gcaatgccgg ttcatatgtc    840
aagttcccca ttactgagct tgtgaccaaa gagttgattc tttttgggtc cttccggtat    900
ggatacaatg actacaagac ctctgtggat atcttggatg aaaattacaa aaacggaaaa    960
```

```
gacaatgcaa tgatagactt cgaggctttg attactcacc ggttctcatt cgacgatgcc      1020
atcaaggcat acgacaaagt gcgttctggt gacggcgctg caaaatgtat cattgatggg      1080
ccagaataa                                                              1089
```

<210> SEQ ID NO 10
<211> LENGTH: 1092
<212> TYPE: DNA
<213> ORGANISM: Pichia stipitis
<220> FEATURE:
<223> OTHER INFORMATION: exemplary xylitol dehydrogenase from Pichia
      stipitis (No more XYL2 gene sequence available in Metschnikowia
      spp.)

<400> SEQUENCE: 10

```
atgactgcta accct tcctt ggtgttgaac aagatcgacg acatttcgtt cgaaacttac       60
gatgccccag aaatctctga acctaccgat gtcctcgtcc aggtcaagaa aaccggtatc      120
tgtggttccg acatccactt ctacgcccat ggtagaatcg gtaacttcgt tttgaccaag      180
ccaatggtct tgggtcacga atccgccggt actgttgtcc aggttggtaa gggtgtcacc      240
tctcttaagg ttggtgacaa cgtcgctatc gaaccaggta ttccatccag attctccgac      300
gaatacaaga gcggtcacta caacttgtgt cctcacatgg ccttcgccgc tactcctaac      360
tccaaggaag gcgaaccaaa cccaccaggt accttatgta agtacttcaa gtcgccagaa      420
gacttcttgg tcaagttgcc agaccacgtc agctggaac tcggtgctct tgttgagcca      480
ttgtctgttg gtgtccacgc ctccaagttg ggttccgttg ctttcggcga ctacgttgcc      540
gtctttggtg ctggtcctgt tggtcttttg gctgctgctg tcgccaagac cttcggtgct      600
aagggtgtca tcgtcgttga cattttcgac aacaagttga agatggccaa ggacattggt      660
gctgctactc acaccttcaa ctccaagacc ggtggttctg aagaattgat caaggctttc      720
ggtggtaacg tgccaaacgt cgttttggaa tgtactggtg ctgaaccttg tatcaagttg      780
ggtgttgacg ccattgcccc aggtggtcgt ttcgttcaag ttggtaacgc tgctggtcca      840
gtcagcttcc caatcaccgt tttcgccatg aaggaattga ctttgttcgg ttctttcaga      900
tacggattca acgactacaa gactgctgtt ggaatctttg acactaacta ccaaaacggt      960
agagaaaatg ctccaattga cttttgaacaa ttgatcaccc acagatacaa gttcaaggac     1020
gctattgaag cctacgactt ggtcagagcc ggtaagggtg ctgtcaagtg tctcattgac     1080
ggccctgagt aa                                                         1092
```

<210> SEQ ID NO 11
<211> LENGTH: 318
<212> TYPE: PRT
<213> ORGANISM: Metschnikowia
<220> FEATURE:
<223> OTHER INFORMATION: XYL1 protein from H0 Metschnikowia sp.

<400> SEQUENCE: 11

Met Ala Thr Ile Lys Leu Asn Ser Gly Tyr Asp Met Pro Gln Val Gly
1               5                   10                  15

Phe Gly Cys Trp Lys Val Thr Asn Ser Thr Cys Ala Asp Thr Ile Tyr
            20                  25                  30

Asn Ala Ile Lys Val Gly Tyr Arg Leu Phe Asp Gly Ala Glu Asp Tyr
        35                  40                  45

Gly Asn Glu Lys Glu Val Gly Glu Gly Ile Asn Arg Ala Ile Asp Glu
    50                  55                  60

Gly Leu Val Ala Arg Asp Glu Leu Phe Val Val Ser Lys Leu Trp Asn 65                  70                  75                  80
Asn Phe His His Pro Asp Asn Val Glu Lys Ala Leu Asp Lys Thr Leu
                    85                  90                  95
Gly Asp Leu Asn Val Glu Tyr Leu Asp Leu Phe Leu Ile His Phe Pro
                100                 105                 110
Ile Ala Phe Lys Phe Val Pro Phe Glu Glu Lys Tyr Pro Pro Gly Phe
            115                 120                 125
Tyr Cys Gly Glu Gly Asp Lys Phe Ile Tyr Glu Asp Val Pro Leu Leu
        130                 135                 140
Asp Thr Trp Arg Ala Leu Glu Lys Phe Val Lys Gly Lys Ile Arg
145                 150                 155                 160
Ser Ile Gly Ile Ser Asn Phe Ser Gly Ala Leu Ile Gln Asp Leu Leu
                165                 170                 175
Arg Gly Ala Glu Ile Pro Pro Ala Val Leu Gln Ile Glu His His Pro
            180                 185                 190
Tyr Leu Gln Gln Pro Arg Leu Ile Glu Tyr Val Gln Ser Lys Gly Ile
        195                 200                 205
Ala Ile Thr Ala Tyr Ser Ser Phe Gly Pro Gln Ser Phe Val Glu Leu
    210                 215                 220
Asp His Pro Lys Val Lys Glu Cys Val Thr Leu Phe Glu His Glu Asp
225                 230                 235                 240
Ile Val Ser Ile Ala Lys Ala His Asp Lys Ser Ala Gly Gln Val Leu
                245                 250                 255
Leu Arg Trp Ala Thr Gln Arg Gly Leu Ala Val Ile Pro Lys Ser Asn
            260                 265                 270
Lys Thr Glu Arg Leu Leu Leu Asn Leu Asn Val Asn Asp Phe Asp Leu
        275                 280                 285
Ser Glu Ala Glu Leu Glu Gln Ile Ala Lys Leu Asp Val Gly Leu Arg
    290                 295                 300
Phe Asn Asn Pro Trp Asp Trp Asp Lys Ile Pro Ile Phe His
305                 310                 315

<210> SEQ ID NO 12
<211> LENGTH: 318
<212> TYPE: PRT
<213> ORGANISM: Spathaspora passalidarum
<220> FEATURE:
<223> OTHER INFORMATION: exemplary xylose reductase from Spathaspora
      passalidarum CBS 10155; Xyl1.1p

<400> SEQUENCE: 12

Met Ala Thr Ile Lys Leu Ser Ser Gly His Leu Met Pro Leu Val Gly
1               5                   10                  15
Phe Gly Cys Trp Lys Val Asp Asn Ala Thr Ala Ala Asp Gln Ile Tyr
            20                  25                  30
Asn Ala Ile Lys Ala Gly Tyr Arg Leu Phe Asp Gly Ala Glu Asp Tyr
        35                  40                  45
Gly Asn Glu Lys Glu Val Gly Asp Gly Leu Lys Arg Ala Ile Asp Glu
    50                  55                  60
Gly Leu Val Lys Arg Glu Glu Leu Phe Ile Thr Ser Lys Leu Trp Asn
65                  70                  75                  80
Asn Tyr His Asp Pro Lys Asn Val Glu Thr Ala Leu Asn Arg Thr Leu
                85                  90                  95
Ser Asp Leu Gln Leu Asp Tyr Val Asp Leu Phe Leu Ile His Phe Pro
            100                 105                 110

```
Ile Ala Phe Lys Phe Val Pro Leu Glu Glu Lys Tyr Pro Gly Phe
            115                 120                 125

Tyr Cys Gly Asp Gly Asn Asn Phe His Tyr Glu Asn Val Pro Leu Leu
130                 135                 140

Asp Thr Trp Lys Ala Leu Glu Lys Leu Val Gln Ala Gly Lys Ile Lys
145                 150                 155                 160

Ser Ile Gly Ile Ser Asn Phe Pro Gly Ala Leu Ile Tyr Asp Leu Val
                165                 170                 175

Arg Gly Ala Thr Ile Lys Pro Ala Val Leu Gln Ile Glu His His Pro
            180                 185                 190

Tyr Leu Gln Gln Pro Lys Leu Ile Glu Tyr Val Gln Lys Gln Gly Ile
        195                 200                 205

Ala Ile Thr Ala Tyr Ser Ser Phe Gly Pro Gln Ser Phe Leu Glu Leu
210                 215                 220

Asn Gln Asn Arg Ala Leu Asn Thr Pro Thr Leu Phe Glu His Asp Thr
225                 230                 235                 240

Ile Lys Ser Ile Ser Thr Arg Leu Asn Lys Thr Pro Ala Gln Val Leu
                245                 250                 255

Leu Arg Trp Ala Thr Gln Arg Asn Ile Ala Val Ile Pro Lys Ser Asn
            260                 265                 270

Asn Pro Ala Arg Leu Ala Gln Asn Leu Asp Val Thr Ser Phe Asp Leu
        275                 280                 285

Thr Glu Glu Asp Phe Asn Ala Ile Ser Ala Leu Asp Ile Asn Leu Arg
290                 295                 300

Phe Asn Asp Pro Trp Asp Trp Asp Asn Ile Pro Ile Phe Val
305                 310                 315

<210> SEQ ID NO 13
<211> LENGTH: 317
<212> TYPE: PRT
<213> ORGANISM: Spathaspora passalidarum
<220> FEATURE:
<223> OTHER INFORMATION: exemplary xylose reductase from Spathaspora
      passalidarum UFMGCMY469;  Xyl1.2p

<400> SEQUENCE: 13

Met Ser Phe Lys Leu Ser Ser Gly Tyr Glu Met Pro Lys Ile Gly Phe
1               5                   10                  15

Gly Thr Trp Lys Met Asp Lys Ala Thr Ile Pro Gln Gln Ile Tyr Asp
            20                  25                  30

Ala Ile Lys Gly Gly Ile Arg Ser Phe Asp Gly Ala Glu Asp Tyr Gly
        35                  40                  45

Asn Glu Lys Glu Val Gly Leu Gly Tyr Lys Lys Ala Ile Glu Asp Gly
    50                  55                  60

Leu Val Lys Arg Gly Asp Leu Phe Ile Thr Ser Lys Leu Trp Asn Asn
65                  70                  75                  80

Phe His Asp Pro Lys Asn Val Glu Lys Ala Leu Asp Arg Thr Leu Ala
                85                  90                  95

Asp Leu Gln Leu Asp Tyr Val Asp Leu Phe Leu Ile His Phe Pro Ile
            100                 105                 110

Ala Phe Lys Phe Val Pro Leu Glu Glu Arg Tyr Pro Pro Cys Phe Tyr
        115                 120                 125

Cys Gly Asp Gly Asp Asn Phe His Tyr Glu Asp Val Pro Leu Leu Glu
    130                 135                 140

Thr Trp Lys Ala Leu Glu Ala Leu Val Lys Lys Gly Lys Ile Arg Ser
145                 150                 155                 160
```

```
Leu Gly Val Ser Asn Phe Thr Gly Ala Leu Leu Asp Leu Leu Arg
                165                 170                 175

Gly Ala Thr Ile Lys Pro Ala Val Leu Gln Val Glu His His Pro Tyr
            180                 185                 190

Leu Gln Gln Pro Arg Leu Ile Glu Phe Ala Gln Lys Gln Gly Ile Val
        195                 200                 205

Val Thr Ala Tyr Ser Ser Phe Gly Pro Gln Ser Phe Thr Glu Leu Asn
    210                 215                 220

Gln Asn Arg Ala Asn Asn Thr Pro Arg Leu Phe Asp His Glu Val Ile
225                 230                 235                 240

Lys Lys Ile Ala Ala Arg Arg Gly Arg Thr Pro Ala Gln Val Ile Leu
                245                 250                 255

Arg Trp Ala Thr Gln Arg Asn Val Val Ile Ile Pro Lys Ser Asp Thr
            260                 265                 270

Pro Glu Arg Leu Val Glu Asn Leu Ala Val Phe Asp Phe Asp Leu Thr
        275                 280                 285

Glu Glu Asp Phe Lys Glu Ile Ala Ala Leu Asp Ala Asn Leu Arg Phe
    290                 295                 300

Asn Asp Pro Trp Asp Trp Asp His Ile Pro Ile Phe Val
305                 310                 315

<210> SEQ ID NO 14
<211> LENGTH: 318
<212> TYPE: PRT
<213> ORGANISM: Metschnikowia
<220> FEATURE:
<223> OTHER INFORMATION: exemplary xylose reductase from Metschnikowia
      bicuspidata var. bicuspidate NRRL YB-4993

<400> SEQUENCE: 14

Met Ser Thr Ile Lys Leu Asn Ser Gly Tyr Glu Met Pro Gln Val Gly
1               5                   10                  15

Phe Gly Cys Trp Lys Val Thr Asn Asp Thr Cys Ala Asp Thr Ile Tyr
            20                  25                  30

Asn Ala Ile Lys Val Gly Tyr Arg Leu Phe Asp Gly Ala Gln Asp Tyr
        35                  40                  45

Gly Asn Glu Lys Glu Val Gly Gln Gly Leu Asn Arg Ala Ile Asp Glu
    50                  55                  60

Gly Leu Val Ala Arg Asp Glu Leu Phe Val Val Ser Lys Leu Trp Asn
65                  70                  75                  80

Asn Phe His His Pro Asp Asn Val Glu Lys Ala Leu Asp Lys Thr Leu
                85                  90                  95

Gly Asp Leu Asn Val Glu Tyr Leu Asp Leu Phe Leu Ile His Phe Pro
            100                 105                 110

Ile Ala Phe Lys Phe Val Pro Phe Glu Glu Lys Tyr Pro Pro Gly Phe
        115                 120                 125

Tyr Cys Gly Asp Gly Asp Lys Phe His Tyr Glu Asp Val Pro Leu Leu
    130                 135                 140

Asp Thr Trp Arg Ala Leu Glu Lys Met Val Lys Gly Lys Ile Arg
145                 150                 155                 160

Ser Ile Gly Ile Ser Asn Phe Ser Gly Ala Leu Ile Gln Asp Leu Leu
                165                 170                 175

Arg Gly Ala Glu Ile Ala Pro Ala Val Leu Gln Ile Glu His His Pro
            180                 185                 190

Tyr Leu Gln Gln Pro Arg Leu Val Glu Tyr Val Lys Ser Lys Gly Ile
```

```
                195                 200                 205

Ala Ile Thr Ala Tyr Ser Ser Phe Gly Pro Gln Ser Phe Ile Glu Leu
    210                 215                 220

Asp His Pro Lys Val Lys Glu Cys Val Thr Leu Phe Asp His Asp Thr
225                 230                 235                 240

Ile Leu Ser Val Ala Arg Ala His Asn Lys Ser Ala Gly Gln Val Leu
                245                 250                 255

Leu Arg Trp Ala Thr Gln Arg Gly Leu Ala Val Ile Pro Lys Ser Asn
            260                 265                 270

Lys Thr Glu Arg Leu Val Gln Asn Leu Glu Val Asn Asp Phe Asp Leu
            275                 280                 285

Ser Asp Ala Glu Leu Lys Ser Ile Ser Lys Leu Asp Val Gly Leu Arg
            290                 295                 300

Phe Asn Asn Pro Trp Asp Trp Asp Lys Ile Pro Ile Phe His
305                 310                 315
```

<210> SEQ ID NO 15
<211> LENGTH: 318
<212> TYPE: PRT
<213> ORGANISM: Clavispora lusitaniae
<220> FEATURE:
<223> OTHER INFORMATION: exemplary xylose reductase from Clavispora
      lusitaniae ATCC 42720

<400> SEQUENCE: 15

```
Met Ala Thr Ile Lys Leu Asn Ser Gly Tyr Glu Met Pro Gln Val Gly
1               5                   10                  15

Phe Gly Cys Trp Lys Val Asp Asn Lys Thr Cys Ala Asp Gln Ile Tyr
            20                  25                  30

Asn Ala Ile Lys Val Gly Tyr Arg Leu Phe Asp Gly Ala Glu Asp Tyr
        35                  40                  45

Gly Asn Glu Lys Glu Val Gly Glu Gly Ile Asn Arg Ala Ile Ala Asp
    50                  55                  60

Gly Leu Val Ala Arg Asp Glu Leu Phe Val Val Ser Lys Leu Trp Asn
65                  70                  75                  80

Asn Phe His His Pro Asp Asn Val Glu Lys Ala Leu Asp Lys Thr Leu
                85                  90                  95

Ser Asp Leu Asn Leu Glu Tyr Leu Asp Leu Phe Leu Ile His Phe Pro
            100                 105                 110

Ile Ala Phe Lys Phe Val Pro Phe Glu Glu Lys Tyr Pro Pro Gly Phe
        115                 120                 125

Tyr Cys Gly Asp Thr Asn Lys Phe Ile Tyr Glu Asp Val Pro Ile Ile
130                 135                 140

Asp Thr Trp Arg Ala Leu Glu Lys Leu Val Lys Gly Lys Ile Arg
145                 150                 155                 160

Ser Ile Gly Val Ser Asn Phe Asn Gly Ser Leu Leu Leu Asp Leu Leu
                165                 170                 175

Arg Ala Ala Lys Ile Lys Pro Ala Val Leu Gln Ile Glu His His Pro
            180                 185                 190

Tyr Leu Gln Gln Pro Gln Leu Ile Lys Trp Val Lys Ser Lys Gly Ile
        195                 200                 205

Ala Val Thr Ala Tyr Ser Ser Phe Gly Pro Gln Ser Phe Val Glu Leu
    210                 215                 220

Asn His Pro Lys Val Gly Ser Cys Thr Thr Leu Phe Glu His Glu Asp
225                 230                 235                 240
```

```
Ile Val Ser Ile Ala Lys Lys His Gly Lys Ser Pro Gly Gln Val Leu
                245                 250                 255

Leu Arg Trp Ala Thr Gln Asn Gly Leu Ala Val Ile Pro Lys Ser Asn
            260                 265                 270

Lys Thr Glu Arg Leu Val Gln Asn Leu Asn Val Asn Asp Phe Asp Leu
        275                 280                 285

Ser Ala Ser Asp Leu Ser Ala Ile Ala Lys Leu Asp Ile Gly Leu Arg
    290                 295                 300

Phe Asn Asp Pro Trp Asp Trp Asp Glu Ile Pro Ile Phe His
305                 310                 315

<210> SEQ ID NO 16
<211> LENGTH: 317
<212> TYPE: PRT
<213> ORGANISM: Meyerozyma guilliermondii
<220> FEATURE:
<223> OTHER INFORMATION: exemplary xylose reductase from Meyerozyma
      guilliermondii

<400> SEQUENCE: 16

Met Ser Ile Lys Leu Asn Ser Gly Tyr Asp Met Pro Ser Val Gly Phe
1               5                   10                  15

Gly Cys Trp Lys Val Asp Asn Ala Thr Cys Ala Asp Thr Ile Tyr Asn
            20                  25                  30

Ala Ile Lys Val Gly Tyr Arg Leu Phe Asp Gly Ala Glu Asp Tyr Gly
        35                  40                  45

Asn Glu Lys Glu Val Gly Asp Gly Ile Asn Arg Ala Leu Asp Glu Gly
    50                  55                  60

Leu Val Ala Arg Asp Glu Leu Phe Val Val Ser Lys Leu Trp Asn Ser
65                  70                  75                  80

Phe His Asp Pro Lys Asn Val Glu Lys Ala Leu Asp Lys Thr Leu Ser
                85                  90                  95

Asp Leu Lys Val Asp Tyr Leu Asp Leu Phe Leu Ile His Phe Pro Ile
            100                 105                 110

Ala Phe Lys Phe Val Pro Phe Glu Glu Lys Tyr Pro Pro Gly Phe Tyr
        115                 120                 125

Cys Gly Asp Gly Asp Lys Phe His Tyr Glu Asp Val Pro Leu Ile Asp
    130                 135                 140

Thr Trp Arg Ala Leu Glu Lys Leu Val Glu Lys Gly Lys Ile Arg Ser
145                 150                 155                 160

Ile Gly Ile Ser Asn Phe Ser Gly Ala Leu Ile Gln Asp Leu Leu Arg
                165                 170                 175

Ser Ala Lys Ile Lys Pro Ala Val Leu Gln Ile Glu His His Pro Tyr
            180                 185                 190

Leu Gln Gln Pro Arg Leu Val Glu Tyr Val Gln Ser Gln Gly Ile Ala
        195                 200                 205

Ile Thr Ala Tyr Ser Ser Phe Gly Pro Gln Ser Phe Val Glu Leu Asp
    210                 215                 220

His Pro Arg Val Lys Asp Val Lys Pro Leu Phe Glu His Asp Val Ile
225                 230                 235                 240

Lys Ser Val Ala Gly Lys Val Lys Thr Pro Ala Gln Val Leu Leu
                245                 250                 255

Arg Trp Ala Thr Gln Arg Gly Leu Ala Val Ile Pro Lys Ser Asn Asn
            260                 265                 270

Pro Asp Arg Leu Leu Ser Asn Leu Lys Val Asn Asp Phe Asp Leu Ser
        275                 280                 285
```

```
Gln Glu Asp Phe Gln Glu Ile Ser Lys Leu Asp Ile Glu Leu Arg Phe
        290                 295                 300

Asn Asn Pro Trp Asp Trp Asp Lys Ile Pro Thr Phe Ile
305                 310                 315
```

<210> SEQ ID NO 17
<211> LENGTH: 324
<212> TYPE: PRT
<213> ORGANISM: Candida tropicalis
<220> FEATURE:
<223> OTHER INFORMATION: exemplary xylose reductase from Candida tropicalis

<400> SEQUENCE: 17

```
Met Ser Thr Thr Val Asn Thr Pro Thr Ile Lys Leu Asn Ser Gly Tyr
1               5                   10                  15

Glu Met Pro Leu Val Gly Phe Gly Cys Trp Lys Val Thr Asn Ala Thr
            20                  25                  30

Ala Ala Asp Gln Ile Tyr Asn Ala Ile Lys Thr Gly Tyr Arg Leu Phe
        35                  40                  45

Asp Gly Ala Glu Asp Tyr Gly Asn Glu Lys Glu Val Gly Glu Gly Ile
    50                  55                  60

Asn Arg Ala Ile Lys Asp Gly Leu Val Lys Arg Glu Glu Leu Phe Ile
65                  70                  75                  80

Thr Ser Lys Leu Trp Asn Asn Phe His Asp Pro Lys Asn Val Glu Thr
                85                  90                  95

Ala Leu Asn Lys Thr Leu Ser Asp Leu Asn Leu Asp Tyr Val Asp Leu
            100                 105                 110

Phe Leu Ile His Phe Pro Ile Ala Phe Lys Phe Val Pro Ile Glu Glu
        115                 120                 125

Lys Tyr Pro Pro Gly Phe Tyr Cys Gly Asp Gly Asp Asn Phe His Tyr
    130                 135                 140

Glu Asp Val Pro Leu Leu Asp Thr Trp Lys Ala Leu Glu Lys Leu Val
145                 150                 155                 160

Glu Ala Gly Lys Ile Lys Ser Ile Gly Ile Ser Asn Phe Thr Gly Ala
                165                 170                 175

Leu Ile Tyr Asp Leu Ile Arg Gly Ala Thr Ile Lys Pro Ala Val Leu
            180                 185                 190

Gln Ile Glu His His Pro Tyr Leu Gln Gln Pro Lys Leu Ile Glu Tyr
        195                 200                 205

Val Gln Lys Ala Gly Ile Ala Ile Thr Gly Tyr Ser Ser Phe Gly Pro
    210                 215                 220

Gln Ser Phe Leu Glu Leu Glu Ser Lys Arg Ala Leu Asn Thr Pro Thr
225                 230                 235                 240

Leu Phe Glu His Glu Thr Ile Lys Ser Ile Ala Asp Lys His Gly Lys
                245                 250                 255

Ser Pro Ala Gln Val Leu Leu Arg Trp Ala Thr Gln Arg Asn Ile Ala
            260                 265                 270

Val Ile Pro Lys Ser Asn Asn Pro Glu Arg Leu Ala Gln Asn Leu Ser
        275                 280                 285

Val Val Asp Phe Asp Leu Thr Lys Asp Leu Asp Asn Ile Ala Lys
    290                 295                 300

Leu Asp Ile Gly Leu Arg Phe Asn Asp Pro Trp Asp Trp Asp Asn Ile
305                 310                 315                 320

Pro Ile Phe Val
```

<210> SEQ ID NO 18
<211> LENGTH: 318
<212> TYPE: PRT
<213> ORGANISM: Scheffersomyces stipitis
<220> FEATURE:
<223> OTHER INFORMATION: exemplary xylose reductase from Scheffersomyces stipitis CBS 6054

<400> SEQUENCE: 18

Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315

<210> SEQ ID NO 19
<211> LENGTH: 957
<212> TYPE: DNA
<213> ORGANISM: Metschnikowia
<220> FEATURE:
<223> OTHER INFORMATION: XYL1 gene from H0 Metschnikowia sp

<400> SEQUENCE: 19

```
atggctacta tcaaattgaa ctctggatac gacatgcccc aagtgggttt tgggtgctgg      60
aaagtaacta acagtacatg tgctgatacg atctacaacg cgatcaaagt tggctacaga     120
ttatttgatg gcgctgaaga ttacgggaac gagaaagagg tgggcgaagg aatcaacagg     180
gccattgacg aaggcttggt ggcacgtgac gagttgttcg tggtgtccaa gctctggaac     240
aacttccatc atccagacaa cgtcgagaag gcgttggaca agactttggg cgacttgaat     300
gtcgagtact tggacttgtt cttgatccat ttcccaattg cgttcaaatt cgtgcccttt     360
gaggagaaat acccgcccgg cttctactgt ggagaaggcg ataagtttat ctacgaggat     420
gtgcctttgc ttgacacgtg gcgggcattg gagaagtttg tgaagaaggg taagatcaga     480
tccatcggaa tctcgaactt ttccggcgcg ttgatccagg acttgctcag gggcgccgag     540
atcccccctg ccgtgttgca gattgagcac cacccatact gcagcagcc cagattgatt     600
gagtatgtgc agtccaaggg tattgccatc acagcctact cctcttttgg cccacagtcg     660
tttgtggagt tggaccaccc caaggtcaag gagtgtgtca cgcttttcga gcacgaagac     720
attgttccca tcgctaaagc tcacgacaag tccgcgggcc aggtattatt gaggtgggcc     780
acgcaaaggg tcttgccgt gattccaaag tcaaacaaaa ccgagcgttt gttgctgaat     840
ttgaatgtga acgattttga tctctctgaa gcagaattgg agcaaatcgc aaagttggac     900
gtgggcttgc gcttcaacaa ccctgggac tgggacaaga ttccaatctt ccattaa        957
```

<210> SEQ ID NO 20
<211> LENGTH: 957
<212> TYPE: DNA
<213> ORGANISM: Spathaspora passalidarum
<220> FEATURE:
<223> OTHER INFORMATION: exemplary xylose reductase from Spathaspora passalidarum CBS 10155; XYL1.1

<400> SEQUENCE: 20

```
atggctacta ttaaattatc ctcaggtcac ttgatgcctt tagttggttt cggttgttgg      60
aaggtcgaca cgctaccgc tgctgaccaa atctacaacg ctatcaaggc tggttacaga     120
ttattcgacg gtgctgaaga ttacggtaac gaaaaggaag tcggtgacgg tttaaagaga     180
gccattgatg aaggtctcgt caagagagaa gaattattca tcacctctaa gttatggaac     240
aactaccacg acccaaagaa cgttgaaact gctttaaaca gaaccttatc cgatttacaa     300
ttggactacg ttgatttatt cttgatccac ttcccaattg ctttcaagtt cgttccatta     360
gaagaaaaat acccaccagg tttctactgt ggtgacggta caacttcca ctatgaaaat      420
gttccattat tggacacttg gaaggccttg gaaaagttag ttcaagctgg taagatcaag     480
tctatcggta tctctaactt ccctggtgct ttaatctacg acttggtcag aggtgctacc     540
atcaagccag ctgttttaca aattgaacac caccccatact acaacaacc aaagttgatt    600
gaatacgtcc aaaagcaagg tattgctatt accgcttact cttctttcgg tcctcaatct     660
ttcttggaat tgaaccaaaa cagagcttta aacaccccaa ccttgtttga acacgacacc     720
atcaagtcta tctctaccag attaaacaag accccagctc aagtcttatt aagatgggcc    780
acccaaagaa acattgctgt tattccaaag tctaacaacc cagctagatt agctcaaaac    840
ttggacgtca cctcttttga cttgaccgaa gaagacttca cgctatctc tgctttggac     900
atcaacttga gattcaacga cccatgggac tgggacaaca ttccaatctt cgtttaa        957
```

<210> SEQ ID NO 21
<211> LENGTH: 954
<212> TYPE: DNA
<213> ORGANISM: Spathaspora passalidarum
<220> FEATURE:
<223> OTHER INFORMATION: exemplary xylose reductase from Spathaspora passalidarum UFMGCMY469; XYL1.2

<400> SEQUENCE: 21

```
atgtctttta aattatcttc aggttatgaa atgccaaaaa tcggttttgg tacttggaag      60
atggacaagg ccaccattcc tcagcaaatt tacgatgcta tcaagggtgg tatcagatca     120
ttcgatggtg ctgaagatta tggtaacgaa aggaagttg gtcttggtta caagaaggct      180
attgaagacg tcttgttaa gagaggagat ctttttatta cctccaagtt atggaataac     240
ttccatgacc caagaatgt ggaaaaggct ttagacagaa ctttagctga tttgcaattg     300
gattacgtcg acttatttt aattcatttc ccaattgctt tcaagtttgt tccattggaa     360
gaaagatacc caccttgctt ctactgtggt gatggtgaca acttccatta tgaagatgtc     420
ccattattgg aaacctggaa ggctttagaa gccttggtta agaagggtaa gattagatca     480
cttggtgttt ctaacttcac tggtgctttg ttgttagatt tacttagagg tgctaccatt     540
aagccagctg ttttgcaagt cgaacatcat ccatacttgc aacaaccaag attaattgaa     600
tttgctcaaa agcaaggtat tgttgtcact gcttactctt catttggtcc tcaatctttc     660
actgaattga ccaaaacag agctaacaac actccaagat gtttgaccca cgaagtcata     720
aagaagattg ctgctagaag gggcagaact ccagctcaag ttatcttaag atgggccacc     780
caaagaaatg tcgtgattat ccaaaaatcc gatactccag aaagattggt cgaaaacttg     840
gctgtctttg actttgactt aactgaagaa gatttcaaag aaattgctgc cttggatgct     900
aatttgagat taatgaccc atgggactgg gaccatattc caatctttgt ttaa            954
```

<210> SEQ ID NO 22
<211> LENGTH: 957
<212> TYPE: DNA
<213> ORGANISM: Metschnikowia
<220> FEATURE:
<223> OTHER INFORMATION: exemplary xylose reductase from Metschnikowia bicuspidata var. bicuspidate NRRL YB-4993

<400> SEQUENCE: 22

```
atgagcacta tcaaattgaa ctcgggctac gaaatgcccc aagtgggctt tggctgctgg      60
aaggtgacaa cgacacttg cgcggatact atctacaatg ccatcaaagt ggggtacaga     120
ttgttcgatg gtgcccaaga ctacggaaat gaaaagaag ttggccaggg actcaacaga      180
gcgatcgatg aaggattggt ggcacgtgat gagttatttg tggtatccaa gctttggaac     240
aatttccatc acccagacaa tgttgaaaag gccctagaca agacattggg tgacttgaac     300
gtcgaatact tggacttatt tctcatccac tttcccattg ctttcaaatt tgttcccttt     360
gaggaaaagt accccctgg ttctactgc ggtgacggcg acaaattcca ttacgaggac      420
gtgcctttgc tcgacacgtg gcgggctttg gagaaatgg tcaagaaagg taaaatcaga     480
tccattggta tttcgaactt ttctggagct ttgatccaag acttgcttag ggcgctgaa      540
attgctcccg ctgttctaca aattgaacac caccctatact gcaacagcc ccggttggtt    600
gagtatgtga atcaaaggg cattgctatt actgcctact cgtcttttgg cccacagtct     660
tttatcgagt tagatcaccc taaagtaaag gaatgcgtca ctttgtttga ccatgacaca     720
attttgtccg ttgccagagc acacaataag tctgccggcc aagttttgtt gagatgggcc     780
```

```
actcaaagag gtcttgcagt tattcccaaa tctaacaaga cagaacgctt ggtgcaaaac      840
ttggaggtaa acgactttga cctttctgac gctgagttga agtccatctc caagctagat      900
gtggggttgc gtttcaacaa cccttgggac tgggacaaga ttcctatctt ccactga         957
```

<210> SEQ ID NO 23
<211> LENGTH: 957
<212> TYPE: DNA
<213> ORGANISM: Clavispora lusitaniae
<220> FEATURE:
<223> OTHER INFORMATION: exemplary xylose reductase from Clavispora
      lusitaniae ATCC 42720

<400> SEQUENCE: 23

```
atggccacta ttaagttgaa ctcaggatac gagatgcctc aggttggttt cggctgctgg      60
aaagtcgaca caaaacctg tgctgaccaa atctacaatg ccatcaaagt cggttacaga      120 tgtttgacg gcgctgaaga ttatggtaac gaaaagaag ttggcgaagg tatcaacaga      180
gccattgctg atggcttggt tgctcgtgac gagttattcg ttgtctcgaa gctctggaac      240
aacttccatc accctgacaa tgtggaaaaa gctttggaca agacattgag cgacttgaac      300
ctcgagtacc ttgacttgtt tttgatccat ttcccaattg ctttcaagtt tgttcctttc      360
gaagaaaagt accctccagg attctactgt ggagacacca acaagttcat ttacgaagac      420
gttccaatca ttgacacttg gagagctttg gaaaagttgg tggaaaaggg aaagattaga      480
tccattggtg tttccaactt caatggctcc ttgcttctcg acttgcttag agctgctaag      540
atcaagcctg ctgttttgca aatcgagcac cacccatact gcaacaacc acagttgatc      600 aaatgggtca agagcaaagg aattgctgtg actgcgtact cttcgtttgg tcctcaatca      660
ttcgttgagt tgaaccaccc taaggtcggt agctgcacca cattgttcga acacgaagac      720
attgtctcca tcgccaaaaa gcatggaaag agccctggcc aagtcttgtt gagatgggct      780
actcagaacg gtcttgctgt tattccaaag tccaacaaaa ccgaacgttt ggttcagaac      840
ttgaatgtca acgattttga cctttctgct ctggacttga gtgccattgc taaattggac      900
attggcttgc gtttcaatga tccatgggac tgggatgaaa tcccaatctt ccactag        957
```

<210> SEQ ID NO 24
<211> LENGTH: 954
<212> TYPE: DNA
<213> ORGANISM: Meyerozyma guilliermondii
<220> FEATURE:
<223> OTHER INFORMATION: exemplary xylose reductase from Meyerozyma
      guilliermondii

<400> SEQUENCE: 24

```
atgtctatca agttaaactc tggatatgac atgccctcgg tggttttgg ctgctggaag       60 gtcgacaatg ccacctgtgc cgacaccatc tacaatgcca tcaaggtggg atacagatta      120
tttgacggag ccgaggatta cggtaacgaa aaggaagtgg agatggtat taatagagca      180 ctcgatgagg gcttggttgc cagagatgag cttttcgttg tttccaagct ctggaactcg      240
ttccatgacc ccaaaaacgt ggaaaaggcg ttggacaaaa cattgagcga cttgaaggtg      300
gactaccttg acttgttctt gatccacttt ccaattgctt tcaagtttgt tcccttcgag      360
gagaaatatc ctccaggatt ctactgtgga gatgggaca agttccacta cgaggacgtg      420
ccactcatcg acacctggag agcattggag aagttggtgg agaagggtaa aatcagatcc      480
attggtattt ccaactttag tggtgcgttg atccaggact gttgagaag tgccaaaatc      540 aagccagcag tgttgcagat cgaacaccac ccttacttgc agcaaccaag attggttgag      600
```

```
tacgttcaat ctcaaggcat cgccatcacc gcatactcgt ctttcggacc ccaatctttc      660
gtggaattgg accaccctcg tgtcaaggat gtcaagccat tgttcgagca cgacgtcatc      720
aagtccgttg ctggcaaagt caagaagacc ccagcacagg tgttgttgag atgggccact      780
caaagaggac ttgccgtgat tcccaagtcg aacaatcccg ataggttgtt gagcaacttg      840
aaggtgaacg actttgattt gtcgcaagaa gacttccaag aaatctccaa gttggacatt      900
gaattgagat caacaatcc ttgggactgg acaagattc aactttcat ctaa              954
```

<210> SEQ ID NO 25
<211> LENGTH: 975
<212> TYPE: DNA
<213> ORGANISM: Candida tropicalis
<220> FEATURE:
<223> OTHER INFORMATION: exemplary xylose reductase from Candida
      tropicalis

<400> SEQUENCE: 25

```
atgtctacta ctgttaatac tcctactatt aaattaaact ccggttatga atgccatta       60 gttggtttcg gatgttggaa agtcaccaat gccactgccg ctgaccaaat ctacaatgcc     120
attaaaactg gttacagatt atttgatggt gctgaagatt acggtaacga aaagaagtt     180 ggtgaaggta tcaacagagc cattaaagat ggattagtta aagagaaga attattcatc     240 acttctaaat tatggaacaa tttccatgat ccaagaatgt tgaaactgc tttaaacaaa     300 actttaagtg acttgaactt ggactatgtt gatttattct tgattcattt cccaattgct     360
tttaaatttg ttccaattga agaaaaatac ccacctggtt tctactgtgg tgatggtgat     420
aacttccact atgaagatgt tccattatta gatacttgga agctttgga aaaattggtt     480 gaagctggta agatcaaatc tattggtatt tccaatttca ctggtgctttt gatttacgat     540 ttgatcagag gtgctactat caaaccagct gttttacaaa ttgaacatca cccatacttg     600
caacaaccaa aattgattga atatgttcaa aaagctggta ttgccattac tggttactct     660
tcatttggtc cacaatcatt cttggaatta gaatccaaga gagctttgaa tacccccaact     720 ttatttgaac atgaaactat taatcaatt gctgataaac atggtaaatc tccagctcaa     780
gttttattaa gatgggctac tcaaagaaat attgctgtta ttccaaaatc aaacaatcca     840
gaaagattag ctcaaaactt gtctgttgtt gactttgact tgactaagga tgatttggac     900
aatattgcta aattggacat tggtttgaga ttcaatgatc catgggactg gacaacatt     960 ccaatctttg tttaa                                                     975
```

<210> SEQ ID NO 26
<211> LENGTH: 957
<212> TYPE: DNA
<213> ORGANISM: Scheffersomyces stipitis
<220> FEATURE:
<223> OTHER INFORMATION: exemplary xylose reductase from Scheffersomyces
      stipitis CBS 6054

<400> SEQUENCE: 26

```
atgccttcta ttaagttgaa ctctggttac gacatgccag ccgtcggttt cggctgttgg       60
aaagtcgacg tcgacacctg ttctgaacag atctaccgtg ctatcaagac cggttacaga     120
ttgttcgacg gtgccgaaga ttacgccaac gaaaagttag ttggtgccgg tgtcaagaag     180
gccattgaca aggtatcgt caagcgtgaa gacttgttcc ttacctccaa gttgtggaac     240
aactaccacc acccagacaa cgtcgaaaag gccttgaaca gaaccctttc tgacttgcaa     300
```

-continued

```
gttgactacg ttgacttgtt cttgatccac ttcccagtca ccttcaagtt cgttccatta    360
gaagaaaagt acccaccagg attctactgt ggtaagggtg acaacttcga ctacgaagat    420
gttccaattt tagagacctg gaaggctctt gaaaagttgg tcaaggccgg taagatcaga    480
tctatcggtg tttctaactt cccaggtgct ttgctcttgg acttgttgag aggtgctacc    540
atcaagccat ctgtcttgca agttgaacac cacccatact tgcaacaacc aagattgatc    600
gaattcgctc aatcccgtgg tattgctgtc accgcttact cttcgttcgg tcctcaatct    660
ttcgttgaat tgaaccaagg tagagctttg aacacttctc cattgttcga gaacgaaact    720
atcaaggcta tcgctgctaa gcacggtaag tctccagctc aagtcttgtt gagatggtct    780
tcccaaagag gcattgccat cattccaaag tccaacactg tcccaagatt gttggaaaac    840
aaggacgtca acagcttcga cttggacgaa caagatttcg ctgacattgc caagttggac    900
atcaacttga gattcaacga cccatgggac tgggacaaga ttcctatctt cgtctaa      957
```

<210> SEQ ID NO 27
<211> LENGTH: 543
<212> TYPE: PRT
<213> ORGANISM: Metschnikowia
<220> FEATURE:
<223> OTHER INFORMATION: Xyt1p for H0 Metschnikowia sp.

<400> SEQUENCE: 27

```
Met Gly Tyr Glu Glu Lys Leu Val Ala Pro Ala Leu Lys Phe Lys Asn
1               5                   10                  15

Phe Leu Asp Lys Thr Pro Asn Ile His Asn Val Tyr Val Ile Ala Ala
                20                  25                  30

Ile Ser Cys Thr Ser Gly Met Met Phe Gly Phe Asp Ile Ser Ser Met
            35                  40                  45

Ser Val Phe Val Asp Gln Gln Pro Tyr Leu Lys Met Phe Asp Asn Pro
        50                  55                  60

Ser Ser Val Ile Gln Gly Phe Ile Thr Ala Ser Met Ser Leu Gly Ser
65                  70                  75                  80

Phe Phe Gly Ser Leu Thr Ser Thr Phe Ile Ser Glu Pro Phe Gly Arg
                85                  90                  95

Arg Ala Ser Leu Phe Ile Cys Gly Ile Leu Trp Val Ile Gly Ala Ala
                100                 105                 110

Val Gln Ser Ser Ser Gln Asn Arg Ala Gln Leu Ile Cys Gly Arg Ile
            115                 120                 125

Ile Ala Gly Trp Gly Ile Gly Phe Gly Ser Ser Val Ala Pro Val Tyr
        130                 135                 140

Gly Ser Glu Met Ala Pro Arg Lys Ile Arg Gly Thr Ile Gly Gly Ile
145                 150                 155                 160

Phe Gln Phe Ser Val Thr Val Gly Ile Phe Ile Met Phe Leu Ile Gly
                165                 170                 175

Tyr Gly Cys Ser Phe Ile Gln Gly Lys Ala Ser Phe Arg Ile Pro Trp
                180                 185                 190

Gly Val Gln Met Val Pro Gly Leu Ile Leu Leu Ile Gly Leu Phe Phe
            195                 200                 205

Ile Pro Glu Ser Pro Arg Trp Leu Ala Lys Gln Gly Tyr Trp Glu Asp
        210                 215                 220

Ala Glu Ile Ile Val Ala Asn Val Gln Ala Lys Gly Asn Arg Asn Asp
225                 230                 235                 240

Ala Asn Val Gln Ile Glu Met Ser Glu Ile Lys Asp Gln Leu Met Leu
                245                 250                 255
```

```
Asp Glu His Leu Lys Glu Phe Thr Tyr Ala Asp Leu Phe Thr Lys Lys
            260                 265                 270

Tyr Arg Gln Arg Thr Ile Thr Ala Ile Phe Ala Gln Ile Trp Gln Gln
        275                 280                 285

Leu Thr Gly Met Asn Val Met Met Tyr Ile Val Tyr Ile Phe Gln
    290                 295                 300

Met Ala Gly Tyr Ser Gly Asn Thr Asn Leu Val Pro Ser Leu Ile Gln
305                 310                 315                 320

Tyr Ile Ile Asn Met Ala Val Thr Val Pro Ala Leu Phe Cys Leu Asp
                325                 330                 335

Leu Leu Gly Arg Arg Thr Ile Leu Leu Ala Gly Ala Ala Phe Met Met
            340                 345                 350

Ala Trp Gln Phe Gly Val Ala Gly Ile Leu Ala Thr Tyr Ser Glu Pro
        355                 360                 365

Ala Tyr Ile Ser Asp Thr Val Arg Ile Thr Ile Pro Asp Asp His Lys
    370                 375                 380

Ser Ala Ala Lys Gly Val Ile Ala Cys Cys Tyr Leu Phe Val Cys Ser
385                 390                 395                 400

Phe Ala Phe Ser Trp Gly Val Gly Ile Trp Val Tyr Cys Ser Glu Val
                405                 410                 415

Trp Gly Asp Ser Gln Ser Arg Gln Arg Gly Ala Ala Leu Ala Thr Ser
            420                 425                 430

Ala Asn Trp Ile Phe Asn Phe Ala Ile Ala Met Phe Thr Pro Ser Ser
        435                 440                 445

Phe Lys Asn Ile Thr Trp Lys Thr Tyr Ile Ile Tyr Ala Thr Phe Cys
    450                 455                 460

Ala Cys Met Phe Ile His Val Phe Phe Phe Pro Glu Thr Lys Gly
465                 470                 475                 480

Lys Arg Leu Glu Glu Ile Gly Gln Leu Trp Asp Glu Gly Val Pro Ala
                485                 490                 495

Trp Arg Ser Ala Lys Trp Gln Pro Thr Val Pro Leu Ala Ser Asp Ala
            500                 505                 510

Glu Leu Ala His Lys Met Asp Val Ala His Ala Glu His Ala Asp Leu
        515                 520                 525

Leu Ala Thr His Ser Pro Ser Ser Asp Glu Lys Thr Gly Thr Val
    530                 535                 540

<210> SEQ ID NO 28
<211> LENGTH: 524
<212> TYPE: PRT
<213> ORGANISM: Metschnikowia
<220> FEATURE:
<223> OTHER INFORMATION: Gxf1p from H0 Metschnikowia sp.

<400> SEQUENCE: 28

Met Ser Gln Asp Glu Leu His Thr Lys Ser Gly Val Glu Thr Pro Ile
1               5                   10                  15

Asn Asp Ser Leu Leu Glu Glu Lys His Asp Val Thr Pro Leu Ala Ala
            20                  25                  30

Leu Pro Glu Lys Ser Phe Lys Asp Tyr Ile Ser Ile Ser Ile Phe Cys
        35                  40                  45

Leu Phe Val Ala Phe Gly Gly Phe Val Phe Gly Phe Asp Thr Gly Thr
    50                  55                  60

Ile Ser Gly Phe Val Asn Met Ser Asp Phe Lys Thr Arg Phe Gly Glu
65                  70                  75                  80
```

```
Met Asn Ala Gln Gly Glu Tyr Tyr Leu Ser Asn Val Arg Thr Gly Leu
                85                  90                  95

Met Val Ser Ile Phe Asn Val Gly Cys Ala Val Gly Gly Ile Phe Leu
            100                 105                 110

Cys Lys Ile Ala Asp Val Tyr Gly Arg Ile Gly Leu Met Phe Ser
        115                 120                 125

Met Val Val Tyr Val Val Gly Ile Ile Gln Ile Ala Ser Thr Thr
130                 135                 140

Lys Trp Tyr Gln Tyr Phe Ile Gly Arg Leu Ile Ala Gly Leu Ala Val
145                 150                 155                 160

Gly Thr Val Ser Val Ile Ser Pro Leu Phe Ile Ser Glu Val Ala Pro
                165                 170                 175

Lys Gln Leu Arg Gly Thr Leu Val Cys Cys Phe Gln Leu Cys Ile Thr
            180                 185                 190

Leu Gly Ile Phe Leu Gly Tyr Cys Thr Thr Tyr Gly Thr Lys Thr Tyr
            195                 200                 205

Thr Asp Ser Arg Gln Trp Arg Ile Pro Leu Gly Ile Cys Phe Ala Trp
        210                 215                 220

Ala Leu Phe Leu Val Ala Gly Met Leu Asn Met Pro Glu Ser Pro Arg
225                 230                 235                 240

Tyr Leu Val Glu Lys Ser Arg Ile Asp Asp Ala Arg Lys Ser Ile Ala
                245                 250                 255

Arg Ser Asn Lys Val Ser Glu Glu Asp Pro Ala Val Tyr Thr Glu Val
                260                 265                 270

Gln Leu Ile Gln Ala Gly Ile Asp Arg Glu Ala Leu Ala Gly Ser Ala
            275                 280                 285

Thr Trp Met Glu Leu Val Thr Gly Lys Pro Lys Ile Phe Arg Arg Val
        290                 295                 300

Ile Met Gly Val Met Leu Gln Ser Leu Gln Gln Leu Thr Gly Asp Asn
305                 310                 315                 320

Tyr Phe Phe Tyr Tyr Gly Thr Thr Ile Phe Lys Ala Val Gly Leu Gln
                325                 330                 335

Asp Ser Phe Gln Thr Ser Ile Ile Leu Gly Ile Val Asn Phe Ala Ser
            340                 345                 350

Thr Phe Val Gly Ile Tyr Ala Ile Glu Arg Met Gly Arg Arg Leu Cys
            355                 360                 365

Leu Leu Thr Gly Ser Ala Cys Met Phe Val Cys Phe Ile Ile Tyr Ser
        370                 375                 380

Leu Ile Gly Thr Gln His Leu Tyr Lys Asn Gly Phe Ser Asn Glu Pro
385                 390                 395                 400

Ser Asn Thr Tyr Lys Pro Ser Gly Asn Ala Met Ile Phe Ile Thr Cys
                405                 410                 415

Leu Tyr Ile Phe Phe Phe Ala Ser Thr Trp Ala Gly Val Tyr Cys
            420                 425                 430

Ile Val Ser Glu Ser Tyr Pro Leu Arg Ile Arg Ser Lys Ala Met Ser
        435                 440                 445

Val Ala Thr Ala Ala Asn Trp Met Trp Gly Phe Leu Ile Ser Phe Phe
450                 455                 460

Thr Pro Phe Ile Thr Ser Ala Ile His Phe Tyr Gly Phe Val Phe
465                 470                 475                 480

Thr Gly Cys Leu Ala Phe Ser Phe Phe Tyr Val Tyr Phe Val Val
            485                 490                 495
```

```
Glu Thr Lys Gly Leu Ser Leu Glu Glu Val Asp Ile Leu Tyr Ala Ser
            500                 505                 510

Gly Thr Leu Pro Trp Lys Ser Ser Gly Trp Val Pro
            515                 520

<210> SEQ ID NO 29
<211> LENGTH: 454
<212> TYPE: PRT
<213> ORGANISM: Artificial Sequence
<220> FEATURE:
<223> OTHER INFORMATION: Delta-Gxf1p (variant of Gxf1p with shorter
      N-terminus) from H0 Metschnikowia sp.

<400> SEQUENCE: 29

Met Ser Asp Phe Lys Thr Arg Phe Gly Glu Met Asn Ala Gln Gly Glu
1               5                   10                  15

Tyr Tyr Leu Ser Asn Val Arg Thr Gly Leu Met Val Ser Ile Phe Asn
            20                  25                  30

Val Gly Cys Ala Val Gly Gly Ile Phe Leu Cys Lys Ile Ala Asp Val
            35                  40                  45

Tyr Gly Arg Arg Ile Gly Leu Met Phe Ser Met Val Val Tyr Val Val
        50                  55                  60

Gly Ile Ile Ile Gln Ile Ala Ser Thr Thr Lys Trp Tyr Gln Tyr Phe
65                  70                  75                  80

Ile Gly Arg Leu Ile Ala Gly Leu Ala Val Gly Thr Val Ser Val Ile
            85                  90                  95

Ser Pro Leu Phe Ile Ser Glu Val Ala Pro Lys Gln Leu Arg Gly Thr
            100                 105                 110

Leu Val Cys Cys Phe Gln Leu Cys Ile Thr Leu Gly Ile Phe Leu Gly
            115                 120                 125

Tyr Cys Thr Thr Tyr Gly Thr Lys Thr Tyr Thr Asp Ser Arg Gln Trp
        130                 135                 140

Arg Ile Pro Leu Gly Ile Cys Phe Ala Trp Ala Leu Phe Leu Val Ala
145                 150                 155                 160

Gly Met Leu Asn Met Pro Glu Ser Pro Arg Tyr Leu Val Glu Lys Ser
            165                 170                 175

Arg Ile Asp Asp Ala Arg Lys Ser Ile Ala Arg Ser Asn Lys Val Ser
            180                 185                 190

Glu Glu Asp Pro Ala Val Tyr Thr Glu Val Gln Leu Ile Gln Ala Gly
            195                 200                 205

Ile Asp Arg Glu Ala Leu Ala Gly Ser Ala Thr Trp Met Glu Leu Val
        210                 215                 220

Thr Gly Lys Pro Lys Ile Phe Arg Arg Val Ile Met Gly Val Met Leu
225                 230                 235                 240

Gln Ser Leu Gln Gln Leu Thr Gly Asp Asn Tyr Phe Phe Tyr Tyr Gly
            245                 250                 255

Thr Thr Ile Phe Lys Ala Val Gly Leu Gln Asp Ser Phe Gln Thr Ser
            260                 265                 270

Ile Ile Leu Gly Ile Val Asn Phe Ala Ser Thr Phe Val Gly Ile Tyr
            275                 280                 285

Ala Ile Glu Arg Met Gly Arg Arg Leu Cys Leu Leu Thr Gly Ser Ala
        290                 295                 300

Cys Met Phe Val Cys Phe Ile Ile Tyr Ser Leu Ile Gly Thr Gln His
305                 310                 315                 320

Leu Tyr Lys Asn Gly Phe Ser Asn Glu Pro Ser Asn Thr Tyr Lys Pro
            325                 330                 335
```

```
Ser Gly Asn Ala Met Ile Phe Ile Thr Cys Leu Tyr Ile Phe Phe
            340                 345                 350

Ala Ser Thr Trp Ala Gly Gly Val Tyr Cys Ile Val Ser Glu Ser Tyr
            355                 360                 365

Pro Leu Arg Ile Arg Ser Lys Ala Met Ser Val Ala Thr Ala Ala Asn
            370                 375                 380

Trp Met Trp Gly Phe Leu Ile Ser Phe Phe Thr Pro Phe Ile Thr Ser
385                 390                 395                 400

Ala Ile His Phe Tyr Tyr Gly Phe Val Phe Thr Gly Cys Leu Ala Phe
            405                 410                 415

Ser Phe Phe Tyr Val Tyr Phe Val Val Glu Thr Lys Gly Leu Ser
            420                 425                 430

Leu Glu Glu Val Asp Ile Leu Tyr Ala Ser Gly Thr Leu Pro Trp Lys
            435                 440                 445

Ser Ser Gly Trp Val Pro
        450

<210> SEQ ID NO 30
<211> LENGTH: 548
<212> TYPE: PRT
<213> ORGANISM: Metschnikowia
<220> FEATURE:
<223> OTHER INFORMATION: Gxf2p from H0 Metschnikowia sp.

<400> SEQUENCE: 30

Met Ser Ala Glu Gln Glu Gln Val Ser Gly Thr Ser Ala Thr Ile
1               5                   10                  15

Asp Gly Leu Ala Ser Leu Lys Gln Glu Lys Thr Ala Glu Glu Glu Asp
                20                  25                  30

Ala Phe Lys Pro Lys Pro Ala Thr Ala Tyr Phe Ile Ser Phe Leu
            35                  40                  45

Cys Gly Leu Val Ala Phe Gly Gly Tyr Val Phe Gly Phe Asp Thr Gly
            50                  55                  60

Thr Ile Ser Gly Phe Val Asn Met Asp Asp Tyr Leu Met Arg Phe Gly
65                  70                  75                  80

Gln Gln His Ala Asp Gly Thr Tyr Tyr Leu Ser Asn Val Arg Thr Gly
                85                  90                  95

Leu Ile Val Ser Ile Phe Asn Ile Gly Cys Ala Val Gly Gly Leu Ala
            100                 105                 110

Leu Ser Lys Val Gly Asp Ile Trp Gly Arg Arg Ile Gly Ile Met Val
            115                 120                 125

Ala Met Ile Ile Tyr Met Val Gly Ile Ile Gln Ile Ala Ser Gln
130                 135                 140

Asp Lys Trp Tyr Gln Tyr Phe Ile Gly Arg Leu Ile Thr Gly Leu Gly
145                 150                 155                 160

Val Gly Thr Thr Ser Val Leu Ser Pro Leu Phe Ile Ser Glu Ser Ala
                165                 170                 175

Pro Lys His Leu Arg Gly Thr Leu Val Cys Cys Phe Gln Leu Met Val
            180                 185                 190

Thr Leu Gly Ile Phe Leu Gly Tyr Cys Thr Thr Tyr Gly Thr Lys Asn
            195                 200                 205

Tyr Thr Asp Ser Arg Gln Trp Arg Ile Pro Leu Gly Leu Cys Phe Ala
            210                 215                 220

Trp Ala Leu Leu Leu Ile Ser Gly Met Val Phe Met Pro Glu Ser Pro
225                 230                 235                 240
```

```
Arg Phe Leu Ile Glu Arg Gln Arg Phe Asp Glu Ala Lys Ala Ser Val
            245                 250                 255

Ala Lys Ser Asn Gln Val Ser Thr Glu Asp Pro Ala Val Tyr Thr Glu
        260                 265                 270

Val Glu Leu Ile Gln Ala Gly Ile Asp Arg Glu Ala Leu Ala Gly Ser
    275                 280                 285

Ala Gly Trp Lys Glu Leu Ile Thr Gly Lys Pro Lys Met Leu Gln Arg
290                 295                 300

Val Ile Leu Gly Met Met Leu Gln Ser Ile Gln Gln Leu Thr Gly Asn
305                 310                 315                 320

Asn Tyr Phe Phe Tyr Tyr Gly Thr Thr Ile Phe Lys Ala Val Gly Met
            325                 330                 335

Ser Asp Ser Phe Gln Thr Ser Ile Val Leu Gly Ile Val Asn Phe Ala
        340                 345                 350

Ser Thr Phe Val Gly Ile Trp Ala Ile Glu Arg Met Gly Arg Arg Ser
    355                 360                 365

Cys Leu Leu Val Gly Ser Ala Cys Met Ser Val Cys Phe Leu Ile Tyr
370                 375                 380

Ser Ile Leu Gly Ser Val Asn Leu Tyr Ile Asp Gly Tyr Glu Asn Thr
385                 390                 395                 400

Pro Ser Asn Thr Arg Lys Pro Thr Gly Asn Ala Met Ile Phe Ile Thr
            405                 410                 415

Cys Leu Phe Ile Phe Phe Phe Ala Ser Thr Trp Ala Gly Gly Val Tyr
        420                 425                 430

Ser Ile Val Ser Glu Thr Tyr Pro Leu Arg Ile Arg Ser Lys Gly Met
    435                 440                 445

Ala Val Ala Thr Ala Ala Asn Trp Met Trp Gly Phe Leu Ile Ser Phe
450                 455                 460

Phe Thr Pro Phe Ile Thr Ser Ala Ile His Phe Tyr Tyr Gly Phe Val
465                 470                 475                 480

Phe Thr Gly Cys Leu Ile Phe Ser Phe Phe Tyr Val Phe Phe Phe Val
            485                 490                 495

Arg Glu Thr Lys Gly Leu Ser Leu Glu Glu Val Asp Glu Leu Tyr Ala
        500                 505                 510

Thr Asp Leu Pro Pro Trp Lys Thr Ala Gly Trp Thr Pro Pro Ser Ala
    515                 520                 525

Glu Asp Met Ala His Thr Thr Gly Phe Ala Glu Ala Ala Lys Pro Thr
530                 535                 540

Asn Lys His Val
545

<210> SEQ ID NO 31
<211> LENGTH: 526
<212> TYPE: PRT
<213> ORGANISM: Metschnikowia
<220> FEATURE:
<223> OTHER INFORMATION: Gxs1p from H0 Metschnikowia sp.

<400> SEQUENCE: 31

Met Gly Leu Glu Ser Asn Lys Leu Ile Arg Lys Tyr Ile Asn Val Gly
1               5                   10                  15

Glu Lys Arg Ala Gly Ser Ser Gly Met Gly Ile Phe Val Gly Val Phe
            20                  25                  30

Ala Ala Leu Gly Gly Val Leu Phe Gly Tyr Asp Thr Gly Thr Ile Ser
        35                  40                  45
```

```
Gly Val Met Ala Met Pro Trp Val Lys Glu His Phe Pro Lys Asp Arg
 50                  55                  60

Val Ala Phe Ser Ala Ser Glu Ser Ser Leu Ile Val Ser Ile Leu Ser
 65                  70                  75                  80

Ala Gly Thr Phe Phe Gly Ala Ile Leu Ala Pro Leu Leu Thr Asp Thr
                 85                  90                  95

Leu Gly Arg Arg Trp Cys Ile Ile Ile Ser Ser Leu Val Val Phe Asn
                100                 105                 110

Leu Gly Ala Ala Leu Gln Thr Ala Ala Thr Asp Ile Pro Leu Leu Ile
                115                 120                 125

Val Gly Arg Val Ile Ala Gly Leu Gly Val Gly Leu Ile Ser Ser Thr
130                 135                 140

Ile Pro Leu Tyr Gln Ser Glu Ala Leu Pro Lys Trp Ile Arg Gly Ala
145                 150                 155                 160

Val Val Ser Cys Tyr Gln Trp Ala Ile Thr Ile Gly Ile Phe Leu Ala
                165                 170                 175

Ala Val Ile Asn Gln Gly Thr His Lys Ile Asn Ser Pro Ala Ser Tyr
                180                 185                 190

Arg Ile Pro Leu Gly Ile Gln Met Ala Trp Gly Leu Ile Leu Gly Val
                195                 200                 205

Gly Met Phe Phe Leu Pro Glu Thr Pro Arg Phe Tyr Ile Ser Lys Gly
210                 215                 220

Gln Asn Ala Lys Ala Ala Val Ser Leu Ala Arg Leu Arg Lys Leu Pro
225                 230                 235                 240

Gln Asp His Pro Glu Leu Leu Glu Glu Leu Asp Ile Gln Ala Ala
                245                 250                 255

Tyr Glu Phe Glu Thr Val His Gly Lys Ser Ser Trp Ser Gln Val Phe
                260                 265                 270

Thr Asn Lys Asn Lys Gln Leu Lys Lys Leu Ala Thr Gly Val Cys Leu
                275                 280                 285

Gln Ala Phe Gln Gln Leu Thr Gly Val Asn Phe Ile Phe Tyr Phe Gly
                290                 295                 300

Thr Thr Phe Phe Asn Ser Val Gly Leu Asp Gly Phe Thr Thr Ser Leu
305                 310                 315                 320

Ala Thr Asn Ile Val Asn Val Gly Ser Thr Ile Pro Gly Ile Leu Gly
                325                 330                 335

Val Glu Ile Phe Gly Arg Arg Lys Val Leu Thr Gly Ala Ala Gly
                340                 345                 350

Met Cys Leu Ser Gln Phe Ile Val Ala Ile Val Gly Val Ala Thr Asp
                355                 360                 365

Ser Lys Ala Ala Asn Gln Val Leu Ile Ala Phe Cys Cys Ile Phe Ile
370                 375                 380

Ala Phe Phe Ala Ala Thr Trp Gly Pro Thr Ala Trp Val Val Cys Gly
385                 390                 395                 400

Glu Ile Phe Pro Leu Arg Thr Arg Ala Lys Ser Ile Ala Met Cys Ala
                405                 410                 415

Ala Ser Asn Trp Leu Leu Asn Trp Ala Ile Ala Tyr Ala Thr Pro Tyr
                420                 425                 430

Leu Val Asp Ser Asp Lys Gly Asn Leu Gly Thr Asn Val Phe Phe Ile
                435                 440                 445

Trp Gly Ser Cys Asn Phe Phe Cys Leu Val Phe Ala Tyr Phe Met Ile
450                 455                 460
```

```
Tyr Glu Thr Lys Gly Leu Ser Leu Glu Gln Val Asp Glu Leu Tyr Glu
465                 470                 475                 480

Lys Val Ala Ser Ala Arg Lys Ser Pro Gly Phe Val Pro Ser Glu His
            485                 490                 495

Ala Phe Arg Glu His Ala Asp Val Glu Thr Ala Met Pro Asp Asn Phe
        500                 505                 510

Asn Leu Lys Ala Glu Ala Ile Ser Val Glu Asp Ala Ser Val
    515                 520                 525

<210> SEQ ID NO 32
<211> LENGTH: 526
<212> TYPE: PRT
<213> ORGANISM: Metschnikowia
<220> FEATURE:
<223> OTHER INFORMATION: Hgt12p from H0 Metschnikowia sp

<400> SEQUENCE: 32

Met Gly Leu Glu Ser Asn Lys Leu Ile Arg Lys Tyr Ile Asn Val Gly
1               5                   10                  15

Glu Lys Arg Ala Gly Ser Ser Gly Met Gly Ile Phe Val Gly Val Phe
            20                  25                  30

Ala Ala Leu Gly Gly Val Leu Phe Gly Tyr Asp Thr Gly Thr Ile Ser
        35                  40                  45

Gly Val Met Ala Met Pro Trp Val Lys Glu His Phe Pro Lys Asp Arg
50                  55                  60

Val Ala Phe Ser Ala Ser Glu Ser Ser Leu Ile Val Ser Ile Leu Ser
65                  70                  75                  80

Ala Gly Thr Phe Phe Gly Ala Ile Leu Ala Pro Leu Leu Thr Asp Thr
                85                  90                  95

Leu Gly Arg Arg Trp Cys Ile Ile Ile Ser Ser Leu Val Val Phe Asn
            100                 105                 110

Leu Gly Ala Ala Leu Gln Thr Ala Ala Thr Asp Ile Pro Leu Leu Ile
        115                 120                 125

Val Gly Arg Val Ile Ala Gly Leu Gly Val Gly Leu Ile Ser Ser Thr
130                 135                 140

Ile Pro Leu Tyr Gln Ser Glu Ala Leu Pro Lys Trp Ile Arg Gly Ala
145                 150                 155                 160

Val Val Ser Cys Tyr Gln Trp Ala Ile Thr Ile Gly Ile Phe Leu Ala
                165                 170                 175

Ala Val Ile Asn Gln Gly Thr His Lys Ile Asn Ser Pro Ala Ser Tyr
            180                 185                 190

Arg Ile Pro Leu Gly Ile Gln Met Ala Trp Gly Leu Ile Leu Gly Val
        195                 200                 205

Gly Met Phe Phe Leu Pro Glu Thr Pro Arg Phe Tyr Ile Ser Lys Gly
210                 215                 220

Gln Asn Ala Lys Ala Ala Val Ser Leu Ala Arg Leu Arg Lys Leu Pro
225                 230                 235                 240

Gln Asp His Pro Glu Leu Leu Glu Glu Leu Glu Asp Ile Gln Ala Ala
                245                 250                 255

Tyr Glu Phe Glu Thr Val His Gly Lys Ser Ser Trp Ser Gln Val Phe
            260                 265                 270

Thr Asn Lys Asn Lys Gln Leu Lys Lys Leu Ala Thr Gly Val Cys Leu
        275                 280                 285

Gln Ala Phe Gln Gln Leu Thr Gly Val Asn Phe Ile Phe Tyr Phe Gly
290                 295                 300
```

```
Thr Thr Phe Phe Asn Ser Val Gly Leu Asp Gly Phe Thr Thr Ser Leu
305                 310                 315                 320

Ala Thr Asn Ile Val Asn Val Gly Ser Thr Ile Pro Gly Ile Leu Gly
            325                 330                 335

Val Glu Ile Phe Gly Arg Arg Lys Val Leu Leu Thr Gly Ala Ala Gly
        340                 345                 350

Met Cys Leu Ser Gln Phe Ile Val Ala Ile Val Gly Val Ala Thr Asp
            355                 360                 365

Ser Lys Ala Ala Asn Gln Val Leu Ile Ala Phe Cys Cys Ile Phe Ile
    370                 375                 380

Ala Phe Phe Ala Ala Thr Trp Gly Pro Thr Ala Trp Val Val Cys Gly
385                 390                 395                 400

Glu Ile Phe Pro Leu Arg Thr Arg Ala Lys Ser Ile Ala Met Cys Ala
                405                 410                 415

Ala Ser Asn Trp Leu Leu Asn Trp Ala Ile Ala Tyr Ala Thr Pro Tyr
            420                 425                 430

Leu Val Asp Ser Asp Lys Gly Asn Leu Gly Thr Asn Val Phe Phe Ile
        435                 440                 445

Trp Gly Ser Cys Asn Phe Phe Cys Leu Val Phe Ala Tyr Phe Met Ile
450                 455                 460

Tyr Glu Thr Lys Gly Leu Ser Leu Glu Gln Val Asp Glu Leu Tyr Glu
465                 470                 475                 480

Lys Val Ala Ser Ala Arg Lys Ser Pro Gly Phe Val Pro Ser Glu His
                485                 490                 495

Ala Phe Arg Glu His Ala Asp Val Glu Thr Ala Met Pro Asp Asn Phe
            500                 505                 510

Asn Leu Lys Ala Glu Ala Ile Ser Val Glu Asp Ala Ser Val
        515                 520                 525

<210> SEQ ID NO 33
<211> LENGTH: 548
<212> TYPE: PRT
<213> ORGANISM: Metschnikowia
<220> FEATURE:
<223> OTHER INFORMATION: Hxt5p from H0 Metschnikowia sp.

<400> SEQUENCE: 33

Met Ser Ile Phe Glu Gly Lys Asp Gly Lys Gly Val Ser Ser Thr Glu
1               5                   10                  15

Ser Leu Ser Asn Asp Val Arg Tyr Asp Asn Met Glu Lys Val Asp Gln
            20                  25                  30

Asp Val Leu Arg His Asn Phe Asn Phe Asp Lys Glu Phe Glu Glu Leu
        35                  40                  45

Glu Ile Glu Ala Ala Gln Val Asn Asp Lys Pro Ser Phe Val Asp Arg
    50                  55                  60

Ile Leu Ser Leu Glu Tyr Lys Leu His Phe Glu Asn Lys Asn His Met
65                  70                  75                  80

Val Trp Leu Leu Gly Ala Phe Ala Ala Ala Gly Leu Leu Ser Gly
                85                  90                  95

Leu Asp Gln Ser Ile Ile Ser Gly Ala Ser Ile Gly Met Asn Lys Ala
            100                 105                 110

Leu Asn Leu Thr Glu Arg Glu Ala Ser Leu Val Ser Ser Leu Met Pro
        115                 120                 125

Leu Gly Ala Met Ala Gly Ser Met Ile Met Thr Pro Leu Asn Glu Trp
    130                 135                 140
```

```
Phe Gly Arg Lys Ser Ser Leu Ile Ile Ser Cys Ile Trp Tyr Thr Ile
145                 150                 155                 160

Gly Ser Ala Leu Cys Ala Gly Ala Arg Asp His His Met Met Tyr Ala
            165                 170                 175

Gly Arg Phe Ile Leu Gly Val Gly Val Gly Ile Glu Gly Gly Cys Val
            180                 185                 190

Gly Ile Tyr Ile Ser Glu Ser Val Pro Ala Asn Val Arg Gly Ser Ile
            195                 200                 205

Val Ser Met Tyr Gln Phe Asn Ile Ala Leu Gly Glu Val Leu Gly Tyr
            210                 215                 220

Ala Val Ala Ala Ile Phe Tyr Thr Val His Gly Gly Trp Arg Phe Met
225                 230                 235                 240

Val Gly Ser Ser Leu Val Phe Ser Thr Ile Leu Phe Ala Gly Leu Phe
            245                 250                 255

Phe Leu Pro Glu Ser Pro Arg Trp Leu Val His Lys Gly Arg Asn Gly
            260                 265                 270

Met Ala Tyr Asp Val Trp Lys Arg Leu Arg Asp Ile Asn Asp Glu Ser
            275                 280                 285

Ala Lys Leu Glu Phe Leu Glu Met Arg Gln Ala Ala Tyr Gln Glu Arg
290                 295                 300

Glu Arg Arg Ser Gln Glu Ser Leu Phe Ser Ser Trp Gly Glu Leu Phe
305                 310                 315                 320

Thr Ile Ala Arg Asn Arg Arg Ala Leu Thr Tyr Ser Val Ile Met Ile
            325                 330                 335

Thr Leu Gly Gln Leu Thr Gly Val Asn Ala Val Met Tyr Tyr Met Ser
            340                 345                 350

Thr Leu Met Gly Ala Ile Gly Phe Asn Glu Lys Asp Ser Val Phe Met
            355                 360                 365

Ser Leu Val Gly Gly Ser Leu Leu Ile Gly Thr Ile Pro Ala Ile
370                 375                 380

Leu Trp Met Asp Arg Phe Gly Arg Arg Val Trp Gly Tyr Asn Leu Val
385                 390                 395                 400

Gly Phe Phe Val Gly Leu Val Leu Val Gly Val Gly Tyr Arg Phe Asn
            405                 410                 415

Pro Val Thr Gln Lys Ala Ala Ser Glu Gly Val Tyr Leu Thr Gly Leu
            420                 425                 430

Ile Val Tyr Phe Leu Phe Phe Gly Ser Tyr Ser Thr Leu Thr Trp Val
            435                 440                 445

Ile Pro Ser Glu Ser Phe Asp Leu Arg Thr Arg Ser Leu Gly Met Thr
450                 455                 460

Ile Cys Ser Thr Phe Leu Tyr Leu Trp Ser Phe Thr Val Thr Tyr Asn
465                 470                 475                 480

Phe Thr Lys Met Ser Ala Ala Phe Thr Tyr Thr Gly Leu Thr Leu Gly
            485                 490                 495

Phe Tyr Gly Gly Ile Ala Phe Leu Gly Leu Ile Tyr Gln Val Cys Phe
            500                 505                 510

Met Pro Glu Thr Lys Asp Lys Thr Leu Glu Glu Ile Asp Asp Ile Phe
            515                 520                 525

Asn Arg Ser Ala Phe Ser Ile Ala Arg Glu Asn Ile Ser Asn Leu Lys
            530                 535                 540

Lys Gly Ile Trp
545
```

<210> SEQ ID NO 34
<211> LENGTH: 524
<212> TYPE: PRT
<213> ORGANISM: Metschnikowia
<220> FEATURE:
<223> OTHER INFORMATION: Hxt2.6p from H0 Metschnikowia sp.

<400> SEQUENCE: 34

```
Met Ser Ser Thr Thr Asp Thr Leu Glu Lys Arg Asp Thr Glu Pro Phe
1               5                   10                  15

Thr Ser Asp Ala Pro Val Thr Val His Asp Tyr Ile Ala Glu Glu Arg
            20                  25                  30

Pro Trp Trp Lys Val Pro His Leu Arg Val Leu Thr Trp Ser Val Phe
        35                  40                  45

Val Ile Thr Leu Thr Ser Thr Asn Asn Gly Tyr Asp Gly Ser Met Leu
50                  55                  60

Asn Gly Leu Gln Ser Leu Asp Ile Trp Gln Glu Asp Leu Gly His Pro
65                  70                  75                  80

Ala Gly Gln Lys Leu Gly Ala Leu Ala Asn Gly Val Leu Phe Gly Asn
                85                  90                  95

Leu Ala Ala Val Pro Phe Ala Ser Tyr Phe Cys Asp Arg Phe Gly Arg
            100                 105                 110

Arg Pro Val Ile Cys Phe Gly Gln Ile Leu Thr Ile Val Gly Ala Val
        115                 120                 125

Leu Gln Gly Leu Ser Asn Ser Tyr Gly Phe Phe Leu Gly Ser Arg Ile
130                 135                 140

Val Leu Gly Phe Gly Ala Met Ile Ala Thr Ile Pro Ser Pro Thr Leu
145                 150                 155                 160

Ile Ser Glu Ile Ala Tyr Pro Thr His Arg Glu Thr Ser Thr Phe Ala
                165                 170                 175

Tyr Asn Val Cys Trp Tyr Leu Gly Ala Ile Ile Ala Ser Trp Val Thr
            180                 185                 190

Tyr Gly Thr Arg Asp Leu Gln Ser Lys Ala Cys Trp Ser Ile Pro Ser
        195                 200                 205

Tyr Leu Gln Ala Ala Leu Pro Phe Phe Gln Val Cys Met Ile Trp Phe
210                 215                 220

Val Pro Glu Ser Pro Arg Phe Leu Val Ala Lys Gly Lys Ile Asp Gln
225                 230                 235                 240

Ala Arg Ala Val Leu Ser Lys Tyr His Thr Gly Asp Ser Thr Asp Pro
                245                 250                 255

Arg Asp Val Ala Leu Val Asp Phe Glu Leu His Glu Ile Glu Ser Ala
            260                 265                 270

Leu Glu Gln Glu Lys Leu Asn Thr Arg Ser Ser Tyr Phe Asp Phe Phe
        275                 280                 285

Lys Lys Arg Asn Phe Arg Lys Arg Gly Phe Leu Cys Val Met Val Gly
290                 295                 300

Val Ala Met Gln Leu Ser Gly Asn Gly Leu Val Ser Tyr Tyr Leu Ser
305                 310                 315                 320

Lys Val Leu Asp Ser Ile Gly Ile Thr Glu Thr Lys Arg Gln Leu Glu
                325                 330                 335

Ile Asn Gly Cys Leu Met Ile Tyr Asn Phe Val Ile Cys Val Ser Leu
            340                 345                 350

Met Ser Val Cys Arg Met Phe Lys Arg Val Leu Phe Leu Thr Cys
        355                 360                 365

Phe Ser Gly Met Thr Val Cys Tyr Thr Ile Trp Thr Ile Leu Ser Ala
```

```
            370                 375                 380
Leu Asn Glu Gln Arg His Phe Glu Asp Lys Gly Leu Ala Asn Gly Val
385                 390                 395                 400

Leu Ala Met Ile Phe Phe Tyr Tyr Phe Phe Tyr Asn Val Gly Ile Asn
                405                 410                 415

Gly Leu Pro Phe Leu Tyr Ile Thr Glu Ile Leu Pro Tyr Ser His Arg
                420                 425                 430

Ala Lys Gly Leu Asn Leu Phe Gln Phe Ser Gln Phe Leu Thr Gln Ile
                435                 440                 445

Tyr Asn Gly Tyr Val Asn Pro Ile Ala Met Asp Ala Ile Ser Trp Lys
            450                 455                 460

Tyr Tyr Ile Val Tyr Cys Cys Ile Leu Phe Val Glu Leu Val Ile Val
465                 470                 475                 480

Phe Phe Thr Phe Pro Glu Thr Ser Gly Tyr Thr Leu Glu Glu Val Ala
                485                 490                 495

Gln Val Phe Gly Asp Glu Ala Pro Gly Leu His Asn Arg Gln Leu Asp
                500                 505                 510

Val Ala Lys Glu Ser Leu Glu His Val Glu His Val
            515                 520
```

<210> SEQ ID NO 35
<211> LENGTH: 556
<212> TYPE: PRT
<213> ORGANISM: Metschnikowia
<220> FEATURE:
<223> OTHER INFORMATION: Qup2p from H0 Metschnikowia sp.

<400> SEQUENCE: 35

```
Met Gly Phe Arg Asn Leu Lys Arg Arg Leu Ser Asn Val Gly Asp Ser
1               5                   10                  15

Met Ser Val His Ser Val Lys Glu Glu Asp Phe Ser Arg Val Glu
                20                  25                  30

Ile Pro Asp Glu Ile Tyr Asn Tyr Lys Ile Val Leu Val Ala Leu Thr
            35                  40                  45

Ala Ala Ser Ala Ala Ile Ile Ile Gly Tyr Asp Ala Gly Phe Ile Gly
        50                  55                  60

Gly Thr Val Ser Leu Thr Ala Phe Lys Ser Glu Phe Gly Leu Asp Lys
65                  70                  75                  80

Met Ser Ala Thr Ala Ala Ser Ala Ile Glu Ala Asn Val Val Ser Val
                85                  90                  95

Phe Gln Ala Gly Ala Tyr Phe Gly Cys Leu Phe Phe Tyr Pro Ile Gly
                100                 105                 110

Glu Ile Trp Gly Arg Lys Ile Gly Leu Leu Leu Ser Gly Phe Leu Leu
            115                 120                 125

Thr Phe Gly Ala Ala Ile Ser Leu Ile Ser Asn Ser Ser Arg Gly Leu
        130                 135                 140

Gly Ala Ile Tyr Ala Gly Arg Val Leu Thr Gly Leu Gly Ile Gly Gly
145                 150                 155                 160

Cys Ser Ser Leu Ala Pro Ile Tyr Val Ser Glu Ile Ala Pro Ala Ala
                165                 170                 175

Ile Arg Gly Lys Leu Val Gly Cys Trp Glu Val Ser Trp Gln Val Gly
                180                 185                 190

Gly Ile Val Gly Tyr Trp Ile Asn Tyr Gly Val Leu Gln Thr Leu Pro
            195                 200                 205

Ile Ser Ser Gln Gln Trp Ile Ile Pro Phe Ala Val Gln Leu Ile Pro
```

```
            210                 215                 220
Ser Gly Leu Phe Trp Gly Leu Cys Leu Leu Ile Pro Glu Ser Pro Arg
225                 230                 235                 240

Phe Leu Val Ser Lys Gly Lys Ile Asp Lys Ala Arg Lys Asn Leu Ala
                245                 250                 255

Tyr Leu Arg Gly Leu Ser Glu Asp His Pro Tyr Ser Val Phe Glu Leu
                260                 265                 270

Glu Asn Ile Ser Lys Ala Ile Glu Glu Asn Phe Glu Gln Thr Gly Arg
                275                 280                 285

Gly Phe Phe Asp Pro Leu Lys Ala Leu Phe Phe Ser Lys Lys Met Leu
                290                 295                 300

Tyr Arg Leu Leu Leu Ser Thr Ser Met Phe Met Met Gln Asn Gly Tyr
305                 310                 315                 320

Gly Ile Asn Ala Val Thr Tyr Tyr Ser Pro Thr Ile Phe Lys Ser Leu
                325                 330                 335

Gly Val Gln Gly Ser Asn Ala Gly Leu Leu Ser Thr Gly Ile Phe Gly
                340                 345                 350

Leu Leu Lys Gly Ala Ala Ser Val Phe Trp Val Phe Phe Leu Val Asp
                355                 360                 365

Thr Phe Gly Arg Arg Phe Cys Leu Cys Tyr Leu Ser Leu Pro Cys Ser
                370                 375                 380

Ile Cys Met Trp Tyr Ile Gly Ala Tyr Ile Lys Ile Ala Asn Pro Ser
385                 390                 395                 400

Ala Lys Leu Ala Ala Gly Asp Thr Ala Thr Thr Pro Ala Gly Thr Ala
                405                 410                 415

Ala Lys Ala Met Leu Tyr Ile Trp Thr Ile Phe Tyr Gly Ile Thr Trp
                420                 425                 430

Asn Gly Thr Thr Trp Val Ile Cys Ala Glu Ile Phe Pro Gln Ser Val
                435                 440                 445

Arg Thr Ala Ala Gln Ala Val Asn Ala Ser Ser Asn Trp Phe Trp Ala
                450                 455                 460

Phe Met Ile Gly His Phe Thr Gly Gln Ala Leu Glu Asn Ile Gly Tyr
465                 470                 475                 480

Gly Tyr Tyr Phe Leu Phe Ala Ala Cys Ser Ala Ile Phe Pro Val Val
                485                 490                 495

Val Trp Phe Val Tyr Pro Glu Thr Lys Gly Val Pro Leu Glu Ala Val
                500                 505                 510

Glu Tyr Leu Phe Glu Val Arg Pro Trp Lys Ala His Ser Tyr Ala Leu
                515                 520                 525

Glu Lys Tyr Gln Ile Glu Tyr Asn Glu Gly Glu Phe His Gln His Lys
                530                 535                 540

Pro Glu Val Leu Leu Gln Gly Ser Glu Asn Ser Asp
545                 550                 555

<210> SEQ ID NO 36
<211> LENGTH: 543
<212> TYPE: PRT
<213> ORGANISM: Metschnikowia
<220> FEATURE:
<223> OTHER INFORMATION: Aps1p/Hgt19p from H0 Metschnikowia sp.

<400> SEQUENCE: 36

Met Gly Tyr Glu Glu Lys Leu Val Ala Pro Ala Leu Lys Phe Lys Asn
1               5                   10                  15

Phe Leu Asp Lys Thr Pro Asn Ile His Asn Val Tyr Val Ile Ala Ala
```

```
                    20                  25                  30
Ile Ser Cys Thr Ser Gly Met Met Phe Gly Phe Asp Ile Ser Ser Met
                35                  40                  45
Ser Val Phe Val Asp Gln Gln Pro Tyr Leu Lys Met Phe Asp Asn Pro
            50                  55                  60
Ser Ser Val Ile Gln Gly Phe Ile Thr Ala Ser Met Ser Leu Gly Ser
65                  70                  75                  80
Phe Phe Gly Ser Leu Thr Ser Thr Phe Ile Ser Glu Pro Phe Gly Arg
                85                  90                  95
Arg Ala Ser Leu Phe Ile Cys Gly Ile Leu Trp Val Ile Gly Ala Ala
                100                 105                 110
Val Gln Ser Ser Ser Gln Asn Arg Ala Gln Leu Ile Cys Gly Arg Ile
                115                 120                 125
Ile Ala Gly Trp Gly Ile Gly Phe Gly Ser Ser Val Ala Pro Val Tyr
                130                 135                 140
Gly Ser Glu Met Ala Pro Arg Lys Ile Arg Gly Thr Ile Gly Gly Ile
145                 150                 155                 160
Phe Gln Phe Ser Val Thr Val Gly Ile Phe Ile Met Phe Leu Ile Gly
                165                 170                 175
Tyr Gly Cys Ser Phe Ile Gln Gly Lys Ala Ser Phe Arg Ile Pro Trp
                180                 185                 190
Gly Val Gln Met Val Pro Gly Leu Ile Leu Ile Gly Leu Phe Phe
                195                 200                 205
Ile Pro Glu Ser Pro Arg Trp Leu Ala Lys Gln Gly Tyr Trp Glu Asp
                210                 215                 220
Ala Glu Ile Ile Val Ala Asn Val Gln Ala Lys Gly Asn Arg Asn Asp
225                 230                 235                 240
Ala Asn Val Gln Ile Glu Met Ser Glu Ile Lys Asp Gln Leu Met Leu
                245                 250                 255
Asp Glu His Leu Lys Glu Phe Thr Tyr Ala Asp Leu Phe Thr Lys Lys
                260                 265                 270
Tyr Arg Gln Arg Thr Ile Thr Ala Ile Phe Ala Gln Ile Trp Gln Gln
                275                 280                 285
Leu Thr Gly Met Asn Val Met Met Tyr Tyr Ile Val Tyr Ile Phe Gln
                290                 295                 300
Met Ala Gly Tyr Ser Gly Asn Thr Asn Leu Val Pro Ser Leu Ile Gln
305                 310                 315                 320
Tyr Ile Ile Asn Met Ala Val Thr Val Pro Ala Leu Phe Cys Leu Asp
                325                 330                 335
Leu Leu Gly Arg Arg Thr Ile Leu Leu Ala Gly Ala Ala Phe Met Met
                340                 345                 350
Ala Trp Gln Phe Gly Val Ala Gly Ile Leu Ala Thr Tyr Ser Glu Pro
                355                 360                 365
Ala Tyr Ile Ser Asp Thr Val Arg Ile Thr Ile Pro Asp Asp His Lys
                370                 375                 380
Ser Ala Ala Lys Gly Val Ile Ala Cys Cys Tyr Leu Phe Val Cys Ser
385                 390                 395                 400
Phe Ala Phe Ser Trp Gly Val Gly Ile Trp Val Tyr Cys Ser Glu Val
                405                 410                 415
Trp Gly Asp Ser Gln Ser Arg Gln Arg Gly Ala Ala Leu Ala Thr Ser
                420                 425                 430
Ala Asn Trp Ile Phe Asn Phe Ala Ile Ala Met Phe Thr Pro Ser Ser
                435                 440                 445
```

```
Phe Lys Asn Ile Thr Trp Lys Thr Tyr Ile Ile Tyr Ala Thr Phe Cys
    450                 455                 460

Ala Cys Met Phe Ile His Val Phe Phe Phe Pro Glu Thr Lys Gly
465                 470                 475                 480

Lys Arg Leu Glu Glu Ile Gly Gln Leu Trp Asp Glu Gly Val Pro Ala
                485                 490                 495

Trp Arg Ser Ala Lys Trp Gln Pro Thr Val Pro Leu Ala Ser Asp Ala
                500                 505                 510

Glu Leu Ala His Lys Met Asp Val Ala His Ala Glu His Ala Asp Leu
                515                 520                 525

Leu Ala Thr His Ser Pro Ser Ser Asp Glu Lys Thr Gly Thr Val
                530                 535                 540

<210> SEQ ID NO 37
<211> LENGTH: 539
<212> TYPE: PRT
<213> ORGANISM: Pichia gulliermondii
<220> FEATURE:
<223> OTHER INFORMATION: exemplary xylose transporter from Pichia
      gulliermondii; Axt1p

<400> SEQUENCE: 37

Met Ala Tyr Glu Asp Lys Leu Val Ala Pro Ala Leu Lys Phe Arg Asn
1               5                   10                  15

Phe Leu Asp Lys Thr Pro Asn Ile Tyr Asn Pro Tyr Ile Ile Ser Ile
                20                  25                  30

Ile Ser Cys Ile Ala Gly Met Met Phe Gly Phe Asp Ile Ser Ser Met
            35                  40                  45

Ser Ala Phe Val Ser Leu Pro Ala Tyr Val Asn Tyr Phe Asp Thr Pro
    50                  55                  60

Ser Ala Val Ile Gln Gly Phe Ile Thr Ser Ala Met Ala Leu Gly Ser
65                  70                  75                  80

Phe Phe Gly Ser Ile Ala Ser Ala Phe Val Ser Glu Pro Phe Gly Arg
                85                  90                  95

Arg Ala Ser Leu Leu Thr Cys Ser Trp Phe Trp Met Ile Gly Ala Ala
                100                 105                 110

Ile Gln Ala Ser Ser Gln Asn Arg Ala Gln Leu Ile Ile Gly Arg Ile
            115                 120                 125

Ile Ser Gly Phe Gly Val Gly Phe Gly Ser Ser Val Ala Pro Val Tyr
        130                 135                 140

Gly Ser Glu Met Ala Pro Arg Lys Ile Arg Gly Arg Ile Gly Gly Ile
145                 150                 155                 160

Phe Gln Leu Ser Val Thr Leu Gly Ile Met Ile Met Phe Phe Ile Ser
                165                 170                 175

Tyr Gly Thr Ser His Ile Lys Thr Ala Ala Ala Phe Arg Leu Ala Trp
                180                 185                 190

Ala Leu Gln Ile Ile Pro Gly Leu Leu Met Cys Ile Gly Val Phe Phe
            195                 200                 205

Ile Pro Glu Ser Pro Arg Trp Leu Ala Lys Gln Gly His Trp Asp Glu
        210                 215                 220

Ala Glu Ile Ile Val Ala Lys Ile Gln Ala Lys Gly Asp Arg Glu Asn
225                 230                 235                 240

Pro Asp Val Leu Ile Glu Ile Ser Glu Ile Lys Asp Gln Leu Met Val
                245                 250                 255

Asp Glu Asn Ala Lys Ala Phe Thr Tyr Ala Asp Leu Phe Ser Lys Lys
```

```
            260                 265                 270
Tyr Leu Pro Arg Thr Ile Thr Ala Met Phe Ala Gln Ile Trp Gln Gln
            275                 280                 285

Leu Thr Gly Met Asn Val Met Met Tyr Tyr Ile Val Tyr Ile Phe Glu
            290                 295                 300

Met Ala Gly Tyr Gly Gly Asn Gly Val Leu Val Ser Ser Thr Ile Gln
305                 310                 315                 320

Tyr Val Ile Phe Val Val Thr Phe Val Ser Leu Phe Phe Leu Asp
                325                 330                 335

Lys Phe Gly Arg Arg Lys Ile Leu Leu Val Gly Ala Ala Ser Met Met
            340                 345                 350

Thr Trp Gln Phe Ala Val Ala Gly Ile Leu Ala Arg Tyr Ser Val Pro
            355                 360                 365

Tyr Asp Leu Ser Asp Thr Val Lys Ile Lys Ile Pro Asp Asn His Lys
        370                 375                 380

Ser Ala Ala Lys Gly Val Ile Ala Cys Cys Tyr Leu Phe Val Ala Ser
385                 390                 395                 400

Phe Gly Phe Ser Trp Gly Val Gly Ile Trp Leu Tyr Cys Ser Glu Val
                405                 410                 415

Trp Gly Asp Ser Gln Ser Arg Gln Arg Gly Ala Ala Val Ser Thr Ala
            420                 425                 430

Ser Asn Trp Ile Phe Asn Phe Ala Leu Ala Met Phe Thr Pro Ser Ser
        435                 440                 445

Phe Lys Asn Ile Thr Trp Lys Thr Tyr Cys Ile Tyr Ala Thr Phe Cys
    450                 455                 460

Ala Cys Met Phe Ile His Val Phe Phe Phe Pro Glu Thr Lys Gly
465                 470                 475                 480

Lys Arg Leu Glu Glu Ile Ala Gln Ile Trp Glu Glu Lys Ile Pro Ala
                485                 490                 495

Trp Lys Thr Thr Asn Trp Gln Pro His Val Pro Leu Leu Ser Asp His
            500                 505                 510

Glu Leu Ala Glu Lys Ile Asn Ala Glu His Val Glu Asn Val Asn Ser
        515                 520                 525

Arg Glu Gln Ser Asp Asp Glu Lys Ser Gln Val
    530                 535

<210> SEQ ID NO 38
<211> LENGTH: 547
<212> TYPE: PRT
<213> ORGANISM: Candida intermedia
<220> FEATURE:
<223> OTHER INFORMATION: exemplary xylose transporter from Candida
      intermedia PYCC 4715; Gxf1p

<400> SEQUENCE: 38

Met Ser Gln Asp Ser His Ser Ser Gly Ala Ala Thr Pro Val Asn Gly
1               5                   10                  15

Ser Ile Leu Glu Lys Glu Lys Glu Asp Ser Pro Val Leu Gln Val Asp
            20                  25                  30

Ala Pro Gln Lys Gly Phe Lys Asp Tyr Ile Val Ile Ser Ile Phe Cys
        35                  40                  45

Phe Met Val Ala Phe Gly Gly Phe Val Phe Gly Phe Asp Thr Gly Thr
    50                  55                  60

Ile Ser Gly Phe Val Asn Met Ser Asp Phe Lys Asp Arg Phe Gly Gln
65                  70                  75                  80
```

```
His His Ala Asp Gly Thr Pro Tyr Leu Ser Asp Val Arg Val Gly Leu
                 85                  90                  95

Met Ile Ser Ile Phe Asn Val Gly Cys Ala Val Gly Gly Ile Phe Leu
            100                 105                 110

Cys Lys Val Ala Asp Val Trp Gly Arg Arg Ile Gly Leu Met Phe Ser
        115                 120                 125

Met Ala Val Tyr Val Val Gly Ile Ile Gln Ile Ser Ser Ser Thr
    130                 135                 140

Lys Trp Tyr Gln Phe Phe Ile Gly Arg Leu Ile Ala Gly Leu Ala Val
145                 150                 155                 160

Gly Thr Val Ser Val Val Ser Pro Leu Phe Ile Ser Glu Val Ser Pro
                165                 170                 175

Lys Gln Ile Arg Gly Thr Leu Val Cys Cys Phe Gln Leu Cys Ile Thr
            180                 185                 190

Leu Gly Ile Phe Leu Gly Tyr Cys Thr Thr Tyr Gly Thr Lys Thr Tyr
        195                 200                 205

Thr Asp Ser Arg Gln Trp Arg Ile Pro Leu Gly Leu Cys Phe Ala Trp
    210                 215                 220

Ala Ile Leu Leu Val Val Gly Met Leu Asn Met Pro Glu Ser Pro Arg
225                 230                 235                 240

Tyr Leu Val Glu Lys His Arg Ile Asp Glu Ala Lys Arg Ser Ile Ala
                245                 250                 255

Arg Ser Asn Lys Ile Pro Glu Glu Asp Pro Phe Val Tyr Thr Glu Val
            260                 265                 270

Gln Leu Ile Gln Ala Gly Ile Glu Arg Glu Ala Leu Ala Gly Gln Ala
        275                 280                 285

Ser Trp Lys Glu Leu Ile Thr Gly Lys Pro Lys Ile Phe Arg Arg Val
    290                 295                 300

Ile Met Gly Ile Met Leu Gln Ser Leu Gln Gln Leu Thr Gly Asp Asn
305                 310                 315                 320

Tyr Phe Phe Tyr Tyr Gly Thr Thr Ile Phe Gln Ala Val Gly Leu Lys
                325                 330                 335

Asp Ser Phe Gln Thr Ser Ile Ile Leu Gly Ile Val Asn Phe Ala Ser
            340                 345                 350

Thr Phe Val Gly Ile Tyr Val Ile Glu Arg Leu Gly Arg Arg Leu Cys
        355                 360                 365

Leu Leu Thr Gly Ser Ala Ala Met Phe Ile Cys Phe Ile Ile Tyr Ser
370                 375                 380

Leu Ile Gly Thr Gln His Leu Tyr Lys Gln Gly Tyr Ser Asn Glu Thr
385                 390                 395                 400

Ser Asn Thr Tyr Lys Ala Ser Gly Asn Ala Met Ile Phe Ile Thr Cys
                405                 410                 415

Leu Tyr Ile Phe Phe Phe Ala Ser Thr Trp Ala Gly Gly Val Tyr Cys
            420                 425                 430

Ile Ile Ser Glu Ser Tyr Pro Leu Arg Ile Arg Ser Lys Ala Met Ser
        435                 440                 445

Ile Ala Thr Ala Ala Asn Trp Leu Trp Gly Phe Leu Ile Ser Phe Phe
    450                 455                 460

Thr Pro Phe Ile Thr Ser Ala Ile His Phe Tyr Tyr Gly Phe Val Phe
465                 470                 475                 480

Thr Gly Cys Leu Ala Phe Ser Phe Phe Tyr Val Tyr Phe Phe Val Tyr
                485                 490                 495

Glu Thr Lys Gly Leu Ser Leu Glu Glu Val Asp Glu Met Tyr Ala Ser
```

```
                500               505                510
Gly Val Leu Pro Leu Lys Ser Ala Ser Trp Val Pro Pro Asn Leu Glu
            515                 520                525
His Met Ala His Ser Ala Gly Tyr Ala Gly Ala Asp Lys Ala Thr Asp
            530                 535                540
Glu Gln Val
545

<210> SEQ ID NO 39
<211> LENGTH: 522
<212> TYPE: PRT
<213> ORGANISM: Candida intermedia
<220> FEATURE:
<223> OTHER INFORMATION: exemplary glucose/xylose symporter from Candida
      intermedia Gxs1p

<400> SEQUENCE: 39

Met Gly Leu Glu Asp Asn Arg Met Val Lys Arg Phe Val Asn Val Gly
1               5                   10                  15
Glu Lys Lys Ala Gly Ser Thr Ala Met Ala Ile Ile Val Gly Leu Phe
            20                  25                  30
Ala Ala Ser Gly Gly Val Leu Phe Gly Tyr Asp Thr Gly Thr Ile Ser
            35                  40                  45
Gly Val Met Thr Met Asp Tyr Val Leu Ala Arg Tyr Pro Ser Asn Lys
        50                  55                  60
His Ser Phe Thr Ala Asp Glu Ser Ser Leu Ile Val Ser Ile Leu Ser
65                  70                  75                  80
Val Gly Thr Phe Phe Gly Ala Leu Cys Ala Pro Phe Leu Asn Asp Thr
                85                  90                  95
Leu Gly Arg Arg Trp Cys Leu Ile Leu Ser Ala Leu Ile Val Phe Asn
            100                 105                 110
Ile Gly Ala Ile Leu Gln Val Ile Ser Thr Ala Ile Pro Leu Leu Cys
            115                 120                 125
Ala Gly Arg Val Ile Ala Gly Phe Gly Val Gly Leu Ile Ser Ala Thr
        130                 135                 140
Ile Pro Leu Tyr Gln Ser Glu Thr Ala Pro Lys Trp Ile Arg Gly Ala
145                 150                 155                 160
Ile Val Ser Cys Tyr Gln Trp Ala Ile Thr Ile Gly Leu Phe Leu Ala
                165                 170                 175
Ser Cys Val Asn Lys Gly Thr Glu His Met Thr Asn Ser Gly Ser Tyr
            180                 185                 190
Arg Ile Pro Leu Ala Ile Gln Cys Leu Trp Gly Leu Ile Leu Gly Ile
            195                 200                 205
Gly Met Ile Phe Leu Pro Glu Thr Pro Arg Phe Trp Ile Ser Lys Gly
        210                 215                 220
Asn Gln Glu Lys Ala Ala Glu Ser Leu Ala Arg Leu Arg Lys Leu Pro
225                 230                 235                 240
Ile Asp His Pro Asp Ser Leu Glu Glu Leu Arg Asp Ile Thr Ala Ala
                245                 250                 255
Tyr Glu Phe Glu Thr Val Tyr Gly Lys Ser Ser Trp Ser Gln Val Phe
            260                 265                 270
Ser His Lys Asn His Gln Leu Lys Arg Leu Phe Thr Gly Val Ala Ile
            275                 280                 285
Gln Ala Phe Gln Gln Leu Thr Gly Val Asn Phe Ile Phe Tyr Tyr Gly
        290                 295                 300
```

```
Thr Thr Phe Phe Lys Arg Ala Gly Val Asn Gly Phe Thr Ile Ser Leu
305                 310                 315                 320

Ala Thr Asn Ile Val Asn Val Gly Ser Thr Ile Pro Gly Ile Leu Leu
            325                 330                 335

Met Glu Val Leu Gly Arg Arg Asn Met Leu Met Gly Gly Ala Thr Gly
        340                 345                 350

Met Ser Leu Ser Gln Leu Ile Val Ala Ile Val Gly Val Ala Thr Ser
    355                 360                 365

Glu Asn Asn Lys Ser Ser Gln Ser Val Leu Val Ala Phe Ser Cys Ile
370                 375                 380

Phe Ile Ala Phe Phe Ala Ala Thr Trp Gly Pro Cys Ala Trp Val Val
385                 390                 395                 400

Val Gly Glu Leu Phe Pro Leu Arg Thr Arg Ala Lys Ser Val Ser Leu
            405                 410                 415

Cys Thr Ala Ser Asn Trp Leu Trp Asn Trp Gly Ile Ala Tyr Ala Thr
        420                 425                 430

Pro Tyr Met Val Asp Glu Asp Lys Gly Asn Leu Gly Ser Asn Val Phe
    435                 440                 445

Phe Ile Trp Gly Gly Phe Asn Leu Ala Cys Val Phe Phe Ala Trp Tyr
450                 455                 460

Phe Ile Tyr Glu Thr Lys Gly Leu Ser Leu Glu Gln Val Asp Glu Leu
465                 470                 475                 480

Tyr Glu His Val Ser Lys Ala Trp Lys Ser Lys Gly Phe Val Pro Ser
            485                 490                 495

Lys His Ser Phe Arg Glu Gln Val Asp Gln Gln Met Asp Ser Lys Thr
        500                 505                 510

Glu Ala Ile Met Ser Glu Glu Ala Ser Val
        515                 520

<210> SEQ ID NO 40
<211> LENGTH: 574
<212> TYPE: PRT
<213> ORGANISM: Saccharomyces cerevisiae
<220> FEATURE:
<223> OTHER INFORMATION: exemplary xylose transporter from Saccharomyces
      cerevisiae Gxf2p/Gal2p

<400> SEQUENCE: 40

Met Ala Val Glu Glu Asn Asn Met Pro Val Val Ser Gln Gln Pro Gln
1               5                   10                  15

Ala Gly Glu Asp Val Ile Ser Ser Leu Ser Lys Asp Ser His Leu Ser
            20                  25                  30

Ala Gln Ser Gln Lys Tyr Ser Asn Asp Glu Leu Lys Ala Gly Glu Ser
        35                  40                  45

Gly Ser Glu Gly Ser Gln Ser Val Pro Ile Glu Ile Pro Lys Lys Pro
    50                  55                  60

Met Ser Glu Tyr Val Thr Val Ser Leu Leu Cys Leu Cys Val Ala Phe
65                  70                  75                  80

Gly Gly Phe Met Phe Gly Trp Asp Thr Gly Thr Ile Ser Gly Phe Val
            85                  90                  95

Val Gln Thr Asp Phe Leu Arg Arg Phe Gly Met Lys His Lys Asp Gly
        100                 105                 110

Thr His Tyr Leu Ser Asn Val Arg Thr Gly Leu Ile Val Ala Ile Phe
    115                 120                 125

Asn Ile Gly Cys Ala Phe Gly Gly Ile Ile Leu Ser Lys Gly Gly Asp
130                 135                 140
```

```
Met Tyr Gly Arg Lys Lys Gly Leu Ser Ile Val Ser Val Tyr Ile
145                 150                 155                 160

Val Gly Ile Ile Ile Gln Ile Ala Ser Ile Asn Lys Trp Tyr Gln Tyr
            165                 170                 175

Phe Ile Gly Arg Ile Ile Ser Gly Leu Gly Val Gly Gly Ile Ala Val
            180                 185                 190

Leu Cys Pro Met Leu Ile Ser Glu Ile Ala Pro Lys His Leu Arg Gly
            195                 200                 205

Thr Leu Val Ser Cys Tyr Gln Leu Met Ile Thr Ala Gly Ile Phe Leu
210                 215                 220

Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
            245                 250                 255

Gly Ala Leu Thr Leu Val Pro Glu Ser Pro Arg Tyr Leu Cys Glu Val
            260                 265                 270

Asn Lys Val Glu Asp Ala Lys Arg Ser Ile Ala Lys Ser Asn Lys Val
            275                 280                 285

Ser Pro Glu Asp Pro Ala Val Gln Ala Glu Leu Asp Leu Ile Met Ala
290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
            325                 330                 335

Val Gln Met Phe Gln Gln Leu Thr Gly Asn Asn Tyr Phe Phe Tyr Tyr
            340                 345                 350

Gly Thr Val Ile Phe Lys Ser Val Gly Leu Asp Asp Ser Phe Glu Thr
            355                 360                 365

Ser Ile Val Ile Gly Val Val Asn Phe Ala Ser Thr Phe Phe Ser Leu
370                 375                 380

Trp Thr Val Glu Asn Leu Gly His Arg Lys Cys Leu Leu Leu Gly Ala
385                 390                 395                 400

Ala Thr Met Met Ala Cys Met Val Ile Tyr Ala Ser Val Gly Val Thr
            405                 410                 415

Arg Leu Tyr Pro His Gly Lys Ser Gln Pro Ser Ser Lys Gly Ala Gly
            420                 425                 430

Asn Cys Met Ile Val Phe Thr Cys Phe Tyr Ile Phe Cys Tyr Ala Thr
            435                 440                 445

Thr Trp Ala Pro Val Ala Trp Val Ile Thr Ala Glu Ser Phe Pro Leu
            450                 455                 460

Arg Val Lys Ser Lys Cys Met Ala Leu Ala Ser Ala Ser Asn Trp Val
465                 470                 475                 480

Trp Gly Phe Leu Ile Ala Phe Phe Thr Pro Phe Ile Thr Ser Ala Ile
            485                 490                 495

Asn Phe Tyr Tyr Gly Tyr Val Phe Met Gly Cys Leu Val Ala Met Phe
            500                 505                 510

Phe Tyr Val Phe Phe Phe Val Pro Glu Thr Lys Gly Leu Ser Leu Glu
            515                 520                 525

Glu Ile Gln Glu Leu Trp Glu Glu Gly Val Leu Pro Trp Lys Ser Glu
            530                 535                 540

Gly Trp Ile Pro Ser Ser Arg Arg Gly Asn Asn Tyr Asp Leu Glu Asp
545                 550                 555                 560
```

Leu Gln His Asp Asp Lys Pro Trp Tyr Lys Ala Met Leu Glu
           565                 570

<210> SEQ ID NO 41
<211> LENGTH: 1632
<212> TYPE: DNA
<213> ORGANISM: Metschnikowia
<220> FEATURE:
<223> OTHER INFORMATION: XYT1 from H0 Metschnikowia sp.

<400> SEQUENCE: 41

| | | |
|---|---|---|
| atgggttacg aggaaaagct tgtagcgccc gcgttgaaat caaaaacttt tcttgacaaa | 60 |
| accccaata ttcacaatgt ctatgtcatt gccgccatct cctgtacatc aggtatgatg | 120 |
| tttggatttg atatctcgtc gatgtctgtc tttgtcgacc agcagccata cttgaagatg | 180 |
| tttgacaacc ctagttccgt gattcaaggt ttcattaccg cgctgatgag tttgggctcg | 240 |
| tttttcggct cgctcacatc cacgttcatc tctgagcctt ttggtcgtcg tgcatcgttg | 300 |
| ttcatttgtg gtattctttg ggtaattgga gcagcggttc aaagttcgtc gcagaacagg | 360 |
| gcccaattga tttgtgggcg tatcattgca ggatggggca ttggctttgg gtcatcggtg | 420 |
| gctcctgttt acgggtccga gatggctccg agaaagatca gaggcacgat tggtggaatc | 480 |
| ttccagttct ccgtcaccgt gggtatcttt atcatgttct tgattgggta cggatgctct | 540 |
| ttcattcaag gaaaggcctc ttttccggat ccctgggggtg tgcaaatggt tcccggcctt | 600 |
| atcctcttga ttggacttttt ctttattcct gaatctcccc gttggttggc caaacagggc | 660 |
| tactgggaag acgccgaaat cattgtggcc aatgtgcagg ccaagggtaa ccgtaacgac | 720 |
| gccaacgtgc agattgaaat gtcggagatt aaggatcaat tgatgcttga cgagcacttg | 780 |
| aaggagttta cgtacgctga ccttttcacg aagaagtacc gccagcgcac gatcacggcg | 840 |
| atctttgccc agatctggca acagttgacc ggtatgaatg tgatgatgta ctacattgtg | 900 |
| tacattttcc agatggcagg ctacagcggc aacacgaact tggtgcccag tttgatccag | 960 |
| tacatcatca acatggcggt cacggtgccg gcgcttttct gcttggatct cttgggccgt | 1020 |
| cgtaccattt tgctcgcggg tgccgcgttc atgatggcgt ggcaattcgg cgtggcgggc | 1080 |
| attttggcca cttactcaga accggcatat atctctgaca ctgtgcgtat cacgatcccc | 1140 |
| gacgaccaca gtctgctgc aaaaggtgtg attgcatgct gctatttgtt tgtgtgctcg | 1200 |
| tttgcattct cgtggggtgt cggtatttgg gtgtactgtt ccgaggtttg gggtgactcc | 1260 |
| cagtcgagac aaagaggcgc cgctcttgcg acgtcggcca actggatctt caacttcgcc | 1320 |
| attgccatgt tcacgccgtc ctcattcaag aatatcacgt ggaagacgta tatcatctac | 1380 |
| gccacgttct gtgcgtgcat gttcatacac gtgttttttct ttttcccaga aacaaagggc | 1440 |
| aagcgtttgg aggagatagg ccagctttgg gacgaaggag tcccagcatg gaggtcagcc | 1500 |
| aagtggcagc caacagtgcc gctcgcgtcc gacgcagagc ttgcacacaa gatggatgtt | 1560 |
| gcgcacgcgg agcacgcgga cttattggcc acgcactcgc catcttcaga cgagaagacg | 1620 |
| ggcacggtct aa | 1632 |

<210> SEQ ID NO 42
<211> LENGTH: 1635
<212> TYPE: DNA
<213> ORGANISM: Metschnikowia
<220> FEATURE:
<223> OTHER INFORMATION: GXF1 from H0 Metschnikowia sp.

<400> SEQUENCE: 42

| | |
|---|---|
| atgtctcaag acgaacttca tacaaagtct ggtgttgaaa caccaatcaa cgattcgctt | 60 |
| ctcgaggaga agcacgatgt caccccactc gcggcattgc ccgagaagtc cttcaaggac | 120 |
| tacatttcca tttccatttt ctgtttgttt gtggcatttg gtggttttgt tttcggtttc | 180 |
| gacaccggta cgatttccgg tttcgtcaac atgtccgact tcaagaccag atttggtgag | 240 |
| atgaatgccc agggcgaata ctacttgtcc aatgttagaa ctggtttgat ggtttctatt | 300 |
| ttcaacgtcg gttgcgccgt tggtggtatc ttcctttgta agattgccga tgtttatggc | 360 |
| agaagaattg gtcttatgtt ttccatggtg gtttatgtcg ttggtatcat tattcagatt | 420 |
| gcctccacca ccaaatggta ccaatacttc attggccgtc ttattgctgg cttggctgtg | 480 |
| ggtactgttt ccgtcatctc gccactttc atttccgagg ttgctcctaa acagctcaga | 540 |
| ggtacgcttg tgtgctgctt ccagttgtgt atcaccttgg gtatcttttt gggttactgc | 600 |
| acgacctacg gtacaaagac ttacactgac tccagacagt ggagaatccc attgggtatc | 660 |
| tgtttcgcgt gggctttgtt tttggtggcc ggtatgttga acatgcccga gtctcctaga | 720 |
| tacttggttg agaaatcgag aatcgacgat gccagaaagt ccattgccag atccaacaag | 780 |
| gtttccgagg aagaccccgc cgtgtacacc gaggtgcagc ttatccaggc tggtattgac | 840 |
| agagaggccc ttgccggcag cgccacatgg atggagcttg tgactggtaa gcccaaaatc | 900 |
| ttcagaagag tcatcatggg tgtcatgctt cagtccttgc aacaattgac tggtgacaac | 960 |
| tacttttct actacggaac cacgattttc aaggctgttg gcttgcagga ctctttccag | 1020 |
| acgtcgatta tcttgggtat tgtcaacttt gcctcgactt tgtcggtat ttacgccatt | 1080 |
| gagagaatgg gcagaagatt gtgtttgttg accggatctg cgtgcatgtt tgtgtgtttc | 1140 |
| atcatctact cgctcattgg tacgcagcac ttgtacaaga acggcttctc taacgaacct | 1200 |
| tccaacacat acaagccttc cggtaacgcc atgatcttca tcacgtgtct ttacattttc | 1260 |
| ttctttgcct cgacctgggc cggtggtgtt tactgtatcg tgtccgagtc ttacccattg | 1320 |
| agaatcagat ccaaggccat gtctgtcgcc accgccgcca actggatgtg gggtttcttg | 1380 |
| atctcgttct tcacgccttt catcaccctcc gccatccact tttactacgg ttttgttttc | 1440 |
| actggctgct tggcgttctc cttcttctac gtctacttct ttgtcgtgga gaccaagggt | 1500 |
| cttttccttgg aggaggttga cattttgtac gcttccggta cgcttccatg gaagtcctct | 1560 |
| ggctgggtgc ctcctaccgc ggacgaaatg gcccacaacg ccttcgacaa caagccaact | 1620 |
| gacgaacaag tctaa | 1635 |

<210> SEQ ID NO 43
<211> LENGTH: 1425
<212> TYPE: DNA
<213> ORGANISM: Artificial Sequence
<220> FEATURE:
<223> OTHER INFORMATION: Delta-GXF1 (variant of GXF1 with shorter
      N-terminus) from H0 Metschnikowia sp.

<400> SEQUENCE: 43

| | |
|---|---|
| atgtccgact tcaagaccag atttggtgag atgaatgccc agggcgaata ctacttgtcc | 60 |
| aatgttagaa ctggtttgat ggtttctatt ttcaacgtcg gttgcgccgt tggtggtatc | 120 |
| ttcctttgta agattgccga tgtttatggc agaagaattg gtcttatgtt ttccatggtg | 180 |
| gtttatgtcg ttggtatcat tattcagatt gcctccacca ccaaatggta ccaatacttc | 240 |
| attggccgtc ttattgctgg cttggctgtg ggtactgttt ccgtcatctc gccactttc | 300 |
| atttccgagg ttgctcctaa acagctcaga ggtacgcttg tgtgctgctt ccagttgtgt | 360 |

```
atcaccttgg gtatcttttt gggttactgc acgacctacg gtacaaagac ttacactgac    420
tccagacagt ggagaatccc attgggtatc tgtttcgcgt gggctttgtt tttggtggcc    480
ggtatgttga acatgcccga gtctcctaga tacttggttg agaaatcgag aatcgacgat    540
gccagaaagt ccattgccag atccaacaag gtttccgagg aagacccgc cgtgtacacc     600 gaggtgcagc ttatccaggc tggtattgac agagaggccc ttgccggcag cgccacatgg    660
atggagcttg tgactggtaa gcccaaaatc ttcagaagag tcatcatggg tgtcatgctt    720
cagtccttgc aacaattgac tggtgacaac tactttttct actacggaac cacgattttc    780
aaggctgttg gcttgcagga ctcttttccag acgtcgatta tcttgggtat tgtcaacttt    840
gcctcgactt tgtcggtat ttacgccatt gagagaatgg gcagaagatt gtgtttgttg     900
accggatctg cgtgcatgtt tgtgtgtttc atcatctact cgctcattgg tacgcagcac    960
ttgtacaaga acggcttctc taacgaacct tccaacacat acaagccttc cggtaacgcc   1020
atgatcttca tcacgtgtct ttacattttc ttctttgcct cgacctgggc cggtggtgtt   1080
tactgtatcg tgtccgagtc ttacccattg agaatcagat ccaaggccat gtctgtcgcc   1140
accgccgcca actggatgtg gggtttcttg atctcgttct tcacgccttt catcacctcc   1200
gccatccact tttactacgg ttttgttttc actggctgct tggcgttctc cttcttctac   1260
gtctacttct ttgtcgtgga gaccaagggt cttccttgg aggaggttga cattttgtac    1320
gcttccggta cgcttccatg gaagtcctct ggctgggtgc ctcctaccgc ggacgaaatg   1380
gcccacaacg ccttcgacaa caagccaact gacgaacaag tctaa                    1425
```

<210> SEQ ID NO 44
<211> LENGTH: 1647
<212> TYPE: DNA
<213> ORGANISM: Metschnikowia
<220> FEATURE:
<223> OTHER INFORMATION: GXF2/GAL2 from H0 Metschnikowia sp.

<400> SEQUENCE: 44

```
atgagtgccg aacaggaaca acaagtatcg ggcacatctg ccacgataga tgggctggcg     60
tccttgaagc aagaaaaaac cgccgaggag aagacgcct tcaagcctaa gcccgccacg     120
gcgtactttt tcatttcgtt cctctgtggc ttggtcgcct ttggcggcta cgttttcggt    180
ttcgataccg gtacgatttc cgggtttgtt aacatggacg actatttgat gagattcggc    240
cagcagcacg ctgatggcac gtattacctt ccaacgtga aaccggtttt gatcgtgtcg     300
atcttcaaca ttggctgtgc cgttggtggt cttgcgcttt cgaaagtcgg tgacatttgg    360
ggcagaagaa ttggtattat ggttgctatg atcatctaca tggtgggaat catcatccag    420
atcgcttcac aggataaatg gtaccagtac ttcattggcc gtttgatcac cggattgggt    480
gtcggcacca cgtccgtgct tagtcctctt ttcatctccg agtcggctcc gaagcatttg    540
agaggcaccc ttgtgtgttg tttccagctc atggtcacct gggtatctt tttgggctac    600 tgcacgacct acggtaccaa gaactacact gactcgcgcc agtggcggat tcccttgggt    660 cttttgcttcg catgggctct tttgttgatc tcgggaatgg ttttcatgcc tgaatcccca    720
cgttccttga ttgagcgcca gagattcgac gaggccaagg cttccgtggc caaatcgaac    780
caggtttcga ccgaggaccc cgccgtgtac actgaagtcg agttgatcca ggccggtatt    840
gaccgtgagg cattggccgg atccgctggc tggaaagagc ttatcacggg taagcccaag    900
atgttgcagc gtgtgatttt gggaatgatg ctccagtcga tccagcagct taccggtaac    960
aactactttt tctactatgg taccacgatc ttcaaggccg tgggcatgtc ggactcgttc   1020
```

```
cagacctcga ttgttttggg tattgtcaac ttcgcctcca cttttgtcgg aatctgggcc    1080
atcgaacgca tgggccgcag atcttgtttg cttgttggtt ccgcgtgcat gagtgtgtgt    1140
ttcttgatct actccatctt gggttccgtc aacctttaca tcgacggcta cgagaacacg    1200
ccttccaaca cgcgtaagcc taccggtaac gccatgattt tcatcacgtg tttgttcatc    1260
ttcttcttcg cctccacctg gccggtggt gtgtacagta ttgtgtctga aacataccca    1320
ttgagaatcc gctctaaagg tatggccgtg ccaccgctg ccaactggat gtggggtttc     1380
ttgatttcgt tcttcacgcc tttcatcacc tcggccatcc acttctacta cgggtttgtg    1440
ttcacagggt gtcttatttt ctccttcttc tacgtgttct tctttgttag ggaaaccaag    1500
ggtctctcgt tggaagaggt ggatgagtta tatgccactg acctcccacc atggaagacc    1560
gcgggctgga cgcctccttc tgctgaggat atggcccaca ccaccgggtt tgccgaggcc    1620
gcaaagccta cgaacaaaca cgtttaa                                       1647
```

```
<210> SEQ ID NO 45
<211> LENGTH: 1509
<212> TYPE: DNA
<213> ORGANISM: Metschnikowia
<220> FEATURE:
<223> OTHER INFORMATION: GXS1 from H0 Metschnikowia sp.

<400> SEQUENCE: 45
atgggcattt tcgttggcgt tttcgccgcg cttggcggtg ttctctttgg ctacgatacc      60
ggtaccatct ctggtgtgat ggccatgcct tgggtcaagg aacatttccc aaaagaccgt     120
gttgcattta gtgcttccga gtcgtcgttg attgtgtcta ttttatctgc aggaactttc     180
tttggagcca ttcttgctcc gctcttgacc gatacattgg gtagacgctg gtgtattatc     240
atctcttcgc tcgttgtgtt caatttgggt gctgctttgc agacggctgc cacggatatc     300
ccgctcttga ttgttggtcg tgtcattgcc ggtttagggg ttggtttgat ttcgctgacg     360
attccattgt accagtccga agcgcttccc aaatggatta gaggtgctgt tgtctcgtgc     420
taccaatggg ccattactat tggtatcttt ttggctgccg tgatcaacca gggcactcac     480
aagatcaaca gccctgcgtc gtacagaatt ccattggta ttcagatggc atggggtctt     540
atcttgggtg tcggcatgtt cttcttgccc gagacgcctc gtttctacat ttccaagggc     600
cagaatgcga aggctgctgt tcattggcg cgtttgagaa agcttccgca agatcacccg     660
gagttgttgg aggaattgga agatatccag gcggcatacg agtttgagac tgtccatggc     720
aagtcttcat ggctgcaggt tttccaccaa caagaacaaa c aattgaagaa gttggccacg    780
ggcgtgtgct tgcaggcgtt ccaacaattg actggtgtga acttcatttt ctactttggc     840
acgactttct tcaacagtgt tgggcttgac ggattcacca cctccttggc caccaacatt     900
gtcaatgttg ctcgacgat ccctggtatt ttgggtgttg agattttcgg cagaagaaaa      960
gtgttgttga ccgcgctgc tggtatgtgt ctttcgcaat tcattgttgc cattgttggt     1020
gtagccaccg actccaaggc tgcgaaccaa gttcttattg ccttctgctg cattttcatt     1080
gcgttctttg cagccacctg gggcccacc gcatggggttg tttgtggcga atttttcccc   1140
ttgagaacca gagccaagtc gattgccatg tgcgctgctt cgaactggtt gttgaactgg   1200
gcaattgcat acgccacgcc atacttggtt gactccgata agggtaactt gggcaccaat   1260 gtgttttca tttgggggaag ctgtaacttc ttctgccttg tgtttgccta cttcatgatt   1320
tacgagacca agggtctttc cttggagcag gttgatgagc tttacgagaa ggttgccagc   1380
```

```
gccagaaagt cgcctggctt cgtgccaagc gagcacgctt tcagagagca cgccgatgtg    1440
gagaccgcca tgccagacaa cttcaacttg aaggcggagg cgatttctgt cgaggatgcc    1500
tctgtttaa                                                             1509

<210> SEQ ID NO 46
<211> LENGTH: 1647
<212> TYPE: DNA
<213> ORGANISM: Metschnikowia
<220> FEATURE:
<223> OTHER INFORMATION: HGT12 from H0 Metschnikowia sp.

<400> SEQUENCE: 46
atgagcatct ttgaaggcaa agacgggaag ggggtatcct ccaccgagtc gctttccaat      60
gacgtcagat atgacaacat ggagaaagtt gatcaggatg ttcttagaca caacttcaac     120
tttgacaaag aattcgagga gctcgaaatc gaggcggcgc aagtcaacga caaaccttct     180
tttgtcgaca ggattttatc cctcgaatac aagcttcatt tcgaaaacaa gaaccacatg     240
gtgtggctct gggcgctttt cgcagccgcc gcaggcttat tgtctggctt ggatcagtcc     300
attatttctg gtgcatccat tggaatgaac aaaagcattga acttgactga acgtgaagcc     360
tcattggtgt cttcgcttat gccttttaggc gccatggcag gctccatgat tatgacacct     420
cttaatgagt ggttcggaag aaaatcatcg ttgattattt cttgtatttg gtataccatc     480
ggatccgctt gtgcgctgg cgccagagat caccacatga tgtacgctgg cagatttatt     540
cttggtgtcg gtgtgggtat agaaggtggg tgtgtgggca tttacatttc gagtctgtc     600 ccagccaatg tgcgtggtag tatcgtgtcg atgtaccagt tcaatattgc tttgggtgaa     660
gttctagggt atgctgttgc tgccatttttc tacactgttc atggtggatg gaggttcatg     720
gtggggtctt ctttagtatt ctctactata ttgtttgccg gattgttttt cttgcccgag     780
tcacctcgtt ggttggtgca caaaggcaga aacggaatgg catacgatgt gtggaagaga     840
ttgagagaca taaacgatga aagcgcaaag ttggaatttt tggagatgag acaggctgct     900
tatcaagaga gagaaagacg ctcgcaagag tctttgttct ccagctgggg cgaattattc     960
accatcgcta gaaacagaag agcacttact tactctgtca taatgatcac tttgggtcaa    1020
ttgactggtg tcaatgccgt catgtactac atgtcgactt tgatgggtgc aattggtttc    1080
aacgagaaag actctgtgtt catgtcccct gtgggaggcg ttctttgct tataggtacc    1140 attcctgcca ttttgtggat ggaccgtttc ggcagaagag tttgggggtta taatcttgtt    1200 ggtttcttcg ttggtttggt gctcgttggt gttggctacc gtttcaatcc cgtcactcaa    1260
aaggcggctt cagaaggtgt gtacttgacg ggtctcattg tctatttctt gttctttggt    1320
tcctactcga ccttaacttg ggtcattcca tccgagtctt ttgatttgag aacaagatct    1380
ttgggtatga caatctgttc cactttcctt tactgtggt cttcaccgt cacctacaac    1440 ttcaccaaga tgtccgccgc cttcacatac actgggttga cacttggttt ctacggtggc    1500
attgcgttcc ttggttttgat ttaccaggtc tgcttcatgc ccgagacgaa ggacaagact    1560
ttggaagaaa ttgacgatat cttcaatcgt tctgcgttct ctatcgcgcg cgagaacatc    1620
tccaacttga agaagggtat tggtaa                                         1647

<210> SEQ ID NO 47
<211> LENGTH: 1647
<212> TYPE: DNA
<213> ORGANISM: Metschnikowia
<220> FEATURE:
<223> OTHER INFORMATION: HXT5 from H0 Metschnikowia sp.
```

<400> SEQUENCE: 47

```
atgagcatct tgaaggcaa agacgggaag ggggtatcct ccaccgagtc gctttccaat     60
gacgtcagat atgacaacat ggagaaagtt gatcaggatg ttcttagaca caacttcaac    120
tttgacaaag aattcgagga gctcgaaatc gaggcggcgc aagtcaacga caaaccttct    180
tttgtcgaca ggattttatc cctcgaatac aagcttcatt tcgaaaacaa gaaccacatg    240
gtgtggctct gggcgctttt cgcagccgcc gcaggcttat tgtctggctt ggatcagtcc    300
attatttctg gtgcatccat tggaatgaac aaagcattga acttgactga acgtgaagcc    360
tcattggtgt cttcgcttat gccttttaggc gccatggcag gctccatgat tatgacacct    420
cttaatgagt ggttcggaag aaaatcatcg ttgattattt cttgtatttg gtataccatc    480
ggatccgctt tgtgcgctgg cgccagagat caccacatga gtacgctgg cagatttatt    540
cttggtgtcg gtgtgggtat agaaggtggg tgtgtgggca tttacatttc cgagtctgtc    600
ccagccaatg tgcgtggtag tatcgtgtcg atgtaccagt tcaatattgc tttgggtgaa    660
gttctagggt atgctgttgc tgccatttt ctacactgttc atggtggatg gaggttcatg    720
gtggggtctt ctttagtatt ctctactata ttgtttgccg gattgttttt cttgcccgag    780
tcacctcgtt ggttggtgca caaaggcaga acggaatgg catacgatgt gtggaagaga    840
ttgagagaca taaacgatga agcgcaaag ttggaatttt tggagatgag acaggctgct    900
tatcaagaga gagaaagacg ctcgcaagag tctttgttct ccagctgggg cgaattattc    960
accatcgcta gaaacagaag agcacttact tactctgtca taatgatcac tttgggtcaa   1020
ttgactggtg tcaatgccgt catgtactac atgtcgactt tgatgggtgc aattggtttc   1080
aacgagaaag actctgtgtt catgtcccctt gtgggaggcg ttctttgct tataggtacc   1140
attcctgcca ttttgtggat ggaccgtttc ggcagaagag tttgggatta taatcttgtt   1200
ggtttcttcg ttggtttggt gctcgttggt gttggctacc gttcaatcc cgtcactcaa   1260
aaggcggctt cagaaggtgt gtacttgacg ggtctcattg tctatttctt gttctttggt   1320
tcctactcga ccttaacttg ggtcattcca tccgagtctt ttgatttgag aacaagatct   1380
ttgggtatga caatctgttc cactttcctt tacttgtggt ctttcaccgt cacctacaac   1440
tcaccaagga tgtccgccgc cttcacatac actgggttga cacttggttt ctacggtggc   1500
attgcgttcc ttggtttgat ttaccaggtc tgcttcatgc ccgagacgaa ggacaagact   1560
ttggaagaaa ttgacgatat cttcaatcgt tctgcgttct ctatcgcgcg cgagaacatc   1620
tccaacttga agaagggtat ttggtaa                                       1647
```

<210> SEQ ID NO 48
<211> LENGTH: 1575
<212> TYPE: DNA
<213> ORGANISM: Metschnikowia
<220> FEATURE:
<223> OTHER INFORMATION: HXT2.6 from H0 Metschnikowia sp.

<400> SEQUENCE: 48

```
atgctgagca ctaccgatac cctcgaaaaa agggacaccg agcctttcac ttcagatgct     60
cctgtcacag tccatgacta tatcgcagag gagcgtccgt ggtggaaagt gccgcatttg    120
cgtgtattga cttggtctgt tttcgtgatc accctcacct ccaccaacaa cgggtatgat    180
ggcctgatgt tgaatggatt gcaatccttg gacatttggc aggaggattt gggtcaccct    240
gcgggccaga aattgggtgc cttggccaac ggtgtttttgt ttggtaacct tgctgctgtg    300
```

```
ccttttgctt cgtatttctg cgatcgtttt ggtagaaggc cggtcatttg tttcggacag    360
atcttgacaa ttgttggtgc tgtattacaa ggtttgtcca acagctatgg atttttttg    420 ggttcgagaa ttgtgttggg ttttggtgct atgatagcca ctattccgct gccaacattg    480
atttccgaaa tcgcctaccc tacgcataga gaaacttcca ctttcgccta caacgtgtgc    540
tggtatttgg gagccattat cgcctcctgg gtcacatacg caccagaga tttacagagc    600 aaggcttgct ggtcaattcc ttcttatctc caggccgcct tacctttctt tcaagtgtgc    660
atgatttggt ttgtgccaga gtctcccaga ttcctcgttg ccaagggcaa gatcgaccaa    720
gcaagggctg ttttgtctaa ataccataca ggagactcga ctgacccag agacgttgcg    780 ttggttgact ttgagctcca tgagattgag agtgcattgg agcaggaaaa attgaacact    840
cgctcgtcat actttgactt tttcaagaag agaaacttta gaaagagagg cttcttgtgt    900
gtcatggtcg gtgttgcaat gcagctttct ggaaacggct tagtgtccta ttacttgtcg    960
aaagtgctag actcgattgg aatcactgaa accaagagac agctcgagat caatggctgc   1020
ttgatgatct ataactttgt catctgcgtc tcgttgatga gtgtttgccg tatgttcaaa   1080
agaagagtat tatttctcac gtgtttctca ggaatgacgg tttgctacac gatatggacg   1140
attttgtcag cgcttaatga acagagacac tttgaggata aaggcttggc caatggcgtg   1200
ttggcaatga tcttcttcta ctatttttc tacaacgttg gcatcaatgg attgccattc   1260
ctatacatca ccgagatctt gcctactca cacagagcaa aaggcttgaa tttattccaa   1320
ttctcgcaat ttctcacgca aatctacaat ggctatgtga acccaatcgc catggacgca   1380
atcagctgga agtattacat tgtgtactgc tgtattctct tcgtggagtt ggtgattgtg   1440
tttttcacgt tcccagaaac ttcgggatac actttggagg aggtcgccca ggtatttggt   1500
gatgaggctc ccgggctcca caacagacaa ttggatgttg cgaaagaatc actcgagcat   1560
gttgagcatg tttga                                                    1575
```

<210> SEQ ID NO 49
<211> LENGTH: 1692
<212> TYPE: DNA
<213> ORGANISM: Metschnikowia
<220> FEATURE:
<223> OTHER INFORMATION: QUP2 from H0 Metschnikowia sp.

<400> SEQUENCE: 49

```
atgggctttc gcaacttaaa gcgcaggctc tcaaatgttg gcgactccat gtcagtgcac     60
tctgtgaaag aggaggaaga cttctcccgc gtggaaatcc cggatgaaat ctacaactat    120
aagatcgtcc ttgtggcttt aacagcggcg tcggctgcca tcatcatcgg ctacgatgca    180
ggcttcattg gtggcacggt ttcgttgacg gcgttcaaac tggaatttgg cttggacaaa    240
atgtctgcga cggcggcttc tgctatcgaa gccaacgttg tttccgtgtt ccaggccggc    300
gcctactttg ggtgtctttt cttctatccg attggcgaga tttggggccg taaaatcggt    360
cttcttcttt ccggctttct tttgacgttt ggtgctgcta tttctttgat tcgaactcg    420 tctcgtggcc ttggtgccat atatgctgga agagtactaa caggtttggg gattggcgga    480
tgtctgagtt tggccccaat ctacgtttct gaaatcgcgc tgcagcaat cagaggcaag    540 cttgtgggct gctgggaagt gtcatggcag gtgggcggca ttgttggcta ctggatcaat    600
tacggagtct tgcagactct tccgattagc tcacaacaat ggatcatccc gtttgctgta    660
caattgatcc catcggggct tttctgggc ctttgtcttt tgattccaga gctgccacgt    720
tttcttgtat cgaagggaaa gatcgataag gcgcgcaaaa acttagcgta cttgcgtgga    780
```

```
cttagcgagg accacccta ttctgtttt gagttggaga acattagtaa ggccattgaa      840
gagaacttcg agcaaacagg aaggggtttt ttcgacccat tgaaagcttt gttttcagc      900 aaaaaaatgc tttaccgcct tctcttgtcc acgtcaatgt tcatgatgca gaatggctat     960
ggaatcaatg ctgtgacata ctactcgccc acgatcttca aatccttagg cgttcagggc   1020
tcaaacgccg gtttgctctc aacaggaatt ttcggtcttc ttaaaggtgc cgcttcggtg   1080
ttctgggtct ttttcttggt tgacacattc ggccgccggt tttgtctttg ctacctctct   1140
ctcccctgct cgatctgcat gtggtatatt ggcgcataca tcaagattgc caacccttca   1200
gcgaagcttg ctgcaggaga cacagccacc accccagcag gaactgcagc gaaagcgatg   1260
ctttacatat ggacgatttt ctacggcatt acgtggaatg gtacgacctg ggtgatctgc   1320
gcggagattt tcccccagtc ggtgagaaca gccgcgcagg ccgtcaacgc ttcttctaat   1380
tggttctggg ctttcatgat cggccacttc actggccagg cgctcgagaa tattgggtac   1440
ggatactact tcttgtttgc ggcgtgctct gcaatcttcc ctgtggtagt ctggtttgtg   1500
taccccgaaa caagggtgt gcctttggag gccgtggagt atttgttcga ggtgcgtcct   1560
tggaaagcgc actcatatgc tttgagaag taccagattg agtacaacga gggtgaattc   1620
caccaacata gcccgaagt actcttacaa gggtctgaaa actcggacac gagcgagaaa   1680
agcctcgcct ga                                                      1692

<210> SEQ ID NO 50
<211> LENGTH: 1887
<212> TYPE: DNA
<213> ORGANISM: Metschnikowia
<220> FEATURE:
<223> OTHER INFORMATION: APS1/HGT19 from H0 Metschnikowia sp

<400> SEQUENCE: 50
atgtcagaaa agcctgttgt gtcgcacagc atcgacacga cgctgtctac gtcatcgaaa     60
caagtctatg acggtaactc gcttcttaag accctgaatg agcgcgatgg cgaacgcggc    120
aatatcttgt cgcagtacac tgaggaacag gccatgcaaa tgggccgcaa ctatgcgttg    180
aagcacaatt tagatgcgac actctttgga aaggcggccg cggtcgcaag aaacccatac    240
gagttcaatt cgatgagttt tttgaccgaa gaggaaaaag tcgcgcttaa cacggagcag    300
accaagaaat ggcacatccc aagaaagttg gtggaggtga ttgcattggg gtccatggcc    360
gctgcggtgc agggtatgga tgagtcggtg gtgaatggtg caacgctttt ctaccccacg    420
gcaatgggta tcacagatat caagaatgcc gatttgattg aaggtttgat caacggtgcg    480
ccctatcttt gctgcgccat catgtgctgg acatctgatt actggaacag gaagttgggc    540
cgtaagtgga ccattttctg gacatgtgcc atttctgcaa tcatgtatct ggcaaggt      600 ctcgtcaatt tgaaatggta ccatttgttc attgcgcgtt tctgcttggg tttcggtatc    660
ggtgtcaagt ctgccaccgt gcctgcgtat gctgccgaaa ccaccccggc caaaatcaga    720
ggctcgttgg tcatgctttg gcagttcttc accgctgtcg gaatcatgct tggttacgtg    780
gcgtctttgg cattctatta cattggtgac aatggcattt ctggcggctt gaactggaga    840
ttgatgctag gatctgcatg tcttccagct atcgttgtgt tagtccaagt tccgtttgtt    900
ccagaatccc ctcgttggct catgggtaag gaaagacacg ctgaagcata tgattcgctc    960
cggcaattgc ggtcagtga aatcgaggcg gcccgtgact gtttctacca gtacgtgttg   1020
ttgaaagagg agggctctta tggaacgcag ccattcttca gcagaatcaa ggagatgttc   1080
```

| | |
|---|---|
| accgtgagaa gaaacagaaa tggtgcattg ggcgcgtgga tcgtcatgtt catgcagcag | 1140 |
| ttctgtggaa tcaacgtcat tgcttactac tcgtcgtcga tcttcgtgga gtcgaatctt | 1200 |
| tctgagatca aggccatgtt ggcgtcttgg gggttcggta tgatcaattt cttgtttgca | 1260 |
| attccagcgt tctacaccat tgacacgttt ggccgacgca acttgttgct cactactttc | 1320 |
| cctcttatgg cggtattctt actcatggcc ggattcgggt tctggatccc gttcgagaca | 1380 |
| aacccacacg gccgtttggc ggtgatcact attggtatct atttgtttgc atgtgtctac | 1440 |
| tctgcgggcg agggaccagt tcccttcaca tactctgccg aagcattccc gttgtatatc | 1500 |
| cgtgacttgg gtatgggctt tgccacggcc acgtgttggt tcttcaactt cattttggca | 1560 |
| ttttcctggc ctagaatgaa gaatgcattc aagcctcaag gtgcctttgg ctggtatgcc | 1620 |
| gcctggaaca ttgttggctt cttcttagtg ttatggttct tgcccgagac aaagggcttg | 1680 |
| acgttggagg aattggacga agtgtttgat gtgcctttga gaaaacacgc gcactaccgt | 1740 |
| accaaagaat tagtatacaa cttgcgcaaa tacttcttga ggcagaaccc taagccattg | 1800 |
| ccgccacttt atgcacacca agaatggct gttaccaacc cagaatggtt ggaaaagacc | 1860 |
| gaggtcacgc acgaggagaa tatctag | 1887 |

<210> SEQ ID NO 51
<211> LENGTH: 1620
<212> TYPE: DNA
<213> ORGANISM: Pichia gulliermondii
<220> FEATURE:
<223> OTHER INFORMATION: exemplary xylose transporter from Pichia gulliermondii AXT1

<400> SEQUENCE: 51

| | |
|---|---|
| atggcttacg aggacaaact agtggctccg gccttgaagt ttagaaactt tcttgacaaa | 60 |
| actcccaata tctacaatcc atatatcatt tctataatct cgtgcattgc gggtatgatg | 120 |
| ttcggttttg atatttcttc aatgtcagcg tttgtcagtt taccagcata cgtgaattat | 180 |
| ttcgatacac cttcagcagt gattcaagga tttatcacat ctgccatggc tttgggttca | 240 |
| tttttcgggt caattgcttc tgcgtttgtg tctgagccat ttggaagacg agcttcctta | 300 |
| ctaacttgtt cgtggttttg gatgatagga gcagccatcc aagcgtcttc gcagaaccga | 360 |
| gctcaattga ttattggtcg gattatatct ggatttgggg ttggtttcgg gtcgtctgtg | 420 |
| gctcccgtat atggctccga gatggcacct agaaaaatta gggaagaat tggtggaatt | 480 |
| tttcaattat ctgtcaccct cggtatcatg attatgttct tcataagtta cggaacttct | 540 |
| catattaaga ctgcggcagc tttcaggtta gcctgggcac tccagatcat tcctggactc | 600 |
| ctcatgtgta ttggtgtctt ctttattcca gaatctccta gatggttggc caaacaaggt | 660 |
| cactgggacg aagccgaaat cattgtagcc aaaattcaag ccaaaggaga tcgagaaaat | 720 |
| cccgatgttt tgattgaaat ttcggaaata aagaccaat tgatggttga cgagaatgcc | 780 |
| aaagccttta cctatgctga cttgtttcg aaaaatatc ttcccagaac catcacagcc | 840 |
| atgttcgctc aaatctggca acaattgaca ggaatgaatg tcatgatgta ctatatcgtt | 900 |
| tacattttcg aaatggctgg ctacggtgga aatggagtgt tggtatcatc gacaattcag | 960 |
| tacgttatct ttgtcgttgt tacatttgtc tcattattct ttttgacaa atttggaaga | 1020 |
| agaaaaattt tacttgtcgg agcagcttcc atgatgacct ggcagtttgc agtggcaggg | 1080 |
| atcttggcca ggtactcggt cccgtacgat ctcagcgata ctgtcaaaat taaaattcct | 1140 |
| gacaatcaca atcggctgc aaaaggtgtc attgcatgct gctatctttt cgtagcatcg | 1200 |

```
ttcggatttt cctggggagt tggtatctgg ttatactgct ctgaagtctg ggagactca    1260 caatcgagac agagaggagc cgctgtgtca actgcttcaa attggatttt caattttgcg    1320
ctcgccatgt tcacaccatc ttcgtttaaa aatatcacct ggaagacata ctgtatttat    1380
gccactttct gcgcatgtat gttcatccat gtgttcttct tcttcccaga aaccaagggg    1440
aagcgcttgg aagaaattgc tcaaatttgg gaagaaaaaa ttccagcttg gaaaaccacc    1500
aactggcaac tcatgttccc tttgttgtcg gaccacgaac ttgcggaaaa gatcaatgcc    1560
gaacatgtgg agaacgtgaa ttctagggaa caatcggatg acgagaagtc gcaggtataa    1620
```

<210> SEQ ID NO 52
<211> LENGTH: 1644
<212> TYPE: DNA
<213> ORGANISM: Candida intermedia
<220> FEATURE:
<223> OTHER INFORMATION: exemplary xylose transporter from Candida
      intermedia PYCC 4715 GXF1

<400> SEQUENCE: 52

```
atgtcacaag attcgcattc ttctggtgcc gctacaccag tcaatggttc catccttgaa      60
aaggaaaaag aagactctcc agttcttcaa gttgatgccc acaaaaaggg tttcaaggac     120
tacattgtca tttctatctt ctgttttatg gttgccttcg gtggtttcgt cttcggtttc     180
gacactggta ccatttccgg tttcgtgaac atgtctgact taaagacag attcggtcaa      240 caccacgctg atggtactcc ttacttgtcc gacgttagag ttggtttgat gatttctatt     300
ttcaacgttg gttgcgctgt cggtggtatt ttcctctgca aggtcgctga tgtctggggt     360
agaagaattg gtcttatgtt ctccatggct gtctacgttg ttggtattat tattcagatc     420
tcttcatcca ccaagtggta ccagttcttc attggtcgtc ttattgctgg tttggctgtt     480
ggtaccgttt ctgtcgtttc cccacttttc atctctgagg tttctccaaa gcaaattaga     540
ggtactttag tgtgctgctt ccagttgtgt atcaccttgg gtatcttctt gggttactgt     600
actacttacg gtactaagac ctacactgac tctagacagt ggagaattcc tttgggtttg     660
tgtttcgctt gggctatctt gttggttgtc ggtatgttga acatgccaga gtctccaaga     720
tacttggttg agaagcacag aattgatgag gccaagagat ccattgccag atccaacaag     780
atccctgagg aggacccatt cgtctacact gaggttcagc ttattcaggc cggtattgag     840 agaagcttt ggctggtca ggcatcttgg aaggagttga tcactggtaa gccaaagatc      900
ttcagaagag ttatcatggg tattatgctt cagtccttgc aacagttgac cggtgacaac     960
tacttcttct actacggtac taccattttc caggctgtcg gtttgaagga ttcttttccag    1020 acttctatca ttttgggtat tgtcaacttt gcttccacct tcgttggtat ctatgtcatt    1080
gagagattgg gtagaagatt gtgtcttttg accggttccg ctgctatgtt catctgtttc    1140
atcatctact ctttgattgg tactcagcac ttgtacaagc aaggttactc caacgagacc    1200
tccaacactt acaaggcttc tggtaacgct atgatcttca tcacttgtct ttacattttc    1260
ttctttgctt ctacctgggc tggtggtgtt tactgtatca tttccgagtc ctacccattg    1320
agaattagat ccaaggccat gtctattgct ccgctgcta actggttgtg ggtttcttg     1380 atttccttct tcactccatt catcaccagt gccatccact tctactacgg tttcgttttc    1440
actggttgtt tggctttctc tttcttctac gtctacttct tcgtctacga aaccaagggt    1500 cttttctttgg aggaggttga tgagatgtac gcttccggtg ttcttccact caagtctgcc    1560
agctgggttc caccaaatct tgagcacatg gctcactctg ccggttacgc tggtgctgac    1620
```

```
aaggccaccg acgaacaggt ttaa                                          1644
```

<210> SEQ ID NO 53
<211> LENGTH: 1644
<212> TYPE: DNA
<213> ORGANISM: Candida intermedia
<220> FEATURE:
<223> OTHER INFORMATION: exemplary glucose/xylose symporter from Candida
      intermedia GXS1

<400> SEQUENCE: 53

```
atgtcacaag attcgcattc ttctggtgcc gctacaccag tcaatggttc catccttgaa     60
aaggaaaaag aagactctcc agttcttcaa gttgatgccc acaaaaaggg tttcaaggac    120
tacattgtca tttctatctt ctgttttatg gttgccttcg gtggtttcgt cttcggtttc    180
gacactggta ccatttccgg tttcgtgaac atgtctgact taaagacag attcggtcaa    240
caccacgctg atggtactcc ttacttgtcc gacgttagag ttggtttgat gatttctatt    300
ttcaacgttg ttgcgctgt cggtggtatt ttcctctgca aggtcgctga tgtctggggt    360
agaagaattg gtcttatgtt ctccatggct gtctacgttg ttggtattat tattcagatc    420
tcttcatcca ccaagtggta ccagttcttc attggtcgtc ttattgctgg tttggctgtt    480
ggtaccgttt ctgtcgtttc cccacttttc atctctgagg tttctccaaa gcaaattaga    540
ggtactttag tgtgctgctt ccagttgtgt atcaccttgg gtatcttctt gggttactgt    600
actacttacg gtactaagac ctacactgac tctagacagt ggagaattcc tttgggtttg    660
tgtttcgctt gggctatctt gttggttgtc ggtatgttga acatgccaga gtctccaaga    720
tacttggttg agaagcacag aattgatgag gccaagagat ccattgccag atccaacaag    780
atccctgagg aggacccatt cgtctacact gaggttcagc ttattcaggc cggtattgag    840
agagaagctt ggctggtca ggcatcttgg aaggagttga tcactggtaa gccaaagatc    900
ttcagaagag ttatcatggg tattatgctt cagtccttgc aacagttgac cggtgacaac    960
tacttcttct actacggtac taccattttc caggctgtcg gtttgaagga ttctttccag   1020
acttctatca ttttgggtat tgtcaacttt gcttccacct tcgttggtat ctatgtcatt   1080
gagagattgg gtagaagatt tgtgtctttg accggttccg ctgctatgtt catctgtttc   1140
atcatctact ctttgattgg tactcagcac ttgtacaagc aaggttactc caacgagacc   1200
tccaacactt acaaggcttc tggtaacgct atgatcttca tcacttgtct ttacattttc   1260
ttcttgctt ctacctgggc tggtggtgtt tactgtatca tttccgagtc ctacccattg   1320
agaattagat ccaaggccat gtctattgct accgctgcta actggttgtg gggttcttg   1380
atttccttct tcactccatt catcaccagt gccatccact tctactacgg tttcgttttc   1440
actggttgtt tggctttctc tttcttctac gtctacttct tcgtctacga aaccaagggt   1500
cttttctttgg aggaggttga tgagatgtac gcttccggtg ttcttccact caagtctgcc   1560
agctgggttc caccaaatct tgagcacatg gctcactctg ccggttacgc tggtgctgac   1620
aaggccaccg acgaacaggt ttaa                                         1644
```

<210> SEQ ID NO 54
<211> LENGTH: 1725
<212> TYPE: DNA
<213> ORGANISM: Saccharomyces cerevisiae
<220> FEATURE:
<223> OTHER INFORMATION: exemplary xylose transporter from Saccharomyces
      cerevisiae GAL2/GXF2

<400> SEQUENCE: 54

```
atggcagttg aggagaacaa tatgcctgtt gtttcacagc aaccccaagc tggtgaagac    60
gtgatctctt cactcagtaa agattcccat ttaagcgcac aatctcaaaa gtattctaat   120
gatgaattga agccggtga gtcagggtct gaaggctccc aaagtgttcc tatagagata   180
cccaagaagc ccatgtctga atatgttacc gtttccttgc tttgtttgtg tgttgccttc   240
ggcggcttca tgtttggctg ggataccggt actatttctg ggtttgttgt ccaaacagac   300
tttttgagaa ggtttggtat gaaacataag gatggtaccc actatttgtc aaacgtcaga   360
acaggtttaa tcgtcgccat tttcaatatt ggctgtgcct ttggtggtat tatactttcc   420
aaaggtggag atatgtatgg ccgtaaaaag ggtctttcga ttgtcgtctc ggtttatata   480
gttggtatta tcattcaaat tgcctctatc aacaagtggt accaatattt cattggtaga   540
atcatatctg gtttgggtgt cggcggcatc gccgtcttat gtcctatgtt gatctctgaa   600
attgctccaa agcacttgag aggcacacta gtttcttgtt atcagctgat gattactgca   660
ggtatctttt tgggctactg tactaattac ggtacaaaga gctattcgaa ctcagttcaa   720
tggagagttc cattagggct atgtttcgct tggtcattat ttatgattgg cgctttgacg   780
ttagttcctg aatccccacg ttatttatgt gaggtaaata aggtagaaga cgccaagcgt   840
tccattgcta agtctaacaa ggtgtcacca gaggatcctg ccgtccaggc agagttagat   900
ctgatcatgg ccgtatagaa gctgaaaaa ctggctggca atgcgtcctg gggggaatta   960
ttttccacca agaccaaagt atttcaacgt tgttgatgg gtgtgtttgt tcaaatgttc  1020
caacaattaa ccgtaacaa ttattttttc tactacggta ccgttatttt caagtcagtt  1080
ggcctggatg attcctttga aacatccatt gtcattggtg tagtcaactt tgcctccact  1140
ttctttagtt tgtggactgt cgaaaacttg ggacatcgta atgtttact tttgggcgct  1200 gccactatga tggcttgtat ggtcatctac gcctctgttg gtgttactag attatatcct  1260
cacggtaaaa gccagccatc ttctaaaggt gccggtaact gtatgattgt ctttacctgt  1320
ttttatattt tctgttatgc cacaacctgg gcgccagttg cctgggtcat cacagcagaa  1380
tcattcccac tgagagtcaa gtcgaaatgt atggcgttgg cctctgcttc caattgggta  1440
tgggggttct tgattgcatt tttcacccca ttcatcacat ctgccattaa cttctactac  1500
ggttatgtct tcatgggctg tttggttgcc atgtttttttt atgtctttttt ctttgttcca  1560 gaaactaaag gcctatcgtt agaagaaatt caagaattat gggaagaagg tgttttacct  1620
tggaaatctg aaggctggat tccttcatcc agaagaggta ataattacga tttagaggat  1680
ttacaacatg acgacaaacc gtggtacaag gccatgctag aataa                 1725
```

<210> SEQ ID NO 55
<211> LENGTH: 573
<212> TYPE: DNA
<213> ORGANISM: Artificial Sequence
<220> FEATURE:
<223> OTHER INFORMATION: Codon optimized antibiotics gene sequence of
    MeNAT

<400> SEQUENCE: 55

```
atgggtacca ccttggacga caccgcctac agatacagaa cctccgtccc aggtgacgcc    60
gaggccatcg aggccttgga cggttccttc accaccgaca ccgtcttcag agtcaccgcc   120
accggtgacg gtttcacctt gagagaggtc ccagtggacc caccattgac caaggtcttc   180
ccagacgacg agtccgacga cgagtccgac gacggtgagg acggtgaccc agactccaga   240
accttcgtcg cctacggtga cgacggtgac ttggccggtt tcgtggtcgt ctcctactcc   300
```

```
ggttggaaca gaagattgac cgtcgaggac atcgaggtcg ccccagagca cagaggtcac    360
ggtgtcggta gagccttgat gggtttggcc accgagttcg ccagagagag aggtgccggt    420
cacttgtggt tggaggtcac caacgtcaac gccccagcca tccacgccta cagaagaatg    480
ggtttcacct tgtgcggttt ggacactgcc ttgtacgacg gcaccgcctc tgacggtgag    540
caggctttgt acatgtccat gccatgtcca taa                                 573
```

```
<210> SEQ ID NO 56
<211> LENGTH: 1032
<212> TYPE: DNA
<213> ORGANISM: Artificial Sequence
<220> FEATURE:
<223> OTHER INFORMATION: Codon optimized antibiotics gene sequence of
      MeHPH

<400> SEQUENCE: 56
```

```
atgggtacca agaagcctga gttgaccact acttctgttg agaagttctt gatcgaaaag     60
ttcgactctg tttctgactt gatgcagttg tccgagggtg aggagtccag agctttctcc    120
ttcgacgttg gtggtagagg ttacgtcttg agagtcaact cctgtgccga cggtttctac    180
aaggacagat acgtctacag acacttcgcc tccgctgctt gccaatccc agaggtcttg     240 gacatcggtg agttctctga gtctttgacc tactgtatct ccagaagagc cagggtgtc    300 accttgcagg acttgccaga gaccgagttg ccagccgtct gcagccagt cgctgaggct    360 atggacgcta cgctgctgc cgacttgtct cagacttctg gtttcggtca attcggtcca    420
cagggtatcg gtcagtacac cacttggaga gacttcatct gtgccatcgc cgacccacac    480
gtctaccact ggcagaccgt tatggacgac accgtttctg cctctgttgc ccaggctttg    540
gacgagttga tgttgtgggc tgaggactgt ccagaggtta gacacttggt tcacgctgac    600
ttcggttcca caacgtcttt gaccgacaac ggtagaatca ccgctgtcat cgactggtct    660
gaggctatgt tcggtgactc ccagtacgag gtcgccaaca tcttcttctg gagaccttgg    720
ttggcctgta tggagcagca gaccagatac ttcgagagaa gacacccaga gttggctggt    780
tctccaagat tgagagctta catgttgaga tcggtttggg accagttgta ccagtccttg    840
gttgacggta acttcgacga cgctgcctgg gctcagggta gatgtgacgc tatcgtcaga    900
tctggtgctg gcaccgttgg tagaacccag atcgctagaa gatccgctgc tgtctggacc    960
gacggttgtg tcgaggtttt ggctgactct ggtaacagaa gaccatccac cagaccaaga   1020
gccaaggagt aa                                                       1032
```

```
<210> SEQ ID NO 57
<211> LENGTH: 813
<212> TYPE: DNA
<213> ORGANISM: Artificial Sequence
<220> FEATURE:
<223> OTHER INFORMATION: Codon optimized antibiotics gene sequence of
      MeKAN

<400> SEQUENCE: 57
```

```
atgggtacca aggaaaagac tcacgtttcg agaccaagat tgaactccaa catggatgct     60
gatttgtacg gttacaaatg ggctagagat aacgtcggtc aatctggtgc gactatctac    120
agactttacg gcaagcccga tgcgccagag ttgttcttga agcatggcaa aggttccgtt    180
gccaacgacg ttaccgatga gatggtcaga cttaactggt tgacggaatt tatgcctctt    240
cctaccatca agcacttcat ccgtactcct gatgacgcct ggttgctcac cactgcgatc    300
```

```
ccaggcaaaa ccgctttcca ggtcttggag aatacccctg attctggtga acattgtt      360 gacgcgttgg ccgtgttctt gcgtagattg cactcgattc ctgtttgtaa ctgtcctttc    420
aactccgacc gtgtgttcag actcgctcag gcccaatcca gaatgaacaa cggtttggtt    480
gacgcgtctg actttgatga cgagcgtaac ggctggcctg ttgagcaggt ctggaaagag    540
atgcacaagc tcttgccatt ctctccagat tccgtcgtta ctcacggtga tttctctctt    600
gacaacctta ttttcgacga gggtaagttg atcggttgta ttgatgttgg tagagtcggt    660
atcgctgaca gataccagga tcttgccatc ctctggaact gcctcggtga gttctctcct    720
tccttgcaga agagactttt ccagaagtac ggtattgata accctgatat gaacaagttg    780
cagttccact tgatgctcga cgagttcttt tga                                 813

<210> SEQ ID NO 58
<211> LENGTH: 387
<212> TYPE: DNA
<213> ORGANISM: Artificial Sequence
<220> FEATURE:
<223> OTHER INFORMATION: Codon optimized antibiotics gene sequence of
      MeBLE

<400> SEQUENCE: 58
atgggtaccg ccgaccaagc gacgcccaac ttgccatcca gagatttcga ttccacggct     60
gccttctacg aaagattggg cttcggtatc gttttcagag acgccggttg gatgatcctc    120
cagagaggtg atctcaagtt ggagttcttc gcccacccag gtctcgatcc actcgcttcc    180
tggttcagct gctgtttgag attggacgac ctcgcggagt tctacagaca gtgcaaatcc    240
gtcggcatcc aggaaaccag cagcggttac ccaagaatcc acgctccaga gttgcaggag    300
tggggtggca cgatggccgc tttggttgac ccagacggta cgctcttgcg tttgatccag    360
aacgagttgc ttgctggcat ctcctga                                        387

<210> SEQ ID NO 59
<211> LENGTH: 1025
<212> TYPE: DNA
<213> ORGANISM: Artificial Sequence
<220> FEATURE:
<223> OTHER INFORMATION: Codon optimized antibiotics gene sequence of
      XYL2up

<400> SEQUENCE: 59
accggatgca cacgaaagga gtatgtgcca gcgaagcaac aacgccaagt gtcacggatg     60
acgagtatga cgatgaaaca gacgtggaga actgtaatgg aggggaacct gaatcaagag    120
tgagacaata cagaacatgt gcagatgata ttttaagtgt tcagagcctt gactaaagca    180
gttgattcaa gacgtatagt acctttgaag tacctatata aaagtaataa gaggtactcg    240
gcacacgttg accaatctta tgttttggca tgactacgat gtaccgtaga gtgttcaatt    300
tgatgtttag atcaatctat tagcgactgc ggaaagtaag ggagagccct aagaactgaa    360
tccccgcatt gccggcgtcg accgcagtga accaacgta agtctattat gtcgaatgtg     420
aacaacgagc caagtgcata gattgggtct ccccgcgacg cacaagcgga gactccggag    480
agtcacacat gtggctgaga cggcaaaaag tgggctgatt caagagcaac gcattccaaa    540
acatcagatt ttcacaagct tgaataaat ttttattcgc ctgacaatta cgagcgtact    600
gcggcgatgt aagtgaatcg gatgccccc atttgtttca tgcgcagccg caatataata    660
aaaaaaaagg ggccgatcta tgacgtaatg gctatttcag cgcttttatt cgagatctga    720
agctcgtcac ttgctgaagt tcgtaatata ttctaacaca aataaattcc gacgtggcgc    780
```

```
atgaaactga gtttatgagg gtcaagcagg ataagaattt acgaaaggct taacgcgtgc    840
gttatgaact gaataacctt cgtgtcaaca acaaactggg gtttcccgc  gctgagtttt    900 cccgagaatc attgctgcgc gaagactccg acactctgca gtatgcgtgg gatgctataa    960 attatgacg  acgacgtatt ccactttttt tccttttctt taatcagccg acaccatatc   1020
cgaaa                                                               1025
```

<210> SEQ ID NO 60
<211> LENGTH: 200
<212> TYPE: DNA
<213> ORGANISM: Artificial Sequence
<220> FEATURE:
<223> OTHER INFORMATION: Codon optimized antibiotics gene sequence of
      XYL2N

<400> SEQUENCE: 60

```
atgcctgcta acccatcctt ggttttgaac aaagtgaacg acatcacgtt cgagaactac     60
gaggttccgt tactcacaga ccccaacgat gtattggttc aggtgaaaaa gactggaatc    120
tgtggatctg acatccacta ctacacccac ggcagaattg gcgacttcgt gttgacaaag    180
ccaatggttt tgggccacga                                                200
```

<210> SEQ ID NO 61
<211> LENGTH: 780
<212> TYPE: DNA
<213> ORGANISM: Artificial Sequence
<220> FEATURE:
<223> OTHER INFORMATION: Codon optimized antibiotics gene sequence of
      XYL2 C

<400> SEQUENCE: 61

```
agtggccact acaacttgtg cccacacatg tgttttgccg ccacgcccaa ctctaacccc     60
gacgagccaa acccgccagg gactttgtgc aaatattaca gtccccagc  ggacttcttg    120 gtgaaattgc ctgagcacgt ctcccttgag ttgggcgcta tggtcgagcc tttgactgtc    180
ggtgtgcacg cctcgcgttt gggccgtgtc acttttggtg accacgttgt ggttttcggt    240
gctggcccag tcggtatcct tgcggctgcc gtggccagaa agtttggcgc tgccagcgtg    300
actatcgtcg acatcttcga cagcaaattg gaattggcca gtccattgg  cgcggccact    360 cacacattca actcaatgac tgagggtgtt ctttcggagg ctttgcccgc gggcgtgaga    420
cctgacgttg tattggagtg cactggagca gagatctgtg tgcagcaagg tgtacttgcg    480
ttgaaggctg gtgccgcca  cgtgcaagtt ggaaatgccg gctcctatct caaattcccc    540
atcaccgaat tgttaccaa  ggagttgact ctctttggat ccttccgtta cggttacaac    600
gactacaaga cgtcggtcgc catcttggac gagaattaca gaacgggaa  ggagaatgcg    660 ttggtggact ttgaagcctt gattactcac cgtttcccct tcaagaatgc cattgaggct    720
tacgacgcgg tgcgcgctgg cgacggagct gtcaagtgta tcattgacgg cccagagtaa    780
```

<210> SEQ ID NO 62
<211> LENGTH: 200
<212> TYPE: DNA
<213> ORGANISM: Artificial Sequence
<220> FEATURE:
<223> OTHER INFORMATION: Codon optimized antibiotics gene sequence of
      XYL2C-prime

<400> SEQUENCE: 62

```
ccttccgtta cggttacaac gactacaaga cgtcggtcgc catcttggac gagaattaca     60
```

```
agaacgggaa ggagaatgcg ttggtggact ttgaagcctt gattactcac cgtttcccct    120
tcaagaatgc cattgaggct tacgacgcgg tgcgcgctgg cgacggagct gtcaagtgta    180
tcattgacgg cccagagtaa                                                200
```

<210> SEQ ID NO 63
<211> LENGTH: 553
<212> TYPE: DNA
<213> ORGANISM: Artificial Sequence
<220> FEATURE:
<223> OTHER INFORMATION: Codon optimized antibiotics gene sequence of
    XYL2 d

<400> SEQUENCE: 63

```
cgatgaaata aaaagataat acttgctctt actccattta tagactaatg tacgctgctt     60
cacgatagtt ttcctcacga tagtttattt aggctcgtcg agtctcgccg tctcgcatgc    120
tcatgagatc gttggcgagc tctctttctt gtctgctccg gccattcatg gtggaggcta    180
ttgaattttc aaactttgac agtgatgagt gcctaccgaa ggttgcatat tggtaaggca    240
catcgtgcgt gtatgagctt gccggatact gcatgagaaa tgatgctggg accgcagaat    300
tcagcaagtt tgccagcgat gtgcttgtca gtttcgcctc catcacgtca ttcgtagtgg    360
acgcaatagc gcttgaagac tgcgttggcc gaaccagtct gcttccatca gcgtgaatct    420
tgttcagcat acccgacaac atcttcgtct tgtatttgat gtacttcaaa attctgagat    480
acttcaagtc ctcgtctaga ttctcgtcat cccaatcgat atcggtactc tctgcatctt    540
cgacatcgga ctc                                                       553
```

<210> SEQ ID NO 64
<211> LENGTH: 924
<212> TYPE: DNA
<213> ORGANISM: Artificial Sequence
<220> FEATURE:
<223> OTHER INFORMATION: Codon optimized antibiotics gene sequence of
    XYL1

<400> SEQUENCE: 64

```
atgccccaag tggggtttgg gtgctggaaa gtaactaaca gtacatgtgc tgatacgatc     60
tacaacgcga tcaaagttgg ctacagatta tttgatggcg ctgaagatta cgggaacgag    120
aaagaggtgg gcgaaggaat caacagggcc attgacgaag gcttggtggc acgtgacgag    180
ttgttcgtgg tgtccaagct ctggaacaac ttccatcatc agacaacgt cgagaaggcg    240 ttggacaaga ctttgggcga cttgaatgtc gagtacttgg acttgttctt gatccatttc    300
ccaattgcgt tcaaattcgt gccctttgag gagaaatacc cgcccggctt ctactgtgga    360
gaaggcgata agtttatcta cgaggatgtg cctttgcttg acacgtggcg ggcattggag    420
aagtttgtga agaagggtaa gatcagatcc atcggaatct cgaacttttc cggcgcgttg    480
atccaggact tgctcagggg cgccgagatc cccctgccg tgttgcagat tgagcaccac    540
ccatacttgc agcagcccag attgattgag tatgtgcagt ccaagggtat tgccatcaca    600
gcctactcct cttttggccc acagtcgttt gtggagttgg accacccaa ggtcaaggag    660 tgtgtcacgc ttttcgagca cgaagacatt gtttccatcg ctaaagctca cgacaagtcc    720
gcgggccagg tattattgag gtgggcacg caaagggtc ttgccgtgat tccaaagtca    780
aacaaaaccg agcgtttgtt gctgaatttg aatgtgaacg attttgatct ctctgaagca    840
gaattggagc aaatcgcaaa gttggacgtg ggcttgcgct tcaacaaccc ttgggactgg    900
```

```
gacaagattc caatcttcca ctaa                                           924
```

<210> SEQ ID NO 65
<211> LENGTH: 735
<212> TYPE: DNA
<213> ORGANISM: Artificial Sequence
<220> FEATURE:
<223> OTHER INFORMATION: Codon optimized antibiotics gene sequence of
      ADH1 promotor

<400> SEQUENCE: 65

```
ttgtcttgta aagagtcttc ggtcattttt acgccgaatc ggcctctggt gtacaggtgt    60
aatgtaagca gaaagatgta gataatacat agcgtcaacg gttctatcga gtcaggattg   120
actgcggggc caaatgtggg gtatcacgtg tcgatggaaa ctgtcaacaa aagatgaatt   180 ttttttttgat cgtcaacgct gctctaagcg tgaatcaagg atatgcgctt atggggacgt  240
gcgatccgcg ccgcattcac ccgaagaacg tgctctcgat cgatcacccg gcgccgcgca   300
cggcccaatc gagaaagagg gacctcgag ataagcaccc cctttctcga gtatgtaca    360 tattatttac agcgaaatca caaaggccaa gtctactctc tatcacaatg attatttgca   420
cgctagaagt ttgccgcccc tctttcctca ttcaaagctg tttcagaaat gcactcgtaa   480
gcgcatgttc gtatcggcat cgcaggctca aatgcccagg agccgcccgc gcagcccat    540 aaacccattt caggcatatg cgcctagtgg cccgcagcgt gcgcgagcac cgaacatcac   600
cccacagcaa tgtataaaac ccgaacaata taaagcgat ccacatcgct cggtaatgcg   660
tccgttcttt cgttcatcag tatcacttgc attcacttca cgaatccgag ctacaaacat   720
catcgcaatc agaaa                                                    735
```

<210> SEQ ID NO 66
<211> LENGTH: 859
<212> TYPE: DNA
<213> ORGANISM: Artificial Sequence
<220> FEATURE:
<223> OTHER INFORMATION: Codon optimized antibiotics gene sequence of
      PGK1 promoter

<400> SEQUENCE: 66

```
atgttctggg tgtttctggt ttggagactg gctcagagat aaagcaaccg ggtgaataga   60
gatacagttt atttgaggcg gaaagagatc atcaggcata caaatgcgt ttcgagaata   120 aagttttgtt ggaatgcctt tatgcgtgat gttgatgtgg ggatctgtaa agcaacttga   180
cctgcaattg cattgcatgg gcccggtcgt gctcatttgt tggtatgcgc ttatccgggc   240
aaccacgttg ttgaaaagcg cggatgggcc ggagtactca cagcaagggc aatcgaccac   300
atttattctt agcgcccata gttcaggcgt ccggagtcat cagcggatgg tatctgttga   360
aaataaagtc tcctagagtt tttaatgtaa ttacttgcgt tttcgatttt tgtagaaagt   420
tttggagttt gtgggactga actcaggccc aatgcgattt ccgaatctgg agaaacgtag   480
tcgatatgcg attaggggta acaaaaagat ttcatagtca cacaaagatc aattcgacag   540
tattttgcag tgattgcatt gaaggccata atatcattgc aaatagtgtc tatttgggcc   600
cattggtgaa ttctgtctgt gttgagtcat tcaagacaca gcaatcaatt cgattgcagt   660
ctcgcaggtg gtgtggttgt ggtgcgactt gaaaacccg gaggatggta atccgccgag   720
aatgaactcc gagcgaaaac ccgtcagaca tatataaacc ctcacagtgc gcactactcg   780
cctggaaaaa ttagaattcg tttctatcaa ttcatctcca tttgatatca attgattcgc   840
atactaaaat ctataacta                                                859
```

```
<210> SEQ ID NO 67
<211> LENGTH: 283
<212> TYPE: DNA
<213> ORGANISM: Artificial Sequence
<220> FEATURE:
<223> OTHER INFORMATION: Codon optimized antibiotics gene sequence of
      PGK1 terminator

<400> SEQUENCE: 67
gtagttcgat aagtttgaca cttaccgatt gaatacacat tttaatctat gactttcatg        60
tttattatgt atattgaggt ccaaagcgtg taaaagggcg gagacatgtt cacaacttag       120
cggctccact catgattttg gtccacgact cttcagtcaa ttcttcatac ctgttcttgt       180
tcaaccagta gatcaactct ttgccgtcat cgccctttgg taacttttga ttcttgaact       240 gatttttttgg caccttgtga ttgtgagatg cttgtatgta ttg                        283
```